United States Patent
Skov et al.

(10) Patent No.: US 11,434,285 B2
(45) Date of Patent: ***Sep. 6, 2022

(54) ANTI-ABETA ANTIBODIES

(71) Applicant: OTHAIR PROTHENA LIMITED, Dublin (IE)

(72) Inventors: Michael Skov, Belmont, CA (US); Tarlochan S. Nijjar, Orinda, CA (US); Frédérique Bard, Pacifica, CA (US); Robin Barbour, Walnut Creek, CA (US); Wagner Zago, San Carlos, CA (US)

(73) Assignee: OTHAIR PROTHENA LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/510,170

(22) Filed: Oct. 25, 2021

(65) Prior Publication Data

US 2022/0041701 A1 Feb. 10, 2022

Related U.S. Application Data

(63) Continuation of application No. 17/383,765, filed on Jul. 23, 2021.

(60) Provisional application No. 63/219,611, filed on Jul. 8, 2021, provisional application No. 63/187,379, filed on May 11, 2021, provisional application No. 63/086,589, filed on Oct. 1, 2020, provisional application No. 63/055,813, filed on Jul. 23, 2020.

(51) Int. Cl.
| | |
|---|---|
| *C07K 16/00* | (2006.01) |
| *C07K 16/46* | (2006.01) |
| *C07K 16/18* | (2006.01) |
| *C07K 16/28* | (2006.01) |
| *A61K 39/00* | (2006.01) |

(52) U.S. Cl.
CPC .......... *C07K 16/18* (2013.01); *C07K 16/2887* (2013.01); *C07K 16/2896* (2013.01); *C07K 16/462* (2013.01); *A61K 2039/505* (2013.01); *C07K 2317/24* (2013.01); *C07K 2317/34* (2013.01); *C07K 2317/55* (2013.01); *C07K 2317/565* (2013.01); *C07K 2317/732* (2013.01); *C07K 2317/734* (2013.01); *C07K 2317/92* (2013.01); *C07K 2319/02* (2013.01); *C07K 2319/30* (2013.01); *C07K 2319/40* (2013.01)

(58) Field of Classification Search
None
See application file for complete search history.

(56) References Cited

U.S. PATENT DOCUMENTS

| | | |
|---|---|---|
| 5,624,821 A | 4/1997 | Winter et al. |
| 5,834,597 A | 11/1998 | Tso |
| 6,743,427 B1 | 6/2004 | Schenk |
| 6,750,324 B1 | 6/2004 | Schenk et al. |
| 6,761,888 B1 | 7/2004 | Schenk |
| 6,787,637 B1 | 9/2004 | Schenk |
| 7,049,138 B2 | 5/2006 | Seiffert et al. |
| 7,179,892 B2 | 2/2007 | Basi |
| 7,189,819 B2 | 3/2007 | Basi et al. |
| 7,195,761 B2 | 3/2007 | Holtzman et al. |
| 7,256,273 B2 | 8/2007 | Basi et al. |
| 7,335,491 B2 | 2/2008 | Drapeau et al. |
| 7,561,973 B1 | 7/2009 | Welch et al. |
| 7,575,880 B1 | 8/2009 | Schenk et al. |
| 7,582,733 B2 | 9/2009 | Basi et al. |
| 7,629,311 B2 | 12/2009 | Tobinick |
| 7,700,751 B2 | 4/2010 | Basi et al. |
| 7,825,223 B2 | 11/2010 | Godavarti et al. |
| 7,871,615 B2 | 1/2011 | Basi et al. |
| 8,003,097 B2 | 8/2011 | Schroeter et al. |
| 8,005,620 B2 | 8/2011 | Gustafsson et al. |
| 8,126,653 B2 | 2/2012 | Welch et al. |
| 8,128,928 B2 | 3/2012 | Basi et al. |
| 8,173,127 B2 | 5/2012 | Chain |
| 8,227,576 B2 | 7/2012 | Burbidge et al. |
| 8,246,954 B2 | 8/2012 | Pfeifer et al. |
| 8,412,461 B2 | 4/2013 | Gustafsson et al. |
| 8,470,321 B2 | 6/2013 | Ravetch et al. |
| 8,613,920 B2 | 12/2013 | Lieberburg et al. |
| 8,635,029 B2 | 1/2014 | Gustafsson et al. |
| 8,784,810 B2 | 7/2014 | Lieberburg et al. |
| 9,067,981 B1 | 6/2015 | Basi et al. |

(Continued)

FOREIGN PATENT DOCUMENTS

| | | |
|---|---|---|
| EP | 1960428 | 8/2008 |
| EP | 2165714 A1 | 3/2010 |

(Continued)

OTHER PUBLICATIONS

Skov et al. Novel Amyloid Beta Monoclonal Antibodies With Superior Binding Properties: Potential for More Convenient Dosing and Greater Patient Access in Alzheimer's Disease. Presented at the 13th edition of Clinical Trials on Alzheimer's Disease (CtaD2020), Nov. 4-7, 2020, Virtual/Boston, MA. (Year: 2020).*

GlobeNewswire. Prothena presents new data from robust Alzheimer's portfolio at the Alzheimer's Association International Conference 2021. pp. 1-5, Jul. 26, 2021. (Year: 2021).*

(Continued)

*Primary Examiner* — Maher M Haddad
(74) *Attorney, Agent, or Firm* — McDonnell Boehnen Hulbert & Berghoff LLP

(57) ABSTRACT

Antibodies that bind human beta-amyloid peptide, methods of detecting, measuring and treating amyloidogenic disorders with said antibodies, pharmaceutical compositions comprising the antibodies and methods of manufacture are provided.

19 Claims, 39 Drawing Sheets

Specification includes a Sequence Listing.

(56) References Cited

U.S. PATENT DOCUMENTS

| | | |
|---|---|---|
| 9,109,021 B2 | 8/2015 | Dealwis |
| 9,486,559 B2 | 11/2016 | Mazer et al. |
| 9,670,272 B2 | 6/2017 | Nitsch et al. |
| 9,828,420 B2 | 11/2017 | Nitsch et al. |
| 10,131,708 B2 | 11/2018 | Nitsch et al. |
| 10,202,445 B2 | 2/2019 | Nitsch et al. |
| 2010/0291071 A1 | 11/2010 | Matsubara et al. |
| 2015/0315267 A1 | 11/2015 | Bussiere et al. |
| 2019/0153082 A1 | 5/2019 | Nitsch et al. |
| 2019/0263896 A1 | 8/2019 | Nitsch et al. |
| 2021/0079103 A1 | 3/2021 | Soto et al. |

FOREIGN PATENT DOCUMENTS

| | | |
|---|---|---|
| EP | 3487531 A1 | 5/2019 |
| WO | 9404678 | 3/1994 |
| WO | 2002046237 A2 | 6/2002 |
| WO | 2002088306 A2 | 11/2002 |
| WO | 2004029630 A1 | 4/2004 |
| WO | 2005018424 A2 | 3/2005 |
| WO | 2005028511 A2 | 3/2005 |
| WO | 2005123775 A1 | 12/2005 |
| WO | 2006036291 A2 | 4/2006 |
| WO | 2006040153 A2 | 4/2006 |
| WO | 2006041934 A2 | 4/2006 |
| WO | 2006066171 A1 | 6/2006 |
| WO | 2006083689 A2 | 8/2006 |
| WO | 2007062852 A2 | 6/2007 |
| WO | 2006138737 A2 | 12/2007 |
| WO | 2008030251 A1 | 3/2008 |
| WO | 2008060364 A2 | 5/2008 |
| WO | 2008081008 A1 | 7/2008 |
| WO | 2008131298 A2 | 10/2008 |
| WO | 2008156622 A1 | 12/2008 |
| WO | 2009048538 A2 | 4/2009 |
| WO | 2009051220 A1 | 4/2009 |
| WO | 2009099176 A1 | 8/2009 |
| WO | 2009149185 A2 | 12/2009 |
| WO | 2010004434 A2 | 1/2010 |
| WO | 2010006060 A2 | 1/2010 |
| WO | 2010030203 A1 | 3/2010 |
| WO | 2010119704 A1 | 10/2010 |
| WO | 2010127294 A2 | 11/2010 |
| WO | 2011000095 A1 | 1/2011 |
| WO | 2011016238 A1 | 2/2011 |
| WO | 2011031720 A1 | 3/2011 |
| WO | 2011107507 A1 | 9/2011 |
| WO | 2011130377 A2 | 10/2011 |
| WO | 2012016173 A2 | 2/2012 |
| WO | 2012021469 A1 | 2/2012 |
| WO | 2012021475 A2 | 2/2012 |
| WO | 2012136552 A1 | 10/2012 |
| WO | 2013082045 A1 | 6/2013 |
| WO | 2013140349 A1 | 9/2013 |
| WO | 2014007982 A2 | 1/2014 |
| WO | 2014089149 A1 | 6/2014 |
| WO | 2014089500 | 6/2014 |
| WO | 2014089500 A1 | 6/2014 |
| WO | 2015001504 A2 | 1/2015 |
| WO | 2015035190 A1 | 3/2015 |
| WO | 2015120280 A1 | 8/2015 |
| WO | 2015155694 A1 | 10/2015 |
| WO | 2015165961 A1 | 11/2015 |
| WO | 2015172837 A1 | 11/2015 |
| WO | 2016005466 A2 | 1/2016 |
| WO | 2016016278 A2 | 2/2016 |
| WO | 2016040903 A1 | 3/2016 |
| WO | 2016087944 A2 | 6/2016 |
| WO | 2016097305 A1 | 6/2016 |
| WO | 2016137947 A1 | 9/2016 |
| WO | 2017009459 A2 | 1/2017 |
| WO | 2017106383 A1 | 6/2017 |
| WO | 2017123517 A1 | 7/2017 |
| WO | 2017127764 A1 | 7/2017 |
| WO | 2017157961 A1 | 9/2017 |
| WO | 2017186928 A1 | 11/2017 |
| WO | 2017211827 A1 | 12/2017 |
| WO | 2018081460 A1 | 5/2018 |
| WO | 2018083628 A1 | 5/2018 |
| WO | 2018091444 A1 | 5/2018 |
| WO | 2018119001 A1 | 6/2018 |
| WO | 2018141730 A1 | 8/2018 |
| WO | 2018204408 A1 | 11/2018 |
| WO | 2019016213 A1 | 1/2019 |
| WO | 2019040612 A1 | 2/2019 |
| WO | 2019064053 A1 | 4/2019 |
| WO | 2019074840 A1 | 4/2019 |
| WO | 2019157440 A1 | 8/2019 |
| WO | 2020015637 A1 | 1/2020 |
| WO | 2020023530 A2 | 1/2020 |
| WO | 2020037258 A1 | 2/2020 |
| WO | 2020092937 A1 | 5/2020 |
| WO | 2020167376 A1 | 8/2020 |
| WO | 2020193644 A1 | 10/2020 |
| WO | 2020198866 A1 | 10/2020 |
| WO | 2020257745 A1 | 12/2020 |
| WO | 2021078942 A1 | 4/2021 |
| WO | 2021113899 A1 | 6/2021 |
| WO | 2021186245 A1 | 9/2021 |
| WO | 2022020680 A1 | 1/2022 |

OTHER PUBLICATIONS

Miles LA, Crespi GA, Doughty L, Parker MW. Bapineuzumab captures the N-terminus of the Alzheimer's disease amyloid-beta peptide in a helical conformation. Sci Rep. 2013;3:1302. doi: 10.1038/srep01302. PMID: 23416764; PMCID: PMC3575012.

Ward ES, Güssow D, Griffiths AD, Jones PT, Winter G. Binding activities of a repertoire of single immunoglobulin variable domains secreted from *Escherichia coli*. Nature. Oct. 12, 1989;341(6242):544-6. doi: 10.1038/341544a0. PMID: 2677748.

Songsivilai S, Lachmann PJ. Bispecific antibody: a tool for diagnosis and treatment of disease. Clin Exp Immunol. Mar. 1990;79(3):315-21. doi: 10.1111/j.1365-2249.1990.tb08089.x. PMID: 2180597; PMCID: PMC1534963.

Kostelny SA, Cole MS, Tso JY. Formation of a bispecific antibody by the use of leucine zippers J Immunol Mar. 1, 1992;148(5):1547-53. PMID: 1531669.

Chothia C, Lesk AM Canonical structures for the hypervariable regions of immunoglobulins. J Mol Biol. Aug. 20, 1987;196(4):901-17. doi: 10.1016/0022-2836(87)90412-8. PMID: 3681981.

Chothia C, Lesk AM, Tramontane A, Levitt M, Smith-Gill SJ, Air G, Sheriffs, Padlan EA, Davies D, Tulip WR, et al. Conformations of immunoglobulin hypervariable regions. Nature. Dec. 21-28, 1989;342(6252):877-83. doi 10.1038/342877a0. PMID: 2687698.

Greg A. Lazar, Wei Dang, Sher Karki, Omid Vafa, Judy S. Peng, Linus Hyun, Cheryl Chan, Helen S. Chung, Araz Eivazi, Sean C. Yoder, Jost Vielmetter, David F. Carmichael, Robert J. Hayes, Bassil I. Dahiyat, "Engineered antibody Fc variants with enhanced effector function", Proceedings of the National Academy of Sciences Mar. 2006, 103 (11) 4005-4010; DOI: 10.1073/pnas.0508123103.

Hinton PR, Johlfs MG, Xiong JM, Hanestad K, Ong KC, Bullock C, Keller S, Tang MT, Tso JY, Vásquez M, Tsurushita N. Engineered human IgG antibodies with longer serum half-lives in primates. J Biol Chem. Feb. 20, 2004;279(8):6213-6. doi: 10.1074/jbc.C300470200. Epub Dec. 2, 20039. PMID: 14699147.

Kirkland T. M., Colwell D. E., Michalek S. M., et al. (1986) Analysis of the fine specificity and cross-reactivity of monoclonal anti-lipid A antibodies. J. Immunol.137, 3614 3619.

Morel GA, Yarmush DM, Colton CK, Benjamin DC, Yarmush ML. Monoclonal antibodies to bovine serum albumin: affinity and specificity determinations. Mol Immunol. Jan. 1988;25(1):7-15. doi: 10.1016/0161-5890(88)90085-5. PMID: 3343974.

Cheung RC, Trujillo DE, Robinson WS, Greenberg HB, Marion PL. Epitope-specific antibody response to the surface antigen of duck hepatitis B virus in infected ducks. Virology. Jun. 1990;176(2):546-52. doi: 10.1016/0042-6822(90) 90025-m. PMID: 1693247.

Moldenhauer G, Mielke B, Dörken B, Schwartz-Albiez R, Moller P. Identity of HML-1 antigen on intestinal intraepithelial T cells and

(56) References Cited

OTHER PUBLICATIONS of B-ly7 antigen on hairy cell leukaemia. Scand J Immunol. Aug. 1990;32(2):77-82. doi: 10.1111/i.1365-3083.1990.tb02896.x. PMID: 1697100.

Junghans RP, Waldmann TA, Landolfi NF, Avdalovic NM, Schneider WP, Queen C. Anti-Tac-H, a humanized antibody to the interleukin 2 receptor with new features for immunotherapy in malignant and immune disorders. Cancer Res. Mar. 1, 1990;50(5):1495-502. PMID: 2406013.

Nita Deshpande, Kenneth J. Addess, Wolfgang F. Bluhm, Jeffrey C. Merino-Ott, Wayne Townsend-Merino, Qing Zhang, Charlie Knezevich, Lie Xie, Li Chen, Zukang Feng, Rachel Kramer Green, Judith L. Flippen-Anderson, John Westbrook, Helen M. Berman, Philip E. Bourne, The RCSB Protein Data Bank: a redesigned query system and relational database based on the mmCIF schema, Nucleic Acids Research, vol. 33, Issue suppl_1, Jan. 1, 2005, pp. D233-D237, https://doi.org/10.1093/nar/gki057.

Saido TC, Iwatsubo T, Mann DM, Shimada H, Ihara Y, Kawashima S. Dominant and differential deposition of distinct beta-amyloid peptide species, A beta N3(pE), in senile plaques. Neuron. Feb. 1995;14(2):457-66. doi 10.1016/0896-6273(95)90301-1. PMID: 7857653.

Wagner Zago, Manuel Buttini, Thomas A. Comery, Christopher Nishioka, Shyra J. Gardai, Peter Seubert, Dora Games, Frédérique Bard, Dale Schenk, Gene G. Kinney, "Neutralization of Soluble, Synaptotoxic Amyloid β Species by Antibodies Is Epitope Specific" Journal of Neuroscience Feb. 22, 2012, 32 (8) 2696-2702; Doi: 10.1523/JNEUROSCI.1676-11.2012.

Liao et al., Engineering proteinase K using machine learning and synthetic genes, BMC Biotechnology, 2007, vol. 7, 19 pages.

Ehren et al., Protein engineering of improved prolyl endopeptidaases for celiac sprue therapy, Protein Engineering, Design & Selection, 2008, vol. 21, pp. 699-707.

Heinzelman et al., SCHEMA Recombination of a Fungal Cellulase Uncovers a Single Mutation that Contributes Markedly to Stability, Jun. 16, 2009, The Journal of Biological Chemistry, vol. 284, pp. 26229-26233.

Heinzelman et al., A family of thermostable fungal cellulases created by structure-guided recombination, Apr. 7, 2009, PNAS, vol. 206, 5610-5615.

Chen et al., Reconstructed evolutionary adaptive paths give polymerases accepting reversible terminators for sequencing and SNP detection, Feb. 2, 2010, PNAS, vol. 107, 1948-1953.

Midelfort et al., Redesigning and characterizing the substrate specificity and activity of Vibrio fluvialis aminotransferase for the synthesis of imagabalin, Sep. 25, 2012, Protein Engineering, Design & Selection, vol. 26, 25-33.

Musdal et al., Exploring sequence-function space of a poplar glutathione transferase using designed information-rich gene variants, Aug. 30, 2017, Protein Engineering, Design & Selection, vol. 30, 543-549.

Arndt et al., Structural and kinetic basis for the selectivity of aducanumab for aggregated forms of amyloid-β, Apr. 23, 2018, Scientific Reports, 16 pages.

Bard et al., Peripherally administered antibodies against amyloid β-peptide enter the central nervous system and reduce pathology in a mouse model of Alzheimer disease, Aug. 2000, Nature Medicine, vol. 6, 916-920.

Bard et al., Sustained levels of antibodies against Aβ in amyloid-rich regions of the CNS following intravenous dosing in human APP transgenic mice, Experimental Neurology, 2012, 6 pages.

Basi et al., Structural Correlates of Antibodies Associated with Acute Reversal of Amyloid β-related Behavioral Deficits in a Mouse Model of Alzheimer Disease, Nov. 18, 2009, The Journal of Biological Chemistry, vol. 285, pp. 3417-3427.

Lannfelt, Binding profiles of BAN2401 and aducanumab to different Aβ species, Dec. 7, 2019, CTAD, 20 pages.

Blennow et al., Effect of Immunotherpay with Bapineuzumab on Cerebrospinal Fluid Biomarker Levels in Patients with Mild to Modeate Alzheimer Disease, 2012, Arch Neurol., 9 pages.

Bohrmann et al., Gantenerumab: A Novel Human Anti-Aβ Antibody Demonstrates Sustained Cerebral Amyloid-β Binding and Elicits Cell-Mediated Removal of Human Amyloid-β 2012, Journal of Alzheimer's Disease, vol. 28, 49-69.

Brashear et al., Clinical Evaluation of Amyloid-Related Imaging Abnormalities in Bapineuzumab Phase III Studies, 2018, Journal of Alzheimer's Disease, vol. 66, 1409-1424.

Brody et al., A Phase II, Randomized, Double-Blind, Placebo-Controlled Study of Safety, Pharmacokinetics, and Biomarker Results of Subcutaneous Bapineuzumab in Patients with mild to moderate Alzheimer's disease, 2016, Journal of Alzheimer's Disease, vol. 54, 1509-1519.

Colvin et al., Atomic Resolution Structure of Monomorphic Aβ42 Amyloid Fibrils, Jun. 29, 2016, Journal of the American Chemical Society, 9963-9975.

Demattos et al., A Plaque-Specific Antibody Clears Existing b-amyloid Plaques in Alzheimer's Disease Mice, Dec. 6, 2012, Neuron (Cell Press), vol. 76, 13 pages.

Feinberg et al., Crystal structure reveals conservation of amyloid-β conformation recognized by 3D6 following humanization to bapineuzumab, 2014, Alzheimer's Research & Therapy, 13 pages.

Sumner et al., Antibody Engineering for Optimized Immunotherapy in Alzheimer's Disease, Apr. 23, 2018, Frontiers in Neuroscience, vol. 12, 12 pages.

Portron et al., A Phase I Study to Assess the Effect of Speed of Injection on Pain, Tolerability, and Pharmacokinetics After High-vol. Subcutaneous Administration of Gantenerumab in Healthy Volunteers, Nov. 1, 2020, Clinical Therapeutics, vol. 42, pp. 108-120.

Haeberlein et al., Clinical Development of Aducanumab, an Anti-Aβ Human Monoclonal Antibody Being Investigated for the Treatment of Early Alzheimer's Disease, Nov. 4, 2017, The Journal of Prevention of Alzheimer's Disease, vol. 4, 255-263.

Hanan et al., Inhibitory effect of monoclonal antibodies on Alzheimer's β-amyloid peptide aggregation, Jul. 6, 2009, The Journal of Protein Folding Disorders.

Arndt et al., Supplementary Material, Structural and kinetic basis for the selectivity of aducanumab for aggregated forms of amyloid-β, Apr. 23, 2018, Scientific Reports, 12 pages.

Kaplan et al., Selective Targeting of *Amyloidbeta oligomer* Species by PMN310, a Monoclonal Antibody Rationally Designed for Greater Therapeutic Potency in Alzheimer's Disease, Jul. 18, 2019, 1 page.

Ketter et al., Central Review of Amyloid-Related Imaging Abnormalities in Two Phase III Clinical Trials of Bapineuzumab in Mild-To-Moderate Alzheimer's Disease Patients, 2017, Journal of Alzheimer's Disease, vol. 57, 557-573.

Levites et al., Insights into the mechanisms of action of anti-Aβ antibodies in Alzheimer's disease mouse models, Jun. 20, 2018, The FASEB Journal, 16 pages.

Linse et al., Kinetic fingerprints differentiate anti-Aβ therapies, Feb. 27, 2020, 27 pages.

Linse et al., Kinetic fingerprints differentiate the mechanisms of action of anti-Aβ antibodies, Apr. 2020, Nature, Structural & Molecular Biology, 48 pages.

Lord et al., An amyloid-β protofibril-selective antibody prevents amyloid formation in a mouse model of Alzheimer's disease, Aug. 22, 2009, Neurobiology of Disease, vol. 36, 425-434.

Lu et al., Pharmacokinetics, Pharmacodynamics, and Safety of Subcutaneous Bapineuzumab: A Single-Ascending-Dose Study in Patients With Mild to Moderate Alzheimer Disease, 2019, Clinical Pharmacology in Drug Development, vol. 8(3), 326-335.

Mo et al., Efficacy and safety of anti-amyloid-b immunotherapy for Alzheimer's disease: a systematic review and network meta-analysis, 2017, Annals of Clinical and Translational Neurology, vol. 4(12), 931-942.

Penninkilampi et al., Safety and Efficacy of Anti-Amyloid-β Immunotherapy in Alzheimer's Disease: A Systematic Reviewand Meta-Analysis, 2017, J Neuroimmuni Pharmacol, vol. 12, 194-203.

Freeman et al., Pharmacokinetic and Pharmacodynamic Evaluation of PF-04360365, A Humanized Monoclonal Anti-Amyloid Antibody, in Young and Aged Cynomolgus Monkeys, Jul. 1, 2009, 1 page.

(56) References Cited

OTHER PUBLICATIONS

Billinton et al., Preclinical Discovery and Development of MEDI1814, a Monoclonal Antibody Selectively Targeting Beta-Amyloid 42 (Ab42), Jul. 16, 2017, 1 page.
Racke et al., Exacerbation of Cerebral Amyloid Angiopathy—Associated Microhemorrhage in Amyloid Precursor Protein Transgenic Mice by Immunotherapy Is Dependent on Antibody Recognition of Deposited Forms of Amyloid β, Jan. 19, 2005, Journal of Neuroscience, 25(3), 629-636.
Sebollela et al., Elucidating Molecular Mass and Shape of a Neurotoxic Aβ Oligomer, Oct. 24, 2014, American Chemical Society Neuroscience, vol. 5, 1238-1245.
Seubert et al., Antibody Capture of Soluble A β Does Not Reduce Cortical Aβ Amyloidosis in the PDAPP Mouse, 2008, Neurodegenerative Diseases, vol. 5, 65-71.
Sevigny et al., The antibody aducanumab reduces Aβ plaques in Alzheimer's disease, Sep. 1, 2016, Nature, vol. 537, 50-56.
Sevigny et al., Addendum: The antibody aducanumab reduces Aβ plaques in Alzheimer's disease, Sep. 1, 2016, Nature, 1 page.
Sperling et al., Amyloid-related imaging abnormalities in patients with Alzheimer's disease treated with bapineuzumab: a retrospective analysis, Feb. 3, 2012, Lancet Neural, vol. 11, 241-249.
Swanson et al., Pharmacological Characterization of BAN2401-Mediated Ab Protofibril Clearance by Microglia, Jul. 17, 2017, 2 pages.
Goure et al., Targeting the proper amyloid-beta neuronal toxins: a path forward for Alzheimer's disease immunotherapeutics, 2014, Alzheimer's Research & Therapy, vol. 6, 15 pages.
Vaillancourt et al., Aducanumab Reduces Ab Plaques in Alzheimer's Disease, 2016, Nature, vol. 537, 50-56.
Van Dyck, Anti-Amyloid-b Monoclonal Antibodies for Alzheimer's Disease: Pitfalls and Promise, Feb. 15, 2018, vol. 83, 311-319.
Watt et al., Do current therapeutic anti-Aβ antibodies for Alzheimer's disease engage the target?, 2014, vol. 127, 803-810.
Zago et al., Neutralization of Soluble, Synaptotoxic Amyloid β Species by Antibodies is Epitope Specific, Feb. 22, 2012, The Journal of Neuroscience, vol. 32, 2696-2702.
Zago et al., Vascular alterations in PDAPP mice after anti-Ab immunotherapy: Implications for amyloid-related imaging abnormalities, 2013, Alzheimer's & Dementia, vol. 9, 105-115.
Zeng et al., Strategies Targeting Soluble β-Amyloid Oligomers and their Application to Early Diagnosis of Alzheimer's Disease, 2019, Current Alzheimer Research, vol. 16, 1132-1142.

* cited by examiner

FIG 1

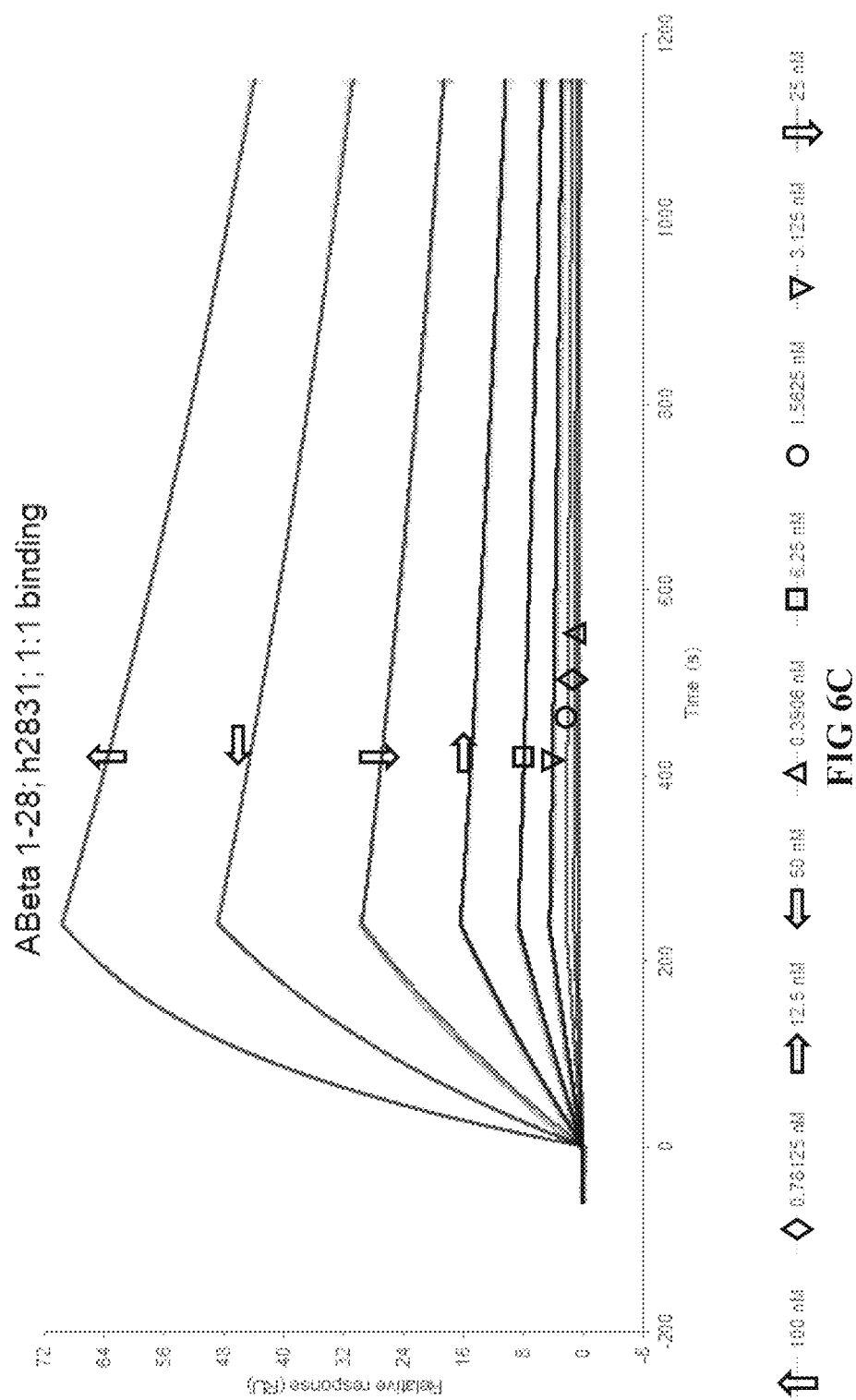

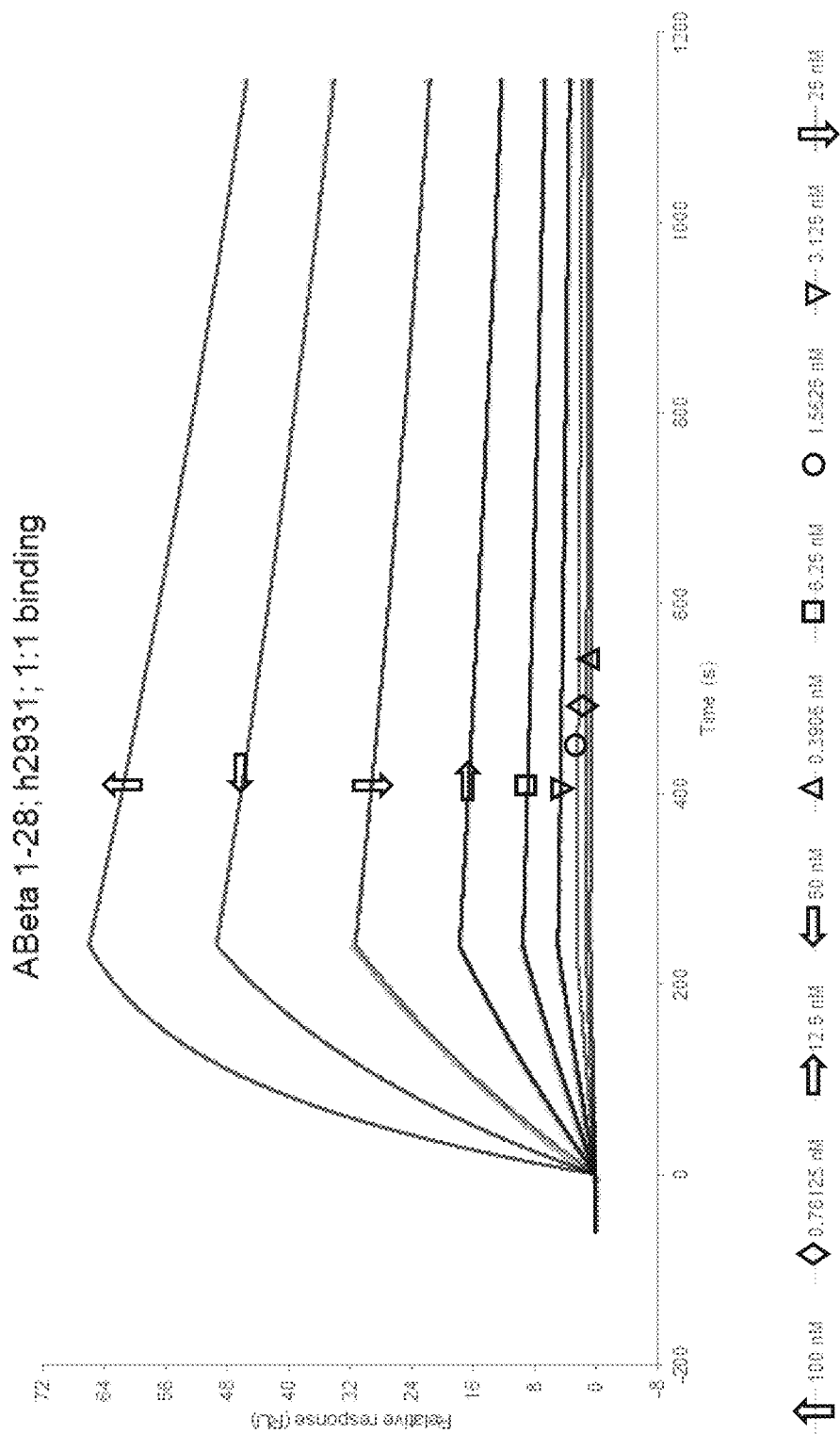

```
                                      +----+----+----+----+
                                      10        20        30        40
hBP_VH       EVQLLESGGGLVQPGGSLRLSCAASGFTFSNYGMSWVRQA    40
Hm27Lm26_VH  ........................................    40
Hm27Lm31_VH  ........................................    40
Hm28Lm31_VH  ..............................F.........    40
Hm29Lm31_VH  ..............................F.........    40

+----+----+----+----+
                                      50        60        70        80
hBP_VH       PGKGLEWVASIRSGGRTYYYSDNVKGRFTISRDNSKNTLY    80
Hm27Lm26_VH  ........................................    80
Hm27Lm31_VH  ...............S........................    80
Hm28Lm31_VH  ........V......S........................    80
Hm29Lm31_VH  ........V...............................    80

+----+----+----+
                                      90       100       110
hBP_VH       LQMNSLRAEDTAVYYCVRYDHYSGSSDYWGQGTLVTVSS    119
Hm27Lm26_VH  .......................................    119
Hm27Lm31_VH  .......................................    119
Hm28Lm31_VH  ..........................F...F........    119
Hm29Lm31_VH  ..........................F...F........    119

CDRs in bold
```

FIG 17

```
                  ----------+---------+---------+---------+
                         10        20        30        40
                  ----------+---------+---------+---------+
hBP_LC            D V V M T Q S P L S L P V T P G E P A S I S C K S S Q S L L D S D G K T Y L N W   40
Hm27Lm26_VL       . . . . . . . . . . . . . . . . . . . . . . . . . . . . . Y . . . . . . . .   40
Hm27Lm31_VL       . . . . . . . . . . . L . . . . . . . . . . . . . . . . . Y . . . . . . . .   40
Hm28Lm31_VL       . . . . . . . . . . . L . . . . . . . . . . . . . . . . . Y . . . . . . . .   40
Hm29Lm31_VL       . . . . . . . . . . . L . . . . . . . . . . . . . . . . . Y . . . . . . . .   40

----------+---------+---------+---------+
                         50        60        70        80
                  ----------+---------+---------+---------+
hBP_LC            L L Q K P G Q S P Q R L I Y L V S K L D S G V P D R F S G S G S G T D F T L K I   80
Hm27Lm26_VL       . . . . . . . . . . . . . K . . N R . . . . . . . . . . . . . . . . . . . .   80
Hm27Lm31_VL       . . . . . . . . . . . . . R . T N R . T . . . . . . . . . . . . . . . . . .   80
Hm28Lm31_VL       . . . . . . . . . . . . . R . T N R . T . . . . . . . . . . . . . . . . . .   80
Hm29Lm31_VL       . . . . . . . . . . . . . R . T N R . T . . . . . . . . . . . . . . . . . .   80

----------+---------+---------+---------+
                         90       100       110       120
                  ----------+---------+---------+---------+
hBP_LC            S R V E A E D V G V Y Y C W Q G T H F P R T F G Q G T K V E I K R T V A A P S V   120
Hm27Lm26_VL       . . . . . . . . . . . . . . . . . . . . . . . . . . . . . . . . . . . . .   112
Hm27Lm31_VL       . . . . . . . . . . . . . . . . . S . . . . . . . . . . . . . . . . . . .   112
Hm28Lm31_VL       . . . . . . . . . . . . . . . . . S . . . . . . . . . . . . . . . . . . .   112
Hm29Lm31_VL       . . . . . . . . . . . . . . . . . S . . . . . . . . . . . . . . . . . . .   112

----------+---------+---------+---------+
                        130       140       150       160
                  ----------+---------+---------+---------+
hBP_LC            F I F P P S D E Q L K S G T A S V V C L L N N F Y P R E A K V Q W K V D N A L Q   160
Hm27Lm26_VL                                                                                       112
Hm27Lm31_VL                                                                                       112
Hm28Lm31_VL                                                                                       112
Hm29Lm31_VL                                                                                       112

----------+---------+---------+---------+
                        170       180       190       200
                  ----------+---------+---------+---------+
hBP_LC            S G N S Q E S V T E Q D S K D S T Y S L S S T L T L S K A D Y E K H K V Y A C E   200
Hm27Lm26_VL                                                                                       112
Hm27Lm31_VL                                                                                       112
Hm28Lm31_VL                                                                                       112
Hm29Lm31_VL                                                                                       112

----------+---------
                        210
                  ----------+---------
hBP_LC            V T H Q G L S S P V T K S F N R G E C                                            219
Hm27Lm26_VL                                                                                       112
Hm27Lm31_VL                                                                                       112
Hm28Lm31_VL                                                                                       112
Hm29Lm31_VL                                                                                       112

CDRs in bold
```

FIG 18

| # H-CDRs | Clone ID | CDR1 aa 26-35 | SEQ ID | CDR2 aa 50-66 | SEQ ID | CDR3 aa 99-108 | SEQ ID | VH SEQ ID |
|---|---|---|---|---|---|---|---|---|
|  | Bapi | GFTFS NYGMS | 16 | SIRSG GGRTY YSDNV KG | 17 | YDHYS GSSDY | 18 | 1 |
| 1 | h2726 | GFTFS NYGMS | 16 | SIRSG SGRTY YSDNV KG | 20 | YDHYS GSSDY | 18 | 3 |
| 2 | h2731 | GFTFS NYGMS | 16 | SIRSG SGRTY YSDNV KG | 20 | YDHYS GSSDY | 18 | 3 |
| 3 | h2831 | GFTFS NFGMS | 19 | SVRSG SGRTY YSDNV KG | 21 | YDHYS GSSDY | 24 | 4 |
| 4 | h2931 | GFTFS NFGMS | 19 | SVRSG SGRTY YSDNV KG | 21 | YDHYT GTSDY | 25 | 5 |
| 5 | h2926 | GFTFS NFGMS | 19 | SIRSG SGRTY YSDNV KG | 21 | YDHYT GTSDY | 25 | 5 |
| 6 | h4921G | GFTFS NFGMS | 19 | SVRSG GGRTY YSDNV KG | 22 | YDHYS GTSDY | 24 | 6 |
| 7 | h2826 | GFTFS NFGMS | 19 | SVRSG SGRTY YSDNV KG | 21 | YDHYS GTSDY | 24 | 4 |
| 8 | h2929 | GFTFS NFGMS | 19 | SVRSG SGRTY YSDNV KG | 21 | YDHYT GTSDY | 25 | 5 |
| 9 | h3818G | GFTFA NYGMS | 20 | SVRSG GSRTY YSDNV KG | 23 | YDHYS GSSDY | 18 | 7 |
| 10 | h2927 | GFTFS NFGMS | 19 | SIRSG SGRTY YSDNV KG | 21 | YDHYT GTSDY | 25 | 5 |
| 11 | h49k3G | GFTFS NFGMS | 19 | SVRSG GGRTY YSDNV KG | 22 | YDHYS GTSDY | 24 | 6 |
| 12 | h4917G | GFTFS NFGMS | 19 | SVRSG GGRTY YSDNV KG | 22 | YDHYS GTSDY | 24 | 6 |
| 13 | h2727 | GFTFS NYGMS | 16 | SIRSG SGRTY YSDNV KG | 20 | YDHYS GSSDY | 18 | 3 |
| 14 | h4918G | GFTFS NFGMS | 19 | SVRSG GGRTY YSDNV KG | 22 | YDHYS GTSDY | 24 | 6 |

FIG 19A

| # L-CDRs | Clone ID | CDR1 aa 24-39 | SEQ ID | CDR2 aa 55-61 | SEQ ID | CDR3 aa 94-102 | SEQ ID | VL SEQ ID |
|---|---|---|---|---|---|---|---|---|
|  | Bapi | KSSQS LLDSD GKTYL N | 26 | LVSKL DS | 27 | WQGTH FPRT | 28 | 2 |
| 1 | h2726 | KSSQS LLDYD GKTYL N | 29 | KVSNR DS | 33 | WQGTH FPRT | 28 | 8 |
| 2 | h2731* | KSSQS LLDYD GKTYL N | 29 | RVTNR DT | 34 | WQGTH FPRS | 38 | 9 |
| 3 | h2831* | KSSQS LLDYD GKTYL N | 29 | RVTNR DT | 34 | WQGTH FPRS | 38 | 9 |
| 4 | h2931* | KSSQS LLDYD GKTYL N | 29 | RVTNR DT | 34 | WQGTH FPRS | 38 | 9 |
| 5 | h2926 | KSSQS LLDYD GKTYL N | 29 | KVSNR DS | 33 | WQGTH FPRT | 28 | 8 |
| 6 | H4921G* | KSSQS LLDSD GKTYL N | 26 | RVTNR DT | 34 | WQGTH FPRT | 28 | 10 |
| 7 | h2826 | KSSQS LLDYD GKTYL N | 29 | KVSNR DS | 33 | WQGTH FPRT | 28 | 8 |
| 8 | h2929 | RSSQS LVDYD GKTYL N | 31 | KVSNR ES | 35 | WQSH FPRSY | 39 | 11 |
| 9 | h3818G* | KSSQS LMDTD GKTYL N | 32 | KVSNR ES | 35 | WQGTH FPRT | 28 | 12 |
| 10 | h2927 | KSSQS LLDSD GKTYL N | 29 | KVSNR DS | 33 | WQGTH FPRS | 38 | 13 |
| 11 | h49k3G* | KSSQS LLDSD GKTYL N | 26 | KVSNR DS | 33 | WQGTH FPRT | 28 | 14 |
| 12 | h4917G* | KSSQS LLDSD GKTYL N | 26 | KVTNR ES | 36 | WQGTH FPRS | 38 | 15 |
| 13 | h2727 | KSSQS LLDYD GKTYL N | 29 | KVSNR DS | 33 | WQGTH FPRS | 38 | 13 |
| 14 | h4918G* | KSSQS LMDTD GKTYL N | 32 | KVSNR ES | 35 | WQGTH FPRT | 28 | 12 |

ANTI-ABETA ANTIBODIES

RELATED APPLICATION

This application is a continuation of U.S. application Ser. No. 17/383,765, filed Jul. 23, 2021, which claims the benefit of U.S. Provisional Patent Application No. 63/055,813, filed Jul. 23, 2020, U.S. Provisional Patent Application No. 63/086,589, filed Oct. 1, 2020, U.S. Provisional Patent Application No. 63/187,379, filed May 11, 2021, and U.S. Provisional Patent Application No. 63/219,611, filed Jul. 8, 2021, all of which are incorporated by reference herein in their entirety.

SEQUENCE LISTING STATEMENT

A computer readable form of the Sequence Listing is filed with this application by electronic submission and is incorporated into this application by reference in its entirety. The Sequence Listing is contained in the file created on Oct. 21, 2021, having the file name "20-1030-US-CON4_Sequence-Listing_ST25.txt" and is 155 kb in size.

FIELD

The present disclosure relates to anti-Amyloid beta (Aβ) antibodies as well as compositions and methods of their use.

BACKGROUND

Alzheimer's disease (AD) is a progressive disease resulting in senile dementia. The disease is generally categorized as late onset, which occurs in old age (65+ years) and early onset, which develops well before the senile period, i.e., between 35 and 60 years. Disease pathology appears to be the same for both types of disease, but abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 μm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed Aβ (Abeta) or β-amyloid peptide. Aβ peptide is a 4-kDa internal fragment of 39-43 amino acids of a larger transmembrane glycoprotein termed amyloid precursor protein (APP). As a result of proteolytic processing of APP by different secretase enzymes, Aβ is primarily found in both a short form, 40 amino acids in length, and a long form, ranging from 42-43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms associated with this type of neural deterioration characterize Alzheimer's disease.

SUMMARY

The present disclosure relates to antibodies (and antibody fragments) that specifically bind to Aβ, methods of producing such antibodies and antibody fragments and associated nucleic acids, methods of treatment of patients with Aβ-related neurological disorders, pharmaceutical formulations and compositions of antibodies that show high affinity binding to Aβ for prophylactic and/or therapeutic use to, for example, treat, reduce the risk of or delay the outset of amyloidogenic disease, prevent, reduce or inhibit markers of amyloidogenic disease, e.g., Aβ plaques, and improve cognition. The present disclosure further relates to methods of detecting amyloid plaques and measuring the efficacy of treatment in patients being treated for amyloidogenic disease. The disclosure is based, at least in part, on the identification and characterization of monoclonal antibodies that specifically bind to Aβ peptide and are effective at reducing plaque burden and neutralizing soluble Aβ species associated with amyloidogenic disorders.

In various aspects, the disclosure are directed to antibodies or fragments thereof that that specifically binds to Aβ peptide. The antibodies and fragments include a heavy chain variable region including heavy chain CDR1, CDR2 and CDR3 and a light chain variable region including light chain CDR1, CDR2 and CDR3, wherein the heavy chain CDR1, CDR2 and CDR3 and the light chain CDR1, CDR2 and CDR3 are as shown for one of the antibodies in Table 1. In addition, the antibodies or fragments or fragments of the disclosure may have a heavy chain variable region that is as shown for one of the antibodies in Table 1 and may have a light chain variable region that is shown for one of the antibodies in Table 1.

In various embodiments of the disclosure, the antibodies and fragments thereof include a heavy chain variable region including heavy chain CDR1, CDR2 and CDR3 and a light chain variable region including light chain CDR1, CDR2 and CDR3, wherein heavy chain CDR1 includes one of SEQ ID NO: 16, 19, or 20, heavy chain CDR2 includes one of SEQ ID NO: 20, 21, 22 or 23, heavy chain CDR3 includes one of SEQ ID NO: 18, 24, or 25, light chain CDR1 includes one of SEQ ID NO: 26, 29, 31, or 32, light chain CDR2 includes one of SEQ ID NO: 33, 34, 35 or 36, and light chain CDR3 includes one of SEQ ID NO: 28, 38 or 39.

The antibody or fragment thereof of the disclosure may include a heavy chain variable region, excluding the CDRs, that is at least 95% or 98% identical an amino acid sequence selected from SEQ ID NO: 3, 4, 5, 6, and 7, and the light chain variable region, excluding the CDRs, that is at least 95% or 98% identical an amino acid sequence selected from SEQ ID NO: 8, 9, 10, 11, 12, 13, 14, and 15. In addition, the heavy chain variable region may be selected from SEQ ID NOs: 3, 4, 5, 6, and 7, and the light chain variable region may be selected from SEQ ID NO: 8, 9, 10, 11, 12, 13, 14 and 15.

In further embodiments, the disclosure is directed to an antibody or fragment thereof that that specifically binds to Aβ peptide, including a heavy chain variable region including heavy chain CDR1, CDR2 and CDR3 and a light chain variable region including light chain CDR1, CDR2 and CDR3, having the following amino acid sequences:

heavy chain CDR1 includes amino acid sequence GFTFSNX$_1$GMS, wherein X$_1$ is Y or F (SEQ ID NO: 88);

heavy chain CDR2 includes amino acid sequence SX$_1$RSGSGRTYYSDNVKG, wherein is X$_1$ is I or V (SEQ ID NO: 89);

heavy chain CDR3 includes amino acid sequence YDHYX$_1$GX$_2$SDY, wherein X$_1$ is S or T and X$_2$ is S or T (SEQ ID NO: 90);

light chain CDR1 includes amino acid sequence KSSQSLLDYDGKTYLN (SEQ ID NO: 91);

light chain CDR2 includes amino acid sequence X$_1$VX$_2$NRDX$_3$, wherein X$_1$ is K or R, X$_2$ is S or T, and X$_3$ is S or T (SEQ ID NO: 92).

light chain CDR3 includes amino acid sequence WQGTHFPRX$_1$, wherein X$_1$ is S or T (SEQ ID NO: 93).

In addition, the light chain CDR3 may be WQGTHFPRX$_1$FX$_2$, wherein X$_1$ is S or T and X$_2$ is F or Y (SEQ ID NO: 94).

Still further, embodiments of the disclosure are directed to an antibody or fragment thereof that specifically binds to Aβ peptide, including a heavy chain variable region including heavy chain CDR1, CDR2 and CDR3 and a light chain variable region including light chain CDR1, CDR2 and CDR3, having the following amino acid sequences:

heavy chain CDR1 includes amino acid sequence GFTFX$_1$NX$_2$GMS, wherein X$_1$ is S or A, and X$_2$ is Y or F (SEQ ID NO: 95);

heavy chain CDR2 includes amino acid sequence SX$_1$RSGX$_2$X$_3$RTYYSDNVKG, wherein is X$_1$ is I or V, X$_2$ is S or G and X$_3$ is S or G (SEQ ID NO: 96);

heavy chain CDR3 includes amino acid sequence YDHYX$_1$GX$_2$SDY, wherein X$_1$ is S or T and X$_2$ is S or T (SEQ ID NO: 90);

light chain CDR1 includes amino acid sequence X$_1$SSQSLX$_2$DX$_3$DGKTYLN, wherein X$_1$ is K or R, X$_2$ is V, M or L, and X$_3$ is Y, T or S (SEQ ID NO: 97);

light chain CDR2 includes amino acid sequence X$_1$VX$_2$NRX$_3$X$_4$, wherein X$_1$ is K or R, X$_2$ is S or T, and X$_3$ is E or D, and X$_4$ is S or T (SEQ ID NO: 98).

light chain CDR3 includes amino acid sequence WQGX$_1$HFPRX$_2$, wherein X$_1$ is S or T, and X$_2$ is S or T (SEQ ID NO: 99).

The light chain CDR3 may also include WQGTHFPRX$_1$FX$_2$X$_3$, wherein X$_1$ is S or T, X$_2$ is S or T and X$_3$ is F or Y (SEQ ID NO: 100).

In further aspects of the disclosure, the antibody or fragment thereof of one is humanized, is human IgG1, or may be a full antibody, a chimeric antibody, a CDR-grafted antibody, or a recombinant antibody. Antibody fragments may include a Fab, Fab', F(ab')2, Fabc, or Fv.

Still further, the antibody or fragment of the disclosure may include a heavy chain constant region including an amino acid sequence at least 95% identical to SEQ ID NO:40, and may include a light chain constant region including an amino acid sequence at least 95% identical to SEQ ID NO:41. The antibody or fragment may specifically bind to an epitope having an amino acid sequence including three or more amino acid positions from amino acids 1-7 of Aβ.

In additional aspects, the disclosure is directed to a nucleic acid encoding the heavy chain and/or light chain of an antibody as described herein.

The disclosure is also directed to a pharmaceutical composition including an antibody or fragment thereof as described herein.

In various embodiments, the disclosure is directed to a method of producing the antibody or fragment thereof as described herein. The method may include (a) culturing cells transformed with nucleic acids encoding the heavy and light chains of the antibody or fragment thereof, so that the cells secrete the antibody or fragment thereof; and (b) purifying the antibody or fragment thereof from cell culture.

In another aspect, the disclosure is directed to a method of producing a cell line producing the antibody or fragment thereof as described herein. The method may include (a) introducing a vector encoding heavy and light chains of the antibody or fragment thereof and a selectable marker into cells; (b) propagating the cells under conditions to select for cells having increased copy number of the vector; (c) isolating single cells from the selected cells; and (d) banking cells cloned from a single cell selected based on yield of antibody or a fragment thereof. The method may also include propagating the cells under selective conditions and screening for cell lines naturally expressing and secreting at least 100 mg/L/10^6 cells/24 h.

Addition aspects of the addition include methods of preventing or treating amyloidogenic disease in a patient. The methods include administering an effective dosage of the antibody or fragment as described herein to the patient. The amyloidogenic disease may be systemic amyloidosis, Alzheimer's disease, mature onset diabetes, Parkinson's disease, Huntington's disease, fronto-temporal dementia, Down's syndrome, or mild cognitive impairment.

When the amyloidogenic disease, the methods of the disclosure may include administering to a patient having the disease the antibody or fragment thereof in a regime effective to treat the disease. In addition, the methods of the disclosure include reducing the risk or delaying the outset of Alzheimer's disease in a patient whose risk of the disease has been determined from a genetic or biochemical marker. The method includes administering to a patient having the disease the antibody or fragment thereof as described herein in a regime effective to reduce the risk or delay the outset of the disease.

Still further, the disclosure is directed to a method for effecting improvement of cognition in a subject having a condition or disease related amyloidogenic disease. The method include including administering to the subject an effective amount of the antibody or fragment thereof as described herein. The amyloidogenic disease may be systemic amyloidosis, Alzheimer's disease, mature onset diabetes, Parkinson's disease, Huntington's disease, fronto-temporal dementia, Down's syndrome, or mild cognitive impairment.

Still further, the disclosure is directed to a method for treating Down's syndrome or clinical or pre-clinical Alzheimer's disease in a human subject. The method include including administering to the subject an effective amount of the antibody or fragment thereof as described herein.

Method of the disclosure also include one or more of inhibiting the formation of amyloid plaque in a human subject, reduce amyloid plaque in the brain of a human subject, inhibiting or reducing amyloid plaque in a subject having or at risk of developing an amyloidogenic disease. The methods include including administering to the subject an effective amount of the antibody or fragment thereof as described herein. In each of these methods, the amyloid plaque may include Aβ$_{1-42}$, pyroglutamate species of Aβ (e.g., Aβ$_{pE3-42}$), or a combination thereof.

In yet another aspect, the disclosure is directed to a method of detecting amyloid plaques in a subject having or at risk of an amyloidogenic disease. The method includes administering to a subject an antibody or fragment as described herein, and detecting the antibody or fragment thereof bound to Aβ in the subject. The amyloidogenic disease is systemic amyloidosis, Alzheimer's disease, mature onset diabetes, Parkinson's disease, Huntington's disease, fronto-temporal dementia, Down's syndrome, or mild cognitive impairment. In the detection methods, the antibody or fragment thereof may be labeled, for example the with a fluorescent label, a paramagnetic label, or a radioactive label. The radioactive label may be detected using positron emission tomography (PET) or single-photon emission computed tomography (SPECT).

A method of measuring efficacy of treatment in a subject being treated for an amyloidogenic disease, including:

(a) measuring a first level of amyloid plaque in the subject prior to treatment by administering to a subject an antibody or fragment thereof of any one of claims 1-18, and detecting a first amount of the antibody or fragment thereof bound to Aβ in the subject, (b) administering the treatment to the subject, (c) measuring a second level of amyloid plaque in the subject after treatment by administering to a subject the antibody or fragment thereof, and detecting the antibody or fragment thereof bound to Aβ in the subject, wherein a decrease in the level of amyloid plaque indicates a positive response to treatment.

Still further, other aspects of the disclosure include a method of measuring efficacy of treatment in a subject being treated for an amyloidogenic disease. The methods includes (a) measuring a first level of amyloid plaque in the subject prior to treatment by administering to a subject an antibody or fragment thereof as described herein, and detecting a first amount of antibody or fragment thereof bound to Aβ in the subject, (b) administering the treatment to the subject, (c) measuring a second level of amyloid plaque in the subject after treatment by administering to a subject the antibody or fragment thereof, and detecting a second amount of antibody or fragment thereof bound to Aβ in the subject. No change in the level of amyloid plaque or a small increase in amyloid plaque indicates a positive response to treatment.

The methods of the disclosure also include reducing, clearing, or promoting clearance of Aβ, or reducing or inhibiting Aβ accumulation or aggregation, in a human subject. Such methods include administering to the subject an effective regime of the antibody or fragment thereof as described herein. The Aβ may be present in the subject's brain tissue.

The methods of the disclosure also include reducing, promoting clearance, or clearing of Aβ in brain tissue of a subject having or at risk of developing an amyloidogenic disease. Such methods include administering to the subject an effective regime of the antibody or fragment thereof as described herein.

The methods of the disclosure also include inhibiting or reducing Aβ accumulation or aggregation in brain tissue of a subject having or at risk of developing an amyloidogenic disease. Such methods include administering to the subject an effective regime of the antibody or fragment thereof as described herein.

A method of inhibiting Aβ accumulation or aggregation in brain tissue of a subject having or at risk of developing an amyloidogenic disease, including administering to the subject an effective regime of the antibody of any one of claims 1 to 18, thereby inhibiting Aβ accumulation or aggregation in brain tissue in the subject. The amyloidogenic disease may be systemic amyloidosis, Alzheimer's disease, mature onset diabetes, Parkinson's disease, Huntington's disease, fronto-temporal dementia, Down's syndrome, or mild cognitive impairment. The Aβ may be Aβ$_{1-42}$, pyroglutamate species of Aβ (e.g., Aβ$_{pE3-42}$), or a combination thereof.

In each of the foregoing methods of the disclosure, the antibody is administered by peripheral administration, which may be intravenous or subcutaneous administration.

BRIEF DESCRIPTION OF THE DRAWINGS

FIG. 1 shows an alignment of three different versions of VL that were designed by incorporating human germline framework residues into bapineuzumab (hBP) VL sequence. Canonical or interface residues were not changed.

FIGS. 6A-6D show BIAcore sensorgrams of binding of h2726 (FIG. 6A), h2731 (FIG. 6B), h2831 (FIG. 6C) and 2931 (FIG. 6D) to Aβ$_{1-28}$ at analyte concentrations from 100 nM to 0.39 nM (2-fold serial dilutions).

FIG. 15A shows spots per neuron and FIG. 15B shows total spot counts (at 40 fields per well).

FIG. 17 shows an alignment of bapineuzumab variable heavy chain sequence and four sequences of the disclosure, 2726, 2731, 2831 and 2931. CDRs are in bold.

FIG. 18 shows an alignment of bapineuzumab light chain sequence and four (variable light chain) sequences of the disclosure, 2726, 2731, 2831 and 2931. CDRs are in bold.

FIGS. 19A and 19B show a CDR table listing the variable heavy and light chain CDR sequences for antibodies of the disclosure. FIG. 19A refers to heavy chain CDRs and FIG. 19B refers to light chain CDRs.

FIG. 20A shows h2931, h2731 and bapineuzumab control, and FIG. 20BA shows h2831, h2726 and bapineuzumab control.

DETAILED DESCRIPTION OF THE INVENTION

Figure 2:
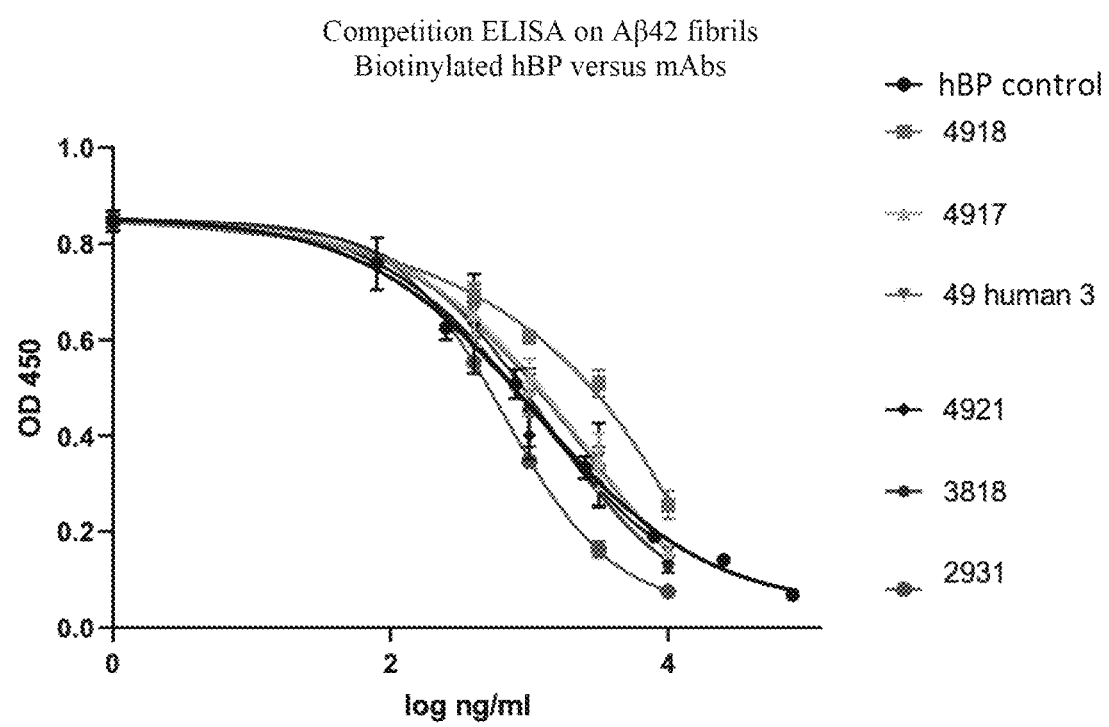
FIG. 2 shows competitive ELISA assay graphs for 4918, 4917, 4921, 3818, 49human3, 2931 and bapineuzumab control for IC$_{50}$ ratio determination relative to bapineuzumab (hBP).

Monoclonal antibodies (mAbs) targeting the N-terminus of amyloid beta (Aβ) have been demonstrated clinically to reduce amyloid plaque burden and one such antibody, aducanumab, showed that significant reduction in plaque burden was associated with slowing of cognitive decline in Alzheimer's disease (AD). Preclinical studies have also indicated that monoclonal antibodies (mAbs) targeting N-terminal epitopes of Aβ elicit an antibody-dependent microglial-mediated Aβ-plaque clearance and neutralization of soluble toxic Aβ oligomers both in vitro and in vivo. It is hypothesized that administration of N-terminal Aβ targeting mAbs slows disease progression via clearance of Aβ plaques and neutralization of soluble Aβ aggregates in patients with AD.

Aβ antibody bapineuzumab (hBP) is a humanized antibody developed from parental murine antibody 3D6. In accordance with various aspects of the disclosure, a multi-pronged approach was applied to construct superior antibodies to hBP. Humanness of hBP was analyzed and a determination was made that light chain humanization could be optimized.

A search was made over the protein sequences in the PDB database [Deshpande et al, 2005] to find structures that would provide a rough structural model of hBP. The crystal structure of hBP fab PDB code 4HIX [Miles, et al., 2013] was utilized for both Vh and Vk structure as it had acceptable resolution and an exact sequence match to hBP Vh and Vk, retaining the same canonical structures for the loops.

IMGT/DomainGapAlignment was performed for the hBP VL as input sequences. to identify human germ line VK gene sequence IGHV2-30*02 as the closest matched to hBP VL. The frameworks of hBP VL share a high degree of sequence similarity with the corresponding framework regions of IGHV2-30*02. Thus, the framework regions of IGHV2-30*02 VL were chosen as the guidance sequence for further optimization of the hBP framework regions. Additional residues in CDR-L2 that do not make any direct contact with the antigen as per hBP 3D structure were also changed to germline sequence resulting in following changes.

Three different versions of VL were designed by incorporating human germline framework residues into hBP VL sequence. Canonical or interface residues were not changed. Also, based on structural observation that P15 is located at a turn and the germline gene has Leu at this position, P15L was tested in one version of the variable light chain.

Based on the 3D structural observations, substitutions at a number of residues in the light chain and heavy chain CDRs and framework were designed. Mutant VL and VH versions were generated and tested for binding in the first round of rational design. Mutations that showed improved binding were combined in the second round of the rational design. Additionally, new mutations guided by further analysis of the structure were also incorporated into the design.

Accordingly, the disclosure provides antibodies (and antibody fragments), nucleic acids encoding and methods of producing such antibodies and antibody fragments, pharmaceutical compositions, and methods for preventing or treating amyloidogenic disease, reducing the risk or delaying the outset of an amyloidogenic disease, effecting improvement of cognition in an subject having a condition related to amyloidogenic disease, inhibiting the formation of Aβ plaque in a subject, reducing Aβ plaque in the brain of a subject, inhibiting or reducing amyloid plaque in a subject at risk of developing an amyloidogenic disease, detecting amyloid plaques, measuring efficacy of a treatment in a subject being treated for an amyloidogenic disease, where amyloidogenic disease comprises Alzheimer's and others as described herein. The disclosure is based, at least in part, on the characterization of a genus of monoclonal antibodies effective at binding beta amyloid protein (Aβ) (e.g., binding soluble and/or aggregated Aβ), mediating phagocytosis (e.g., of aggregated Aβ), reducing plaque burden and/or reducing neuritic dystrophy (e.g., in patient), neutralizing soluble, toxic Aβ species. The antibodies and fragments of the disclosure exhibit greater binding strength (affinity and/or avidity) for pathologic fibrillar Aβ than reported current experimental therapies, and high affinity for soluble toxic Aβ forms. These antibodies may enable more convenient dosing strategies and enhanced patient access.

Before describing particular aspects of the disclosure in more detail, a number of terms are defined.

Definitions

The term "antibody" includes intact antibodies and binding fragments thereof. Typically, fragments compete with the intact antibody from which they were derived for specific binding to the target. Fragments include separate heavy chains, light chains Fab, Fab', F(ab')$_2$, F(ab)c, Fv and single domain antibodies. Single (variable) domain antibodies include VH regions separated from their VL partners (or vice versa) in conventional antibodies (Ward et al., 1989, Nature 341: 544-546) as well as VH regions (sometimes known as VHH) from species such as Camelidae or cartilaginous fish (e.g., a nurse shark) in which VH regions are not associated with VL regions (see, e.g., WO 9404678). Single domain antibodies in which one chain is separated from its natural partners are sometimes known as Dabs and single domain antibodies from Caemelidae or cartilaginous fish are sometimes known as nanobodies. Constant regions or parts of constant regions may or may not be present in single domain antibodies. For example, natural single variable region antibodies from Camelidae include a VHH variable region, and CH2 and CH3 constant regions. Single domain antibodies can be subject of humanization by analogous approaches to conventional antibodies. The Dabs type of antibodies are usually obtained from antibodies of human origin. NANOBODY types of antibody are of Camelidae or shark origin and can be subject to humanization. Fragments can be produced by recombinant DNA techniques, or by enzymatic or chemical separation of intact immunoglobulins. The term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

An immunoglobulin light or heavy chain variable region (also sometimes referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also sometimes referred to herein, respectively, as CDR-L1, CDR-L2, and CDR-L3; CDRs 1, 2, and 3 of a VH domain are also sometimes referred to herein, respectively, as CDR-H1, CDR-H2, and CDR-H3. When the application discloses a VL sequence with R as the C-terminal residue, the R can alternatively be considered as being the N-terminal residue of the light chain constant region. Thus, the application should also be understood as disclosing the VL sequence without the C-terminal R.

The assignment of amino acids to each VL and VH domain is in accordance with any conventional definition of CDRs. Conventional definitions include, the Kabat definition (Kabat, Sequences of Proteins of Immunological Interest (National Institutes of Health, Bethesda, Md., 1987 and 1991), the Chothia definition (Chothia & Lesk, J. Mol. Biol. 196:901-917, 1987; Chothia et al., Nature 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table A). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE A

Conventional Definitions of CDRs Using Kabat Numbering

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
| L2 | L50--L56 | L50--L56 | L50--L56 | L50--L56 | L46--L55 |
| L3 | L89--L97 | L89--L97 | L89--L97 | L89--L97 | L89--L96 |
| H1 | H31--H35B | H26--H32 ... H34* | H26--H35B* | H26--H35B | H30--H35B |
| H2 | H50--H65 | H52--H56 | H50--H65 | H50--H58 | H47--H58 |
| H3 | H95--H102 | H95--H102 | H95--H102 | H95--H102 | H93--H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

In some embodiments, the CDRs of the humanized antibodies of the present invention are of a definition selected from the group of Kabat, Chothia, Kabat/Chothia Composite, AbM and Contact.

One or several amino acids at the amino or carboxy terminus of the light and/or heavy chain, such as a C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine. In some antibodies, the isotype is human IgG2 or IgG4.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

Accordingly, regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The term "epitope" or "antigenic determinant" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. When an epitope is said to be within a range of amino acid residues in a protein (e.g., within residues 1 to 6 of Aβ), the range is inclusive of the residues defining its borders. Certain residues within the range contribute to the epitope, whereas others may not. The residues that form the epitope may or may not be contiguous with one another. Similarly, when an antibody binds to an epitope found within a particular range of amino acids, the antibody need not contact all the amino acids residues within the range, and the residues of the epitope that are contacted by the antibody may or may not be contiguous with one another. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same epitope can be identified in a simple immunoassay showing the ability of one antibody to block or compete with the binding of another antibody to a target antigen, i.e., a competitive binding assay. Competitive binding is determined in an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using I-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75%, or more.

Competition between antibodies is determined by an assay in which an antibody under test inhibits specific binding of a reference antibody (e.g. 3D6, aducanumab, bapineuzumab) to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

Exemplary epitopes or antigenic determinants can be found within the human amyloid precursor protein (APP) but are preferably found within the Aβ peptide of APP. Multiple isoforms of APP exist, for example APP$^{695}$, APP$^{751}$, and APP$^{770}$. Amino acids within APP are assigned numbers according to the sequence of the APP$^{770}$ isoform (see e.g., GenBank Accession No. P05067, also set forth as SEQ ID NO:85).

Aβ (also referred to herein as beta amyloid peptide and A-beta) peptide is a about 4-kDa internal fragment of 39-43 amino acids of APP (Aβ39, Aβ40, Aβ41, Aβ42, and Aβ43). Aβ40, for example, consists of residues 672-711 of APP and Aβ42 consists of residues 673-713 of APP. As a result of proteolytic processing of APP by different secretase enzymes in vivo or in situ, Aβ is found in both a "short form", 40 amino acids in length, and a "long form", ranging from 42-43 amino acids in length. Preferred epitopes or antigenic determinants, as described herein, are located within the N-terminus of the Aβ peptide and include residues within amino acids 1-10 of Aβ, preferably from residues 1-3, 1-4, 1-5, 1-6, 1-7, or 3-7 of Aβ42. Additional referred epitopes or antigenic determinants include residues 2-4, 5, 6, 7, or 8 of Aβ, residues 3-5, 6, 7, 8, or 9 of Aβ, or residues 4-7, 8, 9, or 10 of Aβ42.

"Soluble" or "dissociated" Aβ refers to Aβ species that are either monomeric, aggregated, oligomeric, associated or not with other proteins and lipids, which remain in solution (supernatant) after centrifugation at 100,000×g. "Insoluble" Aβ refers to aggregated Aβ species, amyloid (beta-sheet) or not, that do not remain in solution after 100,000×g centrifugation, for example, Aβ held together by noncovalent bonds. Aβ (e.g., Aβ42) is believed to aggregate, at least in part, due to the presence of hydrophobic residues at the C-terminus of the peptide (part of the transmembrane domain of APP). One method to prepare soluble Aβ is to dissolve lyophilized peptide in neat DMSO with sonication. The resulting solution is centrifuged to remove any insoluble particulates.

"Specific binding" of an antibody mean that the antibody exhibits appreciable affinity for antigen or a preferred epitope and, preferably, does not exhibit significant cross reactivity. "Appreciable" or preferred binding include binding with an affinity of at least $10^6$, $10^7$, $10^8$, $10^9$ M$^{-1}$, or $10^{10}$ M$^{-1}$. Affinities greater $10^7$ M$^{-1}$, preferably greater than $10^8$ M$^{-1}$ are more preferred. Values intermediate of those set forth herein are also intended to be within the scope of the present disclosure and a preferred binding affinity can be indicated as a range of affinities, for example, $10^6$ to $10^{10}$ M$^{-1}$, preferably $10^7$ to $10^{10}$ M$^{-1}$, more preferably $10^8$ to $10^{10}$ M$^{-1}$. An antibody that "does not exhibit significant cross reactivity" is one that will not appreciably bind to an undesirable entity (e.g., an undesirable proteinaceous entity). For example, an antibody that specifically binds to Aβ will appreciably bind Aβ but will not significantly react with non-Aβ proteins or peptides (e.g., non-Aβ proteins or peptides included in plaques). An antibody specific for a preferred epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies.

The term "patient" includes human and other mammalian subjects that receive either prophylactic or therapeutic treatment.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the patient's own immune system.

The term "treatment" as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

The term "amyloidogenic disease" includes any disease associated with (or caused by) the formation or deposition of insoluble amyloid fibrils or amyloid plaques. Exemplary amyloidogenic diseases include, but are not limited to systemic amyloidosis, Alzheimer's disease, mature onset diabetes, Parkinson's disease, Huntington's disease, frontotemporal dementia, Down's syndrome, mild cognitive impairment, prion-related transmissible spongiform encephalopathies (kuru and Creutzfeldt-Jacob disease in humans and scrapie and BSE in sheep and cattle, respectively), and the like. Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ", e.g., in the brain of a subject or patient. The terms "β-amyloid protein", "β-amyloid peptide", "β-amyloid", "Aβ" and "Aβ peptide" are used interchangeably herein.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor.

The term "symptom" refers to a subjective evidence of a disease, such as altered gait, as perceived by the patient. A "sign" refers to objective evidence of a disease as observed by a physician.

Statistical significance means p<0.05.

Anti-Aβ Antibodies

Turning now to various aspects of the disclosure, a first aspect the disclosure is directed to an antibody or fragment thereof that that specifically binds to Aβ peptide. The antibody or fragment includes the heavy chain CDRs and the light chain CDRs from one of the constructs identified herein as h2726, h2731, h2831, h2931, h2926, h4921, h2828, h2929, h3818G, h2927, h49k3G, h4917G h2727, and h4918G. Particular monoclonal antibodies of the disclosure may bind to an epitope within residues 1-6 of Aβ (with the first N terminal residue of natural Aβ designated 1). Some monoclonal antibodies bind to an epitope within amino acids 1-6, some to an epitope within 1-5, and some to an epitope within 1-4. Some antibodies bind to epitopes within amino acids 1-3, 2-5, 3-5, 2-4, 2-5, 2-6, 3-5, or 3-6. When an antibody is said to bind to an epitope within specified residues, such as Aβ 1-6 for example, what is meant is that the antibody specifically binds to a polypeptide containing the specified residues (i.e., Aβ 1-6 in this an example); such antibody does not necessarily contact every residue within Aβ 1-6.

In another aspect, the antibody or fragment includes a heavy chain variable region having a heavy chain CDR1, CDR2 and CDR3 and a light chain variable region comprising a light chain CDR1, CDR2 and CDR3 from the constructs show in Table 1A.

TABLE 1A

| Construct ID | | VH/VL Sequences | SEQ ID | | CDR Sequences | | | SEQ ID |
|---|---|---|---|---|---|---|---|---|
| h2726 | VH | EVQLLESGGGLVQPGGS LRLSCAASGFTFSNYGM SWVRQAPGKGLEWVASI RSGSGRTYYSDNVKGRF TISRDNSKNTLYLQMNS LRAEDTAVYYCVRYDHY SGSSDYWGQGTLVTVSS | 3 | 1 2 3 | GFTFS SIRSG YDHYS | NYGMS SGRTY GSSDY | YSDNV KG | 16 20 18 |
| | VL | DVVMTQSPLSLPVTPGE PASISCKSSQSLLDYDG KTYLNWLLQKPGQSPQR LIYKVSNRDSGVPDRFS GSGSGTDFTLKISRVEA EDVGVYYCWQGTHFPRT FGQGTKVEIK | 8 | 1 2 3 | KSSQS KVSNR WQGTH | LLDYD DS FPRT | GKTYL N | 29 33 28 |
| h2731 | VH | EVQLLESGGGLVQPGGS LRLSCAASGFTFSNYGM SWVRQAPGKGLEWVASI RSGSGRTYYSDNVKGRF TISRDNSKNTLYLQMNS LRAEDTAVYYCVRYDHY SGSSDYWGQGTLVTVSS | 3 | 1 2 3 | GFTFS SIRSG YDHYS | NYGMS SGRTY GSSDY | YSDNV KG | 16 20 18 |
| | VL | DVVMTQSPLSLPVTLGE PASISCKSSQSLLDYDG KTYLNWLLQKPGQSPQR LIYRVTNRDTGVPDRFS GSGSGTDFTLKISRVEA EDVGVYYCWQGTHFPRS FGQGTKVEIK | 9 | 1 2 3 | KSSQS RVTNR WQGTH | LLDYD DT FPRS | GKTYL N | 29 34 38 |
| h2831 | VH | EVQLLESGGGLVQPGGS LRLSCAASGFTFSNFGM SWVRQAPGKGLEWVASV RSGSGRTYYSDNVKGRF | 4 | 1 2 3 | GFTFS SVRSG YDHYS | NFGMS SGRTY GTSDY | YSDNV KG | 19 21 24 |

TABLE 1A-continued

| Construct ID | VH/VL | Sequences | SEQ ID | | CDR Sequences | | | SEQ ID |
|---|---|---|---|---|---|---|---|---|
| | | TISRDNSKNTLYLQMNS LRAEDTAVYYCVRYDHY SGTSDYWGQGTLVTVSS | | | | | | |
| | VL | DVVMTQSPLSLPVTLGE PASISCKSSQSLLDYDG KTYLNWLLQKPGQSPQR LIYRVTNRDTGVPDRFS GSGSGTDFTLKISRVEA EDVGVYYCWQGTHFPRS FGQGTKVEIK | 9 | 1<br>2<br>3 | KSSQS<br>RVTNR<br>WQGTH | LLDYD<br>DT<br>FPRS | GKTYL N | 29<br>34<br>38 |
| h2931 | VH | EVQLLESGGGLVQPGGS LRLSCAASGFTFSNFGM SWVRQAPGKGLEWVASV RSGSGRTYYSDNVKGRF TISRDNSKNTLYLQMNS LRAEDTAVYYCVRYDHY TGTSDYWGQGTLVTVSS | 5 | 1<br>2<br>3 | GFTFS<br>SVRSG<br>YDHYT | NFGMS<br>SGRTY<br>GTSDY | YSDNV KG | 19<br>21<br>25 |
| | VL | DVVMTQSPLSLPVTLGE PASISCKSSQSLLDYDG KTYLNWLLQKPGQSPQR LIYRVTNRDTGVPDRFS GSGSGTDFTLKISRVEA EDVGVYYCWQGTHFPRS FGQGTKVEIK | 9 | 1<br>2<br>3 | KSSQS<br>RVTNR<br>WQGTH | LLDYD<br>DT<br>FPRS | GKTYL N | 29<br>34<br>38 |
| h2926 | VH | EVQLLESGGGLVQPGGS LRLSCAASGFTFSNFGM SWVRQAPGKGLEWVASV RSGSGRTYYSDNVKGRF TISRDNSKNTLYLQMNS LRAEDTAVYYCVRYDHY TGTSDYWGQGTLVTVSS | 5 | 1<br>2<br>3 | GFTFS<br>SVRSG<br>YDHYT | NFGMS<br>SGRTY<br>GTSDY | YSDNV KG | 19<br>21<br>25 |
| | VL | DVVMTQSPLSLPVTPGE PASISCKSSQSLLDYDG KTYLNWLLQKPGQSPQR LIYKVSNRDSGVPDRFS GSGSGTDFTLKISRVEA EDVGVYYCWQGTHFPRT FGQGTKVEIK | 8 | 1<br>2<br>3 | KSSQS<br>KVSNR<br>WQGTH | LLDYD<br>DS<br>FPRT | GKTYL N | 29<br>33<br>28 |
| h4921G | VH | EVQLLESGGGLVQPGGS LRLSCAASGFTFSNFGM SWVRQAPGKGLEWVASV RSGGGRTYYSDNVKGRF TISRDNSKNTLYLQMNS LRAEDTAVYYCVRYDHY SGTSDYWGQGTLVTVSS | 6 | 1<br>2<br>3 | GFTFS<br>SVRSG<br>YDHYS | NFGMS<br>GGRTY<br>GTSDY | YSDNV KG | 19<br>22<br>24 |
| | VL | DVVMTQSPLSLPVTLGE PASISCKSSQSLLDSDG KTYLNWLLQKPGQSPQR LIYRVTNRDTGVPDRFS GSGSGTDFTLKISRVEA EDVGVYYCWQGTHFPRT FGQGTKVEIK | 10 | 1<br>2<br>3 | KSSQS<br>RVTNR<br>WQGTH | LLDSD<br>DT<br>FPRT | GKTYL N | 26<br>34<br>28 |
| h2826 | VH | EVQLLESGGGLVQPGGS LRLSCAASGFTFSNFGM SWVRQAPGKGLEWVASV RSGSGRTYYSDNVKGRF TISRDNSKNTLYLQMNS LRAEDTAVYYCVRYDHY SGTSDYWGQGTLVTVSS | 4 | 1<br>2<br>3 | GFTFS<br>SVRSG<br>YDHYS | NFGMS<br>SGRTY<br>GTSDY | YSDNV KG | 19<br>21<br>24 |
| | VL | DVVMTQSPLSLPVTPGE PASISCKSSQSLLDYDG KTYLNWLLQKPGQSPQR LIYKVSNRDSGVPDRFS GSGSGTDFTLKISRVEA EDVGVYYCWQGTHFPRT FGQGTKVEIK | 8 | 1<br>2<br>3 | KSSQS<br>KVSNR<br>WQGTH | LLDYD<br>DS<br>FPRT | GKTYL N | 29<br>33<br>28 |

TABLE 1A-continued

| Construct ID | | VH/VL Sequences | SEQ ID | | CDR Sequences | SEQ ID |
|---|---|---|---|---|---|---|
| h2929 | VH | EVQLLESGGGLVQPGGS LRLSCAASGFTFSNFGM SWVRQAPGKGLEWVASV RSGSGRTYYSDNVKGRF TISRDNSKNTLYLQMNS LRAEDTAVYYCVRYDHY TGTSDYWGQGTLVTVSS | 5 | 1<br>2<br>3 | GFTFS NFGMS<br>SVRSG SGRTY YSDNV KG<br>YDHYT GTSDY | 19<br>21<br>25 |
| | VL | DVVMTQSPLSLPVTPGE PASISCRSSQSLVDYDG KTYLNWLLQRPGQSPQR LIYKVSNRDSGVPDRFS GSGSGTDFTLKISRVEA EDVGVYYCWQGSHFPRS YGQGTKVEIK | 11 | 1<br>2<br>3 | RSSQS LVDYD GKTYL N<br>KVSNR DS<br>WQGSH FPRS | 31<br>33<br>39 |
| h3818G | VH | EVQLLESGGGLVQPGGS LRLSCAASGFTFANYGM SWVRQAPGKGLEWVASV RSGGSRTYYSDNVKGRF TISRDNSKNTLYLQMNS LRAEDTAVYYCVRYDHY SGSSDYWGQGTLVTVSS | 7 | 1<br>2<br>3 | GFTFA NYGMS<br>SVRSG GSRTY YSDNV KG<br>YDHYS GSSDY | 20<br>23<br>18 |
| | VL | DVVMTQSPLSLPVTLGE PASISCKSSQSLMDTDG KTYLNWLLQKPGQSPQR LIYKVSNRESGVPDRFS GSGSGTDFTLKISRVEA EDVGVYYCWQGTHFPRT FGQGTKVEIK | 12 | 1<br>2<br>3 | KSSQS LMDTD GKTYL N<br>KVSNR ES<br>WQGTH FPRT | 32<br>35<br>28 |
| h2927 | VH | EVQLLESGGGLVQPGGS LRLSCAASGFTFSNFGM SWVRQAPGKGLEWVASV RSGSGRTYYSDNVKGRF TISRDNSKNTLYLQMNS LRAEDTAVYYCVRYDHY TGTSDYWGQGTLVTVSS | 5 | 1<br>2<br>3 | GFTFS NFGMS<br>SVRSG SGRTY YSDNV KG<br>YDHYT GTSDY | 19<br>21<br>25 |
| | VL | DVVMTQSPLSLPVTPGE PASISCKSSQSLLDYDG KTYLNWLLQKPGQSPQR LIYKVSNRDSGVPDRFS GSGSGTDFTLKISRVEA EDVGVYYCWQGTHFPRS FGQGTKVEIK | 13 | 1<br>2<br>3 | KSSQS LLDYD GKTYL N<br>KVSNR DS<br>WQGTH FPRS | 29<br>33<br>38 |
| h49k3G | VH | EVQLLESGGGLVQPGGS LRLSCAASGFTFSNFGM SWVRQAPGKGLEWVASV RSGGGRTYYSDNVKGRF TISRDNSKNTLYLQMNS LRAEDTAVYYCVRYDHY SGTSDYWGQGTLVTVSS | 6 | 1<br>2<br>3 | GFTFS NFGMS<br>SVRSG GGRTY YSDNV KG<br>YDHYS GTSDY | 19<br>22<br>24 |
| | VL | DVVMTQSPLSLPVTLGE PASISCKSSQSLLDSDG KTYLNWLLQKPGQSPQR LIYKVSNRDSGVPDRFS GSGSGTDFTLKISRVEA EDVGVYYCWQGTHFPRT FGQGTKVEIK | 14 | 1<br>2<br>3 | KSSQS LLDSD GKTYL N<br>KVSNR DS<br>WQGTH FPRT | 26<br>33<br>28 |
| h4917G | VH | EVQLLESGGGLVQPGGS LRLSCAASGFTFSNFGM SWVRQAPGKGLEWVASV RSGGGRTYYSDNVKGRF TISRDNSKNTLYLQMNS LRAEDTAVYYCVRYDHY SGTSDYWGQGTLVTVSS | 6 | 1<br>2<br>3 | GFTFS NFGMS<br>SVRSG GGRTY YSDNVKG<br>YDHYS GTSDY | 19<br>22<br>24 |
| | VL | DVVMTQSPLSLPVTLGE PASISCKSSQSLLDSDG KTYLNWLLQKPGQSPQR LIYKVTNRESGVPDRFS | 15 | 1<br>2<br>3 | KSSQS LLDSD GKTYL N<br>KVTNR ES<br>WQGTH FPRS | 26<br>36<br>38 |

TABLE 1A-continued

| Construct ID | VH/VL | Sequences | SEQ ID | | CDR Sequences | SEQ ID |
|---|---|---|---|---|---|---|
| | | GSGSGTDFTLKISRVEA EDVGVYYCWQGTHFPRS FGQGTKVEIK | | | | |
| h2727 | VH | EVQLLESGGGLVQPGGS LRLSCAASGFTFSNYGM SWVRQAPGKGLEWVASI RSGSGRTYYSDNVKGRF TISRDNSKNTLYLQMNS LRAEDTAVYYCVRYDHY SGSSDYWGQGTLVTVSS | 3 | 1<br>2<br>3 | GFTFS NYGMS<br>SIRSG SGRTY YSDNV KG<br>YDHYS GSSDY | 16<br>20<br>18 |
| | VL | DVVMTQSPLSLPVTPGE PASISCKSSQSLLDYDG KTYLNWLLQKPGQSPQR LIYKVSNRDSGVPDRFS GSGSGTDFTLKISRVEA EDVGVYYCWQGTHFPRS FGQGTKVEIK | 13 | 1<br>2<br>3 | KSSQS LLDYD GKTYL N<br>KVSNR DS<br>WQGTH FPRS | 29<br>33<br>38 |
| h4918G | VH | EVQLLESGGGLVQPGGS LRLSCAASGFTFSNFGM SWVRQAPGKGLEWVASV RSGGGRTYYSDNVKGRF TISRDNSKNTLYLQMNS LRAEDTAVYYCVRYDHY SGTSDYWGQGTLVTVSS | 6 | 1<br>2<br>3 | GFTFS NFGMS<br>SVRSG GGRTY YSDNV KG<br>YDHYS GTSDY | 19<br>22<br>24 |
| | VL | DVVMTQSPLSLPVTLGE PASISCKSSQSLMDTDG KTYLNWLLQKPGQSPQR LIYKVSNRESGVPDRFS GSGSGTDFTLKISRVEA EDVGVYYCWQGTHFPRT FGQGTKVEIK | 12 | 1<br>2<br>3 | KSSQS LMDTD GKTYL N<br>KVSNR ES<br>WQGTH FPRT | 32<br>25<br>28 |

In another aspect the antibody or fragment of the disclosure includes a heavy chain variable region (VH) as shown for one of the constructs in Table 1. The antibody or fragment may also include light chain variable region (VL) as shown for one of the constructs in Table 1A.

An alignment of the CDRs for each of the heavy chain and light chain sequences identified in Table 1A and the CDRs from bapineuzumab ("Bapi", "hBP") is show in FIGS. 19A and 19B. In one aspect, the disclosure is directed an antibody or fragment thereof including a heavy chain CDR1, CDR2, and CDR3, wherein CDR1 may be selected from any one of SEQ ID NOS: 16, 19 and 20, wherein CDR2 may be selected from any one of SEQ ID NOS: 17, 20, 21 22, and 23 and wherein CDR3 may be selected from any one of SEQ ID NOS: 18, 24, 25. In addition, the antibody or fragment thereof includes a light chain CDR1, CDR2, and CDR3, wherein CDR1 may be selected from any one of SEQ ID NOS: 26, 29, 31, and 32, wherein CDR2 may be selected from any one of SEQ ID NOS: 27, 33, 34 and 35, and wherein CDR3 may be selected from any one of SEQ ID NOS: 28, 38 and 39. In each of these embodiments, the heavy chain CDRs and the light chain CDRs are not, in combination, simultaneously SEQ ID NOS: 16, 17, 18, 26, 27 and 28.

Analysis of protein modeling information for the antibodies described above identified two changes in the CDRs that, among others, were the contributors to increased avidity/affinity characteristics of the antibodies of the disclosure:

CDR-L1: S32Y (Ser to Tyr at position 32), and
CDR-H2: G55S (Gly to Ser at position 55)

Anti-Aβ antibodies with Tyr at position 32 in CDR-L1 and Ser at position 55 in CDR-H2 that bind the same epitope bound by antibodies listed herein are expected to have the same properties as the listed identified antibodies (See Table 1A and FIG. 19A and FIG. 19B). Antibodies disclosed that do not have Tyr at position 32 in CDR-L1 and Ser at position 55 in CDR-H2 can be modified to possess Tyr at position 32 in CDR-L1 and Ser at position 55 in CDR-H2 and can be expected to confer similar binding properties to such antibodies identified herein.

Examples of a CDR-L1 with Tyr at position 32 include SEQ NOs: 29 and 31. Examples of a CDR-H2 with Ser at position 55 include SEQ Nos: 20 and 21.

As examples, antibodies comprising a CDR-L1 with Tyr at position 32 and a CDR-H2 with Ser at position 55 include antibodies with the CDRs of h2726, h2731, h2727, h2826, h2831, h2926, h2927, h2931, h2929 (See Table 1A). Additional such antibodies include antibodies comprising LC CDRs 1, 2, 3 and HC CDRs 1, 2, 3 as set forth in the table below in Table 1B.

TABLE 1B

| Antibody | HC/LC | | CDR Sequences (HC 1,2,3; LC 1,2,3) | SEQ ID |
|---|---|---|---|---|
| h2729 | HC | 1<br>2<br>3 | GFTFS NYGMS<br>SIRSG SGRTY YSDNV KG<br>YDHYS GSSDY | 16<br>20<br>18 |
| | LC | 1<br>2<br>3 | RSSQS LVDYD GKTYL N<br>KVSNR DS<br>WQGSH FPRS | 31<br>33<br>39 |

TABLE 1B-continued

| Antibody | HC/LC | | CDR Sequences (HC 1,2,3; LC 1,2,3) | SEQ ID |
|---|---|---|---|---|
| H2829 | HC | 1 | GFTFS NFGMS | 19 |
| | | 2 | SVRSG SGRTY YSDNV KG | 21 |
| | | 3 | YDHYS GTSDY | 24 |
| | LC | 1 | RSSQS LVDYD GKTYL N | 31 |
| | | 2 | KVSNR DS | 33 |
| | | 3 | WQGSH FPRS | 39 |
| H2827 | HC | 1 | GFTFS NFGMS | 19 |
| | | 2 | SVRSG SGRTY YSDNV KG | 21 |
| | | 3 | YDHY SGTSDY | 24 |
| | LC | 1 | KSSQS LLDYD GKTYL N | 29 |
| | | 2 | RVTNR DT | 33 |
| | | 3 | WQGTH FPRS | 38 |
| HC-S55/ | HC | 1 | GFTFS NYGMS | 16 |
| LC-Y32 | | 2 | SIRSG SGRTY YSDNV KG | 20 |
| | | 3 | YDHYS GSSDY | 18 |
| | LC | 1 | KSSQS LLDYD GKTYL N | 29 |
| | | 2 | LVSKL DS | 27 |
| | | 3 | WQGTH FPRT | 28 |

In view of the binding properties identified for the antibodies identified herein, consensus sequences can be identified that would be expected to provide similar binding properties. For example, in embodiments of the disclosure, antibodies or binding fragments thereof that that specifically bind to Aβ peptide may include heavy chain variable regions having heavy chain CDR1, CDR2 and CDR3 and a light chain variable regions having light chain CDR1, CDR2 and CDR3, as follows:

heavy chain CDR1 comprises amino acid sequence GFTFSNX$_1$GMS, wherein X$_1$ is Y or F (SEQ ID NO: 88);
heavy chain CDR2 comprises amino acid sequence SX$_1$RSGSGRTYYSDNVKG, wherein is X$_1$ is I or V (SEQ ID NO: 89);
heavy chain CDR3 comprises amino acid sequence YDHYX$_1$GX$_2$SDY, wherein X$_1$ is S or T and X$_2$ is S or T (SEQ ID NO: 90);
light chain CDR1 comprises amino acid sequence KSSQSLLDYDGKTYLN (SEQ ID NO: 91);
light chain CDR2 comprises amino acid sequence X$_1$VX$_2$NRDX$_3$, wherein X$_1$ is K or R, X$_2$ is S or T, and X$_3$ is S or T (SEQ ID NO: 92).
light chain CDR3 comprises amino acid sequence WQGTHFPRX$_1$, wherein X$_1$ is S or T (SEQ ID NO: 93).

In some embodiments, the light chain CDR3 comprises WQGTHFPRX$_1$FX$_2$, wherein X$_1$ is S or T and X$_2$ is F or Y (SEQ ID NO: 94).

Similar consensus sequences that may be expected to provide binding properties similar to the antibodies described herein include a heavy chain variable region having heavy chain CDR1, CDR2 and CDR3 and a light chain variable region having light chain CDR1, CDR2 and CDR3, as follows:

heavy chain CDR1 comprises amino acid sequence GFTFX$_1$NX$_2$GMS, wherein X$_1$ is S or A, and X$_2$ is Y or F (SEQ ID NO: 95);
heavy chain CDR2 comprises amino acid sequence SX$_1$RSGX$_2$X$_3$RTYYSDNVKG, wherein is X$_1$ is I or V, X$_2$ is S or G and X$_3$ is S or G (SEQ ID NO: 96);
heavy chain CDR3 comprises amino acid sequence YDHYX$_1$GX$_2$SDY, wherein X$_1$ is S or T and X$_2$ is S or T (SEQ ID NO: 90);
light chain CDR1 comprises amino acid sequence X$_1$SSQSLX$_2$DX$_3$DGKTYLN, wherein X$_1$ is K or R, X$_2$ is V, M or L, and X$_3$ is Y, T or S (SEQ ID NO: 97);
light chain CDR2 comprises amino acid sequence X$_1$VX$_2$NRX$_3$X$_4$, wherein X$_1$ is K or R, X$_2$ is S or T, and X$_3$ is E or D, and X$_4$ is S or T (SEQ ID NO: 98).
light chain CDR3 comprises amino acid sequence WQGX$_1$HFPRX$_2$, wherein X$_1$ is S or T, and X$_2$ is S or T (SEQ ID NO: 99).

In some embodiments, the light chain CDR3 comprises WQGTHFPRX$_1$FX$_2$X$_3$, wherein X$_1$ is S or T, X$_2$ is S or T and X$_3$ is F or Y (SEQ ID NO: 100).

In addition, the light and heavy variable regions may be at least at least 75% identical to the light and heavy chain variable regions show in Table 1A. For example, the light and heavy chain variable regions may be 75% identical, 80%, identical, 85% identical, 90% identical, 95% identical, 96% identical, 97% identical, 98% identical, 99% identical, of 100% identical to VH and/or VL sequences identified in Table 1A. In various aspects, any sequence variation in the VH and VL may be present outside the CDRs so that the VH and VL sequences of the disclosure include the CDRs identified in Table 1A, but the regions of the VH and VL sequences outside of the CDRs may be at least 75% identical to the regions outside the CDRs of the VH and VL sequences in Table 1A.

For example, the antibody or fragment of the disclosure may include a heavy chain variable region, excluding the CDRS, that is at least 95% identical to one of SEQ ID NOS: 3, 4, 5, 6 and 7, and the light chain variable region, excluding the CDRs, that is at least 95% identical to one of SEQ ID NOS: 8, 9, 10, 11, 12, 13, 14 and 15.

The antibodies and fragments of the disclosure may also include a heavy chain constant region that is at least 75% identical to SEQ ID NO: 40. For example, the heavy chain constant region may be 75% identical, 80%, identical, 85% identical, 90% identical, 95% identical, 96% identical, 97% identical, 98% identical, 99% identical, of 100% identical to SEQ ID NO: 40.

The antibodies and fragments of the disclosure may also include a light chain constant region that is at least 75% identical to SEQ ID NO: 41. For example, the light chain constant region may be 75% identical, 80%, identical, 85% identical, 90% identical, 95% identical, 96% identical, 97% identical, 98% identical, 99% identical, of 100% identical to SEQ ID NO: 41.

A variant antibodies or fragments that are less than 100% identical to the sequences described in Table 1A (plus any constant region) can differ from an anti-Aβ antibody of Table 1A by as few as 1 to 15 amino acid residues, as few as 1 to 10 amino acid residues, such as 6-10, as few as 5, as few as 4, 3, 2, or even 1 amino acid residue. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an Aβ polypeptide).

For example, it is possible to introduce mutations only in framework regions of the antibody molecules. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to immunospecifically bind at least one epitope of an Aβ polypeptide) can be determined using techniques described herein or by routinely modifying techniques known in the art.

In each of the foregoing embodiments, the antibody or fragment of the disclosure may be a humanized antibody as described herein. For example, the antibody may be a human IgG1 antibody. In addition, the antibody may a full antibody, a chimeric antibody, a CDR-grafted antibody, or a recombinant antibody. Fragments of the antibody may be a Fab, Fab', F(ab')2, Fabc, or Fv. Fragments are produced by recombinant DNA techniques, or by enzymatic or chemical separation of intact immunoglobulins.

The antibody or binding fragments, variant, or derivative disclosed herein can be said to bind to Aβ) or a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. In certain embodiments, an antibody of the disclosure can be said to bind Aβ or a fragment or variant thereof with an off rate (k(off)) less than or equal to $5\times10^{4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{7}$ sec$^{-1}$ or $10^{-7}$ sec$^{-1}$.

An antibody or antigen-binding fragment, variant, or derivative disclosed herein can be said to bind a target polypeptide disclosed herein (e.g., Aβ) or a fragment or variant thereof with an on rate (k(on)) of greater than or equal to $10^{3}$ M-1 sec-1, $5\times10^{3}$ M-1 sec-1, $10^{4}$ M-1 sec-1 or $5\times10^{4}$ M-1 sec-1. In certain embodiments, an antibody of the disclosure can be said to bind a target polypeptide disclosed herein (e.g., Aβ) or a fragment or variant thereof with an on rate (k(on)) greater than or equal to $10^{5}$ M-1 sec-1, $5\times10^{5}$ M-1 sec-1, $10^{6}$ M-1 sec-1, or $5\times10^{6}$ M-1 sec-1 or $10^{7}$ M-1 sec-1.

Anti-Aβ antibodies or antigen-binding fragments, variants or derivatives thereof, as described herein can also be described or specified in terms of their binding affinity Aβ. Binding affinities can include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Expression of Recombinant Antibodies

The disclosure is also directed to recombinant polynucleotides encoding antibodies which, when expressed, include the heavy and light chain CDRs of the antibodies of the disclosure. Exemplary polynucleotides, which on expression code for the polypeptide chains comprising the heavy and light chain CDRs of monoclonal antibodies are provided herein (e.g., SEQ ID NO: 42 through SEQ ID NO: 69), which code for the variable light and heavy chain polypeptides, and CDRs thereof, according to SEQ ID NO: 1 through SEQ ID NO: 39. Due to codon degeneracy, other polynucleotide sequences can be readily substituted for those sequences.

Humanized and human antibodies are typically produced by recombinant expression. Nucleic acids encoding humanized light and heavy chain variable regions may be linked to constant regions are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences.

One prokaryotic host useful for cloning the polynucleotides of the present disclosure is *E. coli*. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Additionally, plants (e.g., rice, tobacco) are useful for expression.

Mammalian tissue cell culture may also be used to express and produce the polypeptides of the present disclosure (e.g., polynucleotides encoding immunoglobulins or fragments thereof). Eukaryotic cells can be particularly useful because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas. Preferably, the cells are nonhuman. Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like.

Antibody-coding sequences can be incorporated in transgenes for introduction into the genome of a transgenic animal and subsequent expression in the milk of the transgenic animal. Suitable transgenes include coding sequences for light and/or heavy chains in operable linkage with a promoter and enhancer from a mammary gland specific gene, such as casein or beta lactoglobulin.

Vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present disclosure can be purified according to standard procedures of the art, including ammonium sulfate precipitation, affinity columns (e.g., Protein A), column chromatography, HPLC purification, gel electrophoresis and the like. Substantially pure immunoglobulins of at least about 90 to 95% homogeneity are preferred, and 98 to 99% or more homogeneity most preferred, for pharmaceutical uses.

Increasing the copy number of expression vectors containing polynucleotide sequences of interest is desirable as a way to increase the production of antibodies or antibody fragments. A number of ways to genetically manipulate cells for this purpose and subsequently select the best cells are known in the art. These methods often include an "amplification" step to increase the copy number of the incorporated expression vector to improve the yield obtained for the desired protein. Amplification methods have been previously reported, e.g., by Bebbington and Hentschel (DNA Cloning Volume III (IRL press, 1987)). Any of a number of selectable markers, often in the form of nucleic acid sequences that encode enzymes that are involved in host cell metabolism and are essential for their survival under certain media conditions, can be operably linked to an expression vector, whereby the expression of a desired protein can be promoted upon selection for a selectable marker. Cells selected for a high copy number can be subjected to further amplification methods when the titer of the protein is not acceptably elevated. Such methods can involve subjecting the cells to certain toxic drugs that inhibit the selectable marker (e.g., methotrexate and dihydrofolate reductase, methionine sulphoximine and glutamine synthase, multi-drug resistance/adriamycin). Through such inhibition, cell populations with increased levels of expression of this marker may be selected. This often leads to increased expression levels of similarly functionally linked expression cassettes. Vector copy number in individual cells subjected to the amplification method are assessed until a plateau of protein production is reached, preferably at least about 100 mg/ml/$10^6$ cells/24 hours. Clones that grow through such selection and amplification are subsequently screened for titer/yield to select the best clone and then further evaluated. From such titration and screening, it is common to identify one or a small number of clones for subsequent production of one or more desired proteins and subsequently use it or them alone.

Pharmaceutical Compositions

Several methods of preparing and administering anti-Aβ antibodies, or antigen-binding fragments, variants, or derivatives thereof to a subject in need thereof are known. The route of administration of an anti-Aβ antibody, or antigen-binding fragment, variant, or derivative thereof, can be, for example, peripheral, oral, central (e.g., intrathecal, intracranial), parenteral, by inhalation or topical.

As discussed herein, anti-Aβ antibodies, or antigen-binding fragments, variants, or derivatives thereof can be formulated so as to facilitate administration and promote stability of the active agent. In certain embodiments, pharmaceutical compositions in accordance with the present disclosure comprise a pharmaceutically acceptable, non-toxic, sterile carrier such as physiological saline, non-toxic buffers, preservatives and the like. For the purposes of the instant application, a pharmaceutically effective amount of an anti-Aβ antibody, or antigen-binding fragment, variant, or derivative thereof, shall be held to mean an amount sufficient to achieve effective binding to a target and to achieve a benefit, e.g., reduce brain amyloid plaques without affecting vascular amyloid, or minimizes the occurrence of microhemorrhage during chronic dosing of the anti-Aβ antibody or antigen-binding fragment thereof. In some embodiments, an anti-Aβ antibody or antigen-binding fragment, variant, or derivative thereof can cross the blood-brain barrier in an effective amount to reduce brain amyloid plaques.

The pharmaceutical compositions used in this disclosure comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Prevention of the action of microorganisms can be achieved by various antibacterial and antifungal agents, for example, parabens, chlorobutanol, phenol, ascorbic acid, thimerosal and the like. In many cases, isotonic agents can be included, for example, sugars, polyalcohols or salts in the composition. Prolonged absorption of the injectable compositions can be brought about by including in the composition an agent which delays absorption, for example, aluminum monostearate and gelatin.

Parenteral formulations can be a single bolus dose, an infusion or a loading bolus dose followed with a maintenance dose. These compositions can be administered at specific fixed or variable intervals, e.g., once a day, or on an "as needed" basis.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Furthermore, the pharmaceutical composition of the disclosure can comprise further agents such as dopamine or psychopharmacologic drugs, depending on the intended use of the pharmaceutical composition.

The amount of an anti-Aβ antibody, or fragment, variant, or derivative thereof, to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

The term "peripheral administration" as used herein includes, e.g., intravenous, intraarterial, intraperitoneal, intramuscular, subcutaneous, intranasal, intra-ocular/vitreal, rectal, or vaginal administration. While all these forms of administration are clearly contemplated as being within the scope of the disclosure, an example of a form for administration would be a solution for injection, in particular for subcutaneous, intravenous or intraarterial injection or drip. A suitable pharmaceutical composition for injection can comprise a buffer, a surfactant, optionally a stabilizer agent, etc. Preparations for peripheral administration include sterile aqueous or non-aqueous solutions, suspensions, and emulsions. Preservatives and other additives can also be present such as, for example, antimicrobials, antioxidants, chelating agents, and inert gases and the like.

Therapeutic compositions of the disclosure are typically substantially pure from undesired contaminants. This means that the agent is typically at least 50% w/w pure of interfering proteins and other contaminants arising from its production or purification but does not exclude the possibility that the agent is combined with an excess of pharmaceutical acceptable carrier(s) or other vehicle intended to facilitate its use. Sometimes monoclonal antibodies (or other therapeutic agents) are at least 60%, 70%, 80%, 90%, 95% or 99% w/w pure of interfering proteins and contaminants from production or purification.

Treatment Amenable Patients

The present disclosure is also directed to treatment of Alzheimer's and other amyloidogenic diseases by administration of the antibodies, fragments and pharmaceutical compositions of the disclosure generate a beneficial therapeutic response in a patient (e.g., induction of phagocytosis of Aβ, reduction of plaque burden, inhibition of plaque formation, reduction of neuritic dystrophy, neutralization of soluble, toxic Aβ species, improving cognitive function, and/or reversing, treating or preventing cognitive decline) in the patient, for example, for the prevention or treatment of an amyloidogenic disease. The disclosure is also directed to use of the disclosed antibodies and fragments in the manufacture of a medicament for the treatment or prevention of an amyloidogenic disease.

In one aspect, the disclosure provides methods of preventing or treating a disease associated with amyloid deposits of Aβ in a patient. In one aspect, the amyloid deposits are in the brain or other CNS areas. Such diseases include Alzheimer's disease, Down's syndrome, age-related macular degeneration (AMD), and cognitive impairment. The latter can occur with or without other characteristics of an amyloidogenic disease. Some methods of the disclosure entail administering an effective dosage of an antibody that specifically binds to a component of an amyloid deposit to the patient. Such methods are useful for preventing or treating Alzheimer's disease in human patients The methods can be used on both asymptomatic patients and those currently showing symptoms of disease. The antibodies used in such methods can be humanized, human or fragments thereof (e.g., antigen binding fragments) and can be monoclonal or polyclonal, as described herein. In yet another aspect, the disclosure features administering antibodies prepared from a human immunized with Aβ peptide, which human can be the patient to be treated with antibody.

In another aspect, the disclosure features administering an antibody with a pharmaceutical carrier as a pharmaceutical composition. Alternatively, the antibody can be administered to a patient by administering a polynucleotide encoding at least one antibody chain. The polynucleotide is expressed to produce the antibody chain in the patient. Optionally, the polynucleotide encodes heavy and light chains of the antibody. The polynucleotide is expressed to produce the heavy and light chains in the patient. In exemplary embodiments, the patient is monitored for level of administered antibody in the blood of the patient.

Patients amenable to treatment include individuals at risk of disease but not showing symptoms, as well as patients presently showing symptoms. In the case of Alzheimer's disease, potentially anyone who lives long enough is at risk of Alzheimer's disease. Thus, the present methods include administering prophylactically to the general population without the need for any assessment of the risk of the subject patient. The present methods are especially useful for individuals who have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations, respectively. Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria as discussed in the Examples section.

Treatment in asymptomatic patients can begin at any age (e.g., 10, 20, 30). Usually, however, it is not necessary to begin treatment until a patient reaches 40, 50, 60, or 70.

Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

In Vivo Detection

In another aspect, the disclosure provides methods for detecting amyloid plaques and deposits in a patient having or at risk of developing an amyloidogenic disease. Such methods are useful for diagnosing or confirming amyloidogenic disease or susceptibility to it. For example, the methods can be used in patients with dementia symptoms, wherein observation of abnormal amyloid deposits likely indicates Alzheimer's disease. The methods can also be used in asymptomatic patients. The presence of abnormal deposits of amyloid indicates susceptibility to future symptomatic disease.

In some embodiments, the method comprises administering to a subject/patient an antibody or fragment thereof of the disclosure and detecting the antibody or fragment thereof bound to Aβ.

Antibody and/or antibody fragments thereof can be administered by any suitable means that results in delivery to the tissue to be visualized, e.g., administered directly into the brain by intravenous injection into the patient's body or by intracranial injection. Dosage of the antibody and/or fragment thereof can comprise a therapeutic dose, subtherapeutic dose or a supratherapeutic dose. In some embodiments the antibody or fragment thereof is labeled, comprising a fluorescent label, a paramagnetic label, or a radioactive label. The choice of label depends on the means of detection. For example, fluorescent labels are suitable for visual detection. The use of paramagnetic labels is suitable for tomographic detection without surgical intervention. In some embodiments, the radioactive label is detected using positron emission tomography (PET) or single-photon emission computed tomography (SPECT).

In another aspect, the disclosure provides methods for measuring the efficacy of treatment in a subject being treated for an amyloidogenic disease. In some embodiments, a first level of amyloid plaque in a subject is measured prior to treatment by administering an antibody or fragment thereof of the disclosure and detecting a first amount of the antibody or fragment thereof bound to Aβ in the subject. A treatment can then be administered to the subject, followed by measuring a second level of amyloid plaque in the subject, and detecting the antibody or fragment thereof bound to Aβ in the subject. In some embodiments, a decrease in the level of amyloid plaque indicates a positive response to treatment, and in some embodiments, no change in the level of amyloid plaque or a small increase in amyloid plaque indicates a positive response to treatment. In some embodiments, levels of amyloid plaque can be measured utilizing the methods of detecting amyloid plaques described herein.

In some embodiments, diagnosis of an amyloidogenic disease can be performed, for example, by comparing the number, size and/or intensity of labeled positions from a measured first level (i.e., baseline) to a subsequent second level of amyloid plaque in a subject. An increase over time indicates disease progression, no change indicates, and fewer or less intense amyloid plaques over time indicates remission.

Treatment Regimes

Prophylactic applications: pharmaceutical compositions or medicaments are administered to a patient susceptible to, or otherwise at risk of, Alzheimer's disease or other amyloidogenic disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Patient susceptibility or risk for developing an amyloidogenic disease can be determined, for example, from a genetic marker, a biochemical marker, unspecified hereditary risk or other means. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

In some embodiments, administration of agent reduces or eliminates cognitive impairment in patients that have not yet developed characteristic Alzheimer's, or other amyloidogenic disease cognitive pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved, where "immune response" or "immunological response" includes the development of a humoral (antibody mediated) and/or a cellular (mediated by antigen-specific T cells or their secretion products) response directed against an antigen in a recipient subject. Such a response can be an active response, i.e., induced by administration of immunogen, or a passive response, i.e., induced by administration of immunoglobulin or antibody or primed T-cells.

In some embodiments, antibody is administered on multiple occasions. Intervals between single dosages can be weekly, monthly or yearly. Intervals can also be irregular as indicated by measuring blood levels of antibody to Aβ in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg/kg per dose, especially 0.5 to 2.5 mg/kg per dose. A relatively low dosage is administered at relatively infrequent intervals over a long period of time. Some patients continue to receive treatment for the rest of their lives.

In therapeutic applications, a relatively high dosage (e.g., from about 0.5 to 300 mg/kg of antibody per dose, with dosages of from 5 to 25 mg/kg being more commonly used) at relatively short intervals is sometimes required until progression of the disease is reduced or terminated, and preferably until the patient shows partial or complete amelioration of symptoms of disease. Thereafter, the patent can be administered a prophylactic regime.

Administration: therapeutic agents can be administered by parenteral, topical, intravenous, oral, subcutaneous, intraarterial, intracranial, intraperitoneal, intranasal, intraocular or intramuscular means for prophylactic and/or therapeutic treatment. Intramuscular injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device.

Agents of the disclosure can optionally be administered in combination with other agents that are at least partly effective in treatment of amyloidogenic disease. In the case of Alzheimer's and Down's syndrome, in which amyloid deposits occur in the brain, agents of the disclosure can also be administered in conjunction with other agents that increase passage of the agents of the disclosure across the blood-brain barrier.

The present disclosure will be more fully described by the following non-limiting examples.

```
SEQ ID NO. 40: huIgG1 Constant
ASTKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKSRWQQGNVFSCSV

MHEALHNHYTQKSLSLSPGK

SEQ ID NO. 41: huKappa Constant
RTVAAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

SEQ ID NO. 42: h2726 VH (Variable Heavy) Nucleotide Sequence
GAAGTGCAGCTTCTGGAGAGCGGGGCGGCCTGGTGCAGCCGGGCGGATCCCTGAGACTGTC

CTGTGCCGCGTCCGGTTTTACCTTCTCCAACTACGGAATGTCATGGGTCCGCCAAGCACCCG

GAAAGGGATTGGAATGGGTGGCTTCGATCCGGTCCGGCTCGGGACGGACCTACTACTCCGAT

AACGTCAAGGGCAGATTCACTATTAGCCGGGACAACAGCAAGAATACCCTGTACCTCCAAAT

GAACTCCCTGAGGGCCGAGGACACCGCCGTGTATTACTGCGTGCGCTACGACCACTACTCGG

GTTCCTCTGATTACTGGGGACAGGGGACCCTCGTGACTGTGTCAAGC

SEQ ID NO. 43: h2726 VL (Variable Light) Nucleotide Sequence
GATGTCGTGATGACCCAGTCACCACTGTCCCTTCCTGTGACTCCCGGAGAACCGGCGTCCAT

TTCGTGCAAGAGCAGCCAGTCCCTGCTCGATTATGACGGAAAGACCTACCTGAACTGGTTGC

TCCAAAAGCCTGGGCAGAGCCCCAGAGACTGATCTACAAAGTGTCCAACAGGGACTCGGGC

GTGCCGGACCGCTTCTCGGGGTCCGGTTCCGGTACCGACTTTACGCTGAAGATCTCACGGGT

GGAAGCCGAGGACGTGGGAGTGTACTACTGTTGGCAGGGCACTCACTTCCCGCGGACCTTCG

GACAAGGCACCAAGGTCGAGATCAAG

SEQ ID NO. 44: h2931 VH (Variable Heavy) Nucleotide Sequence
GAAGTGCAGCTCCTGGAGTCCGGGGGTGGACTGGTGCAGCCCGGGGGCAGCCTGAGGCTGAG

CTGCGCCGCGTCAGGATTCACCTTCTCCAACTTCGGAATGTCCTGGGTCAGACAGGCCCCGG

GAAAGGGCCTTGAATGGGTGGCTAGCGTGCGCTCCGGTTCCGGACGGACCTACTACTCGGAC

AACGTGAAGGGCCGGTTTACTATCTCCCGGGACAATTCGAAGAACACCCTGTACCTCCAAAT

GAACTCCTTGCGCGCCGAGGATACCGCAGTGTATTACTGCGTGCGCTACGACCACTACTCTG

GCACTAGCGATTACTGGGGCCAGGGAACTCTGGTCACCGTGTCGTCA

SEQ ID NO. 45: h2931 VL (Variable Light) Nucleotide Sequence
GATGTCGTGATGACTCAGTCACCTCTGTCCCTGCCTGTGACCCTTGGGGAACCCGCCTCGAT

CTCGTGCAAGAGCTCCCAGAGCCTGCTCGACTATGATGGAAAGACCTACCTGAACTGGTTGC

TCCAAAAGCCGGGCCAGAGCCCCCAGAGGCTGATCTACCGCGTGACCAACCGCGACACCGGG
```

-continued

GTGCCGGACCGGTTCTCCGGATCCGGCAGCGGCACTGACTTCACCCTGAAAATTTCCAGAGT

GGAAGCCGAGGACGTGGGAGTGTACTACTGTTGGCAGGGTACTCACTTTCCACGGTCCTTCG

GTCAAGGAACCAAGGTCGAGATCAAG

SEQ ID NO. 46: h2731 VH (Variable Heavy) Nucleotide Sequence
GAAGTGCAGCTTCTGGAGAGCGGGGGCGGCCTGGTGCAGCCGGGCGGATCCCTGAGACTGTC

CTGTGCCGCGTCCGGTTTTACCTTCTCCAACTACGGAATGTCATGGGTCCGCCAAGCACCCG

GAAAGGGATTGGAATGGGTGGCTTCGATCCGGTCCGGCTCGGGACGGACCTACTACTCCGAT

AACGTCAAGGGCAGATTCACTATTAGCCGGGACAACAGCAAGAATACCCTGTACCTCCAAAT

GAACTCCCTGAGGGCCGAGGACACCGCCGTGTATTACTGCGTGCGCTACGACCACTACTCGG

GTTCCTCTGATTACTGGGGACAGGGGACCCTCGTGACTGTGTCAAGC

SEQ ID NO. 47: h2731 VL (Variable Light) Nucleotide Sequence
GATGTCGTGATGACTCAGTCACCTCTGTCCCTGCCTGTGACCCTTGGGGAACCCGCCTCGAT

CTCGTGCAAGAGCTCCCAGAGCCTGCTCGACTATGATGGAAAGACCTACCTGAACTGGTTGC

TCCAAAAGCCGGGCCAGAGCCCCCAGAGGCTGATCTACCGCGTGACCAACCGCGACACCGGG

GTGCCGGACCGGTTCTCCGGATCCGGCAGCGGCACTGACTTCACCCTGAAAATTTCCAGAGT

GGAAGCCGAGGACGTGGGAGTGTACTACTGTTGGCAGGGTACTCACTTTCCACGGTCCTTCG

GTCAAGGAACCAAGGTCGAGATCAAG

SEQ ID NO. 48: h2831 VH (Variable Heavy) Nucleotide Sequence
GAAGTGCAGCTGCTGGAGTCTGGCGGCGGACTGGTGCAGCCCGGGGGATCCCTGCGGCTTTC

CTGCGCCGCATCCGGCTTCACCTTTTCAAACTTCGGAATGTCGTGGGTCAGACAGGCCCCGG

GAAAGGGTCTGGAATGGGTGGCCTCAGTGCGGTCCGGATCGGGTAGAACCTACTACAGCGAT

AACGTGAAGGGCCGGTTCACGATCTCCCGCGACAACTCCAAGAACACCCTGTACTTGCAAAT

GAATAGCCTCAGGGCTGAGGATACCGCGGTCTACTACTGTGTGCGCTATGACCACTACACTG

GAACTAGCGACTACTGGGGCCAGGGGACCCTCGTGACTGTGTCGTCC

SEQ ID NO. 49: h2831 VL (Variable Light) Nucleotide Sequence
GATGTCGTGATGACTCAGTCACCTCTGTCCCTGCCTGTGACCCTTGGGGAACCCGCCTCGAT

CTCGTGCAAGAGCTCCCAGAGCCTGCTCGACTATGATGGAAAGACCTACCTGAACTGGTTGC

TCCAAAAGCCGGGCCAGAGCCCCCAGAGGCTGATCTACCGCGTGACCAACCGCGACACCGGG

GTGCCGGACCGGTTCTCCGGATCCGGCAGCGGCACTGACTTCACCCTGAAAATTTCCAGAGT

GGAAGCCGAGGACGTGGGAGTGTACTACTGTTGGCAGGGTACTCACTTTCCACGGTCCTTCG

GTCAAGGAACCAAGGTCGAGATCAAG

SEQ ID NO. 50: h2926 VH (Variable Heavy) Nucleotide Sequence
GAAGTGCAGCTCCTGGAGTCCGGGGGTGGACTGGTGCAGCCCGGGGGCAGCCTGAGGCTGAG

CTGCGCCGCGTCAGGATTCACCTTCTCCAACTTCGGAATGTCCTGGGTCAGACAGGCCCCGG

GAAAGGGCCTTGAATGGGTGGCTAGCGTGCGCTCCGGTTCCGGACGGACCTACTACTCGGAC

AACGTGAAGGGCCGGTTTACTATCTCCCGGGACAATTCGAAGAACACCCTGTACCTCCAAAT

GAACTCCTTGCGCGCCGAGGATACCGCAGTGTATTACTGCGTGCGCTACGACCACTACTCTG

GCACTAGCGATTACTGGGGCCAGGGAACTCTGGTCACCGTGTCGTCA

SEQ ID NO. 51: h2926 VL (Variable Light) Nucleotide Sequence
GATGTCGTGATGACCCAGTCACCACTGTCCCTTCCTGTGACTCCCGGAGAACCGGCGTCCAT

TTCGTGCAAGAGCAGCCAGTCCCTGCTCGATTATGACGGAAAGACCTACCTGAACTGGTTGC

TCCAAAAGCCTGGGCAGAGCCCCCAGAGACTGATCTACAAAGTGTCCAACAGGGACTCGGGC

GTGCCGGACCGCTTCTCGGGGTCCGGTTCCGGTACCGACTTTACGCTGAAGATCTCACGGGT

-continued
GGAAGCCGAGGACGTGGGAGTGTACTACTGTTGGCAGGGCACTCACTTCCCGCGGACCTTCG

GACAAGGCACCAAGGTCGAGATCAAG

SEQ ID NO. 52: h4921G VH (Variable Heavy) Nucleotide Sequence
GAGGTGCAGCTGCTGGAGTCGGGGGGGGGACTCGTGCAGCCCGGGGGCTCCCTGAGACTCTC

TTGTGCCGCCTCCGGCTTCACTTTTTCAAACTTCGGAATGTCCTGGGTCCGCCAAGCACCGG

GAAAGGGTCTGGAATGGGTCGCCAGCGTGCGGTCCGGCGGCGGACGGACTTACTACTCCGAC

AACGTGAAGGGCCGGTTCACCATCTCAAGGGATAACTCCAAGAATACTCTGTACTTGCAAAT

GAACTCGCTGCGCGCTGAAGATACCGCGGTGTACTATTGCGTGCGCTACGACCACTACTCCG

GTACCAGCGACTACTGGGGACAGGGAACCCTTGTGACCGTGTCGAGC

SEQ ID NO. 53: h4921G VL (Variable Light) Nucleotide Sequence
GATGTCGTGATGACTCAGTCGCCCCTCTCCCTGCCTGTGACTCTGGGGGAACCCGCGTCCAT

TTCGTGCAAGAGCAGCCAGTCCCTGTTGGACTCAGACGGAAAGACCTACCTTAACTGGCTGC

TGCAAAAGCCAGGACAGAGCCCGCAGAGGCTGATCTACCGCGTGACCAACCGGGATACGGGA

GTGCCGGACAGATTCAGCGGCTCGGGTTCCGGCACCGACTTCACCCTCAAAATCTCCCGCGT

CGAGGCCGAGGACGTGGGCGTGTATTACTGTTGGCAGGGAACCCACTTTCCTCGGACCTTCG

GTCAAGGGACTAAGGTCGAAATCAAG

SEQ ID NO. 54: h2826 VH (Variable Heavy) Nucleotide Sequence
GAAGTGCAGCTGCTGGAGTCTGGCGGCGGACTGGTGCAGCCCGGGGGATCCCTGCGGCTTTC

CTGCGCCGCATCCGGCTTCACCTTTTCAAACTTCGGAATGTCGTGGGTCAGACAGGCCCCGG

GAAAGGGTCTGGAATGGGTGGCCTCAGTGCGGTCCGGATCGGGTAGAACCTACTACAGCGAT

AACGTGAAGGGCCGGTTCACGATCTCCCGCGACAACTCCAAGAACACCCTGTACTTGCAAAT

GAATAGCCTCAGGGCTGAGGATACCGCGGTCTACTACTGTGTGCGCTATGACCACTACACTG

GAACTAGCGACTACTGGGGCCAGGGGACCCTCGTGACTGTGTCGTCC

SEQ ID NO. 55: h2826 VL (Variable Light) Nucleotide Sequence
GATGTCGTGATGACCCAGTCACCACTGTCCCTTCCTGTGACTCCCGGAGAACCGGCGTCCAT

TTCGTGCAAGAGCAGCCAGTCCCTGCTCGATTATGACGGAAAGACCTACCTGAACTGGTTGC

TCCAAAAGCCTGGGCAGAGCCCCCAGAGACTGATCTACAAAGTGTCCAACAGGGACTCGGGC

GTGCCGGACCGCTTCTCGGGGTCCGGTTCCGGTACCGACTTTACGCTGAAGATCTCACGGGT

GGAAGCCGAGGACGTGGGAGTGTACTACTGTTGGCAGGGCACTCACTTCCCGCGGACCTTCG

GACAAGGCACCAAGGTCGAGATCAAG

SEQ ID NO. 56: h2929 VH (Variable Heavy) Nucleotide Sequence
GAAGTGCAGCTCCTGGAGTCCGGGGGTGGACTGGTGCAGCCCGGGGGCAGCCTGAGGCTGAG

CTGCGCCGCGTCAGGATTCACCTTCTCCAACTTCGGAATGTCCTGGGTCAGACAGGCCCCGG

GAAAGGGCCTTGAATGGGTGGCTAGCGTGCGCTCCGGTTCCGGACGGACCTACTACTCGGAC

AACGTGAAGGGCCGGTTTACTATCTCCCGGGACAATTCGAAGAACACCCTGTACCTCCAAAT

GAACTCCTTGCGCGCCGAGGATACCGCAGTGTATTACTGCGTGCGCTACGACCACTACTCTG

GCACTAGCGATTACTGGGGCCAGGGAACTCTGGTCACCGTGTCGTCA

SEQ ID NO. 57: h2929 VL (Variable Light) Nucleotide Sequence
GATGTCGTGATGACCCAAAGCCCCCTGTCCCTCCCTGTGACTCCTGGAGAGCCGGCGTCCAT

TTCCTGCCGGTCAAGCCAGTCCTTGGTGGACTACGACGGAAAGACCTACCTCAACTGGCTGC

TGCAGCGCCCCGGGCAGTCGCCGCAGCGGCTTATCTACAAAGTGTCCAACCGCGACTCGGGC

GTGCCGGATAGGTTTTCGGGTTCCGGAAGCGGCACCGACTTCACCCTGAAAATCTCCAGAGT

GGAAGCCGAGGACGTGGGAGTGTACTACTGTTGGCAGGGTTCTCACTTCCCACGGTCATATG

GCCAAGGGACTAAGGTCGAAATCAAG

SEQ ID NO. 58: h3818G VH (Variable Heavy) Nucleotide Sequence
GAAGTGCAGCTCCTGGAGTCCGGCGGTGGACTGGTGCAGCCGGGCGGATCCCTGAGACTGTC

CTGCGCCGCGTCGGGCTTTACTTTCGCAAATTACGGCATGAGCTGGGTCAGACAGGCCCCCG

GGAAGGGTCTGGAATGGGTGGCCAGCGTCCGGAGCGGGGGATCCCGGACCTATTACTCCGAC

AACGTGAAGGGCCGCTTCACCATCTCAAGGGACAACTCCAAGAACACCCTGTACTTGCAAAT

GAACAGCCTTCGGGCTGAGGATACTGCCGTGTACTACTGCGTGCGCTACGACCACTACTCCG

GATCCTCGGATTACTGGGGACAGGGAACCCTCGTGACCGTGTCATCG

SEQ ID NO. 59: h3818G VL (Variable Light) Nucleotide Sequence
GATGTCGTGATGACTCAGTCGCCCCTCTCCCTGCCTGTGACTCTGGGGGAACCCGCGTCCAT

TTCGTGCAAGAGCAGCCAGTCCCTGATGGACACCGACGGAAAGACCTACCTTAACTGGCTGC

TGCAAAAGCCAGGACAGAGCCCGCAGAGGCTGATCTACAAAGTGTCAAACCGGGAGTCCGGA

GTGCCGGACAGATTCAGCGGCTCGGGTTCCGGCACCGACTTCACCCTCAAAATCTCCCGCGT

CGAGGCCGAGGACGTGGGCGTGTATTACTGTTGGCAGGGAACCCACTTTCCTCGGACCTTCG

GTCAAGGGACTAAGGTCGAAATCAAG

SEQ ID NO. 60: h2927 VH (Variable Heavy) Nucleotide Sequence
GAAGTGCAGCTCCTGGAGTCCGGGGGTGGACTGGTGCAGCCCGGGGGCAGCCTGAGGCTGAG

CTGCGCCGCGTCAGGATTCACCTTCTCCAACTTCGGAATGTCCTGGGTCAGACAGGCCCCGG

GAAAGGGCCTTGAATGGGTGGCTAGCGTGCGCTCCGGTTCCGGACGGACCTACTACTCGGAC

AACGTGAAGGGCCGGTTTACTATCTCCCGGGACAATTCGAAGAACACCCTGTACCTCCAAAT

GAACTCCTTGCGCGCCGAGGATACCGCAGTGTATTACTGCGTGCGCTACGACCACTACTCTG

GCACTAGCGATTACTGGGGCCAGGGAACTCTGGTCACCGTGTCGTCA

SEQ ID NO. 61: h2927 VL (Variable Light) Nucleotide Sequence
GATGTCGTGATGACTCAGTCACCGCTCTCCCTCCCTGTGACCCCGGGCGAACCAGCGTCGAT

CTCCTGCAAGAGCAGCCAATCATTGCTGGACTACGACGGAAAGACCTATCTTAACTGGCTGC

TGCAGAAGCCCGGGCAGAGCCCGCAGCGCCTGATCTACAAAGTGTCCAACAGAGACTCCGGA

GTGCCTGATAGGTTCTCGGGTTCCGGCTCCGGTACCGACTTCACTCTGAAAATTTCCCGGGT

GGAAGCCGAGGACGTGGGAGTGTACTACTGTTGGCAGGGCACCCACTTCCCCCGGTCGTTTG

GACAAGGGACCAAGGTCGAGATCAAG

SEQ ID NO. 62: h49K3G VH (Variable Heavy) Nucleotide Sequence
GAGGTGCAGCTGCTGGAGTCGGGGGGGGGACTCGTGCAGCCCGGGGGCTCCCTGAGACTCTC

TTGTGCCGCCTCCGGCTTCACTTTTTCAAACTTCGGAATGTCCTGGGTCCGCCAAGCACCGG

GAAAGGGTCTGGAATGGGTCGCCAGCGTGCGGTCCGGCGGCGGACGGACTTACTACTCCGAC

AACGTGAAGGGCCGGTTCACCATCTCAAGGGATAACTCCAAGAATACTCTGTACTTGCAAAT

GAACTCGCTGCGCGCTGAAGATACCGCGGTGTACTATTGCGTGCGCTACGACCACTACTCCG

GTACCAGCGACTACTGGGGACAGGGAACCCTTGTGACCGTGTCGAGC

SEQ ID NO. 63: h49K3G VL (Variable Light) Nucleotide Sequence
GATGTCGTGATGACTCAGTCGCCCCTCTCCCTGCCTGTGACTCTGGGGGAACCCGCGTCCAT

TTCGTGCAAGAGCAGCCAGTCCCTGTTGGACTCAGACGGAAAGACCTACCTTAACTGGCTGC

TGCAAAAGCCAGGACAGAGCCCGCAGAGGCTGATCTACAAAGTGTCAAACCGGGATTCCGGA

GTGCCGGACAGATTCAGCGGCTCGGGTTCCGGCACCGACTTCACCCTCAAAATCTCCCGCGT

CGAGGCCGAGGACGTGGGCGTGTATTACTGTTGGCAGGGAACCCACTTTCCTCGGACCTTCG

GTCAAGGGACTAAGGTCGAAATCAAG

SEQ ID NO. 64: h4917G VH (Variable Heavy) Nucleotide Sequence
GAGGTGCAGCTGCTGGAGTCGGGGGGGGGACTCGTGCAGCCCGGGGGCTCCCTGAGACTCTC

TTGTGCCGCCTCCGGCTTCACTTTTTCAAACTTCGGAATGTCCTGGGTCCGCCAAGCACCGG

GAAAGGGTCTGGAATGGGTCGCCAGCGTGCGGTCCGGCGGCGGACGGACTTACTACTCCGAC

AACGTGAAGGGCCGGTTCACCATCTCAAGGGATAACTCCAAGAATACTCTGTACTTGCAAAT

GAACTCGCTGCGCGCTGAAGATACCGCGGTGTACTATTGCGTGCGCTACGACCACTACTCCG

GTACCAGCGACTACTGGGGACAGGGAACCCTTGTGACCGTGTCGAGC

SEQ ID NO. 65: h4917G VL (Variable Light) Nucleotide Sequence
GATGTCGTGATGACTCAGTCGCCCCTCTCCCTGCCTGTGACTCTGGGGGAACCCGCGTCCAT

TTCGTGCAAGAGCAGCCAGTCCCTGTTGGACTCAGACGGAAAGACCTACCTTAACTGGCTGC

TGCAAAAGCCAGGACAGAGCCCGCAGAGGCTGATCTACAAAGTGACCAACCGGGAGTCCGGA

GTGCCGGACAGATTCAGCGGCTCGGGTTCCGGCACCGACTTCACCCTCAAAATCTCCCGCGT

CGAGGCCGAGGACGTGGGCGTGTATTACTGTTGGCAGGGAACCCACTTTCCTCGGTCATTCG

GTCAAGGGACTAAGGTCGAAATCAAG

SEQ ID NO. 66: h2727 VH (Variable Heavy) Nucleotide Sequence
GAAGTGCAGCTTCTGGAGAGCGGGGGCGGCCTGGTGCAGCCGGGCGGATCCCTGAGACTGTC

CTGTGCCGCGTCCGGTTTTACCTTCTCCAACTACGGAATGTCATGGGTCCGCCAAGCACCCG

GAAAGGGATTGGAATGGGTGGCTTCGATCCGGTCCGGCTCGGGACGGACCTACTACTCCGAT

AACGTCAAGGGCAGATTCACTATTAGCCGGGACAACAGCAAGAATACCCTGTACCTCCAAAT

GAACTCCCTGAGGGCCGAGGACACCGCCGTGTATTACTGCGTGCGCTACGACCACTACTCGG

GTTCCTCTGATTACTGGGGACAGGGGACCCTCGTGACTGTGTCAAGC

SEQ ID NO. 67: h2727 VL (Variable Light) Nucleotide Sequence
GATGTCGTGATGACTCAGTCACCGCTCTCCCTCCCTGTGACCCCGGGCGAACCAGCGTCGAT

CTCCTGCAAGAGCAGCCAATCATTGCTGGACTACGACGGAAAGACCTATCTTAACTGGCTGC

TGCAGAAGCCCGGGCAGAGCCCGCAGCGCCTGATCTACAAAGTGTCCAACAGAGACTCCGGA

GTGCCTGATAGGTTCTCGGGTTCCGGCTCCGGTACCGACTTCACTCTGAAAATTTCCCGGGT

GGAAGCCGAGGACGTGGGAGTGTACTACTGTTGGCAGGGCACCCACTTCCCCCGGTCGTTTG

GACAAGGGACCAAGGTCGAGATCAAG

SEQ ID NO. 68: h4918G VH (Variable Heavy) Nucleotide Sequence
GAGGTGCAGCTGCTGGAGTCGGGGGGGGGACTCGTGCAGCCCGGGGGCTCCCTGAGACTCTC

TTGTGCCGCCTCCGGCTTCACTTTTTCAAACTTCGGAATGTCCTGGGTCCGCCAAGCACCGG

GAAAGGGTCTGGAATGGGTCGCCAGCGTGCGGTCCGGCGGCGGACGGACTTACTACTCCGAC

AACGTGAAGGGCCGGTTCACCATCTCAAGGGATAACTCCAAGAATACTCTGTACTTGCAAAT

GAACTCGCTGCGCGCTGAAGATACCGCGGTGTACTATTGCGTGCGCTACGACCACTACTCCG

GTACCAGCGACTACTGGGGACAGGGAACCCTTGTGACCGTGTCGAGC

SEQ ID NO. 69: h4918G VL (Variable Light) Nucleotide Sequence
GATGTCGTGATGACTCAGTCGCCCCTCTCCCTGCCTGTGACTCTGGGGGAACCCGCGTCCAT

TTCGTGCAAGAGCAGCCAGTCCCTGATGGACACCGACGGAAAGACCTACCTTAACTGGCTGC

TGCAAAAGCCAGGACAGAGCCCGCAGAGGCTGATCTACAAAGTGTCAAACCGGGAGTCCGGA

GTGCCGGACAGATTCAGCGGCTCGGGTTCCGGCACCGACTTCACCCTCAAAATCTCCCGCGT

CGAGGCCGAGGACGTGGGCGTGTATTACTGTTGGCAGGGAACCCACTTTCCTCGGACCTTCG

GTCAAGGGACTAAGGTCGAAATCAAG

SEQ ID NO. 70: Aducanumab Heavy Chain:
QVQLVESGGGVVQPGRSLRLSCAASGFAFSSYGMHWVRQAPGKGLEWVAVIWFDGTKKYYTD

SVKGRFTISRDNSKNTLYLQMNTLRAEDTAVYYCARDRGIGARRGPYYMDVWGKGTIVIVSS

ASTKGPSVFPLAPSSKSTSGGTAALGCLVKDYFPEPVTVSWNSGALTSGVHTFPAVLQSSGL

YSLSSVVIVPSSSLGTQTYICNVNHKPSNTKVDKRVEPKSCDKTHTCPPCPAPELLGGPSVF

LFPPKPKDTLMISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKSRWQQGNVFSCSV

MHEALHNHYTQKSLSLSPGK

SEQ ID NO. 71: Aducanumab Light Chain:
DIQMTQSPSSLSASVGDRVTITCRASQSISSYLNWYQQKPGKAPKLLIYAASSLQSGVPSRF

SGSGSGTDFTLTISSLQPEDFATYYCQQSYSTPLTFGGGTKVEIKRTVAAPSVFIFPPSDEQ

LKSGTASVVCLLNNFYPREAKVQWKVDNALQSGNSQESVTEQDSKDSTYSLSSTLTLSKADY

EKHKVYACEVTHQGLSSPVTKSFNRGEC

SEQ ID NO. 72: Bapineuzumab HC (Heavy Chain)
EVQLLESGGGLVQPGGSLRLSCAASGFTFSNYGMSWVRQAPGKGLEWVASIRSGGGRTYYSD

NVKGRFTISRDNSKNTLYLQMNSLRAEDTAVYYCVRYDHYSGSSDYWGQGTLVTVSSASTKG

PSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQGNVFSCSVMHEAL

HNHYTQKSLSLSPGK

SEQ ID NO. 73: Bapineuzumab VH (Variable Heavy)
EVQLLESGGGLVQPGGSLRLSCAASGFTFSNYGMSWVRQAPGKGLEWVASIRSGGGRTYYSD

NVKGRFTISRDNSKNTLYLQMNSLRAEDTAVYYCVRYDHYSGSSDYWGQGTLVTVSS

SEQ ID NO: 16: VH_CDR1
GFTFSNYGMS

SEQ ID NO: 17: VH_CDR2
SIRSGGGRTYYSNDYNVKG

SEQ ID NO: 18: VH_CDR3
YDHYSGSSDY

SEQ ID NO. 77: Bapineuzumab LC (Light Chain)
DVVMTQSPLSLPVTPGEPASISCKSSQSLLDSDGKTYLNWLLQKPGQSPQRLIYLVSKLDSG

VPDRFSGSGSGTDFTLKISRVEAEDVGVYYCWQGTHFPRTFGQGTKVEIKRTVAAPSVFIFP

PSDEQLKSGTASVVCLLNNFYPREAKVQWKVDNALQSGNSQESVTEQDSKDSTYSLSSILTL

SKADYEKHKVYACEVTHQGLSSPVTKSFNRGEC

SEQ ID NO. 78: Bapineuzumab VL (Variable Light)
DVVMTQSPLSLPVTPGEPASISCKSSQSLLDSDGKTYLNWLLQKPGQSPQRLIYLVSKLDSG

VPDRFSGSGSGTDFTLKISRVEAEDVGVYYCWQGTHFPRTFGQGTKVEIK

SEQ ID NO: 26: VL_CDR1
KSSQSLLDSDGKTYLN

SEQ ID NO: 27: VL_CDR2
LVSSKLDS

SEQ ID NO: 28: VL_CDR3
WQGTHFPRT

SEQ ID NO. 82: Gantenerumab HC amino acid sequence:
QVELVESGGGLVQPGGSLRLSCAASGFTFSSYAMSWVRQAPGKGLEWVSAINASGTRTYYAD

SVKGRFTISRDNSKNTLYLQMNSLRAEDTAVYYCARGKGNTHKPYGYVRYFDVWGQGTLVTV

SSASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTVDKSRWQQGNVFSC

SVMHEALHNHYTQKSLSLSPGK

SEQ ID NO. 83: Gantenerumab LC amino acid sequence:
DIVLTQSPATLSLSPGERATLSCRASQSVSSSYLAWYQQKPGQAPRLLIYGASSRATGVPAR

FSGSGSGTDFTLTISSLEPEDFATYYCLQIYNMPITFGQGTKVEIKRTVAAPSVFIFPPSDE

QLKSGTASVVCLLNNFYPREAKVQWKVDNALQSGNSQESVTEQDSKDSTYSLSSTLTLSKAD

YEKHKVYACEVTHQGLSSPVTKSFNRGEC

SEQ ID NO. 84: Amyloid Beta (AP) 1-42:
DAEFRHDSGYEVHHQKLVFFAEDVGSNKGAIIGLMVGGVVIA SEQ ID NO. 85: Amyloid Beta (AP) Precursor Protein:
MLPGLALLLLAAWTARALEVPTDGNAGLLAEPQIAMFCGRLNMHMNVQNGKWDSDPSGTKTC

IDTKEGILQYCQEVYPELQITNVVEANQPVTIQNWCKRGRKQCKTHPHFVIPYRCLVGEFVS

DALLVPDKCKFLHQERMDVCETHLHWHTVAKETCSEKSTNLHDYGMLLPCGIDKFRGVEFVC

CPLAEESDNVDSADAEEDDSDVWWGGADTDYADGSEDKVVEVAEEEEVAEVEEEEADDDEDD

EDGDEVEEEAEEPYEEATERTTSIATITTITTESVEEVVREVCSEQAETGPCRAMISRWYFD

VTEGKCAPFFYGGCGGNRNNFDTEEYCMAVCGSAMSQSLLKTTQEPLARDPVKLPTTAASTP

DAVDKYLETPGDENEHAHFQKAKERLEAKHRERMSQVMREWEEAERQAKNLPKADKKAVIQH

FQEKVESLEQEAANERQQLVETHMARVEAMLNDRRRLALENYITALQAVPPRPRHVFNMLKK

YVRAEQKDRQHTLKHFEHVRMVDPKKAAQIRSQVMTHLRVIYERMNQSLSLLYNVPAVAEEI

QDEVDELLQKEQNYSDDVLANMISEPRISYGNDALMPSLTETKTTVELLPVNGEFSLDDLQP

WHSFGADSVPANTENEVEPVDARPAADRGLTTRPGSGLTNIKTEEISEVKMDAEFRHDSGYE

VHHQKLVFFAEDVGSNKGAIIGLMVGGVVIATVIVITLVMLKKKQYTSIHHGVVEVDAAVTP

EERHLSKMQQNGYENPTYKFFEQMQN

SEQ ID NO. 86: huIgG1 Constant Nucleotide Sequence
GCCAGCACTAAGGGGCCTAGCGTCTTTCCGCTGGCCCCGTCCTCCAAGTCCACTTCGGGTGG

AACCGCGGCACTGGGGTGCCTCGTGAAGGACTACTTCCCCGAGCCGGTCACCGTGTCCTGGA

ACTCGGGAGCCCTGACCTCCGGAGTGCATACTTTCCCTGCGGTGCTGCAGTCCTCCGGGCTC

TACTCGCTGTCAAGCGTGGTCACCGTCCCGAGCTCATCCCTGGGTACTCAGACCTACATTTG

CAACGTGAACCACAAACCTTCCAACACCAAGGTCGACAAGAAAGTGGAGCCTAAGAGCTGCG

ACAAGACCCACACCTGTCCCCCGTGTCCCGCCCCTGAGCTGCTGGGCGGCCCCAGCGTGTTC

CTCTTCCCGCCTAAGCCGAAGGACACTCTGATGATCTCGAGAACCCCTGAAGTGACCTGTGT

GGTGGTGGATGTGTCCCACGAGGATCCGGAAGTGAAGTTCAATTGGTACGTGGACGGAGTGG

AAGTCCATAACGCCAAGACCAAGCCCCGCGAGGAACAGTACAACTCAACTTACCGGGTGGTG

TCAGTGCTGACCGTGCTGCACCAAGATTGGCTGAACGGGAAGGAGTACAAGTGCAAAGTCTC

CAACAAGGCGCTGCCGGCCCCCATTGAAAAGACCATCAGCAAGGCTAAGGGCCAGCCCCGGG

AACCACAGGTCTACACCTTGCCCCCTTCCCGGGAGGAAATGACCAAGAACCAAGTGTCGCTG

```
                                -continued
ACGTGCCTGGTCAAGGGCTTTTATCCATCTGACATCGCCGTGGAGTGGGAAAGCAACGGCCA

GCCGGAAAACAACTACAAGACTACCCCGCCTGTGCTGGACTCCGACGGCTCGTTCTTCCTGT

ATTCCAAGCTCACCGTGGATAAGTCCAGATGGCAGCAGGGCAATGTGTTCAGCTGCAGCGTG

ATGCATGAGGCCCTGCACAACCACTACACTCAGAAATCACTGTCCCTTTCCCCCGGAAAGTA

A

SEQ ID NO. 87: huKappa Constant Nucleotide Sequence
CGAACTGTGGCTGCACCATCTGTCTTCATCTTCCCGCCATCTGATGAGCAGTTGAAATCTGG

AACTGCCTCTGTTGTGTGCCTGCTGAATAACTTCTATCCCAGAGAGGCCAAAGTACAGTGGA

AGGTGGATAACGCCCTCCAATCGGGTAACTCCCAGGAGAGTGTCACAGAGCAGGACAGCAAG

GACAGCACCTACAGCCTCAGCAGCACCCTGACGCTGAGCAAAGCAGACTACGAGAAACACAA

AGTCTACGCCTGCGAAGTCACCCATCAGGGCCTGAGCTCGCCCGTCACAAAGAGCTTCAACA

GGGGAGAGTGTTAA
```

EXAMPLES

The following examples have been included to illustrate modes disclosed herein. Certain aspects of the following examples are described in terms of techniques and procedures found or contemplated by the present co-inventors to work well in the practice disclosed herein. In light of the present disclosure and the general level of skill in the art, those of skill appreciate that the following examples are intended to be exemplary only and that numerous changes, modifications, and alterations may be employed without departing from the scope of the disclosure.

"Aducanumab" or "Adu" as used in these experiments refers to an antibody with heavy chain of SEQ ID NO: 70 and light chain of SEQ ID NO: 71, and as set forth in United States patent publication number US 2015/0315267 and PCT publication number WO 2014/089500.

"BAN-2401" and "gantenerumab" as used in these experiments refer to an antibody with heavy chain of SEQ ID NO: 79 and light chain of SEQ ID NO: 80 as set forth, e.g., in European patent number EP 1960428B1.

In the following methods, antibody binding profiles to aggregated or fibrillar Aβ are characterized by ELISA, surface plasmon resonance (SPR) and immunohistochemistry (IHC). The ability to mediate phagocytic plaque clearance is evaluated ex vivo in APP/PS1 transgenic mouse brain as well as AD brain with primary murine microglia by immunofluorescence, ELISA and MSD quantification, and neutralization of Aβ oligomer neuronal binding is assessed in rat primary hippocampal cultures.

Results presented herein: relative to other N-terminal Aβ antibody therapies (bapineuzumab, aducanumab), mAbs of the description exhibited greater apparent affinity for aggregated and fibrillar Aβ in competition or standard binding ELISAs. The enhanced avidity of mAbs of the disclosure for fibrillar Aβ was confirmed by SPR equilibrium binding kinetics, indicating 5-11-fold higher avidity than aducanumab due to slower off-rate kinetics. IHC dose response assessments on frozen human AD brain sections showed greater apparent affinity and plaque area binding than aducanumab, regardless of the individual AD donor tissue tested. In ex vivo activity assays, mAbs of the disclosure were shown to significantly facilitate Aβ plaque reduction by microglial phagocytosis in APP/PS1 mouse tissue and to block soluble Aβ oligomer binding to rat primary neurons in a concentration-dependent manner. In ex vivo functional assays with human AD brain, mAbs from the description were shown to significantly facilitate clearance of pyroglutamyled Aβ, a post-translationally modified component of senile plaques.

Example 1. Aβ Antibody Design

Aβ antibody bapineuzumab (hBP) is a humanized antibody developed from parental murine antibody 3D6. Here, a multipronged approach was applied to construct superior antibodies to hBP. Humanness of hBP was analyzed and a determination was made that light chain humanization could be optimized.

A search was made over the protein sequences in the PDB database [Deshpande et al, 2005] to find structures that would provide a rough structural model of hBP. The crystal structure of hBP fab PDB code 4HIX [Miles, et al., 2013] was utilized for both Vh and Vk structure as it had acceptable resolution (2.2 Å) and an exact sequence match to hBP Vh and Vk, retaining the same canonical structures for the loops.

IMGT/DomainGapAlignment was performed for the hBP VL as input sequences. Human germ line VK gene sequence IGHV2-30*02 is the closest matched to hBP VL. The frameworks of hBP VL share a high degree of sequence similarity with the corresponding framework regions of IGHV2-30*02. Thus, the framework regions of IGHV2-30*02 VL were chosen as the guidance sequence for further optimization of the hBP framework regions. Additionally, three residues in CDR-L2 that do not make any direct contact with the antigen as per hBP 3D structure were also changed to germline sequence resulting in following changes, L50K, K53N and L54R (Kabat).

Figure 1:
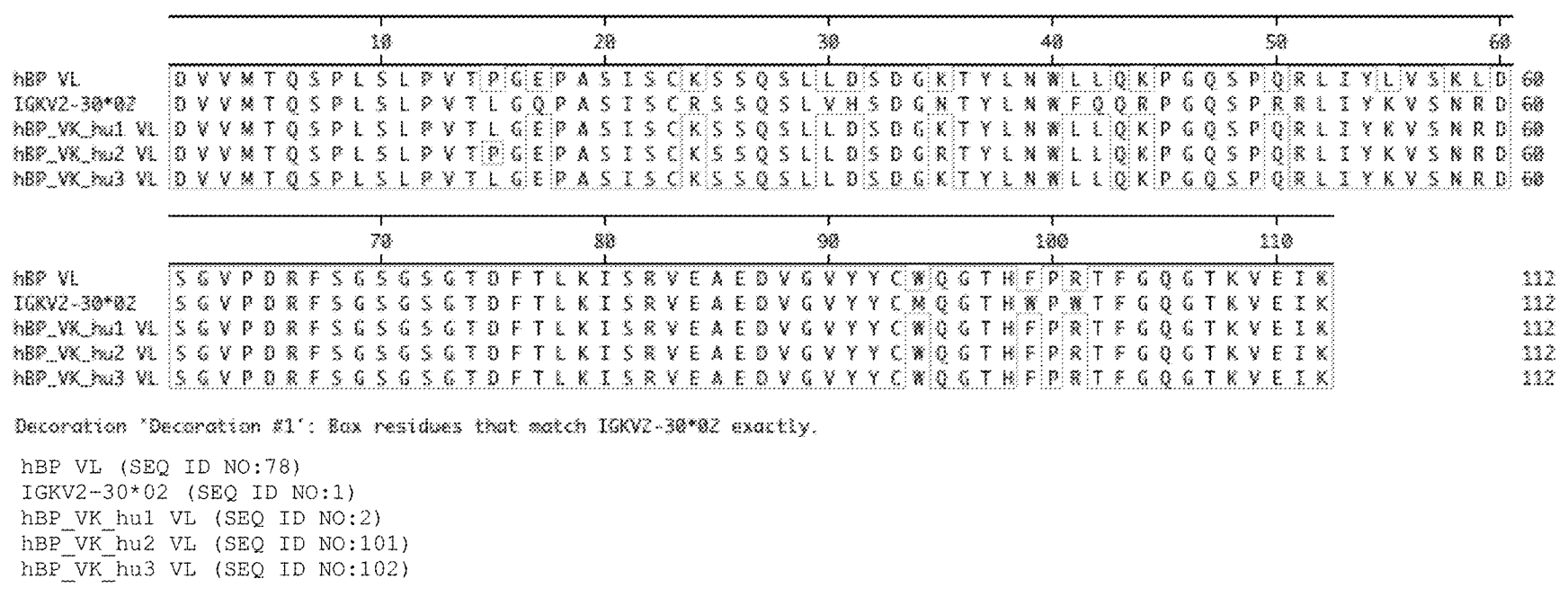

Three different versions of VL were designed by incorporating human germline framework residues into hBP VL sequence. Canonical or interface residues were not changed. An alignment of designed VK version designed is shown in FIG. 1.

Based on structural observation that P15 is located at a turn and the germline gene has Leu at this position, P15L was tested in one version of the variable light chain.

Based on the 3D structural observations, substitutions at a number of residues in the light chain and heavy chain CDRs and framework were designed. In total thirty-one light chain and thirty-two heavy chain mutant VL and VH versions were generated and tested for binding in the first round of rational design. Mutations that showed improved binding were combined in the second round of the rational design. Additionally, new mutations guided by further analysis of the structure were also incorporated into the design.

Rational design based mutagenesis was done for following positions within CDR-H1, T28, S30, N31, Y32 and G33 (Kabat). For CDR-H2 positions I51, G53, G54, T57, S60, D61 and N62 were also mutated (Kabat). CDR-H3 positions D96, H97, S99, S100a and Y102 were subjected to rational mutagenesis (Kabat).

For variable light chain, multiple substitutions were tried at CDR-L1 positions K24, L27c, D27d and S27e (Kabat). Light chain CDR-L2 positions K53 and L54 were subjected to directed and limited mutagenesis (Kabat). CDR-L3 positions were not subjected to substitutions.

A select few positions in the framework regions were also subjected to rational mutagenesis for heavy chain as well as light chain.

Fifty-seven additional heavy chain and thirty-three light chain variants were designed and analyzed with assistance of Atum GPSpro software, which analyzes database of human variable heavy and light chains and, based upon computer learning, suggests query sequence-specific changes.

For the variable heavy domain, a number of substitutions at positions A24, S25, G26, F27, T28, F29, S30, N31, Y32, G33 and M34 were designed and analyzed (Kabat). A majority of these positions were within CDR-H1. Similarly, many of the CDR-H2 residues were subjected to mutagenesis, such as positions A49, S50, I51, R52, S52a, G53, G54, G55, R56, T57, Y58, Y59, S60, D61, N62, V63 and K64 (Kabat). Additionally, multiple substitutions for the amino acids within CDR-H3 were made, for example, positions V93, R94, Y95, D96, H97, Y98, S99, G100, S100a, S100b, D101 and Y102 (Kabat).

Multiple substitutions were also designed for variable light chain CDR-L1 positions K24, S25, S26, Q27, S27a, L27b, L27c, D27d, S27e, D28, G29, K30, T31, Y32, L33 and N34 (Kabat). For CDR-L2, mutagenesis was performed at positions L50, V51, S52, K53, L54, D55 and S56 (Kabat). The majority of CDR-L3 positions such as Q90, G91, T92, H93, F94, P95, R96 and T97 were also rationally substituted with multiple amino acids (Kabat).

All variant antibodies resulting from rational as well as GPSpro design were analyzed for expression, melting point (Tm), affinity, and avidity. Eight antibodies from the rational design and six antibodies from the computer learning campaign were selected for further analysis based on the assays mentioned above.

Example 2. $IC_{50}$ Ratio Determination by Competitive ELISA Assays

An assay based on the competition (inhibition) of binding of a labeled antibody to an antigen-coated plate was used to determine $IC_{50}$ for antibodies of the disclosure.

To generate fibrils, Aβ 1-42 polypeptides, previously treated with HFIP (hexafluoroisopropanol) and dried, were resuspended in DMSO to 5 mM, then further diluted to 100 uM with 10 mM HCl. Samples were incubated at 37° C. for 24 h, and then centrifuged to separate soluble and fibrillar species. The pellet was the resuspended in 1×D-PBS to the original volume and sonicated before use.

Figure 3:
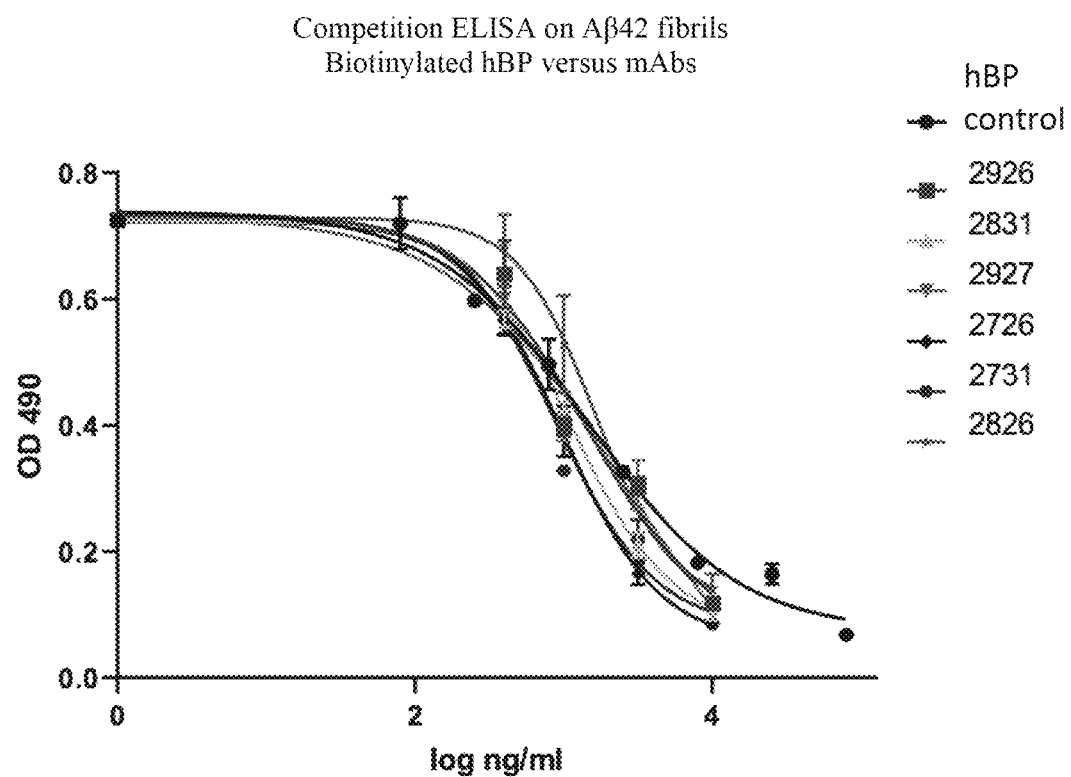
FIG. 3 shows competitive ELISA assay graphs for 2926, 2831, 2927, 2726, 2731, 2826 and bapineuzumab control for IC$_{50}$ ratio determination relative to bapineuzumab (hBP).
Figure 4:
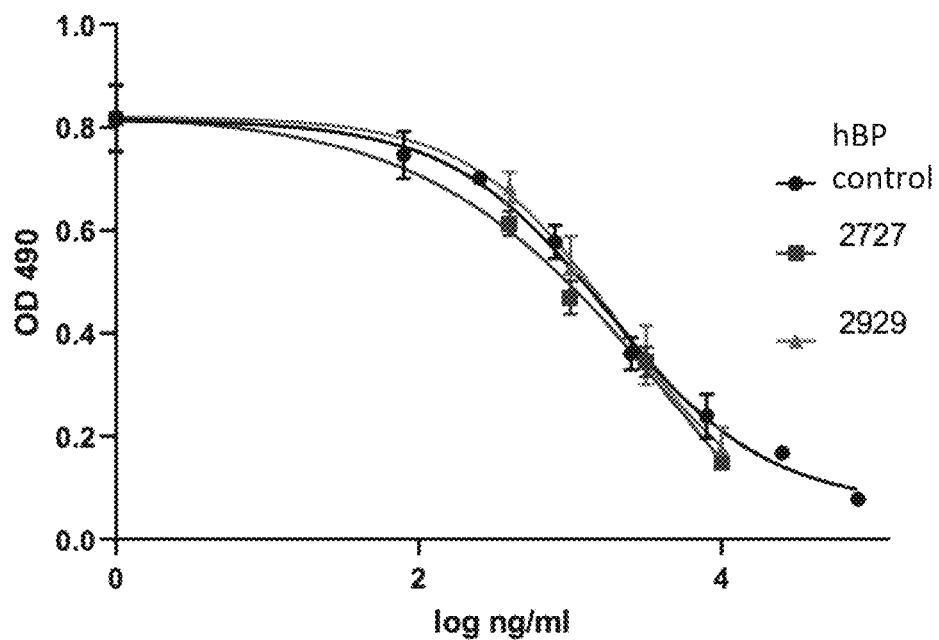
FIG. 4 shows competitive ELISA assay graphs for 2727, 2931 and bapineuzumab control for IC$_{50}$ ratio determination relative to bapineuzumab (hBP).

Plates were coated with 0.5 mg/ml of fibril Aβ 42 and blocked, e.g., with 1% BSA/PBS. Seven 3-fold dilutions of hBP starting at 150 μg/ml (75 μg/ml final concentration) and four 3-fold dilutions of test antibody starting at 20 μg/ml (10 μg/ml final concentration) prepared in 0.1% BSA/PBS were added to wells in triplicate, 50 ul per well. 50 ul of hBP-biotin at 0.75 μg/ml (0.35 μg/ml final concentration) prepared in 0.1% BSA/PBS was added to all wells and plates incubated 2 hours at room temperature then washed 3× with TTBS. 100 ul of GE Streptavidin HRP diluted 1/10,000 was then added and incubated for 30 minutes. Plates were then washed 6× with TTBS. Thermo Fisher o-phenylenediamine dihydrochloride (OPD) substrate was prepared fresh per manufacturers direction, and 100 ul per well was added. The reaction was incubated for 15 minutes and the reaction stopped with 50 ul 2N $H_2SO_4$. Samples were read 490 nM on Spectromax. FIG. 2, FIG. 3 and FIG. 4 illustrate competitive ELISA assay graphs for 4918, 4917, 4921, 3818, 49human3, 2931 and bapineuzumab control (FIG. 2), 2926, 2831, 2927, 2726, 2731, 2826 and bapineuzumab control (FIG. 3) and 2727, 2929 and bapineuzumab control (FIG. 4). $IC_{50}$ for each test antibody are divided by the $IC_{50}$ for hBP to yield an half maximal inhibitory concentration ($IC_{50}$) ratio. A ratio of less than one indicates better performance than hBP. See Table 2.

TABLE 2

| Antibody | Competition ELISA on fibril Aβ42 $IC_{50}$ ratio (test:hBP) |
|---|---|
| h2931 | 0.59 |
| h2731 | 0.61 |
| h2726 | 0.68 |
| h2831 | 0.77 |
| h2926 | 0.99 |
| h4921 | 1.01 |
| h2826 | 1.10 |
| h2929 | 1.16 |
| h3818 | 1.18 |
| h2927 | 1.60 |
| h49_hum3 | 2.16 |
| h49_VK17 | 2.69 |
| h2727 | 3.06 |
| h4918 | ND |
| hBP | 1 |

Example 3. Monoclonal Antibody Potency Determination by Competitive ELISA

Figure 5A:
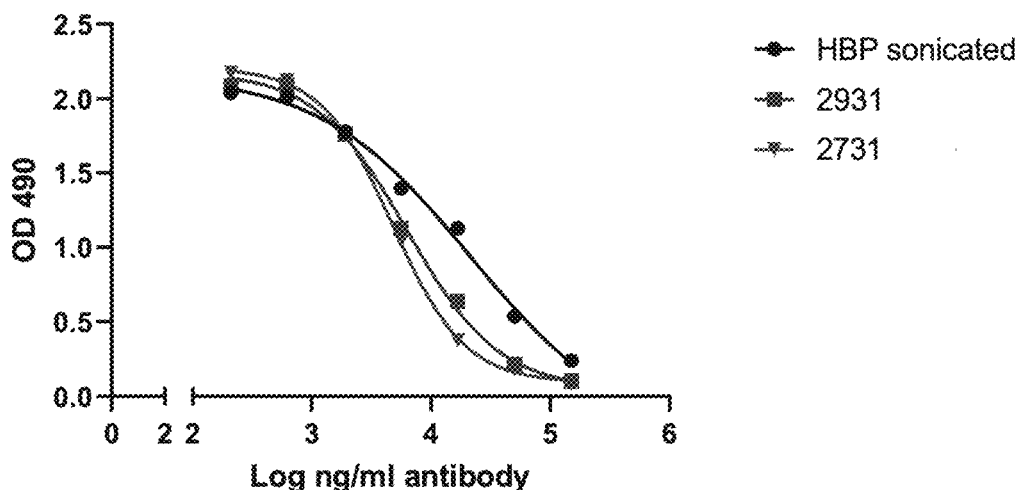
FIG. 5A and FIG. 5B show competitive ELISA assay graphs for 2931, 2731 and bapineuzumab (FIG. 5A) and 2726, 2831 and bapineuzumab (FIG. 5B).
Figure 5B:
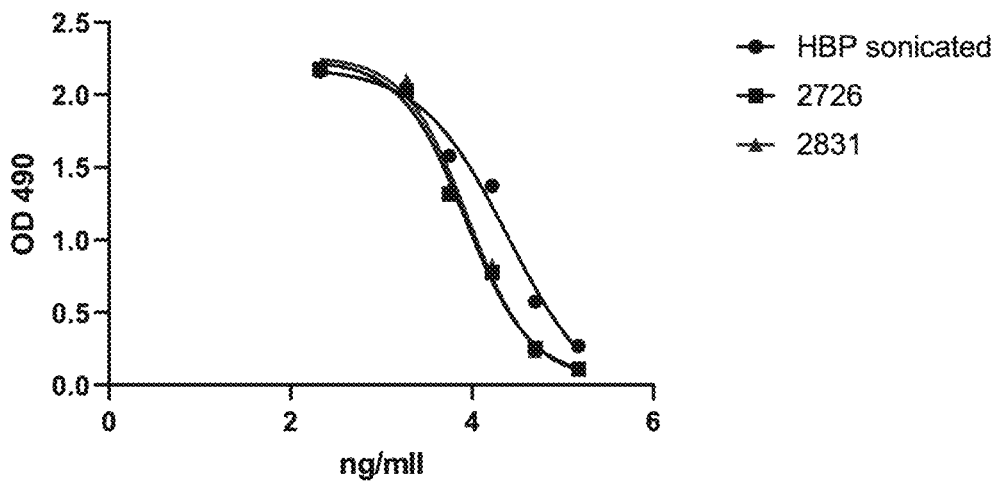
Figure 20A:
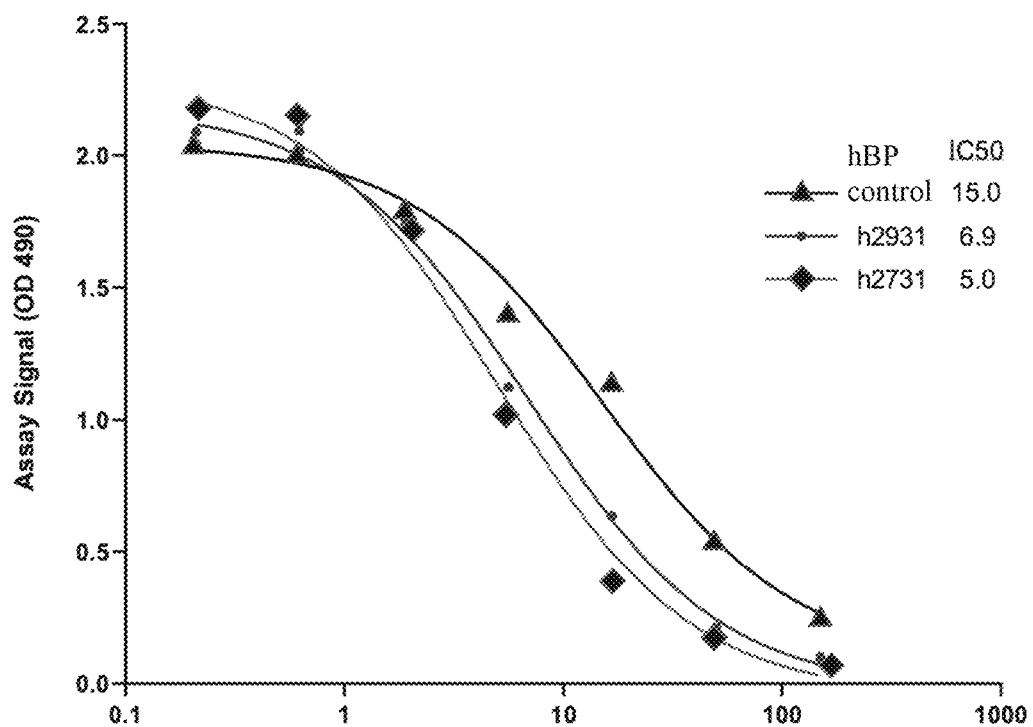
FIGS. 20A and 20B show graphs measuring antibody potency for binding heterogenous aggregated Aβ42 species by competition ELISA.
Figure 20B:
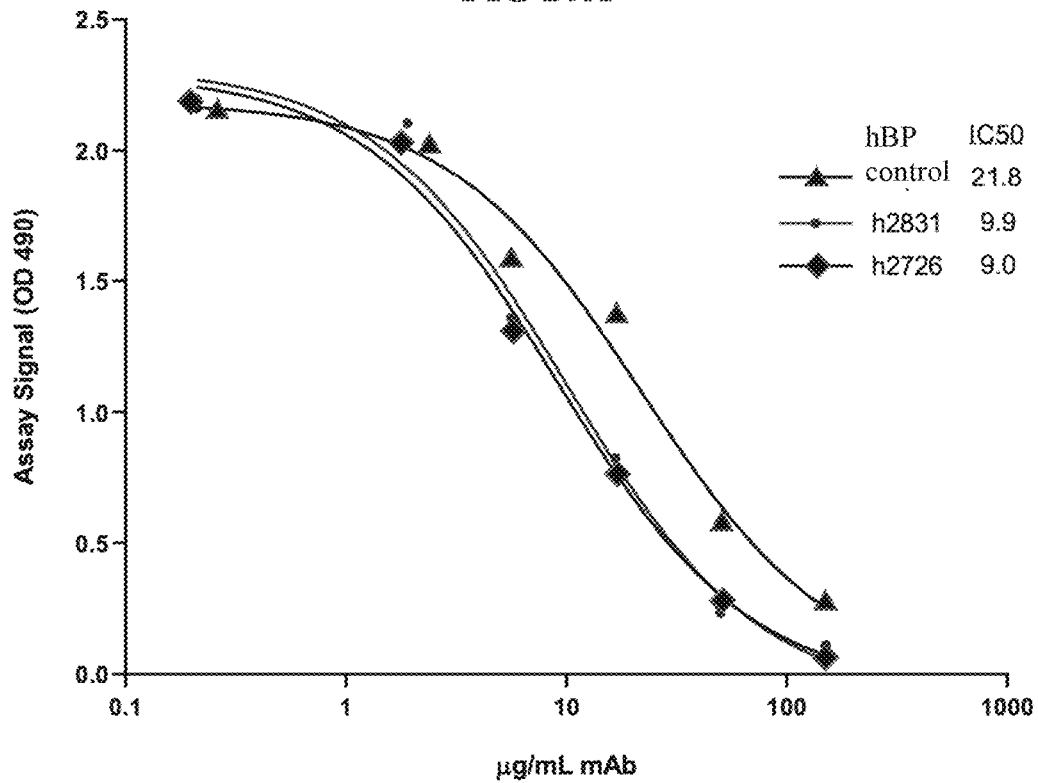

The binding potency of certain monoclonal antibodies of the disclosure and hBP was measured by their ability to compete with biotinylated-bapineuzumab bound to aggregated Aβ42 was assessed by competition ELISA. One mg of Aβ 42 was added to 1 ml of diH2O and was vigorously vortexed and placed on a nutator for 48 hours at room temperature. Plates were coated with 0.5 mg/ml of the heterogeneous Aβ 42 aggregate mixture and blocked, e.g., with 1% BSA/PBS. Seven 3-fold dilutions of hBP starting at 150 μg/ml (75 μg/ml after dilution with hBP-Biotin) and four 3-fold dilutions of test antibody starting at 20 μg/ml (10 μg/ml after dilution with hBP-Biotin) were added to wells in triplicate, 50 ul per well. 50 ul of hBP-biotin at 0.75 μg/ml (0.35 μg/ml after dilution) was added to all wells and plates incubated 2 hours at room temperature then washed 3× with TTBS. 100 ul of GE Streptavidin HRP diluted 1/10,000 was then added and incubated for 30 minutes. Plates were washed six times with TTBS. Thermo Fisher o-phenylenediamine dihydrochloride (OPD) substrate was prepared fresh per manufacturers direction, and 100 ul per well was added. The reaction was incubated for 15 minutes and the reaction stopped with 50 ul 2N $H_2SO_4$. Samples were read 490 nM on Spectromax. FIG. 5A shows a competitive ELISA assay graph for 2931, 2731 and bapineuzumab control; FIG. 5B shows a competitive ELISA assay graph for 2726, 2831 and bapineuzumab control. FIG. 20A shows a competitive ELISA assay graph for 2931, 2731 and bapineuzumab control (data shown in Table 3, rows 1-2); FIG. 20B shows a competitive ELISA assay graph for 2831, 2726 and bapineuzumab control (data shown in Table 3, rows 4-5). For FIG. 20A and FIG. 20B, curves and resulting IC50 estimations represent nonlinear three-parameter least squares fit of data. Individual points are the average of triplicate samples (coefficient of variation <20%).

TABLE 3

| mAb | Bapi | h2931 | h2731 |
|---|---|---|---|
| $IC_{50}$ (μg/mL mAb) | 15.04 | 6.901 | 5.024 |
| mAb | Bapi | h2726 | h2831 |
| $IC_{50}$ (μg/mL mAb) | 21.83 | 9.049 | 9.907 |

Results show that antibodies 2931, 2731, 2726, and 2831 showed greater potency than hBP; ~2-4 lower $IC_{50}$ values than hBP.

Example 4. Characterization of Humanized mAbs or Fabs by BIAcore

To compare the binding characteristics of humanized antibodies or humanized antigen-binding fragments (Fab) to recombinant $A\beta_{1-42}$ fibrils, analysis was performed using a BIAcore T200 (GE Life Sciences).

To generate fibrils, $A\beta_{1-42}$ polypeptides, previously treated with HFIP (hexafluoroisopropanol) and dried, were resuspended in DMSO to 5 mM, then further diluted to 100 uM with 10 mM HCl. Samples were incubated at 37° C. for 24 h, and then centrifuged to separate soluble and fibrillar species. The pellet was the resuspended in D-PBS to the original volume and sonicated before use.

Fibrils were immobilized on sensor chip CM5 (GE Healthcare Life Sciences) via amine coupling to a level to ensure a maximum binding of analyte of approximately 100 RU. Various concentrations of antibodies or Fabs (ranging from 1 nM to 100 nM) were passed over the coupled ligand at 30 μL/min in running buffer (HBS+0.05% P-20, 1 mg/mL BSA) for 300 s association time and 1200 s dissociation time. Regeneration of the chip surface was accomplished by 2 short injections of 10 mM Glycine-HCl at pH 1.7. Data was blank-subtracted to both a sensor not containing ligand and 0 nM analyte concentration. Analysis was performed using a global 1:1 fit with BIAcore Insight Evaluation software (v2.0) with bulk refractive index set to zero RU. Off-rate data ($k_{diss}$; kd) are shown in Table 4 (Fabs) and Table 6 (antibodies).

Similar, small dissociation constants can be seen for the h2726, h2731, h2831 and h2931 Fabs and antibodies in comparison to aducanumab, which demonstrated a significantly larger dissociation constant.

TABLE 4

| Injection variables Analyte 1 Solution | 1:1 binding ka (1/Ms) | kd (1/s) | Apparent KD (M) | Rmax (RU) |
|---|---|---|---|---|
| h2726 | 1.29e+5 | 2.59e−4 | 2.01e−9 | 133.5 |
| h2731 | 1.29e+5 | 2.89e−4 | 2.24e−9 | 134.0 |

TABLE 4-continued

| Injection variables Analyte 1 Solution | 1:1 binding ka (1/Ms) | kd (1/s) | Apparent KD (M) | Rmax (RU) |
|---|---|---|---|---|
| h2831 | 1.08e+5 | 2.48e−4 | 2.31e−9 | 127.1 |
| h2931 | 1.23e+5 | 1.99e−4 | 1.62e−9 | 132.0 |
| hBP | 1.12e+5 | 6.00e−4 | 5.34e−9 | 116.1 |

Example 5. Characterization of Humanized mAbs Affinity Apparent by BIAcore

Determination of binding affinity of anti-Aβ candidates to $A\beta_{1-28}$ (Bachem, Torrance, Calif.) was performed using a Biacore T200. Anti-human Fc antibody was immobilized to a CM3 sensor chip (GE Healthcare Life Sciences) via amine coupling and used to capture Aβ antibodies.

Various concentrations of $A\beta_{1-28}$ (analyte, ranging from concentrations of 100 nM down to 0.39 nM, serial diluted 2-fold each dilution step) were passed over the captured ligand at 50 μl/min in running buffer (HBS+0.05% P-20, 1 mg/mL BSA) for 240 s association time and 900 s dissociation time. Data were blank subtracted to both an irrelevant sensor not containing ligand, and buffer runs containing 0 nM analyte concentration. Analysis was performed using a global 1:1 fit with Biacore Evaluation software (v3.0).

Figure 6A:
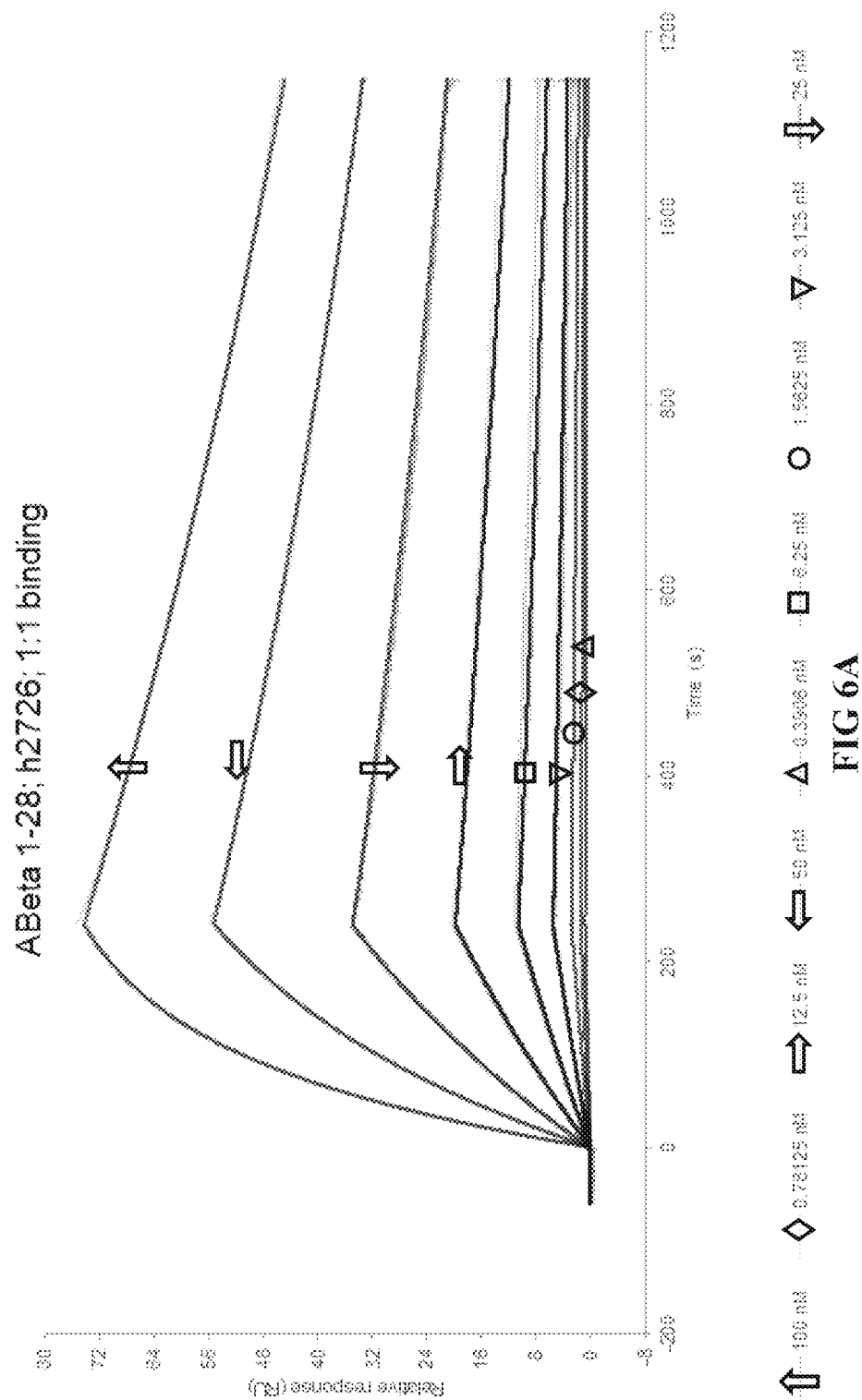
Figure 6B:
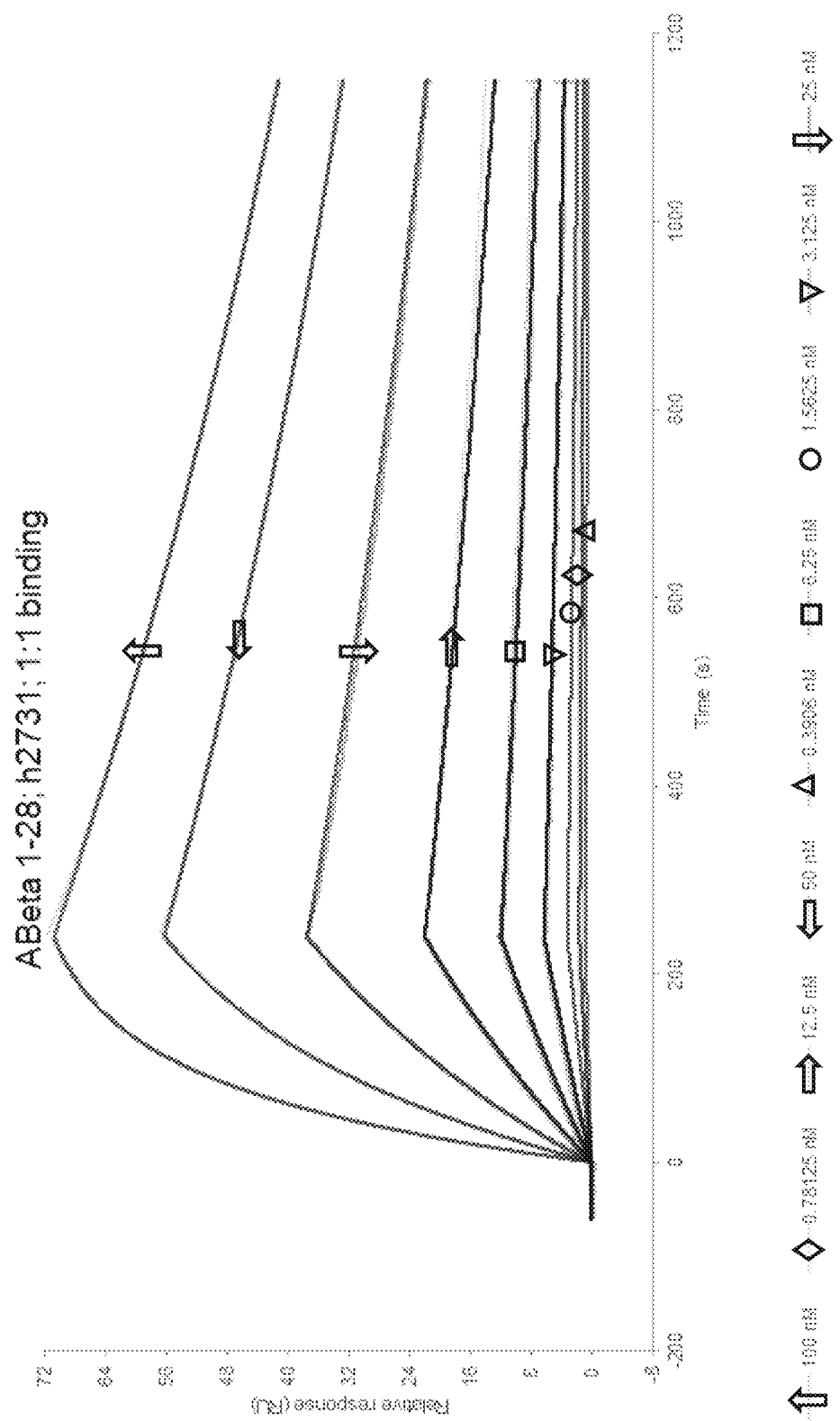

Apparent dissociation constants (KD) are shown in Table 5, where mAbs of the disclosure demonstrated 4-7 nM binding affinity for $A\beta_{1-28}$ monomer. Sensorgrams of binding at concentrations from 0.39 nM through 100 nM are shown in FIG. 6A (h2726), FIG. 6B (h2731), FIG. 6C (h2831) and FIG. 6D (h2931).

TABLE 5

| Injection variables Capture Solution | Analyte 1 Solution | 1:1 binding ka (1/Ms) | kd (1/s) | Apparent KD (M) | Rmax (RU) |
|---|---|---|---|---|---|
| h2726 | $A\beta_{1-28}$ | 9.23e+4 | 5.55e−4 | 6.01e−9 | 87.0 |
| h2731 | $A\beta_{1-28}$ | 1.19e+5 | 5.95e−4 | 5.01e−9 | 78.3 |
| h2831 | $A\beta_{1-28}$ | 7.31e+4 | 5.08e−4 | 6.95e−9 | 88.0 |
| h2931 | $A\beta_{1-28}$ | 9.47e+4 | 4.12e−4 | 4.35e−9 | 76.1 |

Example 6. Characterization of Humanized mAbs Affinity Apparent by BIAcore

To compare the binding characteristics of humanized antibodies to recombinant $A\beta_{1-42}$ fibrils, analysis was performed using a BIAcore T200.

To generate fibrils, $A\beta_{1-42}$ polypeptides, previously treated with HFIP (hexafluoroisopropanol) and dried, were resuspended in DMSO to 5 mM, then further diluted to 100 μM with 10 mM HCl. Samples were incubated at 37° C. for 24 h, and then centrifuged to separate soluble and fibrillar species. The pellet was the resuspended in 1×D-PBS to the original volume and sonicated before use.

Figure 7:
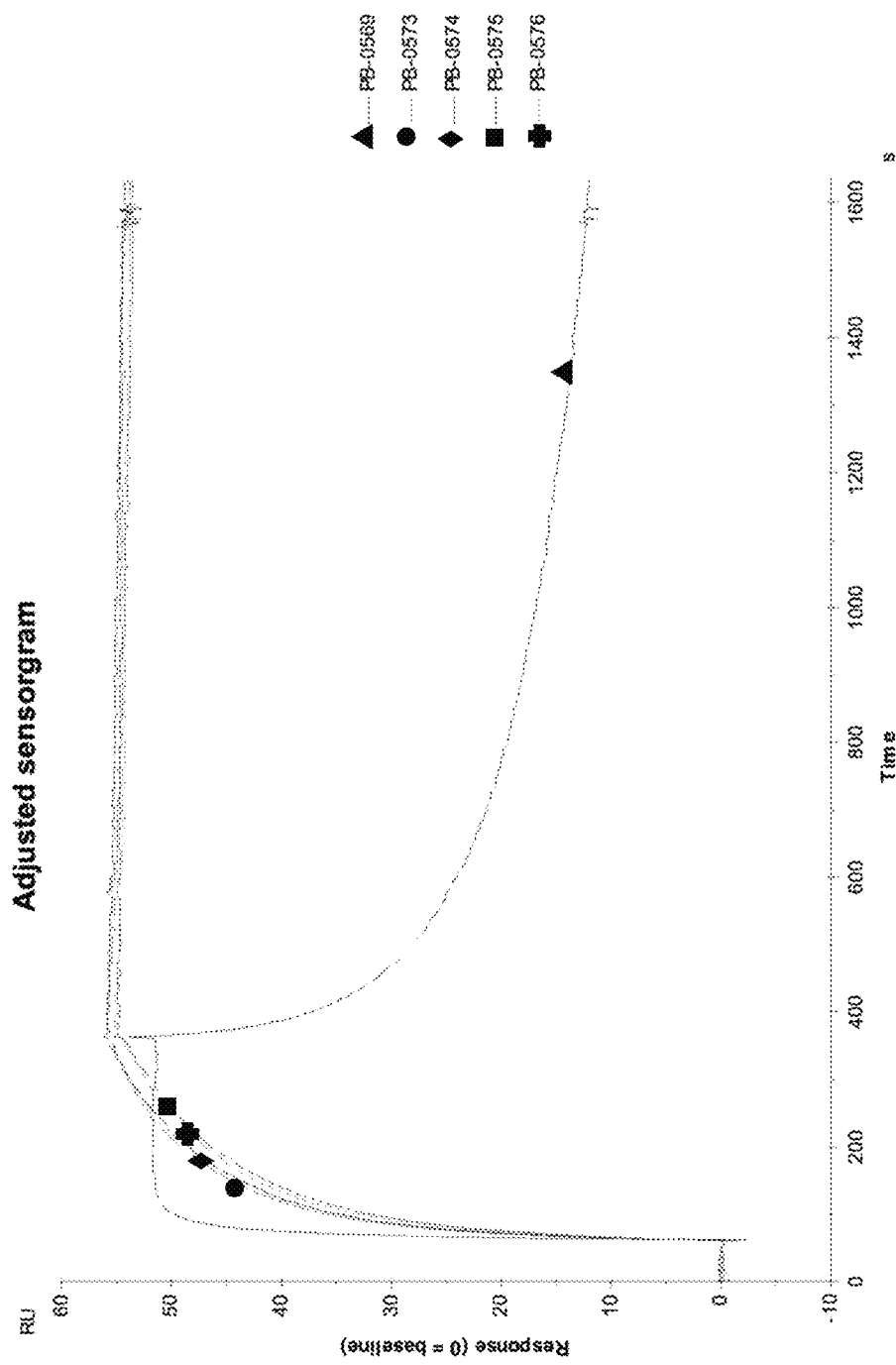
FIG. 7 shows a BIAcore sensorgram comparing binding characteristics of humanized antibodies (PB-0569 (aducanumab), PB-0573 (h2726), PB-0574 (h2731), PB-0575 (h2831), PB-0576 (h2931)) to recombinant Abeta 1-42 (Aβ$_{1-42}$) fibrils.

Fibrils were immobilized on sensor chip CM5 (GE Healthcare Life Sciences) via amine coupling to a level to ensure a maximum binding of analyte of approximately 50 RU. Various concentrations of antibodies (ranging from 0.411 nM to 100 nM) were passed over the coupled ligand at 30 μL/min in running buffer (HBS+0.05% P-20, 1 mg/mL BSA) for 300 s association time and 1200 s dissociation time. Regeneration of the chip surface was accomplished by 2 short injections of 10 mM Glycine-HCl pH 1.7. Data was blank subtracted to both a sensor not containing ligand and 0 nM analyte concentration. Analysis was performed using a global 1:1 fit with BIAcore Insight Evaluation software (v2.0) with bulk refractive index set to zero RU. Apparent dissociation constant (KD) are shown in Table 6 and a comparison sensorgram of binding at 100 nM is shown in FIG. 7.

TABLE 6

| Immobilized ligand | Injection variables Analyte 1 Solution | 1:1 binding ka (1/Ms) | kd (1/s) | Apparent KD (M) | Rmax (RU) |
|---|---|---|---|---|---|
| fibril Aβ 7.5 μg/mL Ace4.5 | Adu | 2.96e+7 | 1.70e−2 | 5.74e−10 | 45.2 |
| fibril Aβ 7.5 μg/mL Ace4.5 | h2726 | 3.93e+5 | 2.12e−5 | 5.40e−11 | 51.0 |
| fibril Aβ 7.5 μg/mL Ace4.5 | h2731 | 3.72e+5 | 2.62e−5 | 7.04e−11 | 50.7 |
| fibril Aβ 7.5 μg/mL Ace4.5 | h2831 | 2.65e+5 | 2.94e−5 | 1.11e−10 | 50.2 |
| fibril Aβ 7.5 μg/mL Ace4.5 | h2931 | 3.35e+5 | 2.05e−5 | 6.12e−11 | 50.0 |

Abeta, amyloid beta, Aβ; ka, association rate constant; kd, dissociation rate constant; KD, apparent equilibrium dissociation constant; mAb, monoclonal antibody; $R_{max}$, maximum response; SPR, surface plasmon resonance.

The enhanced relative avidity of monoclonal antibodies of the disclosure for fibrillar Aβ observed by ELISA was confirmed by SPR equilibrium binding kinetics (Table 6), which indicated a 5- to 11-fold greater avidity (apparent KD) than aducanumab.

This is explained by the different kinetic binding profiles observed in the SPR sensorgram (FIG. 7). Although aducanumab binds Aβ fibrils at a faster association rate (ka), the much slower dissociation rate (kd) of the monoclonal antibodies of the disclosure resulted in greater measured avidity (i.e., lower KD*) than aducanumab.

Example 7. Aβ Fibril Binding by ELISA

The direct binding of certain monoclonal antibodies of the disclosure and aducanumab to $A\beta_{1-42}$ and $A\beta_{pE3-42}$ fibrils was assessed by ELISA. To generate fibrils, $A\beta_{1-42}$ or $A\beta_{pE3-42}$ polypeptides, previously treated with HFIP (hexafluoroisopropanol) and dried, were resuspended in DMSO to 5 mM, then further diluted to 100 uM with 10 mM HCl. Samples were incubated at 37° C. for 24 h, and then centrifuged to separate soluble and fibrillar species. The pellet was the resuspended in 1×D-PBS to the original volume and sonicated before use.

Figure 9:
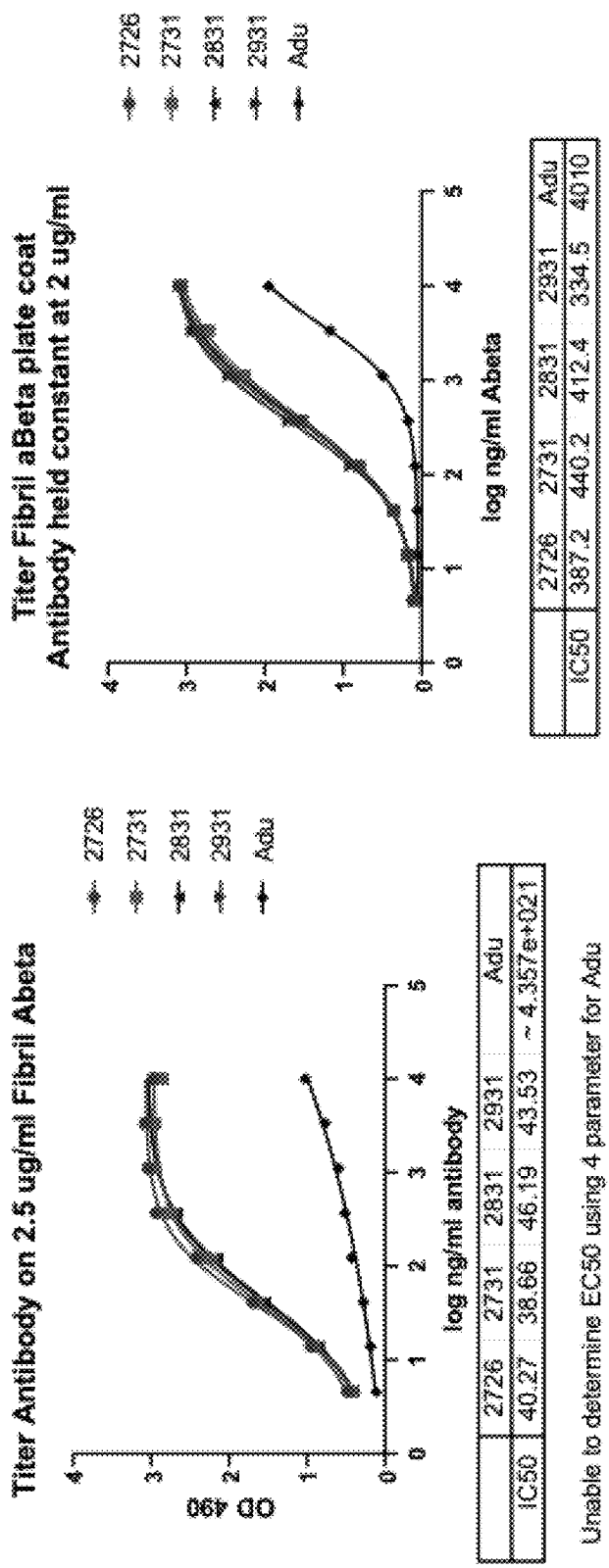
FIG. 9 shows graphs evaluating Aβ fibril binding activity of 2726, 2731, 2831, 2931 versus aducanumab control. Antibody was titrated in a constant concentration of Aβ fibrils (left panel) or Aβ fibrils were titrated in a constant concentration of antibody (right panel), both indicating substantially better binding for 2726, 2731, 2831 and 2931 than for aducanumab.
Figure 21:
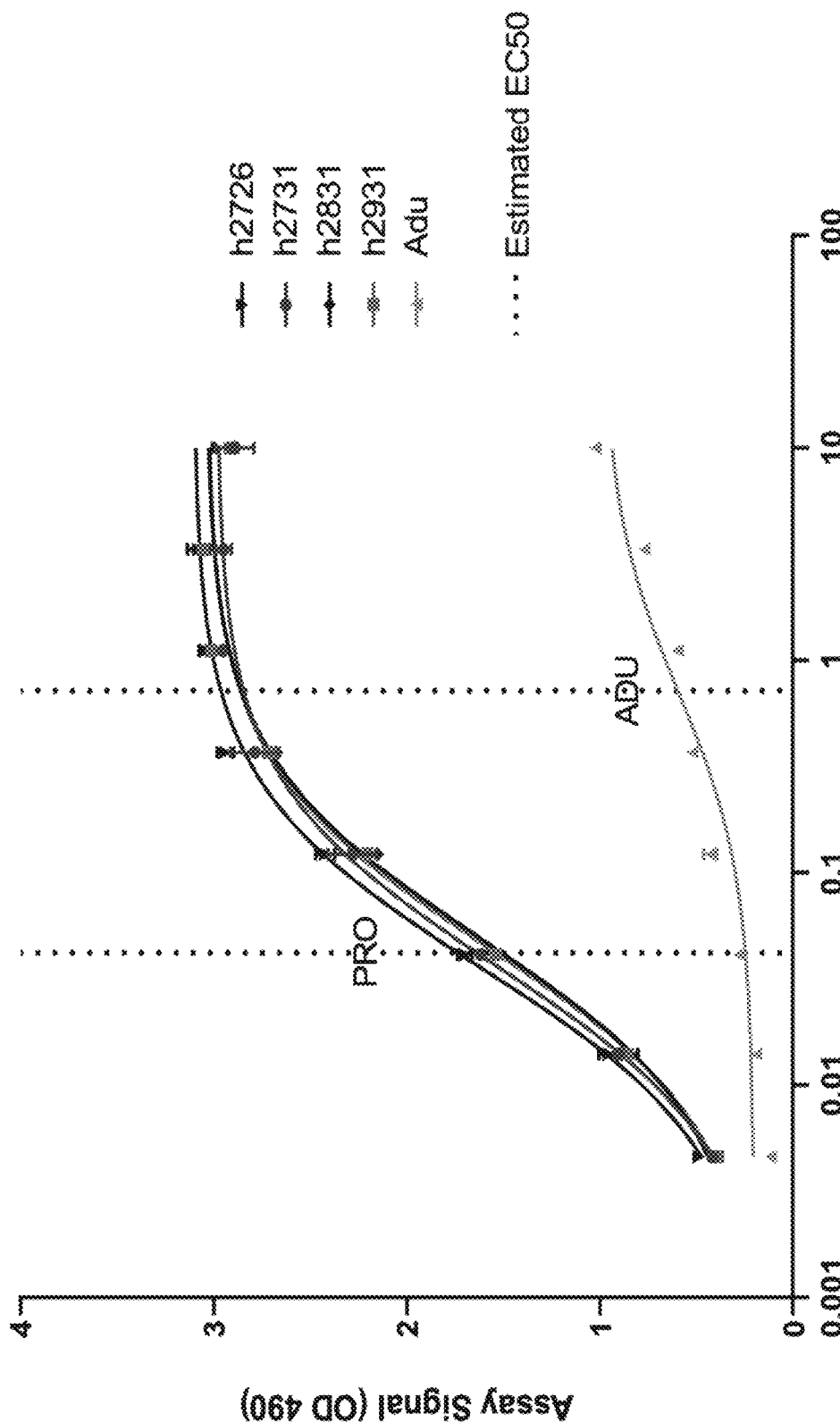
FIG. 21 shows graphs measuring direct binding and relative affinity of antibodies to fibrillar Aβ42 by ELISA.

1.0 μg/ml or 2.5 μg/ml of Aβ fibrils in PBS were coated overnight at room temperature. Plates were blocked 1% BSA/PBS for 1 hour. Antibodies were serially diluted from 10 μg/ml to 4.8 ng/ml in 0.1% BSA-PBS and 0.1% Tween 20 and 100 μl of each dilution was added in duplicate to each antibody and incubated for 2 hrs at room temperature. Plates were washed four times with TBS/Tween 20 and 100 μl of goat anti Human IgG HRP (Jackson ImmunoResearch Laboratories, Inc, West Grove, Pa. or Invitrogen, Carlsbad, Calif.) at 1/5000 dilution was added to each well and incubated 1 hour at room temperature. Plates were wash six times in TBS/Tween 20, and Thermo Fisher o-phenylenediamine dihydrochloride (OPD) tablets and ThermoFisher substrate buffer were prepared per manufacturer's instructions. 100 ul of substrate was added and incubated 15 min. Reaction was stopped with 50 μl $H_2SO_4$. Plates were read at 490 nm on a molecular devices spectromax. FIG. 9A, and FIG. 21. For FIG. 21, curves and resulting $EC_{50}$ estimations represent nonlinear three-parameter least squares fit of the data (data shown in Table 7).

TABLE 7

| mAb | h2726 | h2731 | h2831 | h2931 | Adu |
|---|---|---|---|---|---|
| $EC_{50}$ (μg/mL mAb) | 0.0359 | 0.03671 | 0.04894 | 0.04495 | 0.7241 |

Plates were coated with dilutions of Aβ fibrils in PBS from 10 μg/ml to 4.8 ng/ml overnight at room temperature. Plates were blocked 1% BSA/PBS 1 hour. Antibodies at 2 μg/ml in 0.1% BSA/PBS 0.1% Tween 20 were added in duplicate to the appropriate wells and incubated for 2 hrs at room temperature. Plates were washed 4× with TBS/Tween 20 and then 100 μl of Jackson Goat anti Human IgG HRP 1/5000 dilution was added to each well and incubated 1 hour at room temperature. Plates were wash six times in TBS/Tween 20, and Thermo Fisher o-phenylenediamine dihydrochloride (OPD) tablets and ThermoFisher substrate buffer were prepared per manufacturer's instructions. 100 μl of substrate was and incubated 15 min. Reaction was stopped with 50 μl $H_2SO_4$. Plates were read at 490 nm on a molecular devices spectromax. FIG. 9B, right panel.

Antibodies h2726, h2731, h2831 and h2931, all demonstrated strong affinities to fibrils, with the difference between best and worst performer within 25%. Additionally, these four antibodies all demonstrated significantly greater avidity than aducanumab. For FIG. 21, a 3-fold increase in assay signal (OD490) and a 15 to 20-fold lower estimated $EC_{50}$ indicated increased overall binding and relative avidity of h2726, h2731, h2831 and h2931 mAbs to fibrillar Aβ relative to aducanumab.

Example 8. h2931 Binding of Aβ Oligomer by ELISA

The direct binding of h2931 to Aβ oligomer was assessed by ELISA. To generate oligomers, first lyophilized biotinylated and unlabeled Aβ (Bachem) were each solubilized at 1 mg/mL in 1,1,1,3,3,3-hexafluoroisopropanol (HFIP, Sigma). HFIP was allowed to evaporate from the samples overnight in a fume hood at room temperature. Aliquots were then centrifuged in a speedvac at room temperature to remove all liquid to generate 250 μg aliquots of HFIP films, which were stored at −80° C. until further use.

Oligomers were prepared by solubilizing 250 μg of biotinylated and unlabeled Aβ HFIP pellets in dry DMSO (Sigma) to a final concentration of 5 mM. For unlabeled: biotinylated mixtures, samples were combined in a 9:1 ratio (unlabeled:biotinylated) in an sterile 1.5 mL low-binding microcentrifuge tube (Axygen). DMSO-solubilized samples were then diluted to 100 μM with cold phenol-free neurobasal media (Invitrogen) and incubated for 24 hours at 4° C. After incubation, the oligomers were separated from large insoluble material via centrifugation at 14,000 g for 15 minutes. The top 90% of the supernatant was carefully removed and placed in a new sterile low-binding microcentrifuge tube and stored on ice until use.

Figure 8:
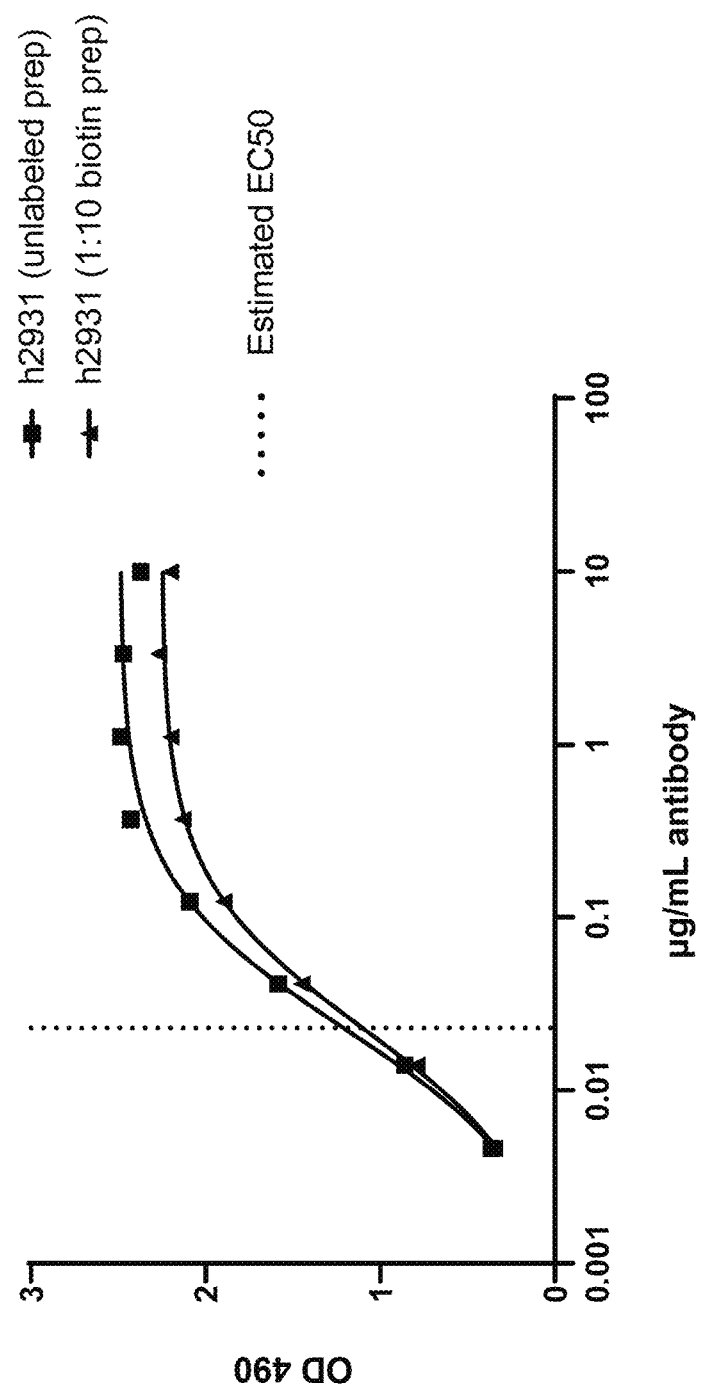
FIG. 8 shows h2931 binds soluble Aβ oligomers with high relative affinity.

2.5 μg/mL of each preparation in PBS was coated 100 ul per well in Costar ELISA high bind plates overnight at room temperature. Plates were aspirated and then 200 μl of 1% BSA in PBS was added in each well and incubated 1 hour at room temperature. h2931 mAb was made at a starting concentration 10 µg/ml in 0.1% BSA/PBS 0.1% tween 20 buffer and serially diluted seven times (1:2 each time) with the same. The samples were incubated for 2 hours at room temperature. Plates were washed 4 times with TBS. 0.1% tween 20. Goat anti-human (H+L) HRP (Jackson Immunoresearch, Pa.) was diluted 1/5000 in 0.1% BSA/PBS 0.1% tween 20, added at 100 µl/well and incubated 1 hour at room temperature. Plates were washed 4 times and o-phenylenediamine dihydrochloride tablets (ThermoFisher) were prepared as per manufacturer instructions. 100 µl was added per well and incubated for 15 minutes at room temperature. Reactions were stopped by the addition of 50 µl of $H_2SO_4$, and samples were read at 490 nM on a Molecular Devices SpectroMax. Curves and resulting $EC_{50}$ estimations represent nonlinear 3-parameter least-squares fit of data using GraphPad Prism software.

mAb h2931 was shown to bind soluble oligomers with high relative affinity, with an estimated $EC_{50}$ of 23 ng/mL or 0.15 nM. FIG. 8.

Example 9. Anti-Aβ Antibodies Binding in AD Brain

Tissue samples. Frozen human AD brain samples were obtained from Banner Sun Health Research Institute, Sun City, Ariz. The tissues are from donors who were confirmed to have high amount of Aβ pathology and staged according to the Braak system at the provider institution (Table 8). In addition, quality control was performed in-house on all tissue blocks to ascertain their pathology level and distribution.

TABLE 8

| AD donor information | | | | |
|---|---|---|---|---|
| Case ID | gender | Expired_age | PMI | Braak score |
| AD 13-75 | M | 77 | 3.62 | VI |
| AD 14-11 | M | 82 | 3.98 | V |
| AD 15-19 | F | 83 | 3.62 | V |
| AD 11-97 | F | 86 | 2.52 | V |

Tissue Sectioning and Fixation. The unfixed frozen brain tissue samples were embedded in Tissue-Tek OCT (Sakura Finetek) in cryomolds dipped in a mixture of 2-methylbutane and dry ice slurry (−60° C.) then stored at −80° C. until sectioning. Serial 10 µm thick cryosections were generated using a Leica 3050S cryostat. The sections were directly thaw-mounted on positively charged glass slides and were stored at −20° C. until use. Prior to immunohistochemistry IHC procedures, the slides were immersed in 10% neutral buffered formalin solution for 10 minutes at 4° C., rinsed in PBS, then incubated for an hour at 37° C. in a glucose oxidase solution (20 mM beta D(+) glucose, 2 mM sodium azide, and 2 units/mL glucose oxidase in 1×PBS). The slides were rinsed 3 times for 5 minutes in PBS before they were transferred onto staining racks for processing in an automated stainer.

Antibody biotinylation. The humanized IgG antibodies were biotinylated using a non-covalent method, by means of incubation with a biotin-conjugated goat anti-human monovalent fab fragment (Jackson ImmunoResearch) in a ratio of 1:4, for 1 hour at room temperature. Unbound excess Fab was absorbed by pre-incubation with human serum for an additional hour before use. The freshly prepared antibodies were then loaded into the stainer for immediate application to tissue sections.

Immunostaining. The staining was performed in an automated Leica Bond Rx Stainer (Leica Biosystems), using the Bond Research Kit (DS980, Leica Biosystems) and the avidin-biotin amplified immuno-peroxidase detection system. Each biotinylated anti-Aβ antibody, or a human IgG control, was applied to the sections, at specified concentrations, for one hour and the staining was visualized using the avidin-biotin amplification system (ABC Elite Standard, PK-6100; Vector Laboratories). Hematoxylin counter-staining of nuclei was subsequently applied to sections before dehydration in an ascending series of alcohols, clearing in xylene, cover-slipping, and air-drying.

Tissue imaging. The stained slides were digitally imaged using a Hamamatsu NanoZoomer 2.0HT slide scanner (Hamamatsu Corporation), and the images were captured in an .ndpi file format using the NanoZoomer Digital Pathology software (NDP.scan, Version 2.7.25). Images included in this report were captured directly from NDP.view and transferred without any enhancement. For morphometry, the digitized slides were analyzed using Halo software (V2.1.1537) to measure the percentage of stained tissue, and the results were plotted using GraphPad Prism 8.

Figure 10:
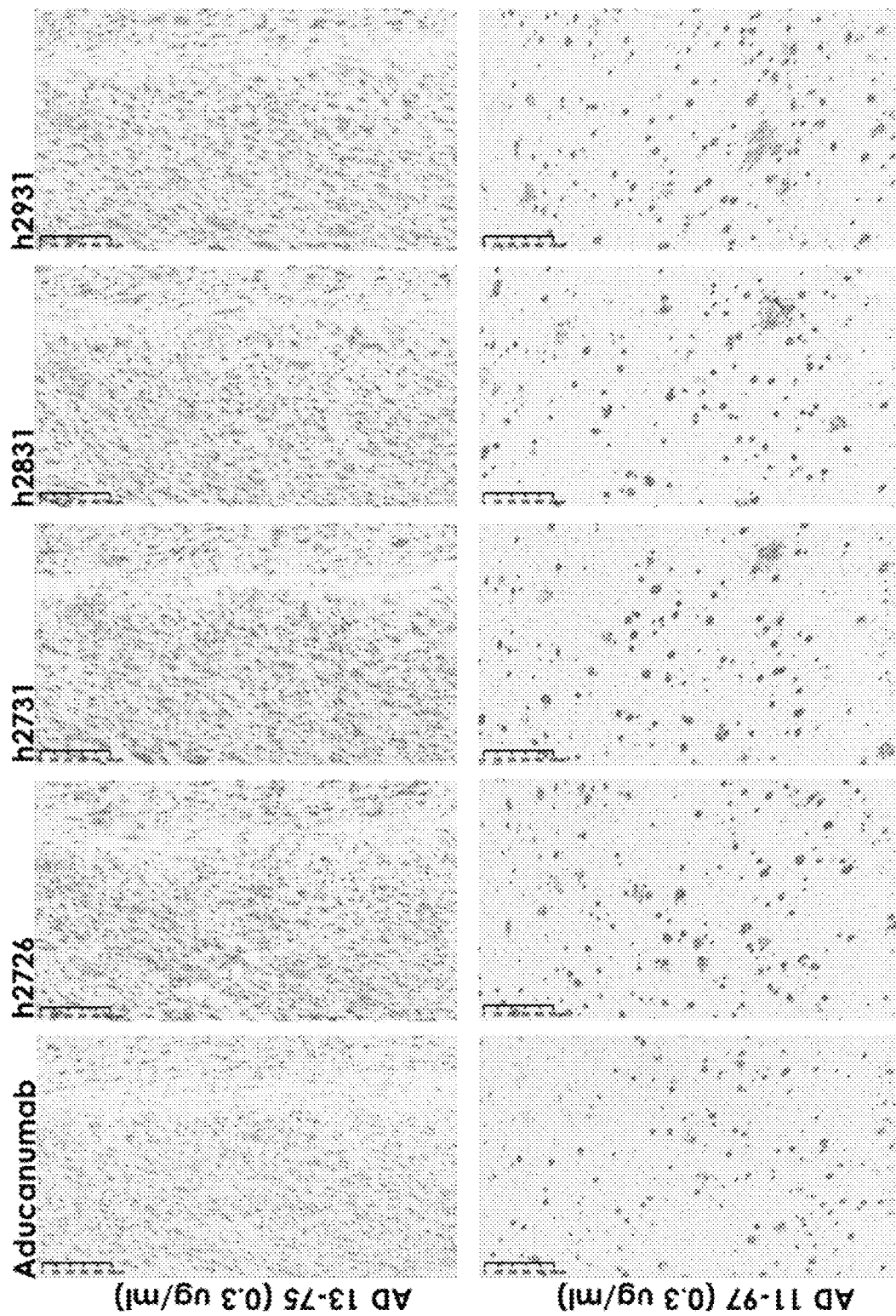
FIG. 10 shows Aβ binding in AD brain. Binding to tissue Aβ pathology appears similar among h2726, h2731, h2831 and h2931 antibodies. Examples of images stained with the four antibodies, h2726, h2731, h2831, h2931, at 0.3 µg/ml show their pattern of staining in two AD brains with different amounts of Aβ pathology (AD 11-97 and AD 13-75). For each brain, the images are from the same area of the section and show comparatively similar intensity and distribution of pathology with all four antibodies. Staining with aducanumab was always the weakest (Scale bar: 500 µm).
Figure 11:
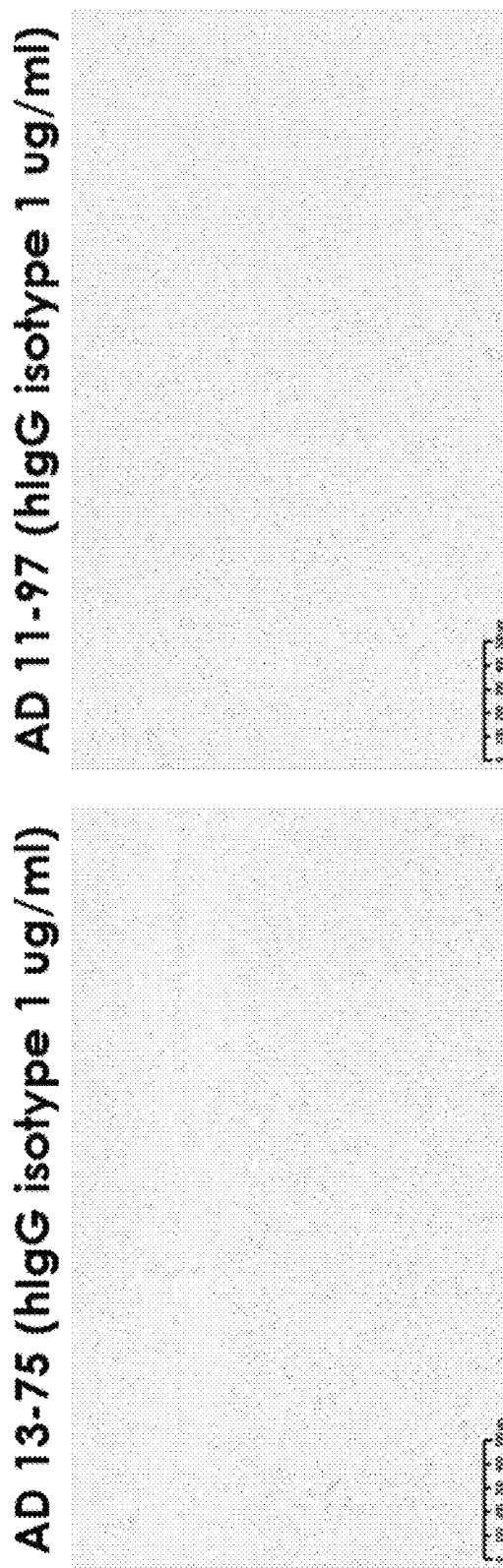
FIG. 11 shows Aβ binding in AD brain of controls. Human IgG isotype control antibody produced no staining in AD brains. As shown in these examples, AD sections incubated with human IgG isotype at 1 µg/ml were devoid of any staining (Scale bar: 500 µm).

Results with h2726, h2731, h2831, h2931 and aducanumab. Four humanized anti-Aβ antibodies of the disclosure, h2726, h2731, h2831 and h2931, as well as aducanumab, were applied to all four AD brains at increasing concentrations: 0.03, 0.1, 0.3, 1, 3 and 9 µg/ml. As shown in FIG. 10 (0.3 µg/mL), the AD brain sections that were incubated with these antibodies exhibited immunopositive structures that are typical for Aβ pathology in AD. Brains AD 13-75 and AD 14-11 have high density of Aβ plaques while the pathology in brains AD 11-97 and AD 15-19 was comparatively sparse. In each brain, the staining produced by the four antibodies, h2726, h2731, h2831 and h2931, at a specific concentration, was comparable in intensity and distribution. Staining with aducanumab was the weakest among samples and concentrations. As exemplified in FIG. 11, sections from all four brains that were incubated with control human IgG isotype at 1 or 9 µg/ml had no pathology staining.

Figure 12:
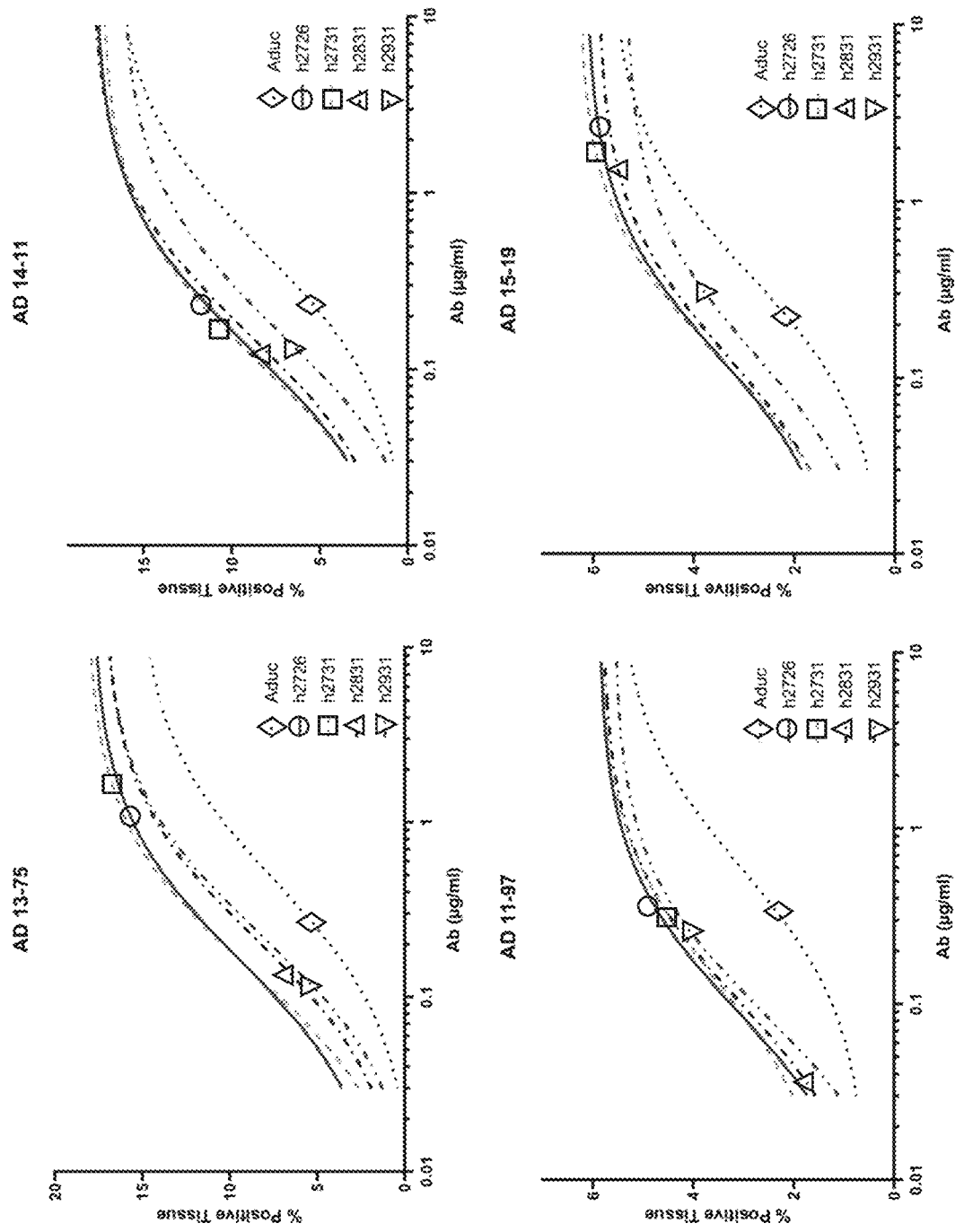
FIG. 12 shows quantification of Aβ binding in AD brain. Quantification of Aβ pathology staining in AD tissues revealed similar binding between h2726, h2731, h2831 and h2931 antibodies. Section from four AD brains were incubated with the antibodies h2726, h2731, h2831, h2931 as well as aducanumab at the following concentrations: 0.03, 0.1, 0.3, 1, 3 and 9 µg/ml. After imaging of sections, the percent of stained tissue area was determined morphometrically using Halo® imaging analysis software. Each graph compares measurements in an AD brain obtained with the five antibodies. The four graphs consistently show that the binding profiles of h2726, h2731, h2831, h2931 antibodies are similar. Measurements obtained with aducanumab were significantly lower.
Figure 22:
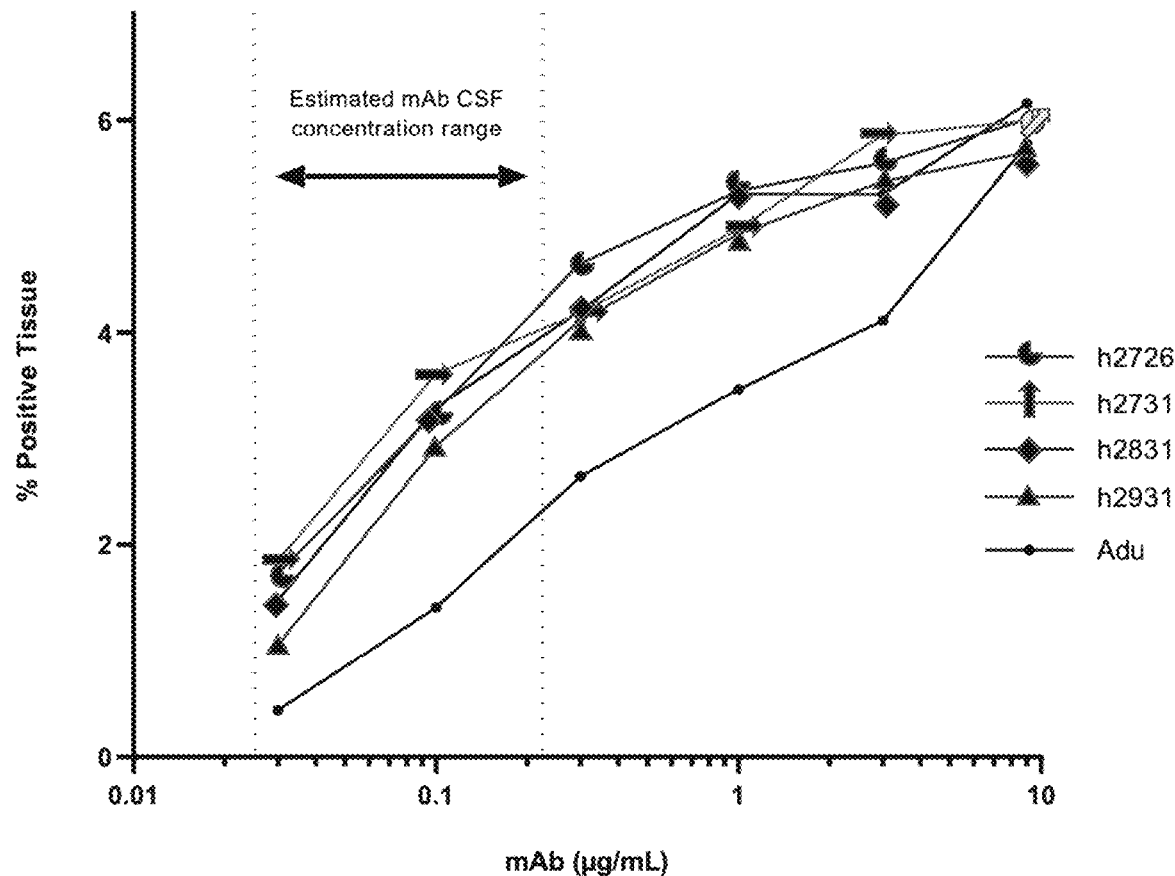
FIG. 22 shows graphs measuring antibody dose response of Aβ plaque area binding measured as percent positive tissue by immunohistochemical staining in AD brain.

The graphs in FIG. 12 and FIG. 22 are plots of the quantification of staining by the five antibodies in all four AD brains. Measurements of the percentage of tissue surface area that was occupied by the stained pathology confirm that, in each AD brain, the four antibodies, h2726, h2731, h2831, h2931, have similar levels of binding, at all concentrations tested. Correspondingly, the data in Table 9 show that, with each brain, the area under the curve and EC50 values remain comparable for the four antibodies. Values obtained with aducanumab were consistently lower among AD brains throughout the concentration range tested.

FIG. 22 showed greater plaque area binding (as a percentage positive tissue stained) than aducanumab, notably, at antibody concentrations that are estimated to be clinically relevant exposures in cerebrospinal fluid with 10 mg/kg aducanumab. Similar plaque area staining was observed at the highest concentration tested, suggesting saturation of binding at this level.

TABLE 9

Area under the curve and half maximal effective concentration ($EC_{50}$)

|  | h2726 | h2731 | h2831 | h2931 |
|---|---|---|---|---|
| Area Under Curve | | | | |
| AD 11-97 | 50.18 | 50.58 | 49.21 | 47.70 |
| AD 15-19 | 52.08 | 52.71 | 49.73 | 44.81 |
| AD 13-75 | 149.3 | 150.4 | 138.7 | 139.1 |
| AD 14-11 | 149.1 | 149.2 | 148.9 | 134.5 |
| EC50 | | | | |
| AD 11-97 | 0.09163 | 0.1346 | 0.1019 | 0.08893 |
| AD 15-19 | 0.1356 | 0.1274 | 0.1328 | 0.1330 |
| AD 13-75 | 0.1615 | 0.1415 | 0.2144 | 0.2273 |
| AD 14-11 | 0.1325 | 0.1102 | 0.1625 | 0.1691 |

Results with Bapineuzumab (hBP)

Figure 13:
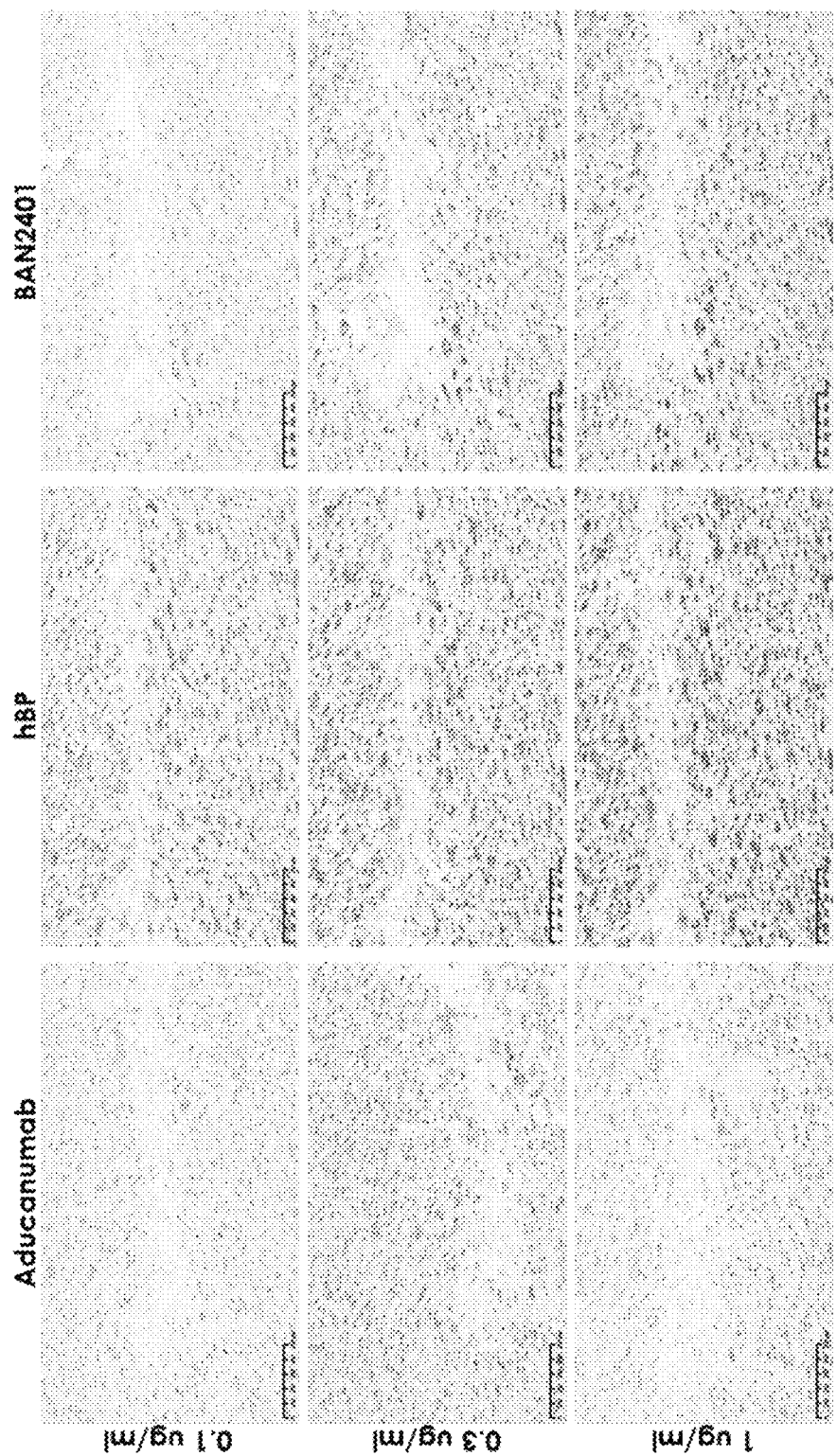
FIG. 13 shows Aβ binding in AD brain. hBP binds to tissue Aβ pathology strongly and in a dose-dependent manner. Images from relatively the same area of the section (Brain AD 13-75) with similar pathology distribution. hBP shows an increase in the amount of staining with concentration, and its binding to Aβ pathology was stronger than that of BAN2401 or aducanumab at each concentration (Scale bar: 500 µm).

Section from brain AD 13-75 were incubated with the humanized antibody hBP as well as aducanumab and BAN2401 at increasing concentrations: 0.03, 0.1, 0.3, 1, 3 and 9 μg/ml. As seen with antibodies h2726, h2731, h2831 and h2931, the level of staining with hBP increased in a dose dependent manner. In addition, hBP staining was stronger than that of aducanumab and BAN2401 at all concentrations tested, as shown in FIG. 13.

Example 10. Ex Vivo Phagocytosis Assays for Determination of ($A\beta_{1-42}$ and $A\beta_{pE3-42}$) Plaque Clearance In the early stages of AD, microglial function is neuroprotective, acting to clear apoptotic cells and pathological protein aggregates, as well as forming a barrier around plaques to restrict their growth and diffusion of synaptotoxic Aβ oligomers. Ex vivo phagocytosis assays quantitate the antibody-mediated microglial clearance response.

Primary microglial culture generation: For dissection of neonatal mouse brain tissue, P1 pups are quickly decapitated with sterile scissors. Meninges are removed and forebrain were immediately immersed into 1-5 ml dissection media (e.g., high glucose DMEM with 20% FBS, P/S) on ice until the desired number of pup brains has been dissected. Preferably limit total procedure time to within 10 minutes to minimize cellular damage.

Tissue was carefully aspirated twice consecutively with new sterile pipettes using a 22G needle, followed by a 25G needle. Sample were centrifuged at 2,500×g for five minutes at 4° C. Supernatant was carefully aspirated and 5 ml of fresh growth media was added (high-glucose DMEM, 10% FBS, P/S and 25 ng/ml recombinant mouse GM-CSF) to the cell pellets. The cell pellets are pipetted up and down approximately 10 times with a sterile 10 ml pipette to dissociate the pellets.

A cell strainer (100 μm pores) was placed onto a fresh 50 ml conical tube and the material was dispensed through the cell strainer into the conical tube. The cell strainer was rinsed with 4-5 ml of fresh media, followed by centrifuging 200×g for five minutes at 4° C.

Cells were plated at a density of two mouse brains per T-75 plastic culture flask. Carefully aspirate supernatant and add 3 ml of fresh growth medium (high-glucose DMEM, 10% FBS, P/S, and 25 ng/ml recombinant mouse GM-CSF) to each cell pellet with 10 ml sterile pipette. Pipette up and down 10 times with a 10 ml pipette to resuspend. Prepare 1 sterile T-75 flask by adding 6 ml of growth medium (high-glucose DMEM, 10% FBS, P/S and 25 ng/ml recombinant mouse granulocyte-monocyte colony-stimulating factor) into each flask, followed by the addition of 6 ml of resuspended cell pellets to obtain 12 ml final in a 5% $CO_2$ incubator at 37° C.

Flasks are incubated undisturbed for five days to allow cells to attach. On the fifth day, the culture media was replaced in each flask with 12 ml of fresh growth medium (high-glucose DMEM, 10% FBS, P/S and 25 ng/ml recombinant mouse GM-CSF). Approximately 10% of the mixed cells plated will attach and grow on the plastic surface. The media was changed twice per week (every 3-4 days) to achieve confluence. Such changes are carried out with very carefully without touching the bottom of the flasks where the cells are attached.

After 7-11 d the flasks were rotated at 200 rpm using a Lab-Line orbital shaker with a 19-mm orbit for 2 h at 37° C. Cell suspensions were centrifuged at 200×g and resuspended in assay medium (hybridoma-serum free medium H-SFM [Life Technologies] plus 1% FBS, glutamine, P/S, and 5 ng/ml recombinant mouse GM-CSF).

Ex vivo assays. Cryostat sections (10 μm in thickness; use the wide blades) of APP/PS1 mouse or human AD brains (postmortem interval, less than 3 h) were 'thaw mounted' onto polylysine-coated, round glass coverslips and placed in wells of 24-well tissue culture plates (CT −30 C OT −20 C). Tissue samples can be warmed with thumb in between sections or by reducing OT to −12 C). The coverslips were washed twice with assay medium. Antibodies (control or against Aβ) were added at a 2× concentration 250 μl in assay medium (20 μg/ml final) for 1 h in tissue culture incubator.

Microglial cells were then seeded at a final density of 800,000 cells/ml (1,600,000 cells/ml stock) in assay medium 250 μl. The cultures were maintained in a humidified incubator at 37° C. in an atmosphere of 5% CO2 for 72 hrs.

Figure 14A:
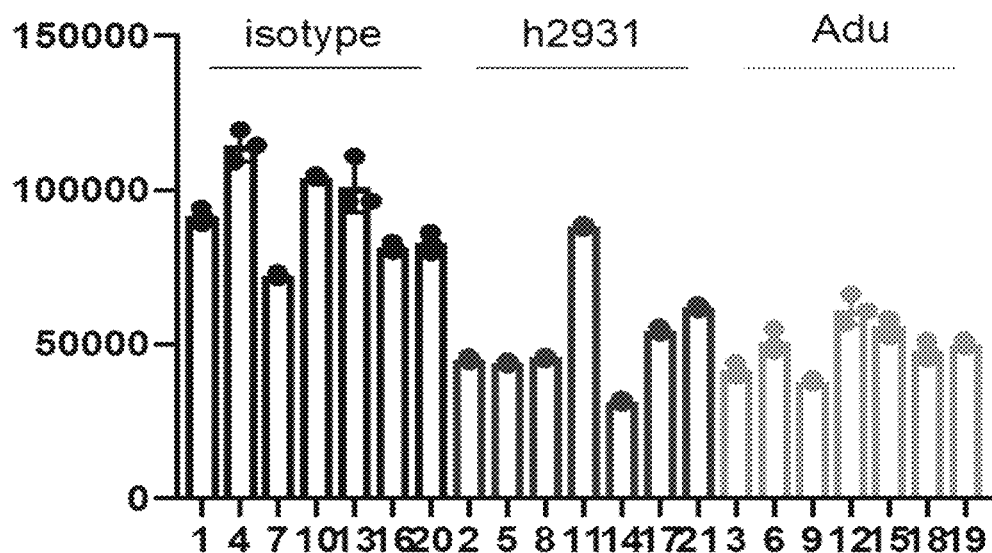
FIGS. 14A and 14B show individual (FIG. 14A) and pooled (FIG. 14B) results from an ex vivo phagocytosis study of h2931 and aducanumab in APP.PS1 Tg mouse tissue with primary murine microglia. h2931 and aducanumab both demonstrate highly significant reductions in $A\beta_{1-42}$ over isotype control.
Figure 14B:
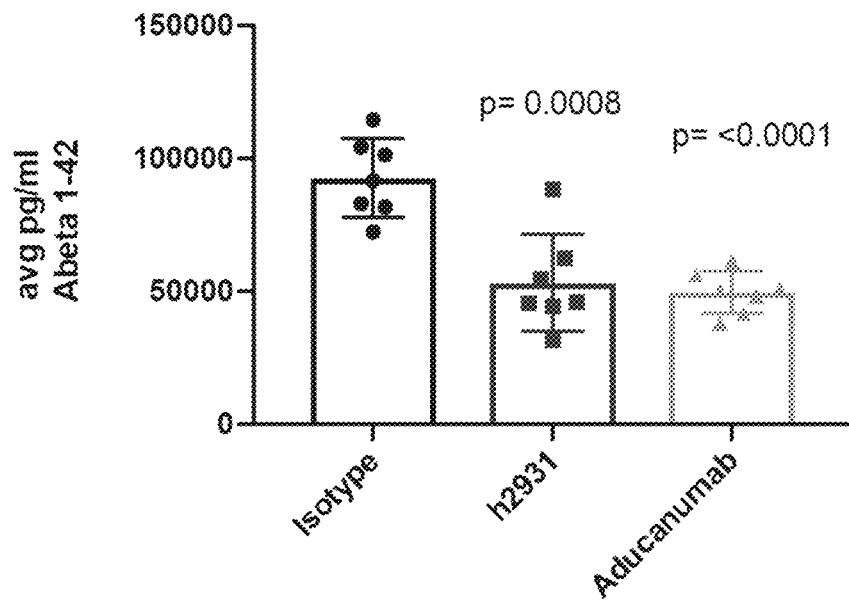
Figure 24:
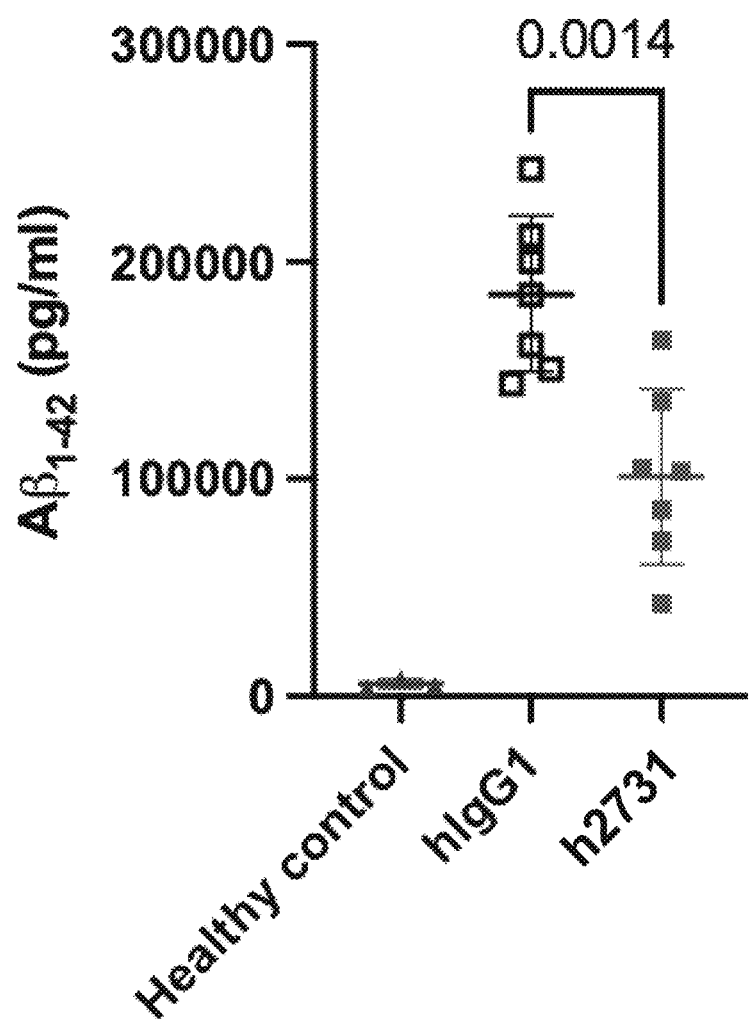
FIG. 24 shows results from an ex vivo phagocytosis study of h2731 in AD tissue with primary murine microglia. h2731 demonstrated highly significant reduction in $A\beta_{1-42}$ indicating the antibody robustly promoted phagocytosis and removal of these species.

Quantification of total Aβ ($A\beta_{1-42}$). Media was carefully aspirated, followed by washing with ice cold PBS. 100 μl 8M urea was added and tissue resuspended by pipetting and scraped off with pipette tip. Suspension was then frozen at −20° C. until ready for analysis. Suspensions were thawed on ice, centrifuged 16,000×g 20 min at 4° C. before dilution and analysis using a V-PLEX Total Aβ42 Peptide (4G8) Kit (Meso Scale Discovery). Results are shown in FIG. 14A, FIG. 14B and FIG. 24. FIG. 14A and FIG. 24 show Aβ level per brain section and FIG. 14B shows the same data as a scatter plot per treatment (data for FIG. 14B shown in Table 10; data for FIG. 24 shown in Table 11). h2731, h2931, and aducanumab demonstrated highly significant reductions in Aβ plaque species over isotype control.

TABLE 10

| mAb (Avg. μg/mL $A\beta_{1-42}$) | Isotype control | h2931 | Aducanumab |
|---|---|---|---|
| Mean | 92619 | 53113 | 49501 |
| SD | 14801 | 18239 | 7961 |

TABLE 11

| Condition | Aβ1-42 (pg/ml) | SD |
|---|---|---|
| Healthy control | 5797.25 | 2022.51 |
| AD brain + hIgG1 isotype | 185138.90 | 35888.64 |
| AD brain + h2731 | 101172.05 | 40194.48 |

Quantification of pyroglutamate-3 Aβ (Aβ$_{pE3-42}$). N-terminal truncated and pyroglutamate-modified Aβ (e.g., Aβ$_{pE3-42}$) has been described as a component of mature senile plaques in AD brain (Saido et al., Neuron 14, 1995). It was unknown whether pyroglutamate-modification of N-terminal Aβ would affect binding of N-terminal antibodies like h2731 and others described herein. Likewise, it was unknown whether these antibodies would have the ability to promote phagocytic-mediated clearance of Aβ$_{pE3-42}$.

Figure 25A:
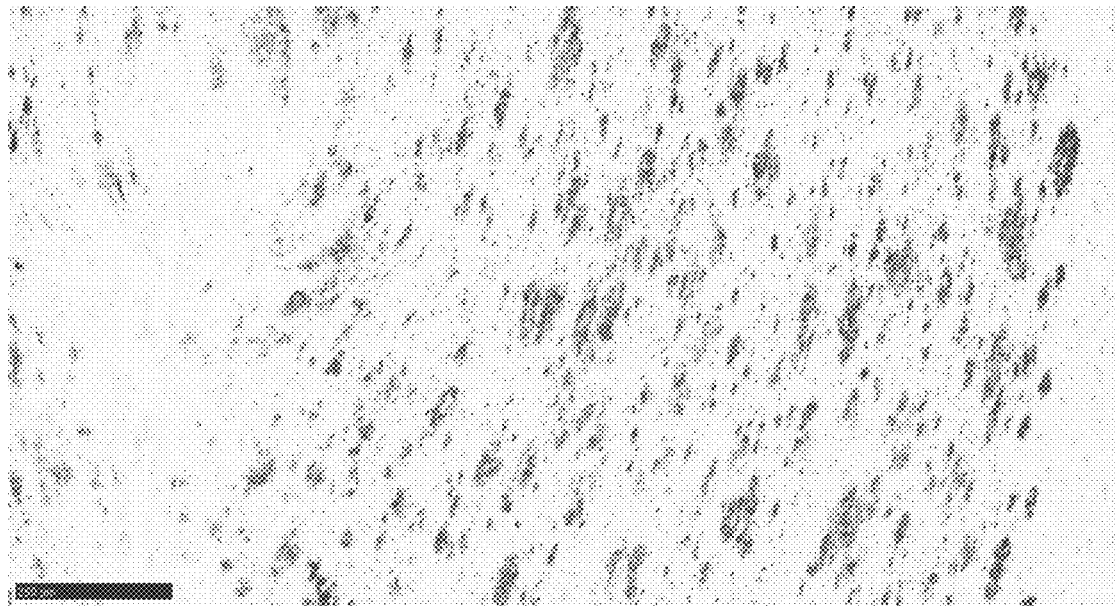
FIGS. 25A and 25B confirm the presence of pyroglutamate-3 Aβ ($A\beta_{pE3-42}$) in AD tissue used for ex vivo phagocytosis assays (FIG. 23A) and demonstrates a similar binding pattern for pyroglutamate-3 Aβ and h2931 (FIGS. 23A and B).
Figure 25B:
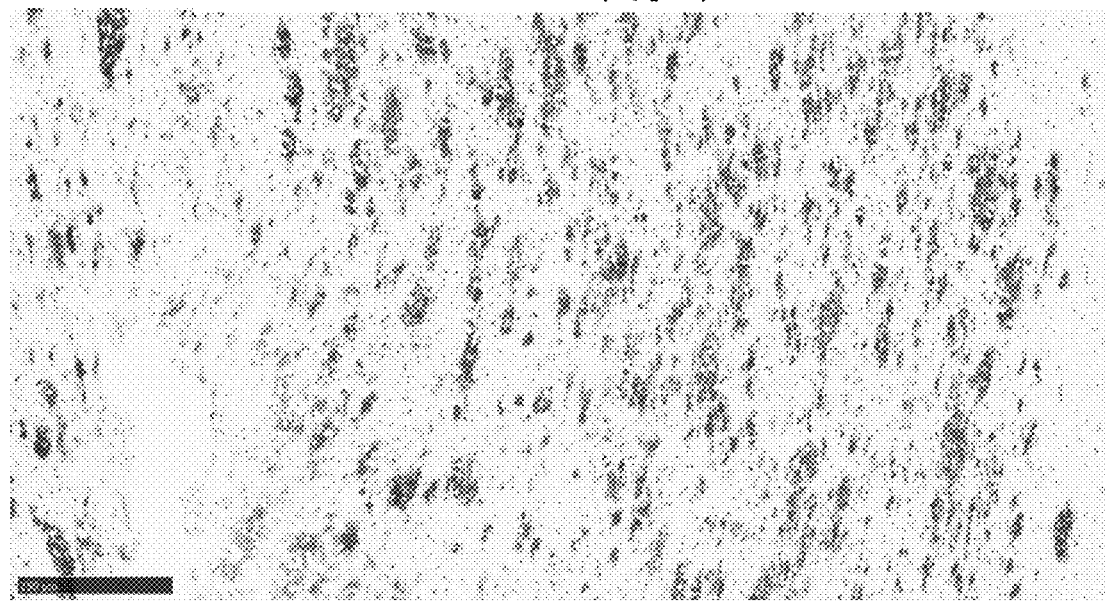

The presence of pyroglutamate-3 Aβ in AD brain used for ex vivo experiments, as well as its similar staining pattern compared to h2931, was confirmed by immunohistochemistry (FIGS. 25A and 25B). To demonstrate removal of pyroglutamate-3 Aβ, a commercial ELISA method was used to measure its removal during ex vivo phagocytosis. Suspensions that were collected following methods above were thawed on ice, centrifuged 16,000×g 20 min at 4° C. before dilution and analysis using a commercial ELISA kit (Amyloid Beta N3pE Aβ, IBL America). Aβ$_{pE3-42}$ ELISA assay is highly specific to Aβ$_{pE3-42}$ when compared to unmodified Aβ$_{1-42}$ (data not shown).

Figure 26A:
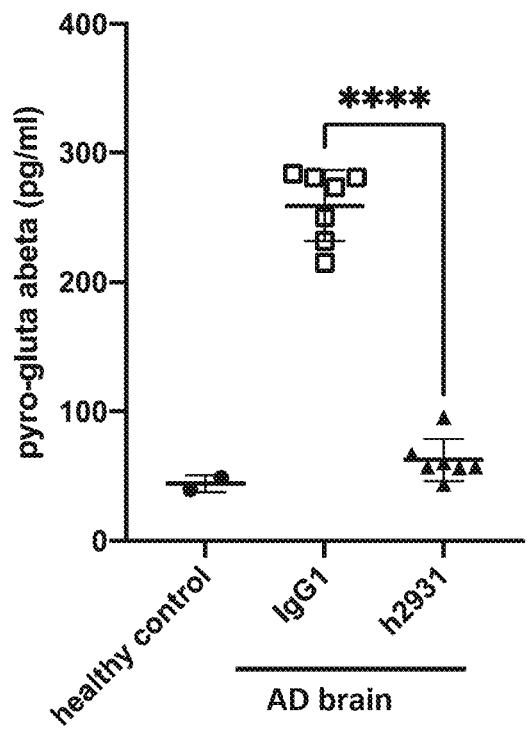
FIGS. 26A and 26B show results from an ex vivo phagocytosis study of h2931 and h2731 in AD tissue with primary murine microglia. h2931 and h2731 both demonstrate highly significant reductions in pyroglutamate-3 Aβ ($A\beta_{pE3-42}$). indicating that both antibodies robustly promote phagocytosis and removal of these species.
Figure 26B:
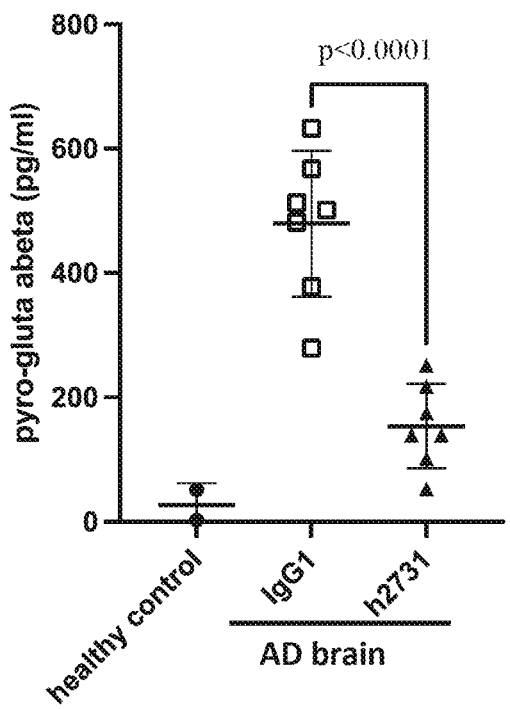

Results are shown in FIG. 26A and FIG. 26B (data shown in Table 12 and Table 13, respectively), which show levels of pyroglutamate-3 Aβ in brain sections after treatment with indicated antibodies, h2931 in FIG. 26A and h2731 in the FIG. 26B, each compared to a healthy control and compared to AD brain treated with IgG1 isotype control. Sections from different AD brains were used for each treatment. h2731 and h2931 both demonstrate highly significant reductions in pyroglutamate-3 Aβ over isotype control.

FIG. 24 and FIG. 26B, taken together, indicate anti-Aβ antibodies of the present invention (e.g., h2731) promote clearance of both Aβ$_{1-42}$ and Aβ$_{pE3-42}$ protein when incubated on AD patient brain sections with primary mouse microglia. These results confirm that these antibodies clear both Aβ$_{1-42}$ and Aβ$_{pE3-42}$ in the human pathology setting.

The N-terminal-targeted anti-Aβ antibodies, facilitated abundant microglia-mediated clearance of Aβ plaque species, including pyroglutamate-modified Aβ, in brain tissue from AD patients. These data support further development of antibodies of the present invention as a subcutaneously administered antibody immunotherapy for Alzheimer's disease.

TABLE 12

| Condition | Ab$_{pE3-42}$ (pg/ml) | Stdev |
|---|---|---|
| Healthy control | 44.20 | 6.39 |
| AD brain + hIgG1 isotype | 259.42 | 27.39 |
| AD brain + h2931 | 62.59 | 16.16 |

TABLE 13

| Condition | Ab$_{pE3-42}$ (pg/ml) | Stdev |
|---|---|---|
| Healthy control | 26.75 | 34.83 |
| AD brain + hIgG1 isotype | 478.91 | 117.80 |
| AD brain + h2731 | 153.76 | 67.59 |

Example 11. Blocking Oligomers in Hippocampal Binding Assay

Aβ Binding Assay in Rat Hippocampal Neurons

E18 primary rat hippocampal neurons were cultured as described by Zago et al. (J. Neurosci 22 Feb. 2012, 32 (8) 2696-2702). Soluble Aβ was pre-incubated with and without antibody on culture DIV14-21 to block neuritic binding to primary neurons.

Fresh unlabeled, biotinylated or (9:1) unlabeled:biotinylated soluble Aβ was prepared one day prior and incubated overnight at 4° C. The Aβ was spun down @ 14,000 RPM for 15 minutes before use.

Each dilution of Aβ solution and antibody at (2×) of the final treatment concentration in one-half of final treatment volume using NeuroBasal-no phenol red (NB-NPR) or NbActiv4-NPR medium were prepared. After combining, the mixture was mixed 3-4 times then pre-incubated for 30 minutes at 37° C.

Immediately before binding assay, the neurons were rinsed with pre-warmed NB-NPR at 150 μL/well. The buffer was aspirated and then antibody/Aβ treatment was added to cells at 60 μL/well then incubated for 30-40 minutes at 37° C. under normal incubator conditions (5% CO2; 9% O2).

The neurons were rinsed twice in 150 μL/well NB-NPR then fixed in 4% paraformaldehyde in 1×DPBS for 20 minutes at room temperature.

The cells were permeabilized in 0.1% Triton X-100 in 1×DPBS for 5 minutes and then blocked in 10% normal goat serum (NGS) for 1 hour at room temperature (RT).

The samples were incubated with microtubule-associated protein 2 (MAP2) and neuronal nuclear protein (NeuN) primary antibodies in 100 μL/well 1×DPBS containing 1% BSA+1% NGS overnight at 4° C. On the next day, the samples were rinsed twice in 150 μL/well 1×DPBS for 5 minutes each wash. Secondary antibody was added for 1 hour @ room temperature in 100 μL/well 1×DPBS+1% BSA+1% NGS.

Figure 15A:
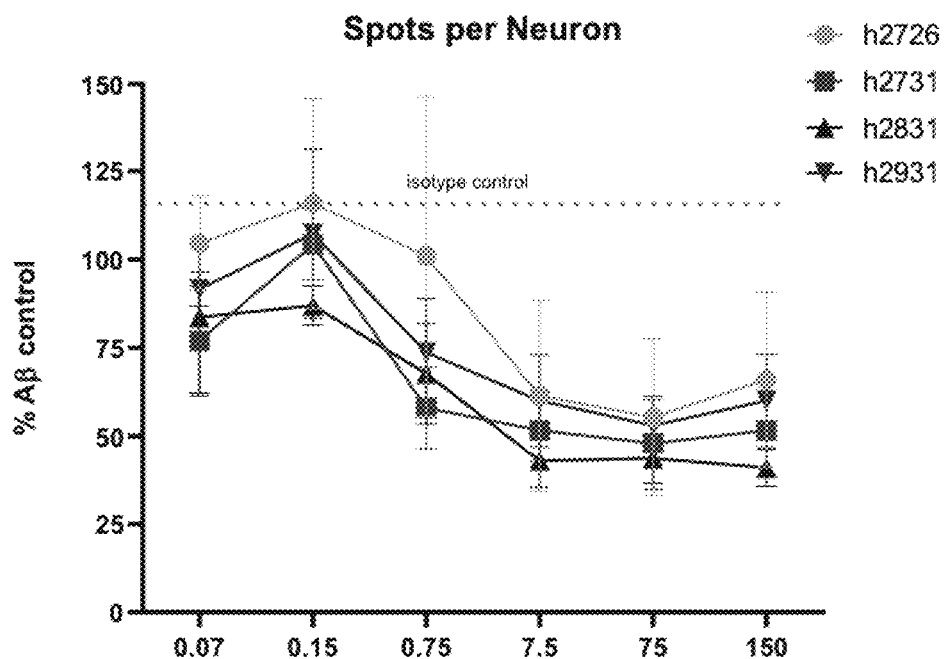
FIGS. 15A and 15B show graphs indicating a reduction of soluble oligomer binding to neurites on rat hippocampal neurons with increasing concentration of h2726, h2731, h2831 and h2931 compared to isotype control, and normalized by +/−Aβ addition.
Figure 15B:
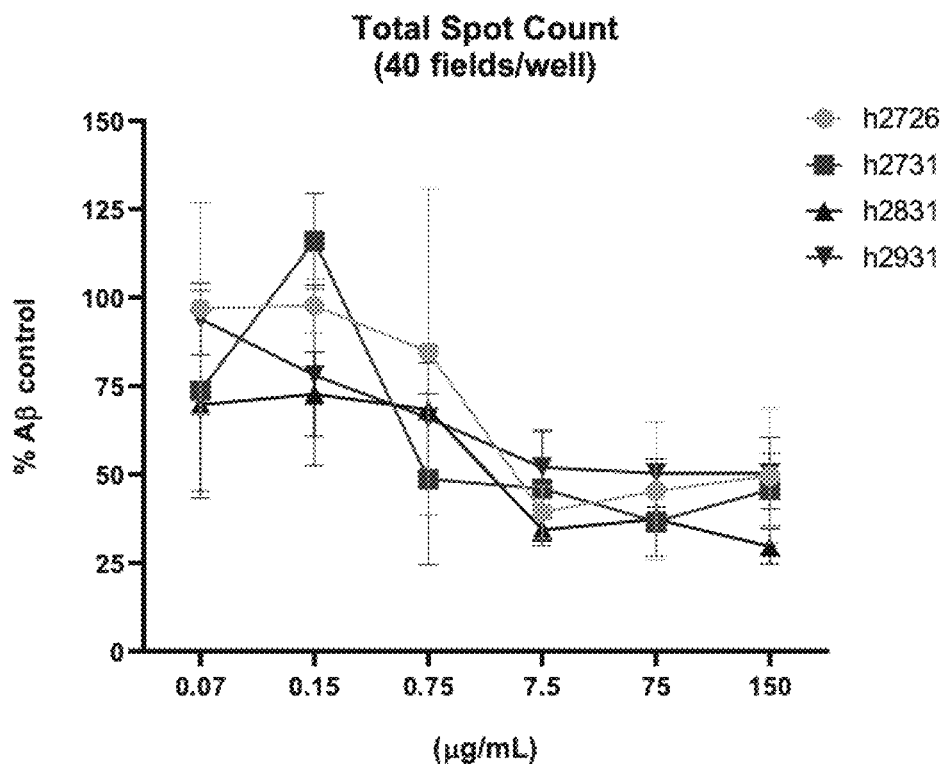
Figure 16:
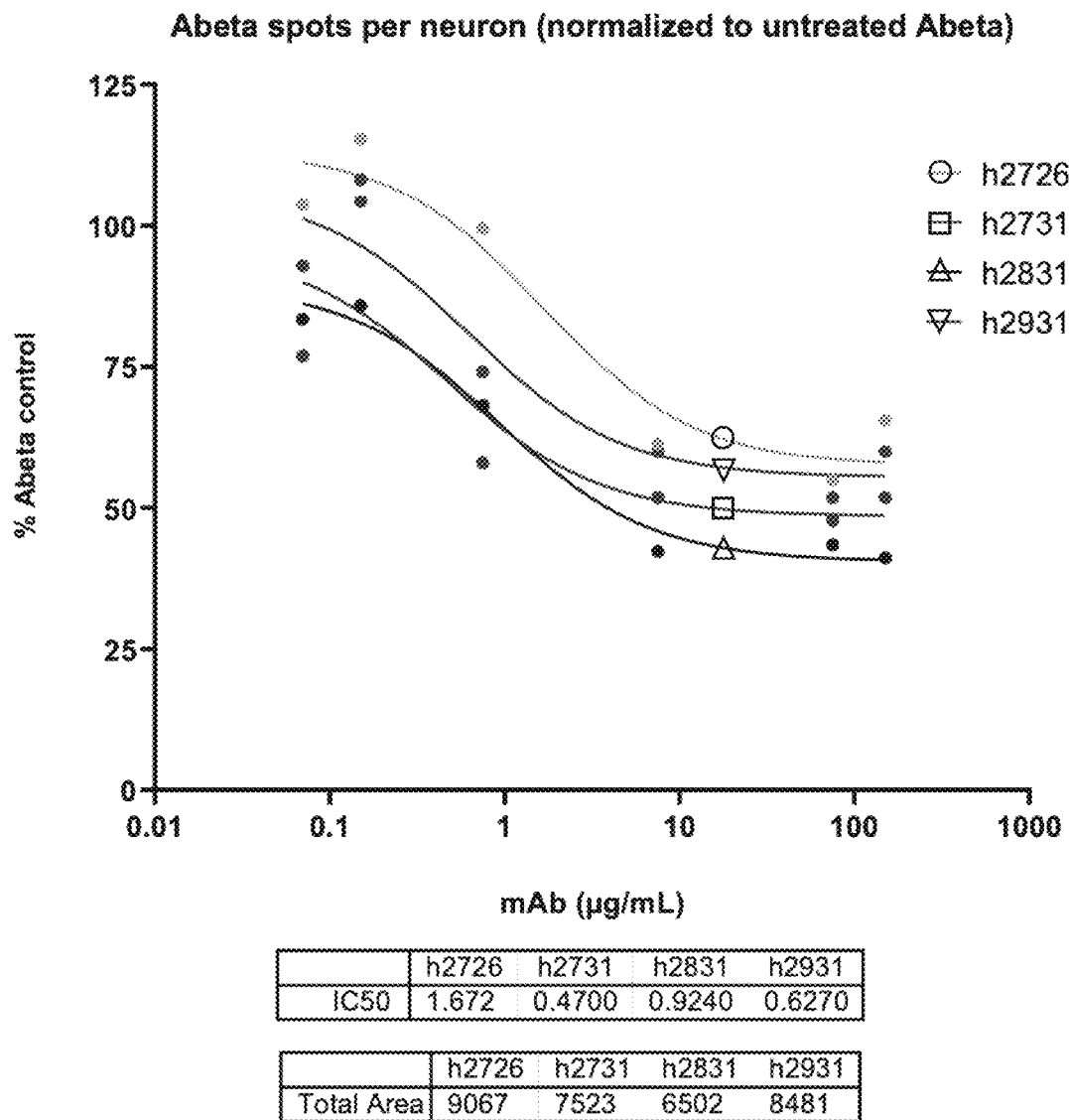
FIG. 16 shows a graph representing the percentage of Aβ spots per neuron with increasing concentration of 2726, 2731, 2831 and 2931 normalized by +/−Aβ addition.
Figure 23:
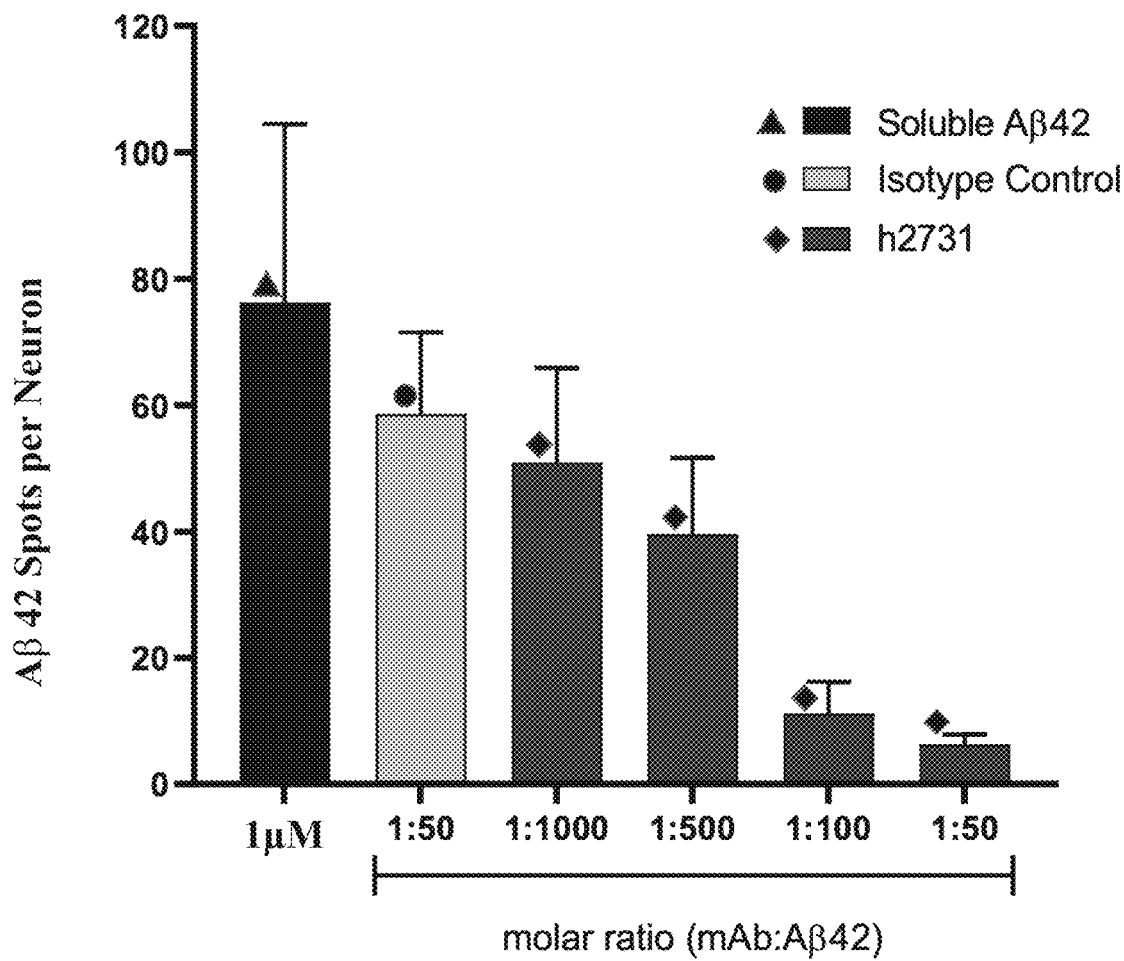
FIG. 23 shows quantification of binding of soluble Aβ to rat hippocampal neurons in the presence of antibody.

High-content imaging (HCI) analysis was performed to quantify soluble Aβ neuritic binding spots using Operetta HCl CLS instrument (Perkin Elmer; modified Neurite Outgrowth algorithm: 40×H$_2$O objective; 25-40 fields per well in microplate format; (n=3) per condition. MAP2 and NeuN neuronal markers were used to each trace neurite tree and count cell body number per optical field (e.g., with microtubule-associated protein 2 (Abcam; Cambridge, UK), and NeuN (EMD Millipore) primary antibodies followed by AlexaFluor (Thermo Fisher Scientific) secondary detection antibodies). Neuritic Aβ spots were detected using various monoclonal and polyclonal Aβ antibodies (e.g., mouse monoclonal anti-Aβ antibody MabN254 (EMD Millipore)) followed by AlexaFluor (Thermo Fisher Scientific) secondary detection antibodies or streptavidin-AF488 for biotinylated Aβ material. FIG. 15A and FIG. 15B show that increasing concentrations of anti-Aβ antibody reduces the number of spots per neuron, indicating activity against Aβ. FIG. 23 shows h2731 effectively blocked the binding of soluble Aβ aggregates to rat hippocampal synapses (Aβ42 spots per neuron) in a concentration-dependent manner. The effect of h2731 was detected at molar mAb:Aβ42 ratios as low as 1:500 (p<0.05) and reached >90% blockade of binding at 1:50 molar ratios (p<0.001) relative to Aβ42 alone (no mAb preincubation). Data shown in Table 14.

TABLE 14

| | Soluble Aβ 1 μM | Isotype Control 1:50 | h2731 1:1000 | h2731 1:500 | h2731 1:100 | h2731 1:50 |
|---|---|---|---|---|---|---|
| Mean (Aβ spots per neuron) | 76.3 | 58.7 | 51.0 | 39.7 | 11.3 | 6.3 |
| SD | 28.2 | 12.9 | 14.9 | 12.1 | 4.9 | 1.5 |

Example 12. Anti-Aβ Antibody Binding to Native and Modified Aβ Species

Cryostat sections of human AD brain were thaw-mounted onto poly-D-lysine coated coverslips and placed in 24-well tissue culture plates and incubated with test antibodies for 1 hour at 37° C. 5% $CO_2$. Primary mouse microglial cells were then seeded at 800,000 cells/ml, and the cultures were maintained at 37° C. 5% $CO_2$ for 72 hours. Media was carefully aspirated, and sections washed with PBS. The sections were resuspended in 8M urea for quantification by ELISA for $Aβ_{pE3-42}$ (Immuno-Biological Laboratories, Minneapolis, Minn.), or MSD for $Aβ_{1-42}$ (Meso Scale Diagnostics, Rockland, Md.). The Immuno-Biological Laboratories $Aβ_{pE3-42}$ ELISA kit specifically detects the pE3-42 species with no detectable signal for full-length Aβ.

Figure 27:
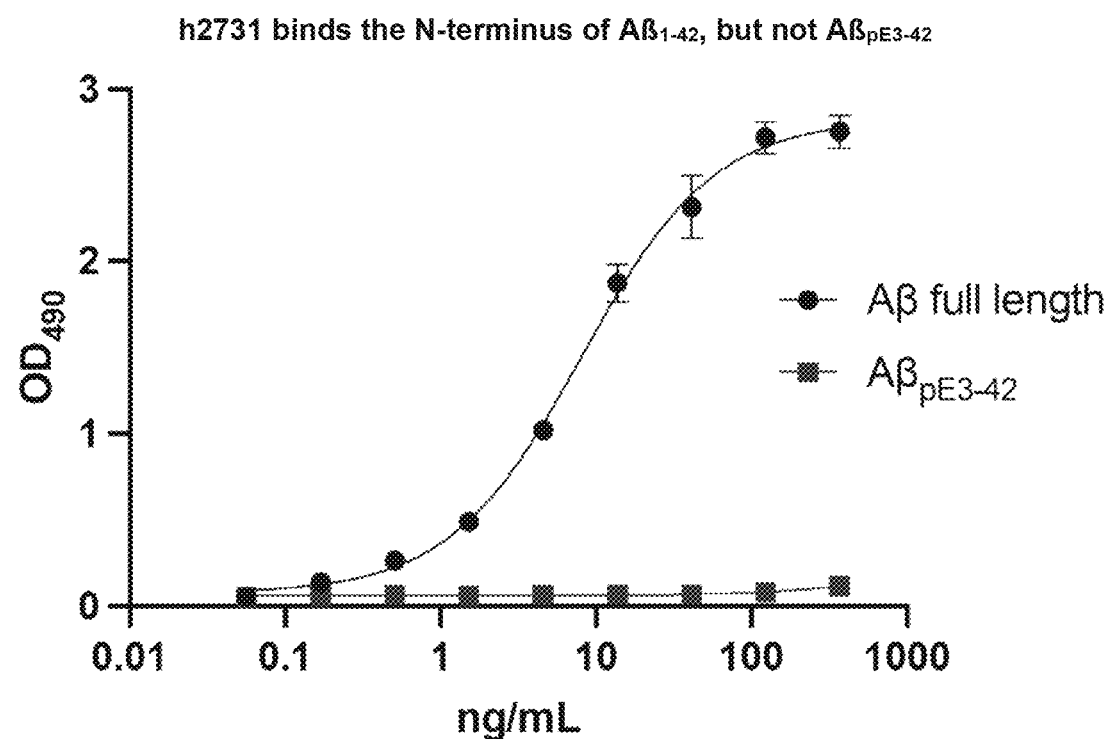
FIG. 27 shows that h2731 binds the N-terminus of $A\beta_{1-42}$ but not $A\beta_{pE3-42}$.

FIG. 27 demonstrates that h2731 binds with high apparent affinity to the N-terminus of full length Aβ but not directly to pyroglutamate-modified Aβ ($Aβ_{pE3-42}$). h2731 bound with a half-maximal effective concentration ($EC_{50}$) of 8.1 ng/mL (54 pM) to fibrillar Aβ species with an unmodified N-terminus ($Aβ_{1-42}$). h2731 demonstrated no detectable binding to $Aβ_{pE3-42}$ up to 100 ng/ml.

Example 13. In Vitro Phagocytic-Mediated Clearance—THP-1 Human Monocyte-Mediated Uptake of $Aβ_{1-42}$ Protofibrils Synthetic protofibrils of $Aβ_{1-42}$ containing an S26C mutation were generated as described in Paranjape et al., ACS Chem. Neurosci. 2012, 3, 302-311. Briefly, Aβ peptides were dissolved in 100% hexafluoroisopropanol (HFIP) (SigmaAldrich, St. Louis, Mo.) at 1 mM, aliquoted into sterile microcentrifuge tubes, and evaporated uncovered at room temperature overnight in a fume hood. The following day, the aliquots were vacuum-centrifuged to remove any residual HFIP and stored in desiccant at −20° C. Some Aβ peptides were treated with 100% trifluoroacetic acid and vacuum centrifuged prior to HFIP treatment. Aβ oligomers and fibrils obtained directly from lyophilized aliquots were prepared by resuspending lyophilized Aβ peptide aliquots in sterile anhydrous dimethyl sulfoxide (DMSO) (Sigma-Aldrich, St. Louis, Mo.) at 5 mM. For oligomer preparation the sample was diluted to 100 μM in sterile ice-cold phenol red-free Ham's F-12 cell culture medium with L-glutamine (F-12, Bioworld, Dublin, Ohio) and incubated for 24 hours at 4° C. For fibril preparation, the sample was diluted to 100 μM in 10 mM HCl and incubated for 24 hours at 37° C. Aβ concentrations in these preparations were based on dry peptide weight.

Mature protofibrils were conjugated to pHrodo Red Maleimide (Thermo Fisher) before use in in vitro phagocytic-mediated clearance assays.

Antibodies at concentrations of 6.25, 3.13, 1.56, 0.78, 0.39, 0.20, 0.098, and 0.049 μg/ml were preincubated for 30 min at room-temperature with pHrodo-$Aβ_{1-42}$ protofibrils, followed by the addition of THP-1 phagocytic cells. After a 3-hour incubation at 37° C. and 5% $CO_2$, antibody-mediated phagocytic-mediated clearance was assessed by measuring cellular pHrodo signal via flow cytometry.

Figure 28A:
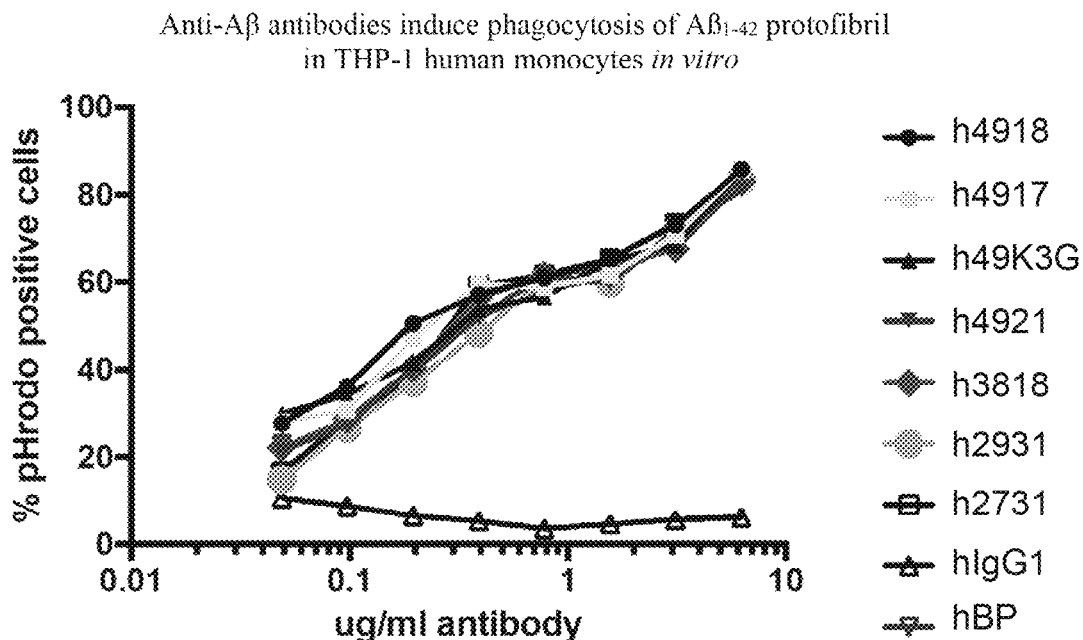
FIGS. 28A and 28B show that antibodies of the present invention induce phagocytosis of $A\beta_{1-42}$ protofibrils in THP-1 human monocytes in vitro.
Figure 28B:
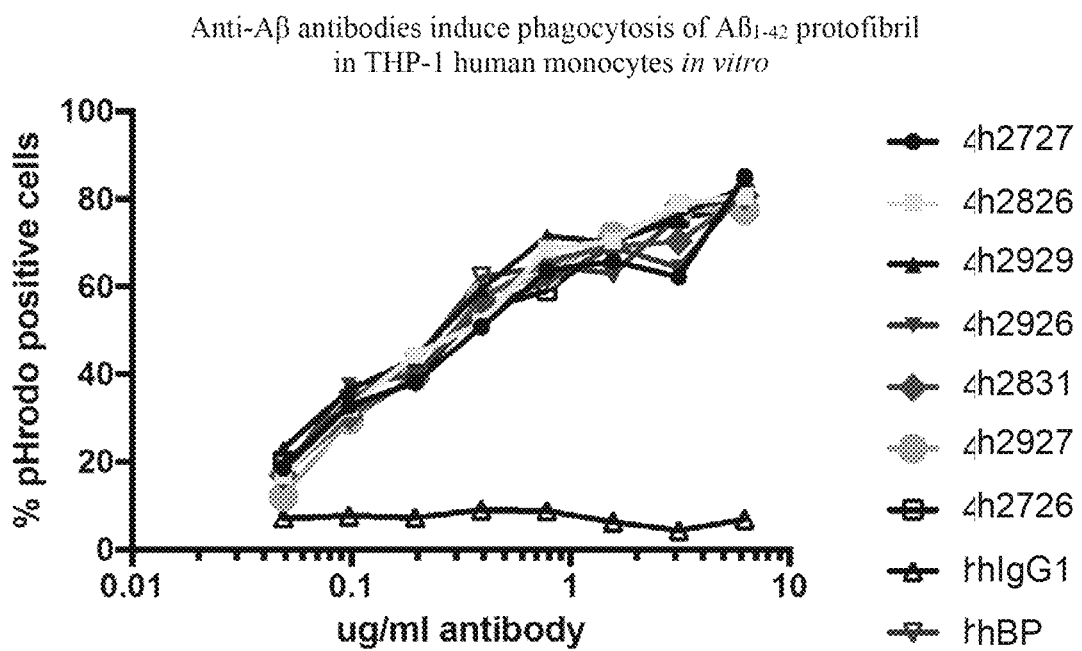

As shown in FIG. 28A and FIG. 28B, anti-Aβ antibodies exhibited $Aβ_{1-42}$ protofibril phagocytic activity in a concentration-dependent fashion. These results suggest that antibodies of the present invention may be able to drive $Aβ_{1-42}$ clearance in brain tissue.

Example 14. Distribution of Total and Pyroglutamate-Modified Aβ in Brain Tissue from Advanced AD Patients Ex vivo IHC methods as described above and herein were conducted on AD brain tissue to determine the distribution of $Aβ_{1-xx}$ (detected with an N-terminal anti-Aβ antibody) and anti-$Aβ_{pE3-42}$.

Figure 29A:
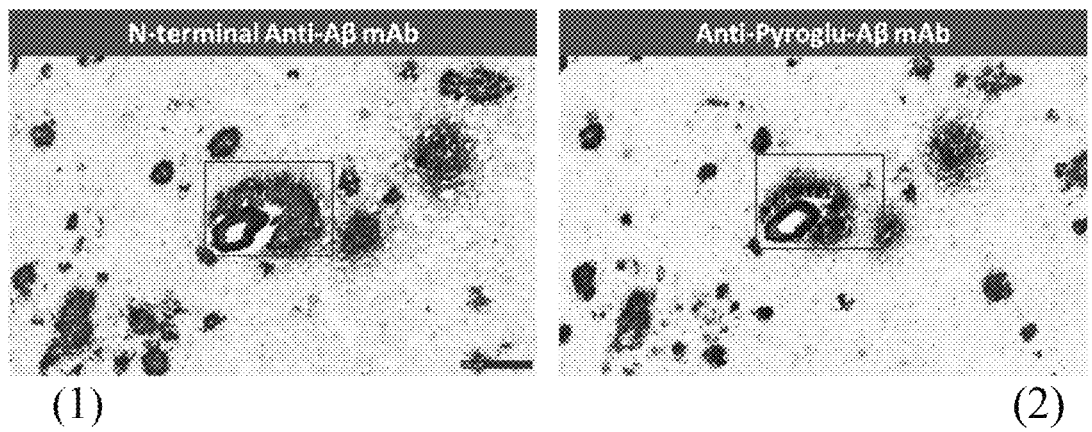
FIG. 29A and FIG. 29B show the distribution pattern of $A\beta_{1-XX}$, as measured by an N-terminal anti-Ab antibody, compared to $A\beta_{pE3-42}$ in human AD brain tissue.

Evaluation of $Aβ_{1-xx}$ and $Aβ_{pE3-42}$ confirmed widespread distribution of both species in tissue from patients with advanced stage AD. The distribution pattern (FIG. 29A(1) and FIG. 29A(2) (and magnified FIG. 29B(1) and FIG. 29B(2), respectively)) and quantification (FIG. 29C) of the percent area covered by $Aβ_{1-xx}$ compared to $Aβ_{pE3-42}$ were consistent with prior studies, suggesting that $Aβ_{pE3-42}$ represents a relatively smaller pool of modified Aβ intermingled with the unmodified Aβ targeted by N-terminal Aβ antibodies. $Aβ_{pE3-42}$ is shown in FIG. 29A(2) and FIG. 29B(2), and intact N-terminal Aβ is shown in FIG. 29A(1) and FIG. 29B(1). Anti-$Aβ_{pE3-42}$ antibody did not cross-react with $Aβ_{1-42}$ (data not shown).

Figure 29B:
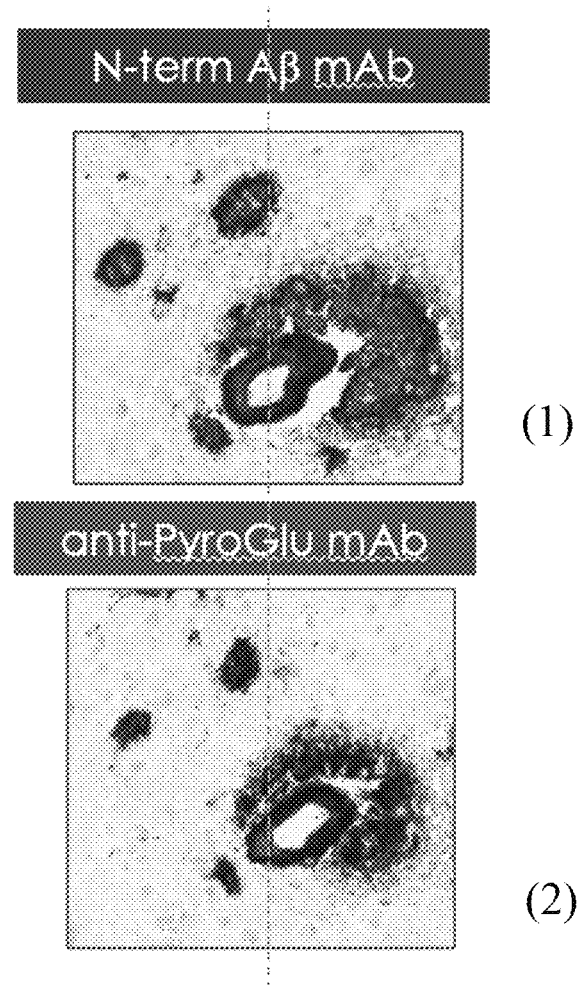
Figure 29C:
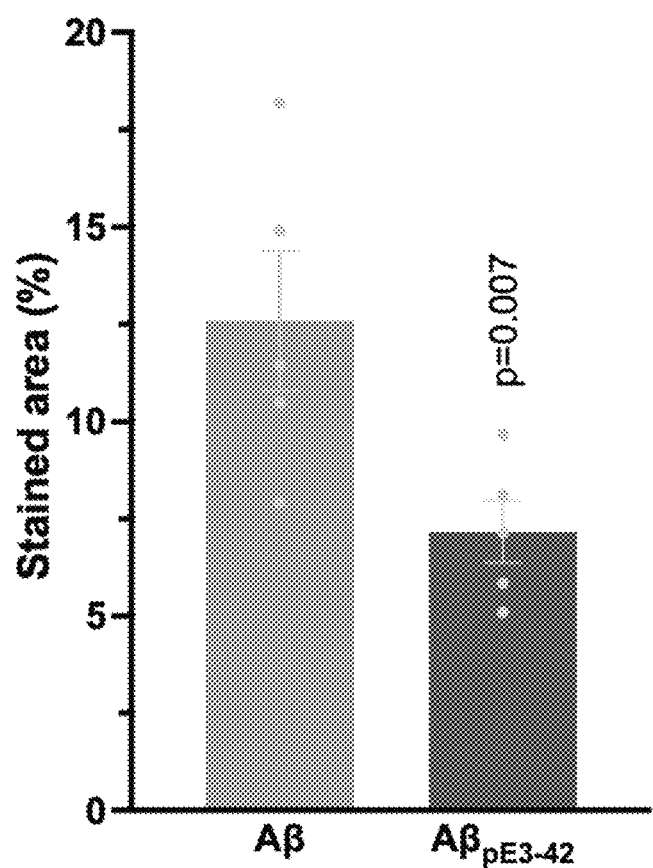
FIG. 29C shows the quantification of the percent area covered by $A\beta_{1-XX}$ compared to $A\beta_{pE3-42}$ in human AD brain tissue.

The box in FIG. 29A(1) and FIG. 29B(1) show an Aβ plaque with intact N-terminal Aβ and modified $Aβ_{pE3-42}$ proximal to blood vessel. Table 15 below reports the quantification of staining in plaques in FIG. 29B(1) and FIG. 29B(2) that is presented as graph in FIG. 29C. The difference between the mean values is statistically significant (p=0.007, paired two-tailed t-test).

TABLE 15

| Antibody | % Area Stained (Mean ± SD; N = 5) |
|---|---|
| anti-N-terminal Aβ antibody | 12.59 ± 4 |
| anti-$Aβ_{pE3-42}$ Aβ antibody | 7.17 ± 1.8 |

Example 15. Anti-Aβ Antibody h2731 Colocalizes with AβpE3-42 in AD Brain

Colocalization of h2731 immunostaining and $Aβ_{pE3-42}$ was assessed by immunofluorescent microscopy. An N-terminal anti-Aβ antibody (in this case h2731) was pre-conjugated to a Cy3-secondary anti-human antibody (Jackson Laboratories) before application to tissues. $Aβ_{pE3-42}$ was detected using a mouse anti-$Aβ_{pE3-42}$ antibody with a 488-AlexaFluor-conjugated anti-mouse secondary antibody. Slides were imaged using a Metamorph-assisted IX81 Olympus microscope connected to a Hamamatsu camera (C10600-10B).

Figure 30:
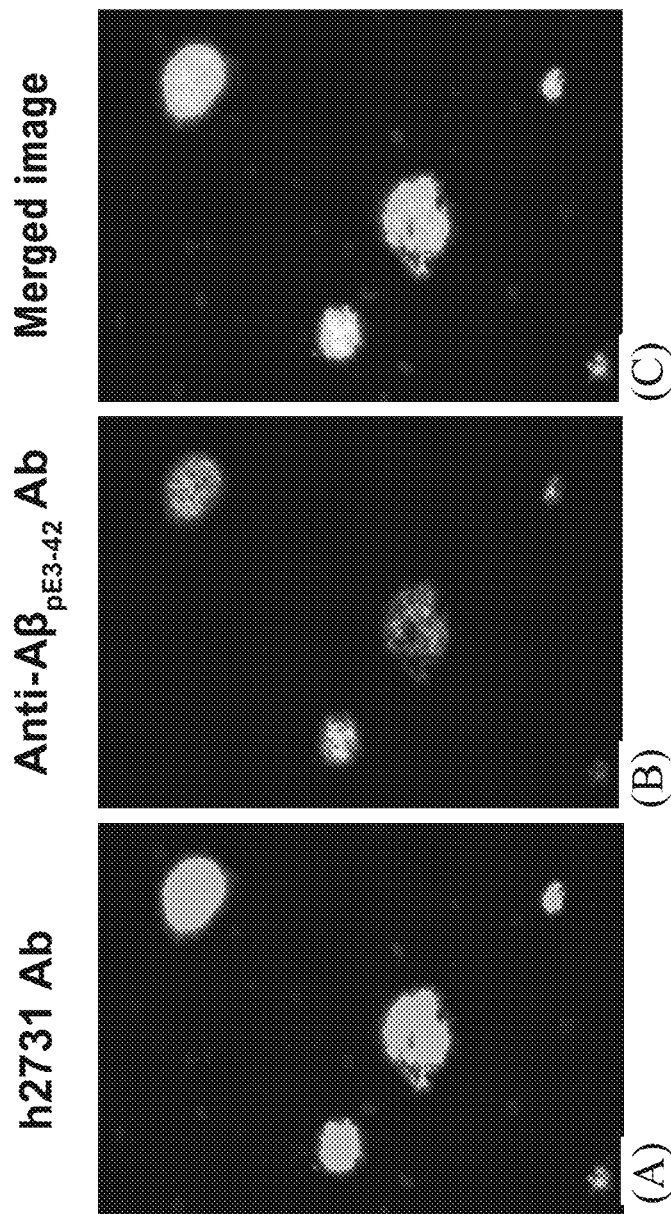
FIG. 30 shows localization of h2731 to Aβ plaques, localization of anti-$A\beta_{pE3-42}$ antibody signal to Aβ plaques, and colocalization of h2731 and anti-$A\beta_{pE3-42}$ antibody signal to Aβ plaques.

FIG. 30 (panel A) shows localization of h2731 to Aβ plaques; FIG. 30 (panel B) shows localization of anti-$Aβ_{pE3-42}$ antibody signal to Aβ plaques; and FIG. 30 (panel C) shows colocalization of h2731 and anti-$Aβ_{pE3-42}$ antibody signal to Aβ plaques. Overlapping signal appears more prominent in dense core regions of the plaques.

Example 16. Anti-Aβ Antibodies of the Present Invention Promote Aβ$_{pE3-42}$ Clearance from AD Brain Tissue Ex Vivo in a Dose-Dependent Manner with Higher Efficacy than Aducanumab Using methods described above and elsewhere herein, the ability of aducanumab and antibodies of the present invention (e.g., h2731) to clear Aβ$_{pE3-42}$ protein from AD brain tissue was assessed.

Figure 31A:
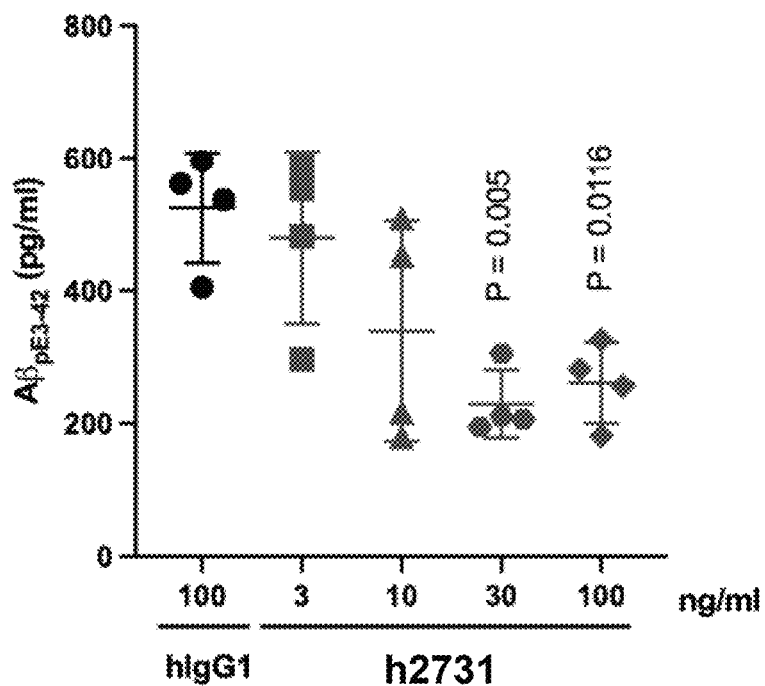
FIG. 31A and FIG. 31B show that anti-Aβ antibody h2731 promotes $A\beta_{pE3-42}$ clearance from AD brain tissue ex vivo in a dose-dependent manner with higher potency than aducanumab.

A physiologically relevant dose-response series of h2731 (3 ng/ml, 10 ng/ml, 30 ng/ml and 100 ng/ml) was incubated with AD patient brain tissue sections and primary mouse microglia for 72 hours. h2731 promoted Aβ$_{pE3-42}$ clearance in a concentration-dependent fashion. Results are presented in Table 16 below and FIG. 31A.

TABLE 16

| Antibody | Concentration (ng/ml) | Ave Aβ$_{pE3-42}$ (pg/ml) (n = 4) | Stdev |
|---|---|---|---|
| hIgG1 isotype | 100 | 524.34 | 83.36 |
| h2731 | 3 | 479.56 | 129.92 |
| h2731 | 10 | 339.06 | 165.44 |
| h2731 | 30 | 229.28 | 51.16 |
| h2731 | 100 | 261.15 | 60.81 | h2731 robustly promotes clearance of Aβ$_{pE3-42}$ from AD patient brain tissue sections by microglial phagocytosis in a concentration-dependent manner and during a relatively short incubation period (72 hours). Thus, the antibodies of the present invention promote ex vivo clearance of Aβ$_{pE3-42}$ from an AD patient brain at a concentration range expected to be reached with subcutaneous administration.

Figure 31B:
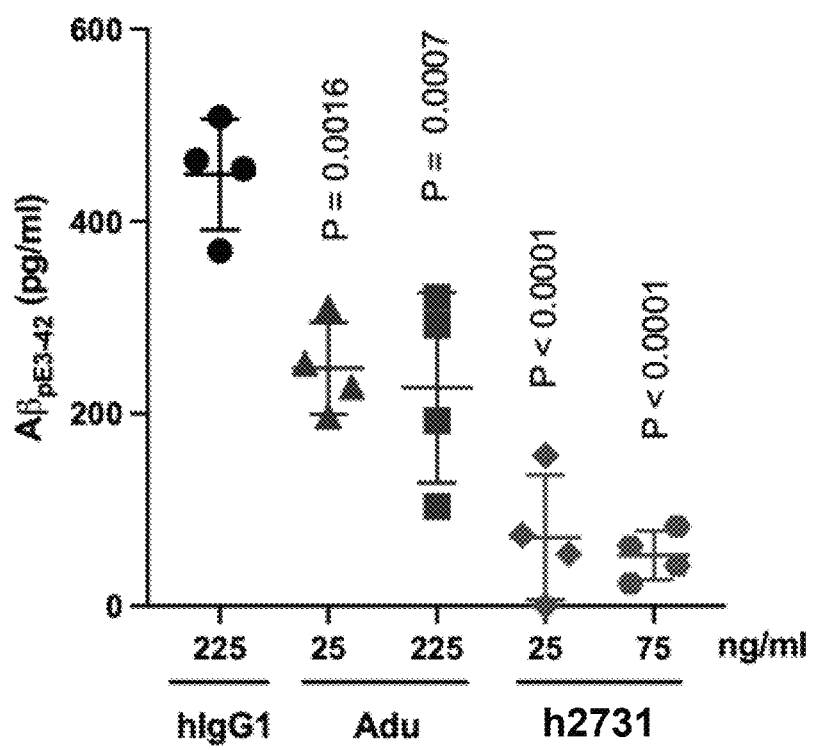

Another series of experiments were conducted comparing h2731 at 25 ng/ml and 75 ng/ml to aducanumab at 25 ng/ml and 225 ng/ml. Results are presented in Table 17 and FIG. 31B.

TABLE 17

| Antibody | Concentration (ng/ml) | Ave Aβ$_{pE3-42}$ (pg/ml) (n = 4) | Stdev |
|---|---|---|---|
| hIgG1 isotype | 225 | 449.11 | 58.14 |
| Adu | 225 | 227.30 | 98.95 |
| Adu | 25 | 247.34 | 48.06 |
| h2731 | 75 | 52.83 | 25.40 |
| h2731 | 25 | 71.31 | 64.93 | h2731 exhibited superior Aβ$_{pE3-42}$ clearance activity when compared to aducanumab, even at 9-fold lower concentrations.

Figure 32A:
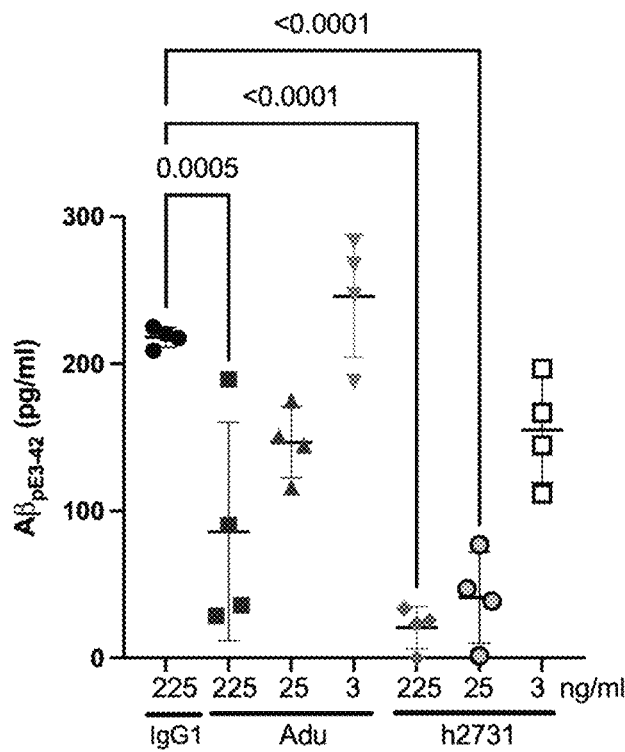
FIG. 32A shows the concentration dependence of h2731 and aducanumab clearance of $A\beta_{pE3-42}$ from AD brain tissue.

Another physiologically relevant dose-response series of h2731 and aducanumab (3 ng/ml, 25 ng/ml, and 225 ng/ml) was incubated with AD patient brain tissue sections and primary mouse microglia for 72 hours, both compared to IgG1 isotype control. While both h2731 and aducanumab promoted Aβ$_{pE3-42}$ clearance in a concentration-dependent fashion, h2731 again did so significantly more potently, with a p-value of <0.0001 at a 9-fold lower concentration than required for aducanumab to reach a p-value of 0.0005. Results are presented in Table 18 below as well as FIG. 32A.

TABLE 18

| Antibody | Concentration (ng/ml) | Ab$_{pE3-42}$ (pg/ml) | Stdev |
|---|---|---|---|
| hIgG1 isotype | 225 | 1.00 | 6.73 |
| Adu | 225 | 85.97 | 74.35 |
| Adu | 25 | 146.70 | 24.30 |
| Adu | 3 | 245.97 | 41.70 |
| h2731 | 225 | 20.60 | 14.44 |
| h2731 | 25 | 41.07 | 31.15 |
| h2731 | 3 | 154.95 | 35.89 |

Figure 32B:
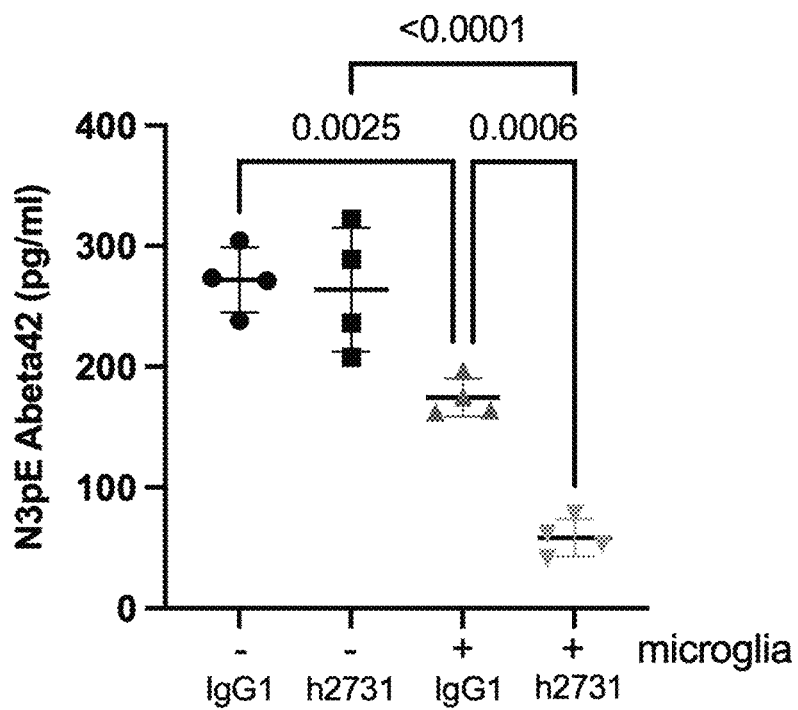
FIG. 32B shows that the effect of h2731 is microglia-dependent.

In order to verify that h2731-mediated ex vivo phagocytosis activity is microglia dependent, a +/−microglia experiment was performed. While microglia alone drive some Aβ$_{pE3-42}$ clearance from AD patient tissue sections, clearance is significantly more robust with the combination of h2731 and microglia. h2731 appears to require the presence of microglia for clearance activity, as h2731 alone has shows no activity without microglia. Results are presented in Table 19 and FIG. 32B.

TABLE 19

| Antibody | Concentration (ng/ml) | Ab$_{pE3-42}$ (pg/ml) | Stdev |
|---|---|---|---|
| hIgG1 isotype | 75 | 271.79 | 27.01 |
| h2731 | 75 | 263.70 | 51.28 |
| hIgG1 + Microglia | 75 | 174.58 | 15.75 |
| h2731 + Microglia | 75 | 58.37 | 15.53 |

Figure 33:
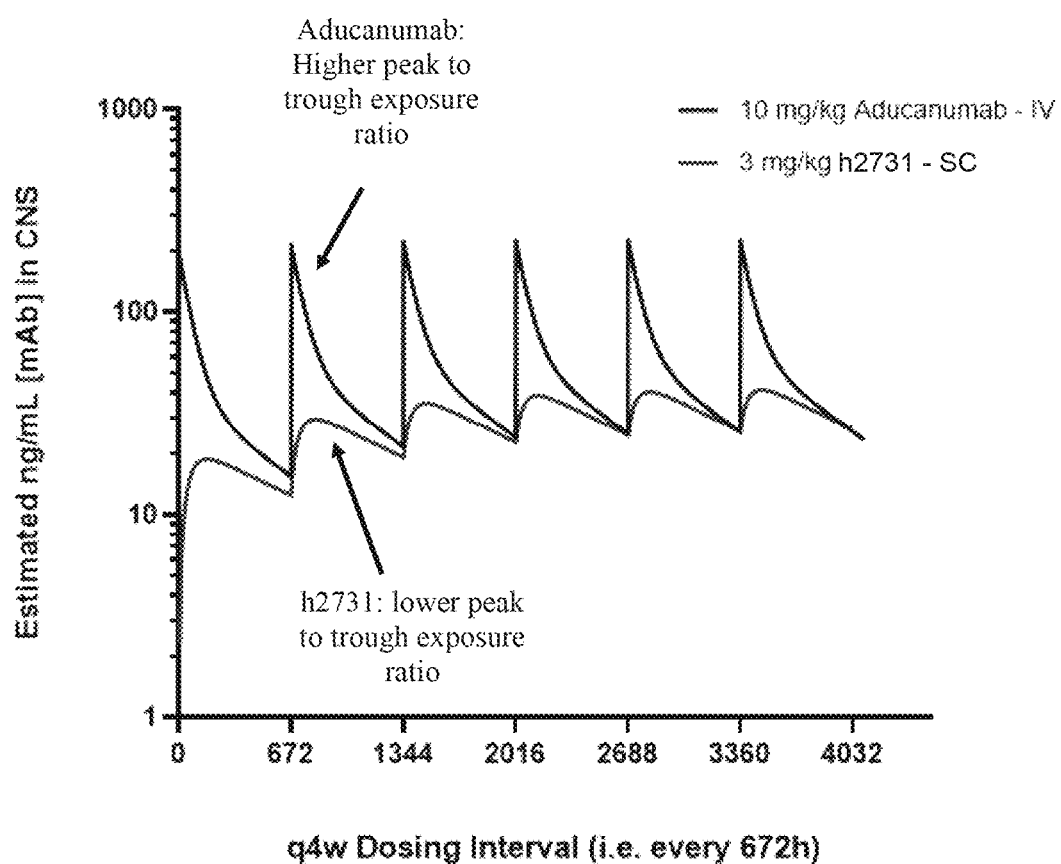
FIG. 33 compares predicted CNS exposure of h2731 and aducanumab with repeated dosing.

The tested antibody concentrations were based on CNS ranges estimated at 0.1% of steady-state plasma minimum and maximum concentrations from modeled pharmacokinetics following monthly administration of 3 mg/kg subcutaneous h2731 (25-75 ng/ml) or 10 mg/kg of intravenous aducanumab (25-225 ng/ml) in humans (FIG. 33).

Antibodies of the present invention promote ex vivo clearance of Aβ$_{pE3-42}$ from an AD patient brain at a concentration range expected to be reached with subcutaneous administration and with greater biological activity than aducanumab.

Figure 34:
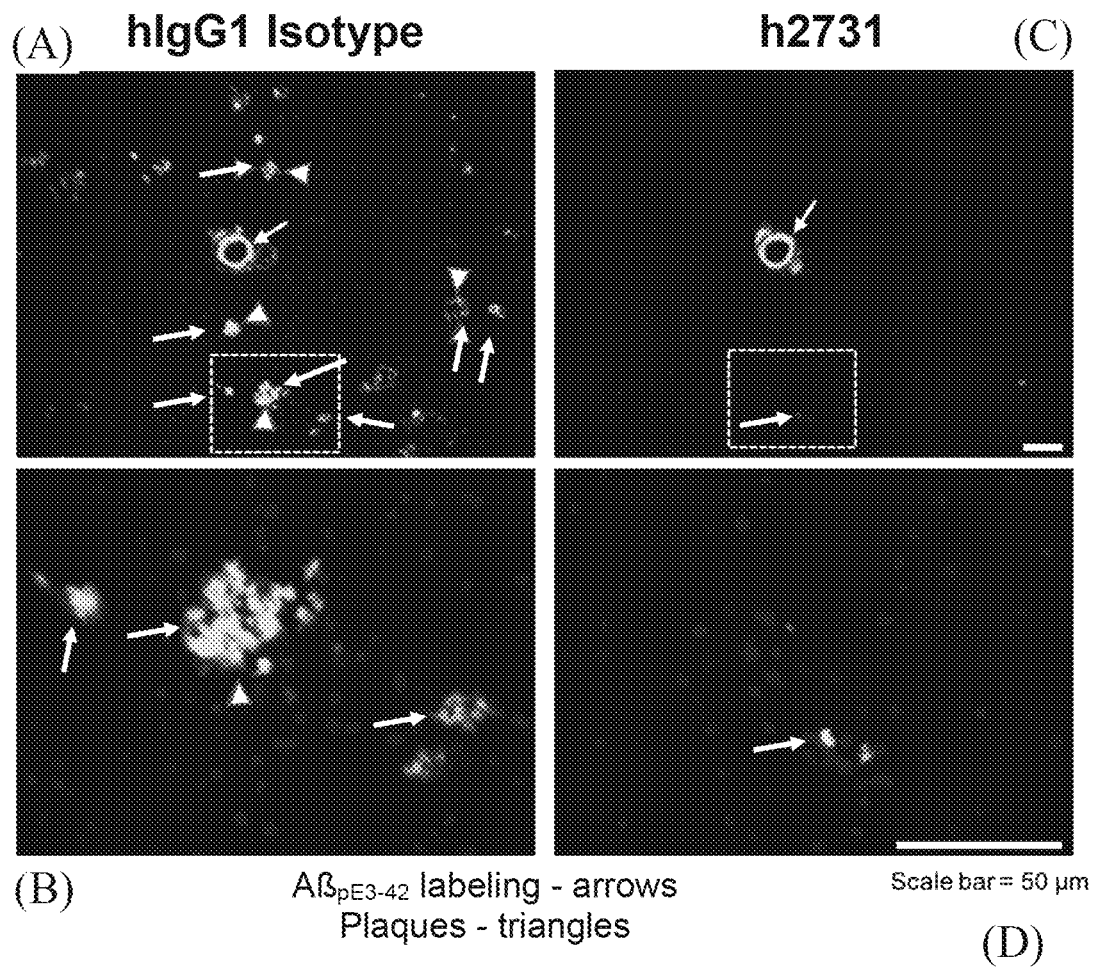
FIG. 34 shows that anti-Aβ antibody h2731 promotes clearance of plaques containing $A\beta_{pE3-42}$ in AD brain tissue ex vivo.

Antibody h2731 reduces Aβ$_{pE3-42}$ staining in AD brain. FIG. 34 shows that Aβ$_{pE3-42}$ (staining indicated by white arrows) was observed in plaques (white triangles) and associated with blood vessels (circular shape in FIG. 34A and FIG. 34C) in AD brain treated with human IgG isotype control antibody (FIG. 34A and FIG. 34B). Treatment with h2731 enhanced microglia-mediated reduction of Aβ$_{pE3-42}$ levels as evidenced by the reduction in plaques (FIG. 34C and FIG. 34D). Antibodies of the present invention, as exemplified by h2731, reduce plaques containing Aβ$_{pE3-42}$ in tissue.

Example 17. h2731 Target Engagement

Female APPxPS1 mice expressing a mutant human amyloid precursor protein (hAPP[V717I]) and a mutant human presenilin 1 (hPS1[A246E]) were used to evaluate the ability of h2731 and aducanumab to traverse the blood-brain-barrier subsequent to peripheral administration and bind to amyloid-beta (Aβ) plaques in the brain. The average age of the animals at the start of the study was 6.7 months. One day prior to drug administration all animals received an injection of an anti-CD4 antibody (20 mg/kg, intravenous) to prevent the formation of anti-drug antibodies in mice receiving h2731 or aducanumab, both of which are fully humanized antibodies. h2731 (3 or 10 mg/kg, subcutaneous, SC) or aducanumab (10 mg/kg, intravenous) were dosed weekly for three weeks and animals were euthanized one week later. Following transcardial perfusion with ice-cold saline, brains were extracted from the mice and flash frozen in 2-methylbutane on dry ice and stored at −80° C.

Serial sagittal 10 μm thick cryosections were generated using a Leica 3050S cryostat. The sections were directly thaw-mounted on positively charged glass slides and were stored at −20° C. until use. Prior to IHC, the slides were immersed in 10% neutral buffered formalin solution for 10 minutes at 4° C., rinsed in PBS, then incubated for an hour at 37° C. in a glucose oxidase solution (20 mM beta D(+) glucose, 2 mM sodium azide, and 2 units/mL glucose oxidase in 1×PBS). The slides were rinsed 3 times for 5 minutes in PBS before they were transferred onto staining racks for processing in an automated stainer. A biotin-SP-conjugated goat anti human IgG (H+L) (Jackson ImmunoResearch Laboratories #109-065-088) was used to detect h2731 or aducanumab in APPxPS1 brain tissue. The staining was performed in an automated Leica Bond Rx Stainer (Leica Biosystems), using the Bond Research Kit (DS980, Leica Biosystems). Hematoxylin counter-staining of nuclei was subsequently applied to sections before dehydration in an ascending series of alcohols, clearing in xylene, cover-slipping, and air-drying. The whole sections were imaged using a NanoZoomer 2.0HT slide scanner (Hamamatsu Corporation, Japan). Morphometric analysis of the digitalized images was carried out using Halo software (V2.1.1537). After delineation of the cerebral cortex as region of interest, the percent of stained tissue area was determined. Data are presented in Table 20.

TABLE 20

|  | h2731 | | Aducanumab |
|---|---|---|---|
|  | 3 mg/kg, SC | 10 mg/kg, SC | 10 mg/kg, IV |
| Plaque Binding (% ROI) | 0.070 ± 0.025 | 0.079 ± 0.034 | 0.060 ± 0.034 |

ROI = region of analysis. All data represent mean ± SD of n = 5 animals per group Reduction in numbers or size of Aβ plaques in Alzheimer's Disease may correlate with slowing or reversing of disease progression. The ability of the anti-Aβ antibodies of the present invention to bind to and clear Aβ in vivo following peripheral administration supports the potential utility of these antibodies as therapeutic agents.

Thus, the antibodies of the present invention promote microglia-mediated clearance of $A\beta_{1-42}$ in brain tissue from patients with AD. Although antibodies of the present invention may not target the pyroglutamate modification directly, they may effectively clear $A\beta_{pE3-42}$ at concentrations predicted to be clinically relevant and with higher potency and greater biologic activity than aducanumab, as exemplified by h2731. Clearance of pyroglutamate species by these antibodies may be due to the ability of microglia to recognize opsonized plaques and engulf large particles with diverse content. The antibodies of the present invention may therefore clear other neurotoxic elements co-deposited in plaques by this same mechanism.

All publications (including GenBank Accession numbers, UniProtKB/Swiss-Prot accession numbers and the like), patents and patent applications cited are herein incorporated by reference in their entirety for all purposes to the same extent as if each individual publication, patent and patent application was specifically and individually indicated to be incorporated by reference in its entirety for all purposes. In the event of any variance in sequences associated with Genbank and UniProtKB/Swiss-Prot accession numbers and the like, the application refers to the sequences associated with the cited accession numbers as of the effective filing date of the application meaning the actual filing date or earlier date of a priority application disclosing the relevant accession number. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

What is claimed is:

1. An antibody or an antigen binding fragment thereof that specifically binds to Aβ peptide, comprising a heavy chain variable region comprising heavy chain CDR1, CDR2, and CDR3 and a light chain variable region comprising light chain CDR1, CDR2, and CDR3, wherein
heavy chain CDR1 comprises the amino acid sequence of SEQ ID NO: 19,
heavy chain CDR2 comprises the amino acid sequence of SEQ ID NO: 21,
heavy chain CDR3 comprises the amino acid sequence of SEQ ID NO: 25,
light chain CDR1 comprises the amino acid sequence of SEQ ID NO: 29,
light chain CDR2 comprises the amino acid sequence of SEQ ID NO: 34, and
light chain CDR3 comprises the amino acid sequence of SEQ ID NO: 38.

2. The antibody or antigen binding fragment thereof of claim 1, wherein the heavy chain variable region, excluding the CDRs, is at least 95% identical to the amino acid sequence of SEQ ID NO: 5, and wherein the light chain variable region, excluding the CDRs, is at least 95% identical to the amino acid sequence of SEQ ID NO: 9.

3. The antibody or antigen binding fragment thereof of claim 2, wherein the heavy chain variable region, excluding the CDRs, is at least 98% identical to the amino acid sequence of SEQ ID NO: 5, and wherein the light chain variable region, excluding the CDRs, is at least 98% identical to the amino acid sequence of SEQ ID NO: 9.

4. The antibody or antigen binding fragment thereof of claim 3, wherein the heavy chain variable region comprises the amino acid sequence of SEQ ID NO: 5, and wherein the light chain variable region comprises the amino acid sequence of SEQ ID NO: 9.

5. The antibody or antigen binding fragment thereof of claim 4 further comprising a heavy chain constant region comprising an amino acid sequence at least 95% identical to SEQ ID NO: 40.

6. The antibody or antigen binding fragment thereof of claim 4 further comprising a light chain constant region comprising an amino acid sequence at least 95% identical to SEQ ID NO: 41.

7. The antibody or antigen binding fragment thereof of claim 5 further comprising a light chain constant region comprising an amino acid sequence at least 95% identical to SEQ ID NO: 41.

8. The antibody or antigen binding fragment thereof of claim 1, wherein the antibody is a humanized IgG1.

9. The antibody or antigen binding fragment thereof of claim 1, wherein the antibody is a full antibody, a chimeric antibody, a CDR-grafted antibody, or a recombinant antibody.

10. The antibody or antigen binding fragment thereof of claim 1, wherein the antigen binding fragment is a Fab, Fab', F(ab')2, Fabc, or Fv.

11. The antibody or antigen binding fragment thereof of claim 1, wherein the antibody or antigen binding fragment thereof specifically binds to an epitope having an amino acid sequence including three or more amino acid positions from amino acids 1-7 of Aβ (SEQ ID NO: 84).

12. A pharmaceutical composition, comprising:
   a pharmaceutically effect amount of the antibody or antigen binding fragment thereof of claim 1; and
   a pharmaceutically acceptable carrier or diluent.

13. A humanized IgG1 antibody or an antigen binding fragment thereof that specifically binds to Aβ peptide, comprising:
   a) a heavy chain comprising a heavy chain variable region comprising the amino acid sequence of SEQ ID NO: 5; and
   b) a light chain comprising a light chain variable region comprising the amino acid sequence of SEQ ID NO: 9.

14. The humanized IgG1 antibody or antigen binding fragment thereof of claim 13, wherein the antibody is a full antibody, a chimeric antibody, a CDR-grafted antibody, or a recombinant antibody.

15. The humanized IgG1 antibody or antigen binding fragment thereof of claim 13, wherein the antigen binding fragment is a Fab, Fab', F(ab')2, Fabc, or Fv.

16. A pharmaceutical composition, comprising:
   a pharmaceutically effective amount of the humanized IgG1 antibody or antigen binding fragment thereof of claim 13; and
   a pharmaceutically acceptable carrier or diluent.

17. A humanized IgG1 antibody that specifically binds to Aβ peptide, comprising:
   a) a heavy chain comprising
      a variable region comprising the amino acid sequence of SEQ ID NO: 5, and
      a constant region comprising the amino acid sequence of SEQ ID NO: 40 with or without the C-terminal lysine; and
   b) a light chain comprising
      a variable region comprising the amino acid sequence of SEQ ID NO: 9, and
      a constant region comprising the amino acid sequence of SEQ ID NO: 41.

18. The humanized IgG1 antibody of claim 17, wherein the antibody is a full antibody, a chimeric antibody, a CDR-grafted antibody, or a recombinant antibody.

19. A pharmaceutical composition, comprising:
   a pharmaceutically effective amount of the humanized IgG1 antibody of claim 17; and
   a pharmaceutically acceptable carrier or diluent.

* * * * *

SEQUENCE LISTING

```
<160> NUMBER OF SEQ ID NOS: 102

<210> SEQ ID NO 1
<211> LENGTH: 112
<212> TYPE: PRT
<213> ORGANISM: Artificial Sequence
<220> FEATURE:
<223> OTHER INFORMATION: Synthetic peptide

<400> SEQUENCE: 1

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Gln Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Gly
                 85                  90                  95

Thr His Trp Pro Trp Thr Phe Gly Gln Gly Thr Lys Val Glu Ile Lys
            100                 105                 110

<210> SEQ ID NO 2
<211> LENGTH: 112
<212> TYPE: PRT
<213> ORGANISM: Artificial Sequence
<220> FEATURE:
<223> OTHER INFORMATION: Synthetic peptide

<400> SEQUENCE: 2

Asp Val Val Met Thr Gln Ser Pro Leu Ser Leu Pro Val Thr Leu Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Val Glu Ile Lys
            100                 105                 110

<210> SEQ ID NO 3
<211> LENGTH: 119
<212> TYPE: PRT
<213> ORGANISM: Artificial Sequence
<220> FEATURE:
<223> OTHER INFORMATION: Synthetic peptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Ser Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: Synthetic peptide

```
<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Ser Trp Val Arg Gln Ala Pro Gly Lys Gly Leu Glu Trp Val
        35                  40                  45

Ala Ser Val Arg Ser Gly Ser Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Thr Ser Asp Tyr Trp Gly Gln Gly
            100                 105                 110

Thr Leu Val Thr Val Ser Ser
        115

<210> SEQ ID NO 5
<211> LENGTH: 119
<212> TYPE: PRT
<213> ORGANISM: Artificial Sequence
<220> FEATURE:
<223> OTHER INFORMATION: Synthetic peptide

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Ser Trp Val Arg Gln Ala Pro Gly Lys Gly Leu Glu Trp Val
        35                  40                  45

Ala Ser Val Arg Ser Gly Ser Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Thr Gly Thr Ser Asp Tyr Trp Gly Gln Gly
            100                 105                 110

Thr Leu Val Thr Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: Synthetic peptide

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Ser Trp Val Arg Gln Ala Pro Gly Lys Gly Leu Glu Trp Val
        35                  40                  45
```

```
Ala Ser Val Arg Ser Gly Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Tyr Asp His Tyr Ser Gly Thr Ser Asp Tyr Trp Gly Gln Gly
                100                 105                 110

Thr Leu Val Thr Val Ser Ser
            115

<210> SEQ ID NO 7
<211> LENGTH: 119
<212> TYPE: PRT
<213> ORGANISM: Artificial Sequence
<220> FEATURE:
<223> OTHER INFORMATION: Synthetic peptide

<400> SEQUENCE: 7

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Asn Tyr
             20                  25                  30

Gly Met Ser Trp Val Arg Gln Ala Pro Gly Lys Gly Leu Glu Trp Val
         35                  40                  45

Ala Ser Val Arg Ser Gly Gly Ser Arg Thr Tyr Tyr Ser Asp Asn Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Tyr Asp His Tyr Ser Gly Ser Ser Asp Tyr Trp Gly Gln Gly
                100                 105                 110

Thr Leu Val Thr Val Ser Ser
            115

<210> SEQ ID NO 8
<211> LENGTH: 112
<212> TYPE: PRT
<213> ORGANISM: Artificial Sequence
<220> FEATURE:
<223> OTHER INFORMATION: Synthetic peptide

<400> SEQUENCE: 8

Asp Val Val Met Thr Gln Ser Pro Leu Ser Leu Pro Val Thr Pro Gly
  1               5                  10                  15

Glu Pro Ala Ser Ile Ser Cys Lys Ser Ser Gln Ser Leu Leu Asp Tyr
             20                  25                  30

Asp Gly Lys Thr Tyr Leu Asn Trp Leu Leu Gln Lys Pro Gly Gln Ser
         35                  40                  45

Pro Gln Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Val Glu Ile Lys
                100                 105                 110
```

<210> SEQ ID NO 9
<211> LENGTH: 112
<212> TYPE: PRT
<213> ORGANISM: Artificial Sequence
<220> FEATURE:
<223> OTHER INFORMATION: Synthetic peptide

<400> SEQUENCE: 9

```
Asp Val Val Met Thr Gln Ser Pro Leu Ser Leu Pro Val Thr Leu Gly
1               5                   10                  15

Glu Pro Ala Ser Ile Ser Cys Lys Ser Ser Gln Ser Leu Leu Asp Tyr
            20                  25                  30

Asp Gly Lys Thr Tyr Leu Asn Trp Leu Leu Gln Lys Pro Gly Gln Ser
        35                  40                  45

Pro Gln Arg Leu Ile Tyr Arg Val Thr Asn Arg Asp Thr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Ser Phe Gly Gln Gly Thr Lys Val Glu Ile Lys
            100                 105                 110
```

<210> SEQ ID NO 10
<211> LENGTH: 112
<212> TYPE: PRT
<213> ORGANISM: Artificial Sequence
<220> FEATURE:
<223> OTHER INFORMATION: Synthetic peptide

<400> SEQUENCE: 10

```
Asp Val Val Met Thr Gln Ser Pro Leu Ser Leu Pro Val Thr Leu Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Arg Val Thr Asn Arg Asp Thr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110
```

<210> SEQ ID NO 11
<211> LENGTH: 112
<212> TYPE: PRT
<213> ORGANISM: Artificial Sequence
<220> FEATURE:
<223> OTHER INFORMATION: Synthetic peptide

<400> SEQUENCE: 11

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Asp Tyr
            20                  25                  30
```

```
Asp Gly Lys Thr Tyr Leu Asn Trp Leu Leu Gln Arg Pro Gly Gln Ser
            35                  40                  45

Pro Gln Arg Leu Ile Tyr Lys Val Ser Asn Arg Asp Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Ser His Phe Pro Arg Ser Tyr Gly Gln Gly Thr Lys Val Glu Ile Lys
            100                 105                 110
```

<210> SEQ ID NO 12
<211> LENGTH: 112
<212> TYPE: PRT
<213> ORGANISM: Artificial Sequence
<220> FEATURE:
<223> OTHER INFORMATION: Synthetic peptide

<400> SEQUENCE: 12

```
Asp Val Val Met Thr Gln Ser Pro Leu Ser Leu Pro Val Thr Leu Gly
 1                5                  10                  15

Glu Pro Ala Ser Ile Ser Cys Lys Ser Ser Gln Ser Leu Met Asp Thr
                 20                  25                  30

Asp Gly Lys Thr Tyr Leu Asn Trp Leu Leu Gln Lys Pro Gly Gln Ser
            35                  40                  45

Pro Gln Arg Leu Ile Tyr Lys Val Ser Asn Arg Glu Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Val Glu Ile Lys
            100                 105                 110
```

<210> SEQ ID NO 13
<211> LENGTH: 112
<212> TYPE: PRT
<213> ORGANISM: Artificial Sequence
<220> FEATURE:
<223> OTHER INFORMATION: Synthetic peptide

<400> SEQUENCE: 13

```
Asp Val Val Met Thr Gln Ser Pro Leu Ser Leu Pro Val Thr Pro Gly
 1                5                  10                  15

Glu Pro Ala Ser Ile Ser Cys Lys Ser Ser Gln Ser Leu Leu Asp Tyr
                 20                  25                  30

Asp Gly Lys Thr Tyr Leu Asn Trp Leu Leu Gln Lys Pro Gly Gln Ser
            35                  40                  45

Pro Gln Arg Leu Ile Tyr Lys Val Ser Asn Arg Asp Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Ser Phe Gly Gln Gly Thr Lys Val Glu Ile Lys
            100                 105                 110
```

<210> SEQ ID NO 14

```
<211> LENGTH: 112
<212> TYPE: PRT
<213> ORGANISM: Artificial Sequence
<220> FEATURE:
<223> OTHER INFORMATION: Synthetic peptide

<400> SEQUENCE: 14

Asp Val Val Met Thr Gln Ser Pro Leu Ser Leu Pro Val Thr Leu Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

<210> SEQ ID NO 15
<211> LENGTH: 112
<212> TYPE: PRT
<213> ORGANISM: Artificial Sequence
<220> FEATURE:
<223> OTHER INFORMATION: Synthetic peptide

<400> SEQUENCE: 15

Asp Val Val Met Thr Gln Ser Pro Leu Ser Leu Pro Val Thr Leu Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Lys Val Thr Asn Arg Glu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Ser Phe Gly Gln Gly Thr Lys Val Glu Ile Lys
            100                 105                 110

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Gly Phe Thr Phe Ser Asn Tyr Gly Met Ser
1               5                   10

<210> SEQ ID NO 17
<211> LENGTH: 19
<212> TYPE: PRT
<213> ORGANISM: Artificial Sequence
<220> FEATURE:
```

<223> OTHER INFORMATION: Synthetic peptide

<400> SEQUENCE: 17

Ser Ile Arg Ser Gly Gly Gly Arg Thr Tyr Tyr Ser Asn Asp Tyr Asn
1               5                   10                  15

Val Lys Gly

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Tyr Asp His Tyr Ser Gly Ser Ser Asp Tyr
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Gly Phe Thr Phe Ser Asn Phe Gly Met Ser
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic peptide

<400> SEQUENCE: 20

Ser Ile Arg Ser Gly Ser Gly Arg Thr Tyr Tyr Ser Asp Asn Val Lys
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: Synthetic peptide

<400> SEQUENCE: 21

Ser Val Arg Ser Gly Ser Gly Arg Thr Tyr Tyr Ser Asp Asn Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Synthetic peptide

<400> SEQUENCE: 22

Ser Val Arg Ser Gly Gly Gly Arg Thr Tyr Tyr Ser Asp Asn Val Lys
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide

<400> SEQUENCE: 23

Ser Val Arg Ser Gly Gly Ser Arg Thr Tyr Tyr Ser Asp Asn Val Lys
1               5                   10                  15

Gly

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Tyr Asp His Tyr Ser Gly Thr Ser Asp Tyr
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Tyr Asp His Tyr Thr Gly Thr Ser Asp Tyr
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Synthetic peptide

<400> SEQUENCE: 26

Lys Ser Ser Gln Ser Leu Leu Asp Ser Asp Gly Lys Thr Tyr Leu Asn
1               5                   10                  15

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide

<400> SEQUENCE: 27

Leu Val Ser Ser Lys Leu Asp Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Trp Gln Gly Thr His Phe Pro Arg Thr

```
1               5

<210> SEQ ID NO 29
<211> LENGTH: 16
<212> TYPE: PRT
<213> ORGANISM: Artificial Sequence
<220> FEATURE:
<223> OTHER INFORMATION: Synthetic peptide

<400> SEQUENCE: 29

Lys Ser Ser Gln Ser Leu Leu Asp Tyr Asp Gly Lys Thr Tyr Leu Asn
1               5                   10                  15

<210> SEQ ID NO 30
<211> LENGTH: 4
<212> TYPE: PRT
<213> ORGANISM: Artificial Sequence
<220> FEATURE:
<223> OTHER INFORMATION: Synthetic peptide

<400> SEQUENCE: 30

Ala Gly Ala Gly
1

<210> SEQ ID NO 31
<211> LENGTH: 16
<212> TYPE: PRT
<213> ORGANISM: Artificial Sequence
<220> FEATURE:
<223> OTHER INFORMATION: Synthetic peptide

<400> SEQUENCE: 31

Arg Ser Ser Gln Ser Leu Val Asp Tyr Asp Gly Lys Thr Tyr Leu Asn
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetic peptide

<400> SEQUENCE: 32

Lys Ser Ser Gln Ser Leu Met Asp Thr Asp Gly Lys Thr Tyr Leu Asn
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Lys Val Ser Asn Arg Asp Ser
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34

Arg Val Thr Asn Arg Asp Thr
1               5
```

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide

<400> SEQUENCE: 35

Lys Val Ser Asn Arg Glu Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

Lys Val Thr Asn Arg Glu Ser
1               5

<210> SEQ ID NO 37
<211> LENGTH: 4
<212> TYPE: PRT
<213> ORGANISM: Artificial Sequence
<220> FEATURE:
<223> OTHER INFORMATION: Synthetic peptide

<400> SEQUENCE: 37

Gly Ala Gly Ala
1

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Trp Gln Gly Thr His Phe Pro Arg Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Trp Gln Gly Ser His Phe Pro Arg Ser
1               5

<210> SEQ ID NO 40
<211> LENGTH: 330
<212> TYPE: PRT
<213> ORGANISM: Artificial Sequence
<220> FEATURE:
<223> OTHER INFORMATION: Synthetic peptide

<400> SEQUENCE: 40

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 107
<212> TYPE: PRT
<213> ORGANISM: Artificial Sequence
<220> FEATURE:
<223> OTHER INFORMATION: Synthetic peptide

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 42
<211> LENGTH: 357
<212> TYPE: PRT
<213> ORGANISM: Artificial Sequence
<220> FEATURE:
<223> OTHER INFORMATION: Synthetic peptide

<400> SEQUENCE: 42

Gly Ala Ala Gly Thr Gly Cys Ala Gly Cys Thr Thr Cys Thr Gly Gly
 1               5                  10                  15

Ala Gly Ala Gly Cys Gly Gly Gly Gly Cys Gly Gly Cys Cys Thr
                 20                  25                  30

Gly Gly Thr Gly Cys Ala Gly Cys Cys Gly Gly Gly Cys Gly Gly Ala
             35                  40                  45

Thr Cys Cys Cys Thr Gly Ala Gly Ala Cys Thr Gly Thr Cys Cys Thr
 50                  55                  60

Gly Thr Gly Cys Cys Gly Cys Cys Thr Cys Cys Gly Gly Thr Thr Thr
 65              70                  75                  80

Thr Ala Cys Cys Thr Thr Cys Thr Cys Cys Ala Ala Cys Thr Ala Cys
                 85                  90                  95

Gly Gly Ala Ala Thr Gly Thr Cys Ala Thr Gly Gly Gly Thr Cys Cys
             100                 105                 110

Gly Cys Cys Ala Ala Gly Cys Ala Cys Cys Cys Gly Gly Ala Ala Ala
             115                 120                 125

Gly Gly Gly Ala Thr Thr Gly Gly Ala Ala Thr Gly Gly Gly Thr Gly
             130                 135                 140

Gly Cys Thr Thr Cys Gly Ala Thr Cys Cys Gly Gly Thr Cys Gly Gly
 145                 150                 155                 160

Gly Cys Thr Cys Gly Gly Gly Ala Cys Gly Gly Ala Cys Cys Thr Ala
                 165                 170                 175

Cys Thr Ala Cys Thr Cys Gly Ala Thr Ala Cys Gly Thr Cys
             180                 185                 190

Ala Ala Gly Gly Gly Cys Ala Gly Ala Thr Thr Cys Ala Cys Thr Ala
             195                 200                 205

Thr Thr Ala Gly Cys Cys Gly Gly Gly Ala Cys Ala Ala Cys Ala Gly
             210                 215                 220

Cys Ala Ala Gly Ala Thr Ala Cys Cys Thr Gly Thr Ala Cys
 225                 230                 235                 240

Cys Thr Cys Cys Ala Ala Ala Thr Gly Ala Ala Cys Thr Cys Cys
             245                 250                 255

Thr Gly Ala Gly Gly Cys Cys Gly Ala Gly Ala Cys Ala Cys
             260                 265                 270

Cys Gly Cys Cys Gly Thr Gly Thr Ala Thr Ala Cys Thr Gly Cys
             275                 280                 285

Gly Thr Gly Cys Gly Cys Thr Ala Cys Gly Ala Cys Cys Ala Cys Thr
 290                 295                 300

```
Ala Cys Thr Cys Gly Gly Thr Thr Cys Thr Cys Thr Gly Ala
305                 310                 315                 320

Thr Thr Ala Cys Thr Gly Gly Gly Ala Cys Ala Gly Gly Gly
                325                 330                 335

Ala Cys Cys Thr Cys Gly Thr Gly Ala Cys Thr Gly Thr Gly Thr
                340                 345                 350

Cys Ala Ala Gly Cys
        355

<210> SEQ ID NO 43
<211> LENGTH: 336
<212> TYPE: PRT
<213> ORGANISM: Artificial Sequence
<220> FEATURE:
<223> OTHER INFORMATION: Synthetic peptide

<400> SEQUENCE: 43

Gly Ala Thr Gly Thr Cys Gly Thr Gly Ala Thr Gly Ala Cys Cys Cys
1               5                   10                  15

Ala Gly Thr Cys Ala Cys Cys Ala Cys Thr Gly Thr Cys Cys Cys Thr
                20                  25                  30

Thr Cys Cys Thr Gly Thr Gly Ala Cys Thr Cys Cys Gly Gly Ala
            35                  40                  45

Gly Ala Ala Cys Cys Gly Gly Cys Gly Thr Cys Cys Ala Thr Thr Thr
        50                  55                  60

Cys Gly Thr Gly Cys Ala Ala Gly Ala Gly Cys Ala Gly Cys Cys Ala
65                  70                  75                  80

Gly Thr Cys Cys Cys Thr Gly Cys Thr Cys Gly Ala Thr Thr Ala Thr
                85                  90                  95

Gly Ala Cys Gly Gly Ala Ala Cys Ala Cys Cys Thr Ala Cys Cys
                100                 105                 110

Thr Gly Ala Ala Cys Thr Gly Gly Thr Thr Cys Thr Cys Cys Ala
            115                 120                 125

Ala Ala Ala Gly Cys Cys Thr Gly Gly Cys Ala Gly Ala Gly Cys
        130                 135                 140

Cys Cys Cys Cys Ala Gly Ala Gly Ala Cys Thr Gly Ala Thr Cys Thr
145                 150                 155                 160

Ala Cys Ala Ala Ala Gly Thr Gly Thr Cys Ala Ala Cys Ala Gly
                165                 170                 175

Gly Gly Ala Cys Thr Cys Gly Gly Gly Cys Gly Thr Gly Cys Cys Gly
                180                 185                 190

Gly Ala Cys Cys Gly Cys Thr Thr Cys Thr Gly Gly Gly Thr
            195                 200                 205

Cys Cys Gly Gly Thr Thr Cys Cys Gly Thr Ala Cys Cys Gly Ala
        210                 215                 220

Cys Thr Thr Thr Ala Cys Gly Cys Thr Gly Ala Ala Gly Ala Thr Cys
225                 230                 235                 240

Thr Cys Ala Cys Gly Gly Gly Thr Gly Gly Ala Ala Gly Cys Cys Gly
                245                 250                 255

Ala Gly Gly Ala Cys Gly Thr Gly Gly Gly Ala Gly Thr Gly Thr Ala
                260                 265                 270

Cys Thr Ala Cys Thr Gly Thr Thr Gly Gly Cys Ala Gly Gly Gly Cys
            275                 280                 285

Ala Cys Thr Cys Ala Cys Thr Thr Cys Cys Cys Gly Cys Gly Gly Ala
        290                 295                 300
```

```
Cys Cys Thr Thr Cys Gly Gly Ala Cys Ala Ala Gly Gly Cys Ala Cys
305                 310                 315                 320

Cys Ala Ala Gly Gly Thr Cys Gly Ala Gly Ala Thr Cys Ala Ala Gly
                325                 330                 335
```

<210> SEQ ID NO 44
<211> LENGTH: 357
<212> TYPE: PRT
<213> ORGANISM: Artificial Sequence
<220> FEATURE:
<223> OTHER INFORMATION: Synthetic peptide

<400> SEQUENCE: 44

```
Gly Ala Ala Gly Thr Gly Cys Ala Gly Cys Thr Cys Cys Thr Gly Gly
1               5                   10                  15

Ala Gly Thr Cys Cys Gly Gly Gly Gly Thr Gly Gly Ala Cys Thr
            20                  25                  30

Gly Gly Thr Gly Cys Ala Gly Cys Cys Gly Gly Gly Gly Gly Cys
            35                  40                  45

Ala Gly Cys Cys Thr Gly Ala Gly Gly Cys Thr Gly Ala Gly Cys Thr
            50                  55                  60

Gly Cys Gly Cys Gly Cys Gly Thr Cys Ala Gly Gly Ala Thr Thr
65                  70                  75                  80

Cys Ala Cys Cys Thr Thr Cys Thr Cys Cys Ala Gly Cys Thr Thr Cys
                85                  90                  95

Gly Gly Ala Ala Thr Gly Thr Cys Thr Gly Gly Gly Thr Cys Ala
                100                 105                 110

Gly Ala Cys Ala Gly Gly Cys Cys Cys Gly Gly Gly Ala Ala Ala
            115                 120                 125

Gly Gly Gly Cys Cys Thr Thr Gly Ala Ala Thr Gly Gly Gly Thr Gly
130                 135                 140

Gly Cys Thr Ala Gly Cys Gly Thr Gly Cys Gly Cys Thr Cys Gly
145                 150                 155                 160

Gly Thr Thr Cys Cys Gly Gly Ala Cys Gly Gly Ala Cys Cys Thr Ala
                165                 170                 175

Cys Thr Ala Cys Thr Cys Gly Gly Ala Cys Ala Ala Cys Gly Thr Gly
                180                 185                 190

Ala Ala Gly Gly Gly Cys Cys Gly Gly Thr Thr Thr Ala Cys Thr Ala
            195                 200                 205

Thr Cys Thr Cys Cys Gly Gly Gly Ala Cys Ala Ala Thr Thr Cys
            210                 215                 220

Gly Ala Ala Gly Ala Ala Cys Ala Cys Cys Thr Gly Thr Ala Cys Cys
225                 230                 235                 240

Cys Thr Cys Cys Ala Ala Thr Gly Ala Ala Cys Thr Cys Cys Thr
                245                 250                 255

Thr Gly Cys Gly Cys Gly Cys Cys Gly Ala Gly Gly Ala Thr Ala Cys
                260                 265                 270

Cys Gly Cys Ala Gly Thr Gly Thr Ala Thr Ala Cys Thr Gly Cys
            275                 280                 285

Gly Thr Gly Cys Gly Cys Thr Ala Cys Gly Ala Cys Ala Cys Thr
            290                 295                 300

Ala Cys Thr Cys Thr Gly Gly Cys Ala Cys Ala Gly Cys Gly Ala
305                 310                 315                 320

Thr Thr Ala Cys Thr Gly Gly Gly Gly Cys Cys Ala Gly Gly Gly Ala
                325                 330                 335
```

```
Ala Cys Thr Cys Thr Gly Gly Thr Cys Ala Cys Cys Gly Thr Gly Thr
                340                 345                 350

Cys Gly Thr Cys Ala
        355

<210> SEQ ID NO 45
<211> LENGTH: 336
<212> TYPE: PRT
<213> ORGANISM: Artificial Sequence
<220> FEATURE:
<223> OTHER INFORMATION: Synthetic peptide

<400> SEQUENCE: 45

Gly Ala Thr Gly Thr Cys Gly Thr Gly Ala Thr Gly Ala Cys Thr Cys
1               5                   10                  15

Ala Gly Thr Cys Ala Cys Cys Thr Cys Thr Gly Thr Cys Cys Cys Thr
                20                  25                  30

Gly Cys Cys Thr Gly Thr Gly Ala Cys Cys Cys Thr Gly Gly Gly
            35                  40                  45

Gly Ala Ala Cys Cys Cys Gly Cys Cys Thr Cys Gly Ala Thr Cys Thr
        50                  55                  60

Cys Gly Thr Gly Cys Ala Ala Gly Ala Gly Cys Thr Cys Cys Cys Ala
65                  70                  75                  80

Gly Ala Gly Cys Cys Thr Gly Cys Thr Cys Gly Ala Cys Thr Ala Thr
                85                  90                  95

Gly Ala Thr Gly Gly Ala Ala Ala Gly Ala Cys Cys Thr Ala Cys Cys
                100                 105                 110

Thr Gly Ala Ala Cys Thr Gly Gly Thr Thr Gly Cys Thr Cys Cys Ala
            115                 120                 125

Ala Ala Ala Gly Cys Cys Gly Gly Gly Cys Cys Ala Gly Ala Gly Cys
        130                 135                 140

Cys Cys Cys Cys Ala Gly Ala Gly Gly Cys Thr Gly Ala Thr Cys Thr
145                 150                 155                 160

Ala Cys Cys Gly Cys Gly Thr Gly Ala Cys Cys Ala Ala Cys Cys Gly
                165                 170                 175

Cys Gly Ala Cys Ala Cys Cys Gly Gly Gly Thr Gly Thr Cys Cys Gly
                180                 185                 190

Gly Ala Cys Cys Gly Gly Thr Thr Cys Thr Cys Gly Gly Ala Thr
            195                 200                 205

Cys Cys Gly Gly Cys Ala Gly Cys Gly Gly Cys Ala Cys Thr Gly Ala
        210                 215                 220

Cys Thr Thr Cys Ala Cys Cys Cys Thr Gly Ala Ala Ala Ala Thr Thr
225                 230                 235                 240

Thr Cys Cys Ala Gly Ala Gly Thr Gly Gly Ala Ala Gly Cys Cys Gly
                245                 250                 255

Ala Gly Gly Ala Cys Gly Thr Gly Gly Gly Ala Gly Thr Gly Thr Ala
                260                 265                 270

Cys Thr Ala Cys Thr Gly Thr Thr Gly Gly Cys Ala Gly Gly Gly Thr
            275                 280                 285

Ala Cys Thr Cys Ala Cys Thr Thr Thr Cys Cys Ala Cys Gly Gly Thr
        290                 295                 300

Cys Cys Thr Thr Cys Gly Gly Thr Cys Ala Ala Gly Gly Ala Ala Cys
305                 310                 315                 320

Cys Ala Ala Gly Gly Thr Cys Gly Ala Gly Ala Thr Cys Ala Ala Gly
                325                 330                 335
```

<210> SEQ ID NO 46
<211> LENGTH: 357
<212> TYPE: PRT
<213> ORGANISM: Artificial Sequence
<220> FEATURE:
<223> OTHER INFORMATION: Synthetic peptide

<400> SEQUENCE: 46

```
Gly Ala Ala Gly Thr Gly Cys Ala Gly Cys Thr Thr Cys Thr Gly Gly
1               5                   10                  15

Ala Gly Ala Gly Cys Gly Gly Gly Gly Cys Gly Gly Cys Cys Thr
            20                  25                  30

Gly Gly Thr Gly Cys Ala Gly Cys Cys Gly Gly Gly Cys Gly Gly Ala
            35                  40                  45

Thr Cys Cys Cys Thr Gly Ala Gly Ala Cys Thr Gly Thr Cys Cys Thr
        50                  55                  60

Gly Thr Gly Cys Cys Gly Cys Gly Thr Cys Cys Gly Gly Thr Thr Thr
65                  70                  75                  80

Thr Ala Cys Cys Thr Thr Cys Thr Cys Ala Ala Cys Thr Ala Cys
                85                  90                  95

Gly Gly Ala Ala Thr Gly Thr Cys Ala Thr Gly Gly Thr Cys Cys
                100                 105                 110

Gly Cys Cys Ala Ala Gly Cys Ala Cys Cys Gly Gly Ala Ala Ala
            115                 120                 125

Gly Gly Gly Ala Thr Thr Gly Gly Ala Ala Thr Gly Gly Gly Thr Gly
            130                 135                 140

Gly Cys Thr Thr Cys Gly Ala Thr Cys Cys Gly Thr Cys Cys Gly
145                 150                 155                 160

Gly Cys Thr Cys Gly Gly Gly Ala Cys Gly Gly Ala Cys Cys Thr Ala
                165                 170                 175

Cys Thr Ala Cys Thr Cys Cys Gly Ala Thr Ala Ala Cys Gly Thr Cys
            180                 185                 190

Ala Ala Gly Gly Gly Cys Ala Gly Ala Thr Thr Cys Ala Cys Thr Ala
                195                 200                 205

Thr Thr Ala Gly Cys Cys Gly Gly Gly Ala Cys Ala Ala Cys Ala Gly
            210                 215                 220

Cys Ala Ala Gly Ala Ala Thr Ala Cys Cys Thr Gly Thr Ala Cys
225                 230                 235                 240

Cys Thr Cys Cys Ala Ala Ala Thr Gly Ala Ala Cys Thr Cys Cys Cys
            245                 250                 255

Thr Gly Ala Gly Gly Cys Cys Gly Ala Gly Gly Ala Cys Ala Cys
            260                 265                 270

Cys Gly Cys Cys Gly Thr Gly Thr Ala Thr Thr Ala Cys Thr Gly Cys
            275                 280                 285

Gly Thr Gly Cys Gly Cys Thr Ala Cys Gly Ala Cys Cys Ala Cys Thr
            290                 295                 300

Ala Cys Thr Cys Gly Gly Gly Thr Thr Cys Thr Cys Thr Thr Gly Ala
305                 310                 315                 320

Thr Thr Ala Cys Thr Gly Gly Gly Gly Ala Cys Ala Gly Gly Gly Gly
                325                 330                 335

Ala Cys Cys Cys Thr Cys Gly Thr Gly Ala Cys Thr Gly Thr Gly Thr
            340                 345                 350

Cys Ala Ala Gly Cys
        355
```

<210> SEQ ID NO 47
<211> LENGTH: 336
<212> TYPE: PRT
<213> ORGANISM: Artificial Sequence
<220> FEATURE:
<223> OTHER INFORMATION: Synthetic peptide

<400> SEQUENCE: 47

Gly Ala Thr Gly Thr Cys Gly Thr Gly Ala Thr Gly Ala Cys Thr Cys
1               5                   10                  15

Ala Gly Thr Cys Ala Cys Cys Thr Cys Thr Gly Thr Cys Cys Cys Thr
                20                  25                  30

Gly Cys Cys Thr Gly Thr Gly Ala Cys Cys Thr Thr Gly Gly Gly
            35                  40                  45

Gly Ala Ala Cys Cys Cys Gly Cys Cys Thr Gly Ala Thr Cys Thr
        50                  55                  60

Cys Gly Thr Gly Cys Ala Ala Gly Ala Gly Cys Thr Cys Cys Ala
65                  70                  75                  80

Gly Ala Gly Cys Cys Thr Gly Cys Thr Cys Gly Ala Cys Thr Ala Thr
                85                  90                  95

Gly Ala Thr Gly Gly Ala Ala Gly Ala Cys Cys Thr Ala Cys Cys
            100                 105                 110

Thr Gly Ala Ala Cys Thr Gly Gly Thr Thr Gly Cys Thr Cys Cys Ala
        115                 120                 125

Ala Ala Ala Gly Cys Cys Gly Gly Gly Cys Cys Ala Gly Ala Gly Cys
130                 135                 140

Cys Cys Cys Cys Ala Gly Ala Gly Gly Cys Thr Gly Ala Thr Cys Thr
145                 150                 155                 160

Ala Cys Cys Gly Cys Gly Thr Gly Ala Cys Ala Cys Cys Gly
        165                 170                 175

Cys Gly Ala Cys Ala Cys Cys Gly Gly Gly Thr Gly Cys Cys Gly
            180                 185                 190

Gly Ala Cys Cys Gly Gly Thr Thr Cys Thr Cys Cys Gly Gly Ala Thr
        195                 200                 205

Cys Cys Gly Gly Cys Ala Gly Cys Gly Gly Cys Ala Cys Thr Gly Ala
210                 215                 220

Cys Thr Thr Cys Ala Cys Cys Cys Thr Gly Ala Ala Ala Ala Thr Thr
225                 230                 235                 240

Thr Cys Cys Ala Gly Ala Gly Thr Gly Gly Ala Ala Gly Cys Cys Gly
            245                 250                 255

Ala Gly Gly Ala Cys Gly Thr Gly Gly Gly Ala Gly Thr Gly Thr Ala
            260                 265                 270

Cys Thr Ala Cys Thr Gly Thr Gly Gly Cys Ala Gly Gly Gly Thr
            275                 280                 285

Ala Cys Thr Cys Ala Cys Thr Thr Thr Cys Cys Ala Cys Gly Gly Thr
            290                 295                 300

Cys Cys Thr Thr Cys Gly Gly Thr Cys Ala Ala Gly Gly Ala Ala Cys
305                 310                 315                 320

Cys Ala Ala Gly Gly Thr Cys Gly Ala Gly Ala Thr Cys Ala Ala Gly
            325                 330                 335

<210> SEQ ID NO 48
<211> LENGTH: 357
<212> TYPE: PRT
<213> ORGANISM: Artificial Sequence
<220> FEATURE:

<223> OTHER INFORMATION: Synthetic peptide

<400> SEQUENCE: 48

Gly Ala Ala Gly Thr Gly Cys Ala Gly Cys Thr Gly Cys Thr Gly Gly
1               5                   10                  15
Ala Gly Thr Cys Thr Gly Cys Gly Gly Cys Gly Gly Ala Cys Thr
            20                  25                  30
Gly Gly Thr Gly Cys Ala Gly Cys Cys Gly Gly Gly Gly Ala
        35                  40                  45
Thr Cys Cys Cys Thr Gly Cys Gly Gly Cys Thr Thr Thr Cys Cys Thr
50                  55                  60
Gly Cys Gly Cys Cys Gly Cys Ala Thr Cys Cys Gly Gly Cys Thr Thr
65                  70                  75                  80
Cys Ala Cys Cys Thr Thr Thr Thr Cys Ala Ala Ala Cys Thr Thr Cys
                85                  90                  95
Gly Gly Ala Ala Thr Gly Thr Cys Gly Thr Gly Gly Gly Thr Cys Ala
                100                 105                 110
Gly Ala Cys Ala Gly Gly Cys Cys Cys Cys Gly Gly Gly Ala Ala Ala
                115                 120                 125
Gly Gly Gly Thr Cys Thr Gly Gly Ala Ala Thr Gly Gly Gly Thr Gly
                130                 135                 140
Gly Cys Cys Thr Cys Ala Gly Thr Gly Cys Gly Gly Thr Cys Cys Gly
145                 150                 155                 160
Gly Ala Thr Cys Gly Gly Thr Ala Gly Ala Ala Cys Cys Thr Ala
                165                 170                 175
Cys Thr Ala Cys Ala Gly Cys Gly Ala Thr Ala Ala Cys Gly Thr Gly
                180                 185                 190
Ala Ala Gly Gly Gly Cys Cys Gly Gly Thr Thr Cys Ala Cys Gly Ala
                195                 200                 205
Thr Cys Thr Cys Cys Gly Cys Gly Ala Cys Ala Ala Cys Thr Cys
                210                 215                 220
Cys Ala Ala Gly Ala Ala Cys Ala Cys Cys Cys Thr Gly Thr Ala Cys
225                 230                 235                 240
Thr Thr Gly Cys Ala Ala Ala Thr Gly Ala Ala Thr Ala Gly Cys Cys
                245                 250                 255
Thr Cys Ala Gly Gly Gly Cys Thr Gly Ala Gly Gly Ala Thr Ala Cys
                260                 265                 270
Cys Gly Cys Gly Gly Thr Cys Thr Ala Cys Thr Ala Cys Thr Gly Thr
                275                 280                 285
Gly Thr Gly Cys Gly Cys Thr Ala Thr Gly Ala Cys Ala Cys Thr
                290                 295                 300
Ala Cys Ala Cys Thr Gly Gly Ala Ala Cys Thr Ala Gly Cys Gly Ala
305                 310                 315                 320
Cys Thr Ala Cys Thr Gly Gly Gly Cys Cys Ala Gly Gly Gly
                325                 330                 335
Ala Cys Cys Cys Thr Gly Thr Gly Ala Cys Thr Gly Thr Gly
                340                 345                 350
Cys Gly Thr Cys Cys
        355

<210> SEQ ID NO 49
<211> LENGTH: 336
<212> TYPE: PRT
<213> ORGANISM: Artificial Sequence
<220> FEATURE:

<223> OTHER INFORMATION: Synthetic peptide

<400> SEQUENCE: 49

Gly Ala Thr Gly Thr Cys Gly Thr Gly Ala Thr Gly Ala Cys Thr Cys
1               5                   10                  15

Ala Gly Thr Cys Ala Cys Cys Thr Cys Thr Gly Thr Cys Cys Cys Thr
                20                  25                  30

Gly Cys Cys Thr Gly Thr Gly Ala Cys Cys Thr Thr Gly Gly Gly
            35                  40                  45

Gly Ala Ala Cys Cys Cys Gly Cys Cys Thr Cys Gly Ala Thr Cys Thr
        50                  55                  60

Cys Gly Thr Gly Cys Ala Ala Gly Ala Gly Cys Thr Cys Cys Cys Ala
65                  70                  75                  80

Gly Ala Gly Cys Cys Thr Gly Cys Thr Cys Gly Ala Cys Thr Ala Thr
                85                  90                  95

Gly Ala Thr Gly Gly Ala Ala Gly Ala Cys Cys Thr Ala Cys Cys
            100                 105                 110

Thr Gly Ala Ala Cys Thr Gly Gly Thr Thr Gly Cys Thr Cys Cys Ala
        115                 120                 125

Ala Ala Ala Gly Cys Cys Gly Gly Cys Cys Ala Gly Ala Gly Cys
130                 135                 140

Cys Cys Cys Cys Ala Gly Ala Gly Gly Cys Thr Gly Ala Thr Cys Thr
145                 150                 155                 160

Ala Cys Cys Gly Cys Gly Thr Gly Ala Cys Cys Ala Ala Cys Cys Gly
                165                 170                 175

Cys Gly Ala Cys Ala Cys Cys Gly Gly Gly Thr Gly Cys Cys Gly
            180                 185                 190

Gly Ala Cys Cys Gly Gly Thr Thr Cys Thr Cys Cys Gly Gly Ala Thr
        195                 200                 205

Cys Cys Gly Gly Cys Ala Gly Cys Gly Gly Cys Ala Cys Thr Gly Ala
210                 215                 220

Cys Thr Thr Cys Ala Cys Cys Cys Thr Gly Ala Ala Ala Thr Thr
225                 230                 235                 240

Thr Cys Cys Ala Gly Ala Gly Thr Gly Gly Ala Ala Gly Cys Cys Gly
                245                 250                 255

Ala Gly Gly Ala Cys Gly Thr Gly Gly Gly Ala Gly Thr Gly Thr Ala
            260                 265                 270

Cys Thr Ala Cys Thr Gly Thr Thr Gly Gly Cys Ala Gly Gly Gly Thr
        275                 280                 285

Ala Cys Thr Cys Ala Cys Thr Thr Cys Cys Ala Cys Gly Gly Thr
290                 295                 300

Cys Cys Thr Thr Cys Gly Gly Cys Ala Ala Gly Gly Ala Ala Cys
305                 310                 315                 320

Cys Ala Ala Gly Gly Thr Cys Gly Ala Gly Ala Thr Cys Ala Ala Gly
                325                 330                 335

<210> SEQ ID NO 50
<211> LENGTH: 357
<212> TYPE: PRT
<213> ORGANISM: Artificial Sequence
<220> FEATURE:
<223> OTHER INFORMATION: Synthetic peptide

<400> SEQUENCE: 50

Gly Ala Ala Gly Thr Gly Cys Ala Gly Cys Thr Cys Cys Thr Gly Gly
1               5                   10                  15

```
Ala Gly Thr Cys Cys Gly Gly Gly Gly Gly Thr Gly Gly Ala Cys Thr
            20                  25                  30

Gly Gly Thr Gly Cys Ala Gly Cys Cys Cys Gly Gly Gly Gly Gly Cys
        35                  40                  45

Ala Gly Cys Cys Thr Gly Ala Gly Gly Cys Thr Gly Ala Gly Cys Thr
    50                  55                  60

Gly Cys Gly Cys Cys Gly Cys Gly Thr Cys Ala Gly Gly Ala Thr Thr
65                  70                  75                  80

Cys Ala Cys Cys Thr Thr Cys Thr Cys Cys Ala Ala Cys Thr Thr Cys
                85                  90                  95

Gly Gly Ala Ala Thr Gly Thr Cys Cys Thr Gly Gly Gly Thr Cys Ala
            100                 105                 110

Gly Ala Cys Ala Gly Gly Cys Cys Cys Cys Gly Gly Gly Ala Ala Ala
        115                 120                 125

Gly Gly Gly Cys Cys Thr Thr Gly Ala Ala Thr Gly Gly Gly Thr Gly
    130                 135                 140

Gly Cys Thr Ala Gly Cys Gly Thr Gly Cys Gly Cys Thr Cys Cys Gly
145                 150                 155                 160

Gly Thr Thr Cys Cys Gly Gly Ala Cys Gly Gly Ala Cys Cys Thr Ala
                165                 170                 175

Cys Thr Ala Cys Thr Cys Gly Gly Ala Cys Ala Ala Cys Gly Thr Gly
            180                 185                 190

Ala Ala Gly Gly Gly Cys Cys Gly Gly Thr Thr Thr Ala Cys Thr Ala
        195                 200                 205

Thr Cys Thr Cys Cys Cys Gly Gly Gly Ala Cys Ala Ala Thr Thr Cys
    210                 215                 220

Gly Ala Ala Gly Ala Ala Cys Ala Cys Cys Cys Thr Gly Thr Ala Cys
225                 230                 235                 240

Cys Thr Cys Cys Ala Ala Ala Thr Gly Ala Ala Cys Thr Cys Cys Thr
                245                 250                 255

Thr Gly Cys Gly Cys Gly Cys Cys Gly Ala Gly Gly Ala Thr Ala Cys
            260                 265                 270

Cys Gly Cys Ala Gly Thr Gly Thr Ala Thr Thr Ala Cys Thr Gly Cys
        275                 280                 285

Gly Thr Gly Cys Gly Cys Thr Ala Cys Gly Ala Cys Cys Ala Cys Thr
    290                 295                 300

Ala Cys Thr Cys Thr Gly Gly Cys Ala Cys Thr Ala Gly Cys Gly Ala
305                 310                 315                 320

Thr Thr Ala Cys Thr Gly Gly Gly Gly Cys Cys Ala Gly Gly Gly Ala
                325                 330                 335

Ala Cys Thr Cys Thr Gly Gly Thr Cys Ala Cys Cys Gly Thr Gly Thr
            340                 345                 350

Cys Gly Thr Cys Ala
        355
```

<210> SEQ ID NO 51
<211> LENGTH: 336
<212> TYPE: PRT
<213> ORGANISM: Artificial Sequence
<220> FEATURE:
<223> OTHER INFORMATION: Synthetic peptide

<400> SEQUENCE: 51

```
Gly Ala Thr Gly Thr Cys Gly Thr Gly Ala Thr Gly Ala Cys Cys Cys
1               5                   10                  15
```

Ala Gly Thr Cys Ala Cys Cys Ala Cys Thr Gly Thr Cys Cys Cys Thr
            20                  25                  30

Thr Cys Cys Thr Gly Thr Gly Ala Cys Thr Cys Cys Gly Gly Ala
        35                  40                  45

Gly Ala Ala Cys Cys Gly Gly Cys Gly Thr Cys Cys Ala Thr Thr Thr
50                  55                  60

Cys Gly Thr Gly Cys Ala Ala Gly Ala Gly Cys Ala Gly Cys Cys Ala
65                  70                  75                  80

Gly Thr Cys Cys Cys Thr Gly Cys Thr Cys Gly Ala Thr Thr Ala Thr
                85                  90                  95

Gly Ala Cys Gly Gly Ala Ala Gly Ala Cys Cys Thr Ala Cys Cys
            100                 105                 110

Thr Gly Ala Ala Cys Thr Gly Gly Thr Thr Gly Cys Thr Cys Cys Ala
        115                 120                 125

Ala Ala Ala Gly Cys Cys Thr Gly Gly Cys Ala Gly Ala Gly Cys
130                 135                 140

Cys Cys Cys Cys Ala Gly Ala Gly Ala Cys Thr Gly Ala Thr Cys Thr
145                 150                 155                 160

Ala Cys Ala Ala Ala Gly Thr Gly Thr Cys Ala Ala Cys Ala Gly
            165                 170                 175

Gly Gly Ala Cys Thr Cys Gly Gly Gly Cys Gly Thr Gly Cys Cys Gly
        180                 185                 190

Gly Ala Cys Cys Gly Cys Thr Thr Cys Thr Cys Gly Gly Gly Gly Thr
    195                 200                 205

Cys Cys Gly Gly Thr Thr Cys Cys Gly Gly Thr Ala Cys Cys Gly Ala
210                 215                 220

Cys Thr Thr Thr Ala Cys Gly Cys Thr Gly Ala Ala Gly Ala Thr Cys
225                 230                 235                 240

Thr Cys Ala Cys Gly Gly Gly Thr Gly Gly Ala Ala Gly Cys Cys Gly
            245                 250                 255

Ala Gly Gly Ala Cys Gly Thr Gly Gly Gly Ala Gly Thr Gly Thr Ala
        260                 265                 270

Cys Thr Ala Cys Thr Gly Thr Thr Gly Gly Cys Ala Gly Gly Gly Cys
    275 280 285

Ala Cys Thr Cys Ala Cys Thr Thr Cys Cys Cys Gly Cys Gly Gly Ala
290 295 300

Cys Cys Thr Thr Cys Gly Gly Ala Cys Ala Ala Gly Gly Cys Ala Cys
305 310 315 320

Cys Ala Ala Gly Gly Thr Cys Gly Ala Gly Ala Thr Cys Ala Ala Gly
325 330 335

<210> SEQ ID NO 52
<211> LENGTH: 357
<212> TYPE: PRT
<213> ORGANISM: Artificial Sequence
<220> FEATURE:
<223> OTHER INFORMATION: Synthetic peptide

<400> SEQUENCE: 52

Gly Ala Gly Gly Thr Gly Cys Ala Gly Cys Thr Gly Cys Thr Gly Gly
1 5 10 15

Ala Gly Thr Cys Gly Gly Gly Gly Gly Gly Gly Gly Gly Ala Cys Thr
20 25 30

Cys Gly Thr Gly Cys Ala Gly Cys Cys Cys Gly Gly Gly Gly Gly Cys
35 40 45

```
Thr Cys Cys Cys Thr Gly Ala Gly Ala Cys Thr Cys Thr Thr
     50                  55                  60

Gly Thr Gly Cys Cys Gly Cys Cys Thr Cys Cys Gly Cys Thr Thr
 65                  70                  75                  80

Cys Ala Cys Thr Thr Thr Thr Cys Ala Ala Cys Thr Thr Cys
                 85                  90                  95

Gly Gly Ala Ala Thr Gly Thr Cys Cys Thr Gly Gly Thr Cys Cys
                100                 105                 110

Gly Cys Cys Ala Ala Gly Cys Ala Cys Cys Gly Gly Ala Ala Ala
             115                 120                 125

Gly Gly Gly Thr Cys Thr Gly Gly Ala Ala Thr Gly Gly Thr Cys
            130                 135                 140

Gly Cys Cys Ala Gly Cys Gly Thr Gly Cys Gly Gly Thr Cys Cys Gly
145                 150                 155                 160

Gly Cys Gly Gly Cys Gly Gly Ala Cys Gly Gly Ala Cys Thr Thr Ala
                165                 170                 175

Cys Thr Ala Cys Thr Cys Cys Gly Ala Cys Ala Ala Cys Gly Thr Gly
                180                 185                 190

Ala Ala Gly Gly Gly Cys Cys Gly Gly Thr Thr Cys Ala Cys Cys Ala
                195                 200                 205

Thr Cys Thr Cys Ala Ala Gly Gly Gly Ala Thr Ala Ala Cys Thr Cys
     210                 215                 220

Cys Ala Ala Gly Ala Ala Thr Ala Cys Thr Cys Thr Gly Thr Ala Cys

Gly Ala Ala Cys Cys Cys Gly Cys Gly Thr Cys Cys Ala Thr Thr Thr
            50                  55                  60

Cys Gly Thr Gly Cys Ala Ala Gly Ala Gly Cys Ala Gly Cys Cys Ala
65                  70                  75                  80

Gly Thr Cys Cys Cys Thr Gly Thr Thr Gly Gly Ala Cys Thr Cys Ala
                85                  90                  95

Gly Ala Cys Gly Gly Ala Ala Gly Ala Cys Cys Thr Ala Cys Cys
            100                 105                 110

Thr Thr Ala Ala Cys Thr Gly Gly Cys Thr Gly Cys Thr Gly Cys Ala
        115                 120                 125

Ala Ala Ala Gly Cys Cys Ala Gly Gly Ala Cys Ala Gly Ala Gly Cys
    130                 135                 140

Cys Cys Gly Cys Ala Gly Ala Gly Gly Cys Thr Gly Ala Thr Cys Thr
145                 150                 155                 160

Ala Cys Cys Gly Cys Gly Thr Gly Ala Cys Cys Ala Ala Cys Cys Gly
                165                 170                 175

Gly Gly Ala Thr Ala Cys Gly Gly Gly Ala Gly Thr Gly Cys Cys Gly
            180                 185                 190

Gly Ala Cys Ala Gly Ala Thr Thr Cys Ala Gly Cys Gly Gly Cys Thr
        195                 200                 205

Cys Gly Gly Gly Thr Thr Cys Cys Gly Gly Cys Ala Cys Cys Gly Ala
    210                 215                 220

Cys Thr Thr Cys Ala Cys Cys Thr Cys Ala Ala Ala Thr Cys
225                 230                 235                 240

Thr Cys Cys Cys Gly Cys Gly Thr Cys Gly Ala Gly Cys Cys Gly
                245                 250                 255

Ala Gly Gly Ala Cys Gly Thr Gly Gly Gly Cys Gly Thr Gly Thr Ala
            260                 265                 270

Thr Thr Ala Cys Thr Gly Thr Thr Gly Gly Cys Ala Gly Gly Ala
        275                 280                 285

Ala Cys Cys Cys Ala Cys Thr Thr Cys Thr Cys Gly Gly Ala
    290                 295                 300

Cys Cys Thr Thr Cys Gly Gly Thr Cys Ala Ala Gly Gly Gly Ala Cys
305                 310                 315                 320

Thr Ala Ala Gly Gly Thr Cys Gly Ala Ala Thr Cys Ala Ala Gly
                325                 330                 335

<210> SEQ ID NO 54
<211> LENGTH: 357
<212> TYPE: PRT
<213> ORGANISM: Artificial Sequence
<220> FEATURE:
<223> OTHER INFORMATION: Synthetic peptide

<400> SEQUENCE: 54

Gly Ala Ala Gly Thr Gly Cys Ala Gly Cys Thr Gly Cys Thr Gly Gly
1               5                   10                  15

Ala Gly Thr Cys Thr Gly Gly Cys Gly Gly Cys Gly Gly Ala Cys Thr
            20                  25                  30

Gly Gly Thr Gly Cys Ala Gly Cys Cys Gly Gly Gly Gly Gly Ala
        35                  40                  45

Thr Cys Cys Cys Thr Gly Cys Gly Gly Cys Thr Cys Thr Cys Cys Thr
    50                  55                  60

Gly Cys Gly Cys Cys Gly Cys Ala Thr Cys Cys Gly Gly Cys Thr Thr
65                  70                  75                  80

Cys Ala Cys Cys Thr Thr Thr Cys Ala Ala Ala Cys Thr Thr Cys
            85                  90                  95

Gly Gly Ala Ala Thr Gly Thr Cys Gly Thr Gly Gly Thr Cys Ala
            100                 105                 110

Gly Ala Cys Ala Gly Gly Cys Cys Cys Gly Gly Ala Ala Ala
            115                 120                 125

Gly Gly Gly Thr Cys Thr Gly Gly Ala Ala Thr Gly Gly Thr Gly
            130                 135                 140

Gly Cys Cys Thr Cys Ala Gly Thr Cys Gly Gly Thr Cys Cys Gly
145                 150                 155                 160

Gly Ala Thr Cys Gly Gly Thr Ala Gly Ala Cys Cys Thr Ala
            165                 170                 175

Cys Thr Ala Cys Ala Gly Cys Gly Ala Thr Ala Ala Cys Gly Thr Gly
            180                 185                 190

Ala Ala Gly Gly Gly Cys Cys Gly Gly Thr Thr Cys Ala Cys Gly Ala
            195                 200                 205

Thr Cys Thr Cys Cys Gly Cys Gly Ala Cys Ala Ala Cys Thr Cys
            210                 215                 220

Cys Ala Ala Gly Ala Ala Cys Ala Cys Cys Thr Gly Thr Ala Cys
225                 230                 235                 240

Thr Thr Gly Cys Ala Ala Ala Thr Gly Ala Ala Thr Ala Gly Cys Cys
            245                 250                 255

Thr Cys Ala Gly Gly Gly Cys Thr Gly Ala Gly Gly Ala Thr Ala Cys
            260                 265                 270

Cys Gly Cys Gly Gly Thr Cys Thr Ala Cys Thr Ala Cys Thr Gly Thr
            275                 280                 285

Gly Thr Gly Cys Gly Cys Thr Ala Thr Gly Ala Cys Cys Ala Cys Thr
            290                 295                 300

Ala Cys Ala Cys Thr Gly Gly Ala Ala Cys Thr Ala Gly Cys Gly Ala
305                 310                 315                 320

Cys Thr Ala Cys Thr Gly Gly Gly Cys Cys Ala Gly Gly Gly Gly
            325                 330                 335

Ala Cys Cys Cys Thr Cys Gly Thr Gly Ala Cys Thr Gly Thr Gly Thr
            340                 345                 350

Cys Gly Thr Cys Cys
            355

<210> SEQ ID NO 55
<211> LENGTH: 336
<212> TYPE: PRT
<213> ORGANISM: Artificial Sequence
<220> FEATURE:
<223> OTHER INFORMATION: Synthetic peptide

<400> SEQUENCE: 55

Gly Ala Thr Gly Thr Cys Gly Thr Gly Ala Thr Gly Ala Cys Cys Cys
1               5                   10                  15

Ala Gly Thr Cys Ala Cys Cys Ala Cys Thr Gly Thr Cys Cys Cys Thr
            20                  25                  30

Thr Cys Cys Thr Gly Thr Gly Ala Cys Thr Cys Cys Cys Gly Gly Ala
            35                  40                  45

Gly Ala Ala Cys Cys Gly Gly Cys Gly Thr Cys Cys Ala Thr Thr Thr
            50                  55                  60

Cys Gly Thr Gly Cys Ala Ala Gly Ala Gly Cys Ala Gly Cys Cys Ala
65                  70                  75                  80

-continued

Gly Thr Cys Cys Cys Thr Cys Thr Cys Gly Ala Thr Ala Thr
             85                  90                  95

Gly Ala Cys Gly Gly Ala Ala Gly Ala Cys Cys Thr Ala Cys Cys
            100                 105                 110

Thr Gly Ala Ala Cys Thr Gly Gly Thr Thr Gly Cys Thr Cys Cys Ala
            115                 120                 125

Ala Ala Ala Gly Cys Cys Thr Gly Gly Cys Ala Gly Ala Gly Cys
        130                 135                 140

Cys Cys Cys Cys Ala Gly Ala Gly Ala Cys Thr Gly Ala Thr Cys Thr
145                 150                 155                 160

Ala Cys Ala Ala Ala Gly Thr Gly Thr Cys Ala Ala Cys Ala Gly
            165                 170                 175

Gly Gly Ala Cys Thr Cys Gly Gly Gly Cys Gly Thr Gly Cys Cys Gly
            180                 185                 190

Gly Ala Cys Cys Gly Cys Thr Thr Cys Thr Cys Gly Gly Gly Thr
            195                 200                 205

Cys Cys Gly Gly Thr Thr Cys Cys Gly Gly Thr Ala Cys Cys Gly Ala
210                 215                 220

Cys Thr Thr Thr Ala Cys Gly Cys Thr Gly Ala Ala Gly Ala Thr Cys
225                 230                 235                 240

Thr Cys Ala Cys Gly Gly Gly Thr Gly Gly Ala Ala Gly Cys Cys Gly
            245                 250                 255

Ala Gly Gly Ala Cys Gly Thr Gly Gly Gly Ala Gly Thr Gly Thr Ala
            260                 265                 270

Cys Thr Ala Cys Thr Gly Thr Thr Gly Cys Ala Gly Gly Gly Cys
            275                 280                 285

Ala Cys Thr Cys Ala Cys Thr Thr Cys Cys Gly Cys Gly Gly Ala
        290                 295                 300

Cys Cys Thr Thr Cys Gly Gly Ala Cys Ala Ala Gly Gly Cys Ala Cys
305                 310                 315                 320

Cys Ala Ala Gly Gly Thr Cys Gly Ala Gly Ala Thr Cys Ala Ala Gly
            325                 330                 335

<210> SEQ ID NO 56
<211> LENGTH: 357
<212> TYPE: PRT
<213> ORGANISM: Artificial Sequence
<220> FEATURE:
<223> OTHER INFORMATION: Synthetic peptide

<400> SEQUENCE: 56

Gly Ala Ala Gly Thr Gly Cys Ala Gly Cys Thr Cys Thr Gly Gly
1               5                   10                  15

Ala Gly Thr Cys Cys Gly Gly Gly Gly Gly Thr Gly Gly Ala Cys Thr
            20                  25                  30

Gly Gly Thr Gly Cys Ala Gly Cys Cys Gly Gly Gly Gly Gly Cys
            35                  40                  45

Ala Gly Cys Cys Thr Gly Ala Gly Cys Thr Gly Ala Gly Cys Thr
        50                  55                  60

Gly Cys Gly Cys Cys Gly Cys Thr Cys Ala Gly Gly Ala Thr Thr
65                  70                  75                  80

Cys Ala Cys Cys Thr Thr Cys Thr Cys Cys Ala Ala Cys Thr Thr Cys
            85                  90                  95

Gly Gly Ala Ala Thr Gly Thr Cys Cys Thr Gly Gly Gly Thr Cys Ala
            100                 105                 110

Gly Ala Cys Ala Gly Gly Cys Cys Cys Gly Gly Ala Ala Ala
            115                 120                 125

Gly Gly Gly Cys Cys Thr Thr Gly Ala Ala Thr Gly Gly Thr Gly
            130                 135                 140

Gly Cys Thr Ala Gly Cys Gly Thr Gly Cys Gly Thr Cys Cys Gly
145                 150                 155                 160

Gly Thr Thr Cys Cys Gly Gly Ala Cys Gly Gly Ala Cys Cys Thr Ala
                165                 170                 175

Cys Thr Ala Cys Thr Cys Gly Gly Ala Cys Ala Ala Cys Gly Thr Gly
            180                 185                 190

Ala Ala Gly Gly Gly Cys Cys Gly Gly Thr Thr Thr Ala Cys Thr Ala
            195                 200                 205

Thr Cys Thr Cys Cys Gly Gly Gly Ala Cys Ala Ala Th

```
Thr Cys Ala Ala Cys Thr Gly Gly Cys Thr Gly Cys Thr Gly Cys Ala
            115                 120                 125
Gly Cys Gly Cys Cys Cys Gly Gly Cys Ala Gly Thr Cys Gly
        130                 135                 140
Cys Cys Gly Cys Ala Gly Cys Gly Gly Cys Thr Thr Ala Thr Cys Thr
145                 150                 155                 160
Ala Cys Ala Ala Ala Gly Thr Gly Thr Cys Cys Ala Ala Cys Cys Gly
                165                 170                 175
Cys Gly Ala Cys Thr Cys Gly Gly Cys Gly Thr Gly Cys Cys Gly
            180                 185                 190
Gly Ala Thr Ala Gly Gly Thr Thr Thr Thr Cys Gly Gly Gly Thr Thr
            195                 200                 205
Cys Cys Gly Gly Ala Ala Gly Cys Gly Gly Cys Ala Cys Cys Gly Ala
        210                 215                 220
Cys Thr Thr Cys Ala Cys Cys Thr Gly Ala Ala Ala Ala Thr Cys Cys
225                 230                 235                 240
Thr Cys Cys Ala Gly Ala Gly Thr Gly Gly Ala Ala Gly Cys Cys Gly
            245                 250                 255
Ala Gly Gly Ala Cys Gly Thr Gly Gly Ala Gly Thr Gly Thr Ala
            260                 265                 270
Cys Thr Ala Cys Thr Gly Thr Thr Gly Gly Cys Ala Gly Gly Thr
        275                 280                 285
Thr Cys Thr Cys Ala Cys Thr Thr Cys Cys Ala Cys Gly Gly Thr
        290                 295                 300
Cys Ala Thr Ala Thr Gly Gly Cys Cys Ala Ala Gly Gly Ala Cys
305                 310                 315                 320
Thr Ala Ala Gly Gly Thr Cys Gly Ala Ala Ala Thr Cys Ala Ala Gly
                325                 330                 335
```

<210> SEQ ID NO 58
<211> LENGTH: 357
<212> TYPE: PRT
<213> ORGANISM: Artificial Sequence
<220> FEATURE:
<223> OTHER INFORMATION: Synthetic peptide

<400> SEQUENCE: 58

```
Gly Ala Ala Gly Thr Gly Cys Ala Gly Cys Thr Cys Cys Thr Gly Gly
1               5                   10                  15
Ala Gly Thr Cys Cys Gly Gly Cys Gly Gly Thr Gly Gly Ala Cys Thr
            20                  25                  30
Gly Gly Thr Gly Cys Ala Gly Cys Cys Gly Gly Cys Gly Gly Ala
        35                  40                  45
Thr Cys Cys Cys Thr Gly Gly Ala Cys Thr Gly Thr Cys Cys Thr
    50                  55                  60
Gly Cys Gly Cys Cys Gly Cys Thr Cys Gly Gly Gly Cys Thr Thr
65                  70                  75                  80
Thr Ala Cys Thr Thr Thr Cys Gly Cys Ala Ala Ala Thr Thr Ala Cys
                85                  90                  95
Gly Gly Cys Ala Thr Gly Ala Cys Thr Gly Gly Thr Cys Ala
            100                 105                 110
Gly Ala Cys Ala Gly Gly Cys Cys Cys Cys Gly Gly Gly Ala Ala
        115                 120                 125
Gly Gly Gly Thr Cys Thr Gly Gly Ala Ala Thr Gly Gly Gly Thr Gly
                130                 135                 140
```

Gly Cys Cys Ala Gly Cys Gly Thr Cys Cys Gly Gly Ala Gly Cys Gly
145 150 155 160

Gly Gly Gly Gly Ala Thr Cys Cys Cys Gly Gly Ala Cys Cys Thr Ala
165 170 175

Thr Thr Ala Cys Thr Cys Cys Gly Ala Cys Ala Ala Cys Gly Thr Gly
180 185 190

Ala Ala Gly Gly Gly Cys Cys Gly Cys Thr Thr Cys Ala Cys Cys Ala
195 200 205

Thr Cys Thr Cys Ala Ala Gly Gly Gly Ala Cys Ala Ala Cys Thr Cys
210 215 220

Cys Ala Ala Gly Ala Ala Cys Ala Cys Cys Cys Thr Gly Thr Ala Cys
225 230 235 240

Thr Thr Gly Cys Ala Ala Ala Thr Gly Ala Ala Cys Ala Gly Cys Cys
245 250 255

Thr Thr Cys Gly Gly Gly Cys Thr Gly Ala Gly Gly Ala Thr Ala Cys
260 265 270

Thr Gly Cys Cys Gly Thr Gly Thr Ala Cys Thr Ala Cys Thr Gly Cys
275 280 285

Gly Thr Gly Cys Gly Cys Thr Ala Cys Gly Ala Cys Cys Ala Cys Thr
290 295 300

Ala Cys Thr Cys Cys Gly Gly Ala Thr Cys Cys Thr Cys Gly Gly Ala
305 310 315 320

Thr Thr Ala Cys Thr Gly Gly Gly Gly Ala Cys Ala Gly Gly Gly Ala
325 330 335

Ala Cys Cys Cys Thr Cys Gly Thr Gly Ala Cys Cys Gly Thr Gly Thr
340 345 350

Cys Ala Thr Cys Gly
355

<210> SEQ ID NO 59
<211> LENGTH: 336
<212> TYPE: PRT
<213> ORGANISM: Artificial Sequence
<220> FEATURE:
<223> OTHER INFORMATION: Synthetic peptide

<400> SEQUENCE: 59

Gly Ala Thr Gly Thr Cys Gly Thr Gly Ala Thr Gly Ala Cys Thr Cys
1 5 10 15

Ala Gly Thr Cys Gly Cys Cys Cys Cys Thr Cys Thr Cys Cys Cys Thr
20 25 30

Gly Cys Cys Thr Gly Thr Gly Ala Cys Thr Cys Thr Gly Gly Gly Gly
35 40 45

Gly Ala Ala Cys Cys Cys Gly Cys Gly Thr Cys Cys Ala Thr Thr Thr
50 55 60

Cys Gly Thr Gly Cys Ala Ala Gly Ala Gly Cys Ala Gly Cys Cys Ala
65 70 75 80

Gly Thr Cys Cys Cys Thr Gly Ala Thr Gly Gly Ala Cys Ala Cys Cys
85 90 95

Gly Ala Cys Gly Gly Ala Ala Ala Gly Ala Cys Cys Thr Ala Cys Cys
100 105 110

Thr Thr Ala Ala Cys Thr Gly Gly Cys Thr Gly Cys Thr Gly Cys Ala
115 120 125

Ala Ala Ala Gly Cys Cys Ala Gly Gly Ala Cys Ala Gly Ala Gly Cys
130 135 140

Cys Cys Gly Cys Ala Gly Ala Gly Gly Cys Thr Gly Ala Thr Cys Thr
145                 150                 155                 160

Ala Cys Ala Ala Ala Gly Thr Gly Thr Cys Ala Ala Cys Cys Gly
            165                 170                 175

Gly Gly Ala Gly Thr Cys Cys Gly Gly Ala Gly Thr Gly Cys Cys Gly
            180                 185                 190

Gly Ala Cys Ala Gly Ala Thr Thr Cys Ala Gly Cys Gly Gly Cys Thr
            195                 200                 205

Cys Gly Gly Gly Thr Thr Cys Cys Gly Gly Cys Ala Cys Cys Gly Ala
        210                 215                 220

Cys Thr Thr Cys Ala Cys Cys Thr Cys Ala Ala Ala Thr Cys
225                 230                 235                 240

Thr Cys Cys Cys Gly Cys Gly Thr Cys Gly Ala Gly Gly Cys Cys Gly
                245                 250                 255

Ala Gly Gly Ala Cys Gly Thr Gly Gly Cys Gly Thr Gly Thr Ala
            260                 265                 270

Thr Thr Ala Cys Thr Gly Thr Thr Gly Gly Cys Ala Gly Gly Gly Ala
            275                 280                 285

Ala Cys Cys Cys Ala Cys Thr Thr Cys Thr Cys Gly Gly Ala
            290                 295                 300

Cys Cys Thr Thr Cys Gly Gly Thr Cys Ala Ala Gly Gly Ala Cys
305                 310                 315                 320

Thr Ala Ala Gly Gly Thr Cys Gly Ala Ala Thr Cys Ala Ala Gly
                325                 330                 335

<210> SEQ ID NO 60
<211> LENGTH: 357
<212> TYPE: PRT
<213> ORGANISM: Artificial Sequence
<220> FEATURE:
<223> OTHER INFORMATION: Synthetic peptide

<400> SEQUENCE: 60

Gly Ala Ala Gly Thr Gly Cys Ala Gly Cys Thr Cys Thr Gly Gly
1               5                   10                  15

Ala Gly Thr Cys Cys Gly Gly Gly Gly Thr Gly Gly Ala Cys Thr
                20                  25                  30

Gly Gly Thr Gly Cys Ala Gly Cys Cys Gly Gly Gly Gly Gly Cys
            35                  40                  45

Ala Gly Cys Cys Thr Gly Ala Gly Gly Cys Thr Gly Ala Gly Cys
        50                  55                  60

Gly Cys Gly Cys Cys Gly Cys Thr Cys Ala Gly Gly Ala Thr Thr
65                  70                  75                  80

Cys Ala Cys Cys Thr Thr Cys Thr Cys Ala Ala Cys Thr Thr Cys
                85                  90                  95

Gly Gly Ala Ala Thr Gly Thr Cys Cys Thr Gly Gly Gly Thr Cys
            100                 105                 110

Gly Ala Cys Ala Gly Gly Cys Cys Cys Gly Gly Gly Ala Ala Ala
        115                 120                 125

Gly Gly Gly Cys Cys Thr Thr Gly Ala Ala Thr Gly Gly Gly Thr
    130                 135                 140

Gly Cys Thr Ala Gly Cys Gly Thr Gly Cys Gly Thr Cys Cys Gly
145                 150                 155                 160

Gly Thr Thr Cys Cys Gly Gly Ala Cys Gly Gly Ala Cys Cys Thr Ala
                165                 170                 175

```
Cys Thr Ala Thr Cys Gly Gly Ala Cys Ala Ala Cys Gly Thr Gly
                180                 185                 190

Ala Ala Gly Gly Gly Cys Cys Gly Gly Thr Thr Thr Ala Cys Thr Ala
            195                 200                 205

Thr Cys Thr Cys Cys Gly Gly Gly Ala Cys Ala Ala Thr Thr Cys
        210                 215                 220

Gly Ala Ala Gly Ala Ala Cys Ala Cys Cys Cys Thr Gly Thr Ala Cys
225                 230                 235                 240

Cys Thr Cys Cys Ala Ala Ala Thr Gly Ala Ala Cys Thr Cys Cys Thr
                245                 250                 255

Thr Gly Cys Gly Cys Gly Cys Cys Gly Ala Gly Gly Ala Thr Ala Cys
            260                 265                 270

Cys Gly Cys Ala Gly Thr Gly Thr Ala Thr Ala Cys Thr Gly Cys
        275                 280                 285

Gly Thr Gly Cys Gly Cys Thr Ala Cys Gly Ala Cys Cys Ala Cys Thr
            290                 295                 300

Ala Cys Thr Cys Thr Gly Gly Cys Ala Cys Thr Ala Gly Cys Gly Ala
305                 310                 315                 320

Thr Thr Ala Cys Thr Gly Gly Gly Cys Cys Ala Gly Gly Ala
                325

```
Ala Gly Ala Cys Thr Cys Cys Gly Ala Gly Thr Gly Cys Cys Thr
            180                 185                 190

Gly Ala Thr Ala Gly Gly Thr Thr Cys Thr Cys Gly Gly Thr Thr
            195                 200                 205

Cys Cys Gly Gly Cys Thr Cys Cys Gly Thr Ala Cys Cys Gly Ala
            210                 215                 220

Cys Thr Thr Cys Ala Cys Thr Cys Thr Gly Ala Ala Ala Thr Thr
225                 230                 235                 240

Thr Cys Cys Cys Gly Gly Thr Gly Ala Ala Gly Cys Cys Gly
            245                 250                 255

Ala Gly Gly Ala Cys Gly Thr Gly Gly Ala Gly Thr Gly Thr Ala
            260                 265                 270

Cys Thr Ala Cys Thr Gly Thr Thr Gly Gly Cys Ala Gly Gly Cys
            275                 280                 285

Ala Cys Cys Cys Ala Cys Thr Thr Cys Cys Cys Cys Gly Gly Thr
            290                 295                 300

Cys Gly Thr Thr Thr Gly Gly Ala Cys Ala Ala Gly Gly Gly Ala Cys
305                 310                 315                 320

Cys Ala Ala G

```
Thr Cys Thr Cys Ala Ala Gly Gly Ala Thr Ala Ala Cys Thr Cys
    210                 215                 220
Cys Ala Ala Gly Ala Ala Thr Ala Cys Thr Cys Thr Gly Thr Ala Cys
225                 230                 235                 240
Thr Thr Gly Cys Ala Ala Ala Thr Gly Ala Ala Cys Thr Cys Gly Cys
                245                 250                 255
Thr Gly Cys Gly Cys Gly Cys Thr Gly Ala Ala Gly Ala Thr Ala Cys
                260                 265                 270
Cys Gly Cys Gly Gly Thr Gly Thr Ala Cys Thr Ala Thr Thr Gly Cys
        275                 280                 285
Gly Thr Gly Cys Gly Cys Thr Ala Cys Gly Ala Cys Cys Ala Cys Thr
    290                 295                 300
Ala Cys Thr Cys Cys Gly Gly Thr Ala Cys

```
Cys Gly Gly Gly Thr Thr Cys Cys Gly Gly Cys Ala Cys Cys Gly Ala
            210                 215                 220

Cys Thr Thr Cys Ala Cys Cys Thr Cys Ala Ala Ala Thr Cys
225                 230                 235                 240

Thr Cys Cys Cys Gly Cys Gly Thr Cys Gly Ala Gly Gly Cys Cys Gly
                245                 250                 255

Ala Gly Gly Ala Cys Gly Thr Gly Gly Cys Gly Thr Gly Thr Thr Ala
            260                 265                 270

Thr Thr Ala Cys Thr Gly Thr Thr Gly Gly Cys Ala Gly Gly Gly Ala
        275                 280                 285

Ala Cys Cys Cys Ala Cys Thr Thr Thr Cys Cys Thr Cys Gly Gly Ala
        290                 295                 300

Cys Cys Thr Thr Cys Gly Gly Thr Cys Ala Ala Gly Gly Gly Ala Cys
305                 310                 315                 320

Thr Ala Ala Gly Gly Thr Cys Gly Ala Ala Ala Thr Cys Ala Ala Gly
                325                 330                 335
```

<210> SEQ ID NO 64
<211> LENGTH: 357
<212> TYPE: PRT
<213> ORGANISM: Artificial Sequence
<220> FEATURE:
<223> OTHER INFORMATION: Synthetic peptide

<400> SEQUENCE: 64

```
Gly Ala Gly Gly Thr Gly Cys Ala Gly Cys Thr Gly Cys Thr Gly Gly
1               5                   10                  15

Ala Gly Thr Cys Gly Gly Gly Gly Gly Gly Gly Gly Ala Cys Thr Thr
            20                  25                  30

Cys Gly Thr Gly Cys Ala Gly Cys Cys Gly Gly Gly Gly Gly Gly Cys
        35                  40                  45

Thr Cys Cys Cys Thr Gly Ala Gly Ala Cys Thr Cys Thr Cys Thr Thr
    50                  55                  60

Gly Thr Gly Cys Cys Gly Cys Cys Thr Cys Gly Gly Cys Thr Thr Cys
65                  70                  75                  80

Cys Ala Cys Thr Thr Thr Thr Cys Ala Ala Cys Thr Thr Cys
            85                  90                  95

Gly Gly Ala Ala Thr Gly Thr Cys Cys Thr Gly Gly Gly Thr Cys Cys
            100                 105                 110

Gly Cys Cys Ala Ala Gly Cys Ala Cys Cys Gly Gly Gly Ala Ala Ala
        115                 120                 125

Gly Gly Gly Thr Cys Thr Gly Gly Ala Ala Thr Gly Gly Gly Thr Cys
    130                 135                 140

Gly Cys Cys Ala Gly Cys Gly Thr Gly Cys Gly Gly Thr Cys Cys Gly
145                 150                 155                 160

Gly Cys Gly Gly Cys Gly Gly Ala Cys Gly Gly Ala Cys Thr Thr Ala
                165                 170                 175

Cys Thr Ala Cys Thr Cys Cys Gly Ala Cys Ala Ala Cys Gly Thr Gly
            180                 185                 190

Ala Ala Gly Gly Gly Cys Cys Gly Gly Thr Thr Cys Ala Cys Cys Ala
        195                 200                 205

Thr Cys Thr Cys Ala Ala Gly Gly Gly Ala Thr Ala Ala Cys Thr Cys
    210                 215                 220

Cys Ala Ala Gly Ala Ala Thr Ala Cys Thr Cys Thr Gly Thr Ala Cys
225                 230                 235                 240
```

Thr Thr Gly Cys Ala Ala Ala Thr Gly Ala Ala Cys Thr Cys Gly Cys
                245                 250                 255

Thr Gly Cys Gly Cys Gly Cys Thr Gly Ala Ala Gly Ala Thr Ala Cys
                260                 265                 270

Cys Gly Cys Gly Gly Thr Gly Thr Ala Cys Thr Ala Thr Thr Gly Cys
                275                 280                 285

Gly Thr Gly Cys Gly Cys Thr Ala Cys Gly Ala Cys Cys Ala Cys Thr
        290                 295                 300

Ala Cys Thr Cys Cys Gly Gly Thr Ala Cys Cys Ala Gly Cys Gly Ala
305                 310                 315                 320

Cys Thr Ala Cys Thr Gly Gly Gly Ala Cys Ala Gly Gly Gly Ala
                325                 330                 335

Ala Cys Cys Cys Thr Thr Gly Thr Gly Ala Cys Cys Gly Thr Gly Thr
                340                 345                 350

Cys Gly Ala Gly Cys
        355

<210> SEQ ID NO 65
<211> LENGTH: 336
<212> TYPE: PRT
<213> ORGANISM: Artificial Sequence
<220> FEATURE:
<223> OTHER INFORMATION: Synthetic peptide

<400> SEQUENCE: 65

Gly Ala Thr Gly Thr Cys Gly Thr Gly Ala Thr Gly Ala Cys Thr Cys
1               5                   10                  15

Ala Gly Thr Cys Gly Cys Cys Cys Thr Cys Thr Cys Cys Cys Thr
                20                  25                  30

Gly Cys Cys Thr Gly Thr Gly Ala Cys Thr Cys Thr Gly Gly Gly Gly
        35                  40                  45

Gly Ala Ala Cys Cys Cys Gly Cys Gly Thr Cys Ala Thr Thr Thr
        50                  55                  60

Cys Gly Thr Gly Cys Ala Ala Gly Ala Gly Cys Ala Gly Cys Cys Ala
65                  70                  75                  80

Gly Thr Cys Cys Cys Thr Gly Thr Thr Gly Ala Cys Thr Cys Ala
                85                  90                  95

Gly Ala Cys Gly Gly Ala Ala Ala Gly Ala Cys Cys Thr Ala Cys Cys
        100                 105                 110

Thr Thr Ala Ala Cys Thr Gly Gly Cys Thr Gly Cys Thr Gly Cys Ala
        115                 120                 125

Ala Ala Ala Gly Cys Cys Ala Gly Gly Ala Cys Ala Gly Ala Gly Cys
        130                 135                 140

Cys Cys Gly Cys Ala Gly Ala Gly Gly Cys Thr Gly Ala Thr Cys Thr
145                 150                 155                 160

Ala Cys Ala Ala Ala Gly Thr Gly Ala Cys Ala Ala Cys Cys Gly
                165                 170                 175

Gly Gly Ala Gly Thr Cys Cys Gly Gly Ala Thr Gly Cys Cys Gly
        180                 185                 190

Gly Ala Cys Ala Gly Ala Thr Thr Cys Ala Gly Cys Gly Gly Cys Thr
        195                 200                 205

Cys Gly Gly Gly Thr Cys Cys Gly Gly Ala Cys Cys Gly Ala
        210                 215                 220

Cys Thr Thr Cys Ala Cys Cys Cys Thr Cys Ala Ala Ala Thr Cys
225                 230                 235                 240

```
Thr Cys Cys Cys Gly Cys Gly Thr Cys Gly Ala Gly Cys Gly
            245                 250                 255

Ala Gly Gly Ala Cys Gly Thr Gly Gly Cys Gly Thr Gly Thr Ala
        260                 265                 270

Thr Thr Ala Cys Thr Gly Thr Thr Gly Gly Cys Ala Gly Gly Ala
        275                 280                 285

Ala Cys Cys Cys Ala Cys Thr Thr Cys Thr Cys Gly Gly Thr
    290                 295                 300

Cys Ala Thr Thr Cys Gly Gly Thr Cys Ala Ala Gly Gly Ala Cys
305             310                 315                 320

Thr Ala Ala Gly Gly Thr Cys Gly Ala Ala Thr Cys Ala Ala Gly
            325                 330                 335
```

<210> SEQ ID NO 66
<211> LENGTH: 357
<212> TYPE: PRT
<213> ORGANISM: Artificial Sequence
<220> FEATURE:
<223> OTHER INFORMATION: Synthetic peptide

<400> SEQUENCE: 66

```
Gly Ala Ala Gly Thr Gly Cys Ala Gly Cys Thr Thr Cys Thr Gly Gly
1               5                   10                  15

Ala Gly Ala Gly Cys Gly Gly Gly Gly Cys Gly Gly Cys Cys Thr
            20                  25                  30

Gly Gly Thr Gly Cys Ala Gly Cys Cys Gly Gly Cys Gly Gly Ala
        35                  40                  45

Thr Cys Cys Cys Thr Gly Ala Gly Ala Cys Thr Gly Thr Cys Cys Thr
    50                  55                  60

Gly Thr Gly Cys Cys Gly Cys Gly Thr Cys Cys Gly Gly Thr Thr Thr
65                  70                  75                  80

Thr Ala Cys Cys Thr Thr Cys Thr Cys Ala Ala Cys Thr Ala Cys
            85                  90                  95

Gly Gly Ala Ala Thr Gly Thr Cys Ala Thr Gly Gly Gly Thr Cys Cys
            100                 105                 110

Gly Cys Cys Ala Ala Gly Cys Ala Cys Cys Gly Gly Ala Ala Ala
        115                 120                 125

Gly Gly Gly Ala Thr Thr Gly Gly Ala Ala Thr Gly Gly Gly Thr Gly
    130                 135                 140

Gly Cys Thr Thr Cys Gly Ala Thr Cys Cys Gly Gly Thr Cys Cys Gly
145                 150                 155                 160

Gly Cys Thr Cys Gly Gly Gly Ala Cys Gly Gly Ala Cys Cys Thr Ala
            165                 170                 175

Cys Thr Ala Cys Thr Cys Cys Gly Ala Thr Ala Ala Cys Gly Thr Cys
            180                 185                 190

Ala Ala Gly Gly Gly Cys Ala Gly Ala Thr Thr Cys Ala Cys Thr Ala
        195                 200                 205

Thr Thr Ala Gly Cys Cys Gly Gly Gly Ala Cys Ala Ala Cys Ala Gly
    210                 215                 220

Cys Ala Ala Gly Ala Ala Thr Ala Cys Cys Cys Thr Gly Thr Ala Cys
225                 230                 235                 240

Cys Thr Cys Cys Ala Ala Ala Thr Gly Ala Ala Cys Thr Cys Cys
            245                 250                 255

Thr Gly Ala Gly Gly Gly Cys Cys Gly Ala Gly Ala Cys Ala Cys
        260                 265                 270
```

```
Cys Gly Cys Cys Gly Thr Gly Thr Ala Thr Thr Ala Cys Thr Gly Cys
            275                 280                 285

Gly Thr Gly Cys Gly Cys Thr Ala Cys Gly Ala Cys Cys Ala Cys Thr
            290                 295                 300

Ala Cys Thr Cys Gly Gly Gly Thr Thr Cys Cys Thr Cys Thr Gly Ala
305                 310                 315                 320

Thr Thr Ala Cys Thr Gly Gly Gly Ala Cys Ala Gly Gly Gly
            325                 330                 335

Ala Cys Cys Thr Cys Gly Thr Gly Ala Cys Thr Gly Thr Gly Thr
            340                 345                 350

Cys Ala Ala Gly Cys
            355

<210> SEQ ID NO 67
<211> LENGTH: 336
<212> TYPE: PRT
<213> ORGANISM: Artificial Sequence
<220> FEATURE:
<223> OTHER INFORMATION: Synthetic peptide

<400> SEQUENCE: 67

Gly Ala Thr Gly Thr Cys Gly Thr Gly Ala Thr Ala Cys Thr Cys
1               5                   10                  15

Ala Gly Thr Cys Ala Cys Cys Gly Cys Thr Cys Thr Cys Cys Thr
                20                  25                  30

Cys Cys Cys Thr Gly Thr Gly Ala Cys Cys Cys Gly Gly Gly Cys
            35                  40                  45

Gly Ala Ala Cys Cys Ala Gly Cys Thr Gly Ala Thr Cys Thr
            50                  55                  60

Cys Cys Thr Gly Cys Ala Ala Gly Ala Gly Cys Ala Gly Cys Cys Ala
65                  70                  75                  80

Ala Thr Cys Ala Thr Thr Gly Cys Thr Gly Gly Ala Cys Thr Ala Cys
                85                  90                  95

Gly Ala Cys Gly Gly Ala Ala Ala Gly Ala Cys Cys Thr Ala Thr Cys
            100                 105                 110

Thr Thr Ala Ala Cys Thr Gly Gly Cys Thr Gly Cys Thr Gly Cys Ala
            115                 120                 125

Gly Ala Ala Gly Cys Cys Gly Gly Gly Cys Ala Gly Ala Gly Cys
            130                 135                 140

Cys Cys Gly Cys Ala Gly Cys Gly Cys Thr Gly Ala Thr Cys Thr
145                 150                 155                 160

Ala Cys Ala Ala Ala Gly Thr Gly Thr Cys Ala Ala Cys Ala Gly
            165                 170                 175

Ala Gly Ala Cys Thr Cys Cys Gly Ala Gly Thr Cys Cys Thr
            180                 185                 190

Gly Ala Thr Ala Gly Gly Thr Thr Cys Thr Gly Gly Gly Thr Thr
            195                 200                 205

Cys Cys Gly Gly Cys Thr Cys Cys Gly Gly Thr Ala Cys Cys Gly Ala
            210                 215                 220

Cys Thr Thr Cys Ala Cys Thr Cys Thr Gly Ala Ala Ala Thr Thr
225                 230                 235                 240

Thr Cys Cys Cys Gly Gly Gly Thr Gly Ala Ala Gly Cys Cys Gly
            245                 250                 255

Ala Gly Gly Ala Cys Gly Thr Gly Gly Ala Gly Thr Gly Thr Ala
            260                 265                 270
```

-continued

```
Cys Thr Ala Cys Thr Gly Thr Thr Gly Gly Cys Ala Gly Gly Gly Cys
            275                 280                 285

Ala Cys Cys Ala Cys Thr Thr Cys Cys Cys Cys Gly Gly Thr
290                 295                 300

Cys Gly Thr Thr Thr Gly Gly Ala Cys Ala Gly Gly Gly Ala Cys
305                 310                 315                 320

Cys Ala Ala Gly Gly Thr Cys Gly Ala Gly Ala Thr Cys Ala Ala Gly
                325                 330                 335

<210> SEQ ID NO 68
<211> LENGTH: 357
<212> TYPE: PRT
<213> ORGANISM: Artificial Sequence
<220> FEATURE:
<223> OTHER INFORMATION: Synthetic peptide

<400> SEQUENCE: 68

Gly Ala Gly Gly Thr Gly Cys Ala Gly Cys Thr Gly Cys Thr Gly Gly
1               5                   10                  15

Ala Gly Thr Cys Gly Gly Gly Gly Gly Gly Gly Gly Ala Cys Thr
                20                  25                  30

Cys Gly Thr Gly Cys Ala Gly Cys Cys Gly Gly Gly Gly Gly Cys
            35                  40                  45

Thr Cys Cys Cys Thr Gly Ala Gly Ala Cys Thr Cys Thr Cys Thr
50                  55                  60

Gly Thr Gly Cys Cys Gly Cys Cys Thr Cys Gly Gly Cys Thr Thr
65                  70                  75                  80

Cys Ala Cys Thr Thr Thr Thr Cys Ala Ala Cys Thr Thr Cys
                85                  90                  95

Gly Gly Ala Ala Thr Gly Thr Cys Cys Thr Gly Gly Thr Cys Cys
                100                 105                 110

Gly Cys Cys Ala Ala Gly Cys Ala Cys Cys Gly Gly Gly Ala Ala Ala
            115                 120                 125

Gly Gly Gly Thr Cys Thr Gly Gly Ala Ala Thr Gly Gly Thr Cys
            130                 135                 140

Gly Cys Cys Ala Gly Cys Gly Thr Thr Cys Gly Gly Thr Cys Cys Gly
145                 150                 155                 160

Gly Cys Gly Gly Cys Gly Gly Ala Cys Gly Gly Ala Cys Thr Thr Ala
                165                 170                 175

Cys Thr Ala Cys Thr Cys Cys Gly Ala Cys Ala Ala Cys Gly Thr Gly
            180                 185                 190

Ala Ala Gly Gly Gly Cys Cys Gly Gly Thr Thr Cys Ala Cys Cys Ala
            195                 200                 205

Thr Cys Thr Cys Ala Ala Gly Gly Gly Ala Thr Ala Ala Cys Thr Cys
            210                 215                 220

Cys Ala Ala Gly Ala Ala Thr Ala Cys Thr Cys Thr Gly Thr Ala Cys
225                 230                 235                 240

Thr Thr Gly Cys Ala Ala Ala Thr Gly Ala Ala Cys Thr Cys Gly Cys
                245                 250                 255

Thr Gly Cys Gly Cys Gly Cys Thr Gly Ala Ala Gly Ala Thr Ala Cys
            260                 265                 270

Cys Gly Cys Gly Gly Thr Gly Thr Ala Cys Thr Ala Thr Thr Gly Cys
            275                 280                 285

Gly Thr Gly Cys Gly Cys Thr Ala Cys Gly Ala Cys Cys Ala Cys Thr
            290                 295                 300
```

```
Ala Cys Thr Cys Cys Gly Gly Thr Ala Cys Cys Ala Gly Cys Gly Ala
305                 310                 315                 320

Cys Thr Ala Cys Thr Gly Gly Gly Gly Ala Cys Ala Gly Gly Gly Ala
                325                 330                 335

Ala Cys Cys Cys Thr Thr Gly Thr Gly Ala Cys Gly Thr Gly Thr
                340                 345                 350

Cys Gly Ala Gly Cys
        355
```

```
<210> SEQ ID NO 69
<211> LENGTH: 336
<212> TYPE: PRT
<213> ORGANISM: Artificial Sequence
<220> FEATURE:
<223> OTHER INFORMATION: Synthetic peptide

<400> SEQUENCE: 69

Gly Ala Thr Gly Thr Cys Gly Thr Gly Ala Thr Gly Ala Cys Thr Cys
1               5                   10                  15

Ala Gly Thr Cys Gly Cys Cys Cys Thr Cys Thr Cys Cys Cys Thr
                20                  25                  30

Gly Cys Cys Thr Gly Thr Gly Ala Cys Thr Cys Thr Gly Gly Gly
            35                  40                  45

Gly Ala Ala Cys Cys Gly Cys Gly Thr Cys Cys Ala Thr Thr Thr
    50                  55                  60

Cys Gly Thr Gly Cys Ala Ala Gly Ala Gly Cys Ala Gly Cys Cys Ala
65                  70                  75                  80

Gly Thr Cys Cys Cys Thr Gly Ala Thr Gly Ala Cys Ala Cys Cys
                85                  90                  95

Gly Ala Cys Gly Gly Ala Ala Ala Gly Ala Cys Cys Thr Ala Cys Cys
                100                 105                 110

Thr Thr Ala Ala Cys Thr Gly Gly Cys Thr Gly Cys Thr Gly Cys Ala
            115                 120                 125

Ala Ala Ala Gly Cys Cys Ala Gly Gly Ala Cys Ala Gly Ala Gly Cys
                130                 135                 140

Cys Cys Gly Cys Ala Gly Ala Gly Gly Cys Thr Gly Ala Thr Cys Thr
145                 150                 155                 160

Ala Cys Ala Ala Ala Gly Thr Gly Thr Cys Ala Ala Cys Cys Gly
                165                 170                 175

Gly Gly Ala Gly Thr Cys Cys Gly Gly Ala Gly Thr Gly Cys Cys Gly
                180                 185                 190

Gly Ala Cys Ala Gly Ala Thr Thr Cys Ala Gly Cys Gly Gly Cys Thr
            195                 200                 205

Cys Gly Gly Gly Thr Thr Cys Cys Gly Gly Cys Ala Cys Cys Gly Ala
                210                 215                 220

Cys Thr Thr Cys Ala Cys Cys Cys Thr Cys Ala Ala Ala Ala Thr Cys
225                 230                 235                 240

Thr Cys Cys Cys Gly Cys Gly Thr Cys Gly Ala Gly Cys Cys Gly
                245                 250                 255

Ala Gly Gly Ala Cys Gly Thr Gly Gly Cys Gly Thr Gly Thr Ala
                260                 265                 270

Thr Thr Ala Cys Thr Gly Thr Thr Gly Gly Cys Ala Gly Gly Ala
            275                 280                 285

Ala Cys Cys Cys Ala Cys Thr Thr Cys Cys Thr Cys Gly Gly Ala
    290                 295                 300
```

```
Cys Cys Thr Thr Cys Gly Gly Thr Cys Ala Ala Gly Gly Gly Ala Cys
305                 310                 315                 320

Thr Ala Ala Gly Gly Thr Cys Gly Ala Ala Thr Cys Ala Ala Gly
                325                 330                 335

<210> SEQ ID NO 70
<211> LENGTH: 454
<212> TYPE: PRT
<213> ORGANISM: Artificial Sequence
<220> FEATURE:
<223> OTHER INFORMATION: Synthetic peptide

<400> SEQUENCE: 70

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Arg Gly Ile Gly Ala Arg Arg Gly Pro Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335
```

```
Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 71
<211> LENGTH: 214
<212> TYPE: PRT
<213> ORGANISM: Artificial Sequence
<220> FEATURE:
<223> OTHER INFORMATION: Synthetic peptide

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
```

```
<211> LENGTH: 449
<212> TYPE: PRT
<213> ORGANISM: Artificial Sequence
<220> FEATURE:
<223> OTHER INFORMATION: Synthetic peptide

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

Ser Asn Gly Gln Pro Glu Asn Tyr Lys Thr Thr Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 73
<211> LENGTH: 119
<212> TYPE: PRT
<213> ORGANISM: Artificial Sequence
<220> FEATURE:
<223> OTHER INFORMATION: Synthetic peptide

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
                100                 105                 110

Thr Leu Val Thr Val Ser Ser
        115

<210> SEQ ID NO 74
<211> LENGTH: 4
<212> TYPE: PRT
<213> ORGANISM: Artificial Sequence
<220> FEATURE:
<223> OTHER INFORMATION: Synthetic peptide

<400> SEQUENCE: 74

Ala Ala Ala Ala
1

<210> SEQ ID NO 75
<211> LENGTH: 4
<212> TYPE: PRT
<213> ORGANISM: Artificial Sequence
<220> FEATURE:
<223> OTHER INFORMATION: Synthetic peptide

<400> SEQUENCE: 75

Ala Ala Ala Gly
1

<210> SEQ ID NO 76
<211> LENGTH: 4
<212> TYPE: PRT

```
<213> ORGANISM: Artificial Sequence
<220> FEATURE:
<223> OTHER INFORMATION: Synthetic peptide

<400> SEQUENCE: 76

Ala Ala Gly Gly
1

<210> SEQ ID NO 77
<211> LENGTH: 219
<212> TYPE: PRT
<213> ORGANISM: Artificial Sequence
<220> FEATURE:
<223> OTHER INFORMATION: Synthetic peptide

<400> SEQUENCE: 77

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 78
<211> LENGTH: 112
<212> TYPE: PRT
<213> ORGANISM: Artificial Sequence
<220> FEATURE:
<223> OTHER INFORMATION: Synthetic peptide

<400> SEQUENCE: 78

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45
```

Pro Gln Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Val Glu Ile Lys
            100                 105                 110

<210> SEQ ID NO 79
<211> LENGTH: 4
<212> TYPE: PRT
<213> ORGANISM: Artificial Sequence
<220> FEATURE:
<223> OTHER INFORMATION: Synthetic peptide

<400> SEQUENCE: 79

Ala Ala Gly Gly
1

<210> SEQ ID NO 80
<211> LENGTH: 4
<212> TYPE: PRT
<213> ORGANISM: Artificial Sequence
<220> FEATURE:
<223> OTHER INFORMATION: Synthetic peptide

<400> SEQUENCE: 80

Ala Gly Gly Gly
1

<210> SEQ ID NO 81
<211> LENGTH: 4
<212> TYPE: PRT
<213> ORGANISM: Artificial Sequence
<220> FEATURE:
<223> OTHER INFORMATION: Synthetic peptide

<400> SEQUENCE: 81

Gly Gly Gly Gly
1

<210> SEQ ID NO 82
<211> LENGTH: 456
<212> TYPE: PRT
<213> ORGANISM: Artificial Sequence
<220> FEATURE:
<223> OTHER INFORMATION: Synthetic peptide

<400> SEQUENCE: 82

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 83
<211> LENGTH: 215
<212> TYPE: PRT
<213> ORGANISM: Artificial Sequence
<220> FEATURE:
<223> OTHER INFORMATION: Synthetic peptide

<400> SEQUENCE: 83

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 84
<211> LENGTH: 42
<212> TYPE: PRT
<213> ORGANISM: Artificial Sequence
<220> FEATURE:
<223> OTHER INFORMATION: Synthetic peptide

<400> SEQUENCE: 84

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 85
<211> LENGTH: 770
<212> TYPE: PRT
<213> ORGANISM: Artificial Sequence
<220> FEATURE:
<223> OTHER INFORMATION: Synthetic peptide

<400> SEQUENCE: 85

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln

```
                35                  40                  45
Asn Gly Lys Trp Asp Ser Asp Pro Ser Gly Thr Lys Thr Cys Ile Asp
 50                  55                  60
Thr Lys Glu Gly Ile Leu Gln Tyr Cys Gln Glu Val Tyr Pro Glu Leu
65                  70                  75                  80
Gln Ile Thr Asn Val Val Glu Ala Asn Gln Pro Val Thr Ile Gln Asn
                85                  90                  95
Trp Cys Lys Arg Gly Arg Lys Gln Cys Lys Thr His Pro His Phe Val
            100                 105                 110
Ile Pro Tyr Arg Cys Leu Val Gly Glu Phe Val Ser Asp Ala Leu Leu
            115                 120                 125
Val Pro Asp Lys Cys Lys Phe Leu His Gln Glu Arg Met Asp Val Cys
            130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
            195                 200                 205
Trp Trp Gly Gly Ala Asp Thr Asp Tyr Ala Asp Gly Ser Glu Asp Lys
            210                 215                 220
Val Val Glu Val Ala Glu Glu Glu Val Ala Glu Val Glu Glu Glu Glu
225                 230                 235                 240
Glu Ala Asp Asp Asp Glu Asp Asp Glu Asp Gly Asp Glu Val Glu Glu
            245                 250                 255
Glu Ala Glu Glu Pro Tyr Glu Glu Ala Thr Glu Arg Thr Thr Ser Ile
            260                 265                 270
Ala Thr Thr Thr Thr Thr Thr Thr Glu Ser Val Glu Glu Val Val Arg
            275                 280                 285
Glu Val Cys Ser Glu Gln Ala Glu Thr Gly Pro Cys Arg Ala Met Ile
            290                 295                 300
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
            355                 360                 365
Ala Ser Thr Pro Asp Ala Val Asp Lys Tyr Leu Glu Thr Pro Gly Asp
            370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
            435                 440                 445
Glu Arg Gln Gln Leu Val Glu Thr His Met Ala Arg Val Glu Ala Met
            450                 455                 460
```

```
Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
            485                 490                 495

Tyr Val Arg Ala Glu Gln Lys Asp Arg Gln His Thr Leu Lys His Phe
        500                 505                 510

Glu His Val Arg Met Val Asp Pro Lys Lys Ala Ala Gln Ile Arg Ser
    515                 520                 525

Gln Val Met Thr His Leu Arg Val Ile Tyr Glu Arg Met Asn Gln Ser
530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
            565                 570                 575

Leu Ala Asn Met Ile Ser Glu Pro Arg Ile Ser Tyr Gly Asn Asp Ala
        580                 585                 590

Leu Met Pro Ser Leu Thr Glu Thr Lys Thr Thr Val Glu Leu Leu Pro
    595                 600                 605

Val Asn Gly Glu Phe Ser Leu Asp Asp Leu Gln Pro Trp His Ser Phe
610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
            645                 650                 655

Gly Leu Thr Asn Ile Lys Thr Glu Glu Ile Ser Glu Val Lys Met Asp
        660                 665                 670

Ala Glu Phe Arg His Asp Ser Gly Tyr Glu Val His His Gln Lys Leu
    675                 680                 685

Val Phe Phe Ala Glu Asp Val Gly Ser Asn Lys Gly Ala Ile Ile Gly
690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
            725                 730                 735

Glu Val Asp Ala Ala Val Thr Pro Glu Glu Arg His Leu Ser Lys Met
        740                 745                 750

Gln Gln Asn Gly Tyr Glu Asn Pro Thr Tyr Lys Phe Phe Glu Gln Met
    755                 760                 765

Gln Asn
    770

<210> SEQ ID NO 86
<211> LENGTH: 993
<212> TYPE: PRT
<213> ORGANISM: Artificial Sequence
<220> FEATURE:
<223> OTHER INFORMATION: Synthetic peptide

<400> SEQUENCE: 86

Gly Cys Cys Ala Gly Cys Ala Cys Thr Ala Ala Gly Gly Gly Gly Cys
1               5                   10                  15

Cys Thr Ala Gly Cys Gly Thr Cys Thr Thr Thr Cys Cys Gly Cys Thr
            20                  25                  30

Gly Gly Cys Cys Cys Cys Gly Thr Cys Cys Thr Cys Cys Ala Ala Gly
        35                  40                  45
```

-continued

```
Thr Cys Cys Ala Cys Thr Thr Cys Gly Gly Gly Thr Gly Ala Ala
    50                   55                  60
Cys Cys Gly Cys Gly Gly Cys Ala Cys Thr Gly Gly Gly Thr Gly
65              70                  75                  80
Cys Cys Thr Cys Gly Thr Gly Ala Ala Gly Ala Cys Thr Ala Cys
                85                  90                  95
Thr Thr Cys Cys Cys Gly Ala Gly Cys Cys Gly Gly Thr Cys Ala
            100                 105                 110
Cys Cys Gly Thr Gly Thr Cys Cys Thr Gly Gly Ala Ala Cys Thr Cys
        115                 120                 125
Gly Gly Gly Ala Gly Cys Cys Thr Gly Ala Cys Cys Thr Cys Cys
    130                 135                 140
Gly Gly Ala Gly Thr Gly Cys Ala Thr Ala Cys Thr Thr Thr Cys Cys
145                 150                 155                 160
Cys Thr Gly Cys Gly Gly Thr Gly Cys Thr Gly Cys Ala Gly Thr Cys
                165                 170                 175
Cys Thr Cys Cys Gly Gly Gly Cys Thr Cys Thr Ala Cys Thr Cys Gly
            180                 185                 190
Cys Thr Gly Thr Cys Ala Ala Gly Cys Gly Thr Gly Thr Cys Ala
        195                 200                 205
Cys Cys Gly Thr Cys Cys Cys Gly Ala Gly Cys Thr Cys Ala Thr Cys
    210                 215                 220
Cys Cys Thr Gly Gly Gly Thr Ala Cys Thr Cys Ala Gly Ala Cys Cys
225                 230                 235                 240
Thr Ala Cys Ala Thr Thr Thr Gly Cys Ala Ala Cys Gly Thr Gly Ala
                245                 250                 255
Ala Cys Cys Ala Cys Ala Ala Ala Cys Cys Thr Thr Cys Cys Ala Ala
            260                 265                 270
Cys Ala Cys Cys Ala Ala Gly Gly Thr Cys Gly Ala Cys Ala Ala Gly
        275                 280                 285
Ala Ala Ala Gly Thr Gly Gly Ala Gly Cys Cys Thr Ala Ala Gly Ala
    290                 295                 300
Gly Cys Thr Gly Cys Gly Ala Cys Ala Ala Ala Cys Cys Cys Ala
305                 310                 315                 320
Cys Ala Cys Cys Thr Gly Thr Cys Cys Cys Cys Gly Thr Gly Thr
                325                 330                 335
Cys Cys Cys Gly Cys Cys Cys Thr Gly Ala Gly Cys Thr Gly Cys
            340                 345                 350
Thr Gly Gly Gly Cys Gly Gly Cys Cys Cys Ala Gly Cys Gly Thr
        355                 360                 365
Gly Thr Thr Cys Cys Thr Cys Thr Thr Cys Cys Gly Cys Cys Thr
    370                 375                 380
Ala Ala Gly Cys Cys Gly Ala Ala Gly Ala Cys Ala Cys Thr Cys
385                 390                 395                 400
Thr Gly Ala Thr Gly Ala Thr Cys Thr Cys Gly Ala Gly Ala Ala Cys
                405                 410                 415
Cys Cys Cys Thr Gly Ala Ala Gly Thr Gly Ala Cys Cys Thr Gly Thr
            420                 425                 430
Gly Thr Gly Gly Thr Gly Gly Thr Gly Gly Ala Thr Gly Thr Gly
        435                 440                 445
Cys Cys Cys Ala Cys Gly Ala Gly Gly Ala Thr Cys Cys Gly Gly Ala
    450                 455                 460
```

```
Ala Gly Thr Gly Ala Ala Gly Thr Thr Cys Ala Thr Gly Gly
465                 470                 475                 480

Thr Ala Cys Gly Thr Gly Gly Ala Cys Gly Gly Ala Gly Thr Gly Gly
                485                 490                 495

Ala Ala Gly Thr Cys Cys Ala Thr Ala Ala Cys Gly Cys Ala Ala
            500                 505                 510

Gly Ala Cys Cys Ala Ala Gly Cys Cys Cys Gly Cys Gly Ala Gly
            515                 520                 525

Gly Ala Ala Cys Ala Gly Thr Ala Cys Ala Ala Cys Thr Cys Ala Ala
530                 535                 540

Cys Thr Thr Ala Cys Cys Gly Gly Gly Thr Gly Gly Thr Gly Thr Cys
545                 550                 555                 560

Ala Gly Thr Gly Cys Thr Gly Ala Cys Cys Gly Thr Gly Cys Thr Gly
                565                 570                 575

Cys Ala Cys Cys Ala Ala Gly Ala Thr Thr Gly Gly Cys Thr Gly Ala
                580                 585                 590

Ala Cys Gly Gly Gly Ala Ala Gly Gly Ala Gly Thr Ala Cys Ala Ala
            595                 600                 605

Gly Thr Gly Cys Ala Ala Ala Gly Thr Cys Thr Cys Cys Ala Ala Cys
610                 615                 620

Ala Ala Gly Gly Cys Gly Cys Thr Gly Cys Cys Gly Cys Cys Cys
625                 630                 635                 640

Cys Cys Ala Thr Thr Gly Ala Ala Ala Ala Gly Ala Cys Cys Ala Thr
                645                 650                 655

Cys Ala Gly Cys Ala Ala Gly Gly Cys Thr Ala Ala Gly Gly Gly Cys
            660                 665                 670

Cys Ala Gly Cys Cys Cys Gly Gly Ala Ala Cys Cys Ala Cys
            675                 680                 685

Ala Gly Gly Thr Cys Thr Ala Cys Ala Cys Cys Thr Thr Gly Cys Cys
            690                 695                 700

Cys Cys Cys Thr Thr Cys Cys Gly Gly Gly Ala Gly Gly Ala Ala
705                 710                 715                 720

Ala Thr Gly Ala Cys Cys Ala Ala Gly Ala Ala Cys Cys Ala Ala Gly
                725                 730                 735

Thr Gly Thr Cys Gly Cys Thr Gly Ala Cys Gly Thr Gly Cys Cys Thr
                740                 745                 750

Gly Gly Thr Cys Ala Ala Gly Gly Gly Cys Thr Thr Thr Ala Thr
            755                 760                 765

Cys Cys Ala Thr Cys Thr Gly Ala Cys Ala Thr Cys Gly Cys Cys Gly
770                 775                 780

Thr Gly Gly Ala Gly Thr Gly Gly Ala Ala Ala Gly Cys Ala Ala
785                 790                 795                 800

Cys Gly Gly Cys Cys Ala Gly Cys Cys Gly Gly Ala Ala Ala Ala Cys
            805                 810                 815

Ala Ala Cys Thr Ala Cys Ala Ala Gly Ala Cys Cys Ala Cys Cys Cys
            820                 825                 830

Cys Gly Cys Cys Thr Gly Thr Gly Cys Thr Gly Gly Ala Cys Thr Cys
            835                 840                 845

Cys Gly Ala Cys Gly Gly Cys Thr Cys Gly Thr Thr Cys Thr Thr Cys
            850                 855                 860

Cys Thr Gly Thr Ala Thr Thr Cys Cys Ala Ala Gly Cys Thr Cys Ala
865                 870                 875                 880

Cys Cys Gly Thr Gly Gly Ala Thr Ala Ala Gly Thr Cys Cys Ala Gly
```

```
                    885                 890                 895
Ala Thr Gly Gly Cys Ala Gly Cys Ala Gly Gly Cys Ala Ala Thr
                900                 905                 910
Gly Thr Gly Thr Thr Cys Ala Gly Cys Thr Gly Cys Ala Gly Cys Gly
                915                 920                 925
Thr Gly Ala Thr Gly Cys Ala Thr Gly Ala Gly Gly Cys Cys Cys Thr
                930                 935                 940
Gly Cys Ala Cys Ala Ala Cys Cys Ala Cys Thr Ala Cys Ala Cys Thr
945                 950                 955                 960
Cys Ala Gly Ala Ala Ala Thr Cys Ala Cys Thr Gly Thr Cys Cys Cys
                965                 970                 975
Thr Thr Thr Cys Cys Cys Cys Gly Gly Ala Ala Ala Gly Thr Ala
                980                 985                 990
Ala
```

<210> SEQ ID NO 87
<211> LENGTH: 324
<212> TYPE: PRT
<213> ORGANISM: Artificial Sequence
<220> FEATURE:
<223> OTHER INFORMATION: Synthetic peptide

<400> SEQUENCE: 87

```
Cys Gly Ala Ala Cys Thr Gly Thr Gly Cys Thr Gly Cys Ala Cys
1               5                   10                  15
Cys Ala Thr Cys Thr Gly Thr Cys Thr Thr Cys Ala Thr Cys Thr Thr
                20                  25                  30
Cys Cys Cys Gly Cys Cys Ala Thr Cys Thr Gly Ala Thr Gly Ala Gly
                35                  40                  45
Cys Ala Gly Thr Thr Gly Ala Ala Ala Thr Cys Thr Gly Gly Ala Ala
                50                  55                  60
Cys Thr Gly Cys Cys Thr Cys Thr Gly Thr Thr Gly Thr Gly Thr Gly
65                  70                  75                  80
Cys Cys Thr Gly Cys Thr Gly Ala Ala Thr Ala Ala Cys Thr Thr Cys
                85                  90                  95
Thr Ala Thr Cys Cys Cys Ala Gly Ala Gly Ala Gly Gly Cys Cys Ala
                100                 105                 110
Ala Ala Gly Thr Ala Cys Ala Gly Thr Gly Gly Ala Ala Gly Gly Thr
                115                 120                 125
Gly Gly Ala Thr Ala Ala Cys Gly Cys Cys Cys Thr Cys Cys Ala Ala
                130                 135                 140
Thr Cys Gly Gly Gly Thr Ala Ala Cys Thr Cys Cys Cys Ala Gly Gly
145                 150                 155                 160
Ala Gly Ala Gly Thr Gly Thr Cys Ala Cys Ala Gly Ala Gly Cys Ala
                165                 170                 175
Gly Gly Ala Cys Ala Gly Cys Ala Ala Gly Ala Cys Ala Gly Cys
                180                 185                 190
Ala Cys Cys Thr Ala Cys Ala Gly Cys Cys Thr Cys Ala Gly Cys Ala
                195                 200                 205
Gly Cys Ala Cys Cys Cys Thr Gly Ala Cys Gly Cys Thr Gly Ala Gly
                210                 215                 220
Cys Ala Ala Ala Gly Cys Ala Gly Ala Cys Thr Ala Cys Gly Ala Gly
225                 230                 235                 240
Ala Ala Ala Cys Ala Cys Ala Ala Ala Gly Thr Cys Thr Ala Cys Gly
                245                 250                 255
```

```
Cys Cys Thr Gly Cys Gly Ala Ala Gly Thr Cys Ala Cys Cys Ala
                260                 265                 270

Thr Cys Ala Gly Gly Cys Cys Thr Gly Ala Gly Cys Thr Cys Gly
            275                 280                 285

Cys Cys Cys Gly Thr Cys Ala Cys Ala Ala Gly Ala Gly Cys Thr
        290                 295                 300

Thr Cys Ala Ala Cys Ala Gly Gly Gly Ala Gly Ala Gly Thr Gly
305                 310                 315                 320

Thr Thr Ala Ala

<210> SEQ ID NO 88
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: X = Y of F

<400> SEQUENCE: 88

Gly Phe Thr Phe Ser Asn Xaa Gly Met Ser
1               5                   10

<210> SEQ ID NO 89
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: X = I or V

<400> SEQUENCE: 89

Ser Xaa Arg Ser Gly Ser Gly Arg Thr Tyr Tyr Ser Asp Asn Val Lys
1               5                   10                  15
Gly

<210> SEQ ID NO 90
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: X = S or T
<220> FEATURE:
<221> NAME/KEY: misc_feature
<222> LOCATION: (7)..(7)
<223> OTHER INFORMATION: X = S or T

<400> SEQUENCE: 90

Tyr Asp His Tyr Xaa Gly Xaa Ser Asp Tyr
1               5                   10

<210> SEQ ID NO 91
<211> LENGTH: 16
<212> TYPE: PRT
<213> ORGANISM: Artificial Sequence
<220> FEATURE:
<223> OTHER INFORMATION: Synthetic peptide
```

```
<400> SEQUENCE: 91

Lys Ser Ser Gln Ser Leu Leu Asp Tyr Asp Gly Lys Thr Tyr Leu Asn
1               5                   10                  15

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X = K or R
<220> FEATURE:
<221> NAME/KEY: misc_feature
<222> LOCATION: (3)..(3)
<223> OTHER INFORMATION: X = S or T
<220> FEATURE:
<221> NAME/KEY: misc_feature
<222> LOCATION: (7)..(7)
<223> OTHER INFORMATION: X = S or T

<400> SEQUENCE: 92

Xaa Val Xaa Asn Arg Asp Xaa
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: X = S or T

<400> SEQUENCE: 93

Trp Gln Gly Thr His Phe Pro Arg Xaa
1               5

<210> SEQ ID NO 94
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: X = S or T
<220> FEATURE:
<221> NAME/KEY: misc_feature
<222> LOCATION: (11)..(11)
<223> OTHER INFORMATION: X = F or Y

<400> SEQUENCE: 94

Trp Gln Gly Thr His Phe Pro Arg Xaa Phe Xaa
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
```

<223> OTHER INFORMATION: X = S or A
<220> FEATURE:
<221> NAME/KEY: misc_feature
<222> LOCATION: (7)..(7)
<223> OTHER INFORMATION: X = Y or F

<400> SEQUENCE: 95

Gly Phe Thr Phe Xaa Asn Xaa Gly Met Ser
1               5                   10

<210> SEQ ID NO 96
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: X = I or V
<220> FEATURE:
<221> NAME/KEY: misc_feature
<222> LOCATION: (6)..(6)
<223> OTHER INFORMATION: X = S or G
<220> FEATURE:
<221> NAME/KEY: misc_feature
<222> LOCATION: (7)..(7)
<223> OTHER INFORMATION: X = S or G

<400> SEQUENCE: 96

Ser Xaa Arg Ser Gly Xaa Xaa Arg Thr Tyr Tyr Ser Asp Asn Val Lys
1               5                   10                  15

Gly

<210> SEQ ID NO 97
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X = K or R
<220> FEATURE:
<221> NAME/KEY: misc_feature
<222> LOCATION: (7)..(7)
<223> OTHER INFORMATION: X = V, M or L
<220> FEATURE:
<221> NAME/KEY: misc_feature
<222> LOCATION: (9)..(9)
<223> OTHER INFORMATION: X = Y, T or S

<400> SEQUENCE: 97

Xaa Ser Ser Gln Ser Leu Xaa Asp Xaa Asp Gly Lys Thr Tyr Leu Asn
1               5                   10                  15

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: X = K or R
<220> FEATURE:
<221> NAME/KEY: misc_feature
<222> LOCATION: (3)..(3)
<223> OTHER INFORMATION: X = S or T
<220> FEATURE:

```
<221> NAME/KEY: misc_feature
<222> LOCATION: (6)..(6)
<223> OTHER INFORMATION: X = E or D
<220> FEATURE:
<221> NAME/KEY: misc_feature
<222> LOCATION: (7)..(7)
<223> OTHER INFORMATION: X = S or T

<400> SEQUENCE: 98

Xaa Val Xaa Asn Arg Xaa Xaa
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: X = S or T
<220> FEATURE:
<221> NAME/KEY: misc_feature
<222> LOCATION: (9)..(9)
<223> OTHER INFORMATION: X = S or T

<400> SEQUENCE: 99

Trp Gln Gly Xaa His Phe Pro Arg Xaa
1               5

<210> SEQ ID NO 100
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: X = S or T
<220> FEATURE:
<221> NAME/KEY: misc_feature
<222> LOCATION: (11)..(11)
<223> OTHER INFORMATION: X = S or T
<220> FEATURE:
<221> NAME/KEY: misc_feature
<222> LOCATION: (12)..(12)
<223> OTHER INFORMATION: X = F or Y

<400> SEQUENCE: 100

Trp Gln Gly Thr His Phe Pro Arg Xaa Phe Xaa Xaa
1               5                   10

<210> SEQ ID NO 101
<211> LENGTH: 112
<212> TYPE: PRT
<213> ORGANISM: Artificial Sequence
<220> FEATURE:
<223> OTHER INFORMATION: Synthetic peptide

<400> SEQUENCE: 101

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
                20                  25                  30

Asp Gly Arg Thr Tyr Leu Asn Trp Leu Leu Gln Lys Pro Gly Gln Ser
            35                  40                  45

Pro Gln Arg Leu Ile Tyr Leu Val Ser Lys Leu Asp Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Val Glu Ile Lys
                100                 105                 110

<210> SEQ ID NO 102
<211> LENGTH: 112
<212> TYPE: PRT
<213> ORGANISM: Artificial Sequence
<220> FEATURE:
<223> OTHER INFORMATION: Synthetic peptide

<400> SEQUENCE: 102

Asp Val Val Met Thr Gln Ser Pro Leu Ser Leu Pro Val Thr Leu Gly
 1               5                  10                  15

Glu Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Lys Pro Gly Gln Ser
             35                  40                  45

Pro Gln Arg Leu Ile Tyr Leu Val Ser Lys Leu Asp Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Val Glu Ile Lys
                100                 105                 110
```